US012655140B2

(12) United States Patent
Xu et al.

(10) Patent No.: US 12,655,140 B2
(45) Date of Patent: Jun. 16, 2026

(54) COMPOUND CONTAINING STRUCTURE OF A HETEROAROMATIC RING, PHARMACEUTICAL COMPOSITION THEREOF AND APPLICATION THEREOF

(71) Applicant: SHANGHAI YINGLI PHARMACEUTICAL CO., LTD., Shanghai (CN)

(72) Inventors: Zusheng Xu, Shanghai (CN); Yangtong Lou, Shanghai (CN); Tiegang Xie, Shanghai (CN); Linlin Xu, Shanghai (CN); Li Chen, Shanghai (CN); Yanhang Liu, Shanghai (CN); Qingrui Sun, Shanghai (CN)

(73) Assignee: SHANGHAI YINGLI PHARMACEUTICAL CO., LTD., Shanghai (CN)

( * ) Notice: Subject to any disclaimer, the term of this patent is extended or adjusted under 35 U.S.C. 154(b) by 491 days.

(21) Appl. No.: 18/460,207

(22) Filed: Sep. 1, 2023

(65) Prior Publication Data

US 2025/0042891 A1 Feb. 6, 2025

(30) Foreign Application Priority Data

Jun. 16, 2023 (CN) ......................... 202310718341.1

(51) Int. Cl.

| | |
|---|---|
| ***C07D 417/04*** | (2006.01) |
| ***A61P 35/00*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |
| ***C07D 491/044*** | (2006.01) |
| ***C07F 9/24*** | (2006.01) |

(52) U.S. Cl.

CPC ............ *C07D 417/04* (2013.01); *A61P 35/00* (2018.01); *C07D 413/14* (2013.01); *C07D 417/14* (2013.01); *C07D 471/04* (2013.01); *C07D 487/04* (2013.01); *C07D 491/044* (2013.01); *C07F 9/2466* (2013.01); *C07B 2200/05* (2013.01)

(58) Field of Classification Search

CPC .. C07D 487/14; C07D 471/14; C07D 417/14; C07D 413/14; C07D 417/04

See application file for complete search history.

(56) References Cited

U.S. PATENT DOCUMENTS

| | | | |
|---|---|---|---|
| 6,858,638 | B2 | 2/2005 | Damour et al. |
| 7,473,701 | B2 | 1/2009 | Damour et al. |
| 10,508,086 | B2 | 12/2019 | Mcgonagle et al. |

FOREIGN PATENT DOCUMENTS

| | | | |
|---|---|---|---|
| WO | 2008156757 | A1 | 12/2008 |
| WO | 2016092326 | A1 | 6/2016 |
| WO | 2016097749 | A1 | 6/2016 |
| WO | 2021055744 | A1 | 3/2021 |
| WO | 2022138812 | A1 | 6/2022 |
| WO | 2023057389 | A1 | 4/2023 |
| WO | 2023057394 | A1 | 4/2023 |

OTHER PUBLICATIONS

Lala, et al. Cancer and Metastasis Reviews (1998), 17(1), 91-106.*

Golub, et al. Science 286, 531 (1999).*

Cancer [online], [retrieved on Aug. 11, 2023]. Retrieved from the internet, URL https://medlineplus.gov/cancer.html#>.*

* cited by examiner

*Primary Examiner* — Shawquia Jackson

(74) *Attorney, Agent, or Firm* — Panitch Schwarze Belisario & Nadel LLP

(57) ABSTRACT

Disclosed is a compound containing structure of a heteroaromatic ring, pharmaceutical composition thereof and application thereof. The present disclosure provides a compound containing structure of a heteroaromatic ring represented by formula I, a pharmaceutically acceptable salt thereof, a stereoisomer thereof, an isomer thereof or an isotopic compound thereof. The compound containing structure of a heteroaromatic ring is expected to treat and/or prevent various PARG-related diseases.

I

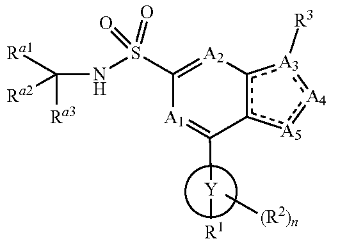

13 Claims, No Drawings

COMPOUND CONTAINING STRUCTURE OF A HETEROAROMATIC RING, PHARMACEUTICAL COMPOSITION THEREOF AND APPLICATION THEREOF

TECHNICAL FIELD

The present disclosure relates to a compound containing structure of a heteroaromatic ring, pharmaceutical composition thereof and application thereof.

BACKGROUND

Cancer cells tend to divide and proliferate uncontrollably, resulting in a higher incidence of DNA damage and defective DNA repair, and are more dependent on DNA damage repair mechanisms than normal cells.

Polyadenosine diphosphate ribose polymerase (PARP), polyadenosine diphosphate ribose hydrolase (PARG) and other proteins play an important role in DNA repair and have become important targets in the development of anti-cancer drugs. PARP can bind to single-strand break sites of DNA, which promotes the production of polyadenosine diphosphate ribose (PAR) chains, thus triggering the repair process. PARG is to degrade PAR on PARP and facilitate the completion of the entire repair cycle. Inhibition of either PARP or PARG affects the entire repair process.

Currently, the research and development of PARP inhibitors has been highly successful, with several drugs approved for marketing, and has demonstrated the feasibility of using DNA repair proteins as targets. At the same time, there is some problem still exist in PARP inhibitors such as not effective to all patients, drug resistance. The research on PARG inhibitors is still in the exploratory stage. There is a lot of room for research in this target direction, which is expected to fill the unmet clinical needs.

CONTENT OF THE PRESENT DISCLOSURE

The present disclosure provides a compound containing structure of a heteroaromatic ring represented by formula I, a pharmaceutically acceptable salt thereof, a stereoisomer thereof, an isomer thereof or an isotopic compound thereof:

I

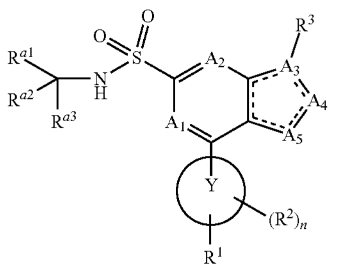

Wherein, “⎓” represents a single bond or a double bond;

Both rings of

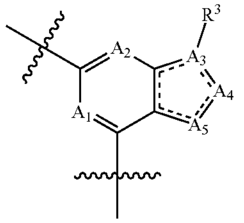

are aromatic;

$A_1$ and $A_2$ are independently N or $CR^{b1}$, $R^{b1}$ is hydrogen or halogen;

$A_3$ is C or N;

$A_4$ is N, $CR^4$ or $NR^4$;

$A_5$ is $NR^5$, N, $CR^5$, S or O;

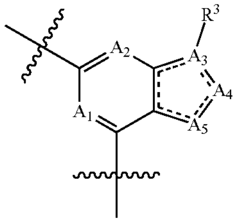

is

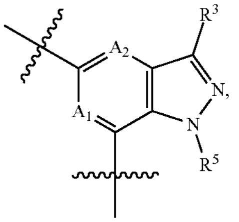

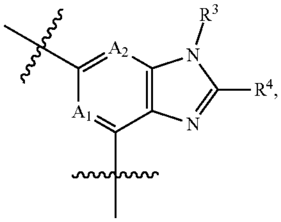

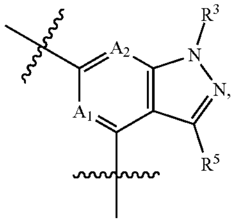

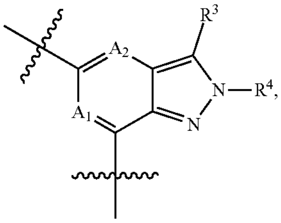

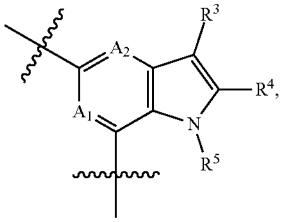

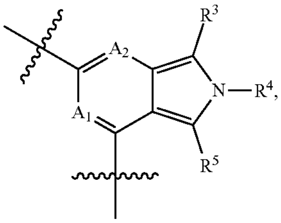

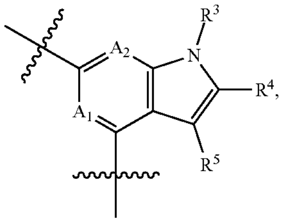

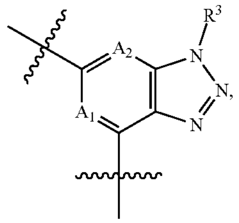

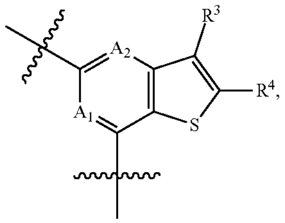

-continued

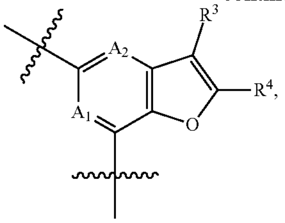

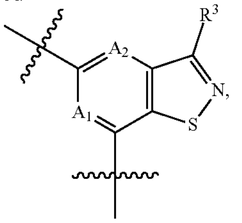

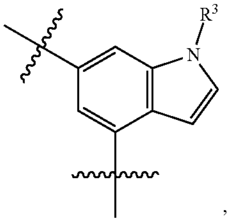

,

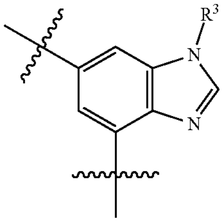

or

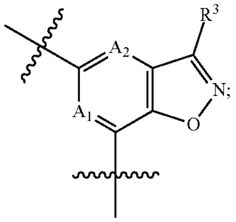

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a-1}$, $—C(═O)R^{a-2}$, $—NR^{a-31}R^{a-32}$, $—C(═O)OR^{a-4}$, $—C(═O)NR^{a-51}R^{a-52}$, or, $C_{1-6}$ alkyl substituted with one or more $R^{a1-1}$, $R^{a1-1}$ is independently halogen, hydroxyl or $—OC_{1-6}$ alkyl;

or, $R^{a-2}$ and $R^{a3}$ together with the carbon atom to which they are attached form $C_{3-7}$ cycloalkane, $C_{3-7}$ cycloalkane substituted with one or more $R^{a2-1}$, "3- to 8-membered heterocycloalkyl containing 1 to 3 heteroatoms independently selected from O, S and N", or, "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, ═O, hydroxyl, $C_{1-6}$ alkyl, $C_{1-6}$ alkyl substituted with one or more halogen, $—OC_{1-6}$ alkyl, or, $—OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogen;

Ring Y is $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, "5- to 6-membered heteroaryl containing 1 to 4 heteroatoms independently selected from O, S and N" fused with "5- to 6-membered heterocycloalkyl containing 1 to 3 heteroatoms independently selected from O, S and N", or, "4- to 8-membered heterocycloalkenyl containing 1 to 3 heteroatoms independently selected from O, S and N";

n is 0, 1, 2, 3, 4, 5 or 6;

$R^2$ is halogen, hydroxyl, cyano, oxo, $C_{1-6}$ alkyl, $C_{1-6}$ alkyl substituted with one or more $R^{2-1}$, $C_{2-6}$ alkenyl, $C_{2-6}$ alkynyl, $—OC_{1-6}$ alkyl, $—SC_{1-6}$ alkyl, $—OC_{1-6}$ alkyl substituted with one or more $R^{2-2}$, $—C(═O)R^{2a}$, $—NR^{2b1}R^{2b2}$, $—C(═O)OR^{2c}$, $—C(═O)NR^{2d1}R^{2d2}$, $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N"; or, when n is 2, 3, 4, 5 or 6, two optional $R^2$ are connected, together with the atoms to which they are attached, independently form 3- to 8-membered carbon ring or "3- to 8-membered heterocycle containing 1 to 3 heteroatoms independently selected from O, S and N";

$R^{2-1}$ and $R^{2-2}$ are independently halogen, cyano, $C_{1-6}$ alkyl-O—, hydroxyl, $—C(═O)R^{22a}$, $—NR^{22b1}R^{22b2}$, $—C(═O)OR^{22c}$, $—C(═O)NR^{22d1}R^{22d2}$, $—S(O)_2NR^{22e1}R^{22e2}$ or $—S(O)_2R^{22f}$;

$R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$ and $R^{22f}$ are independently hydrogen, $C_{1-6}$ alkyl, or, $C_{1-6}$ alkyl substituted with one or more halogen;

$R^1$ is

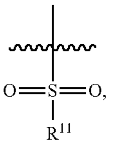

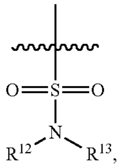

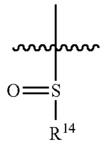

,

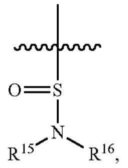

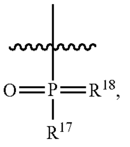

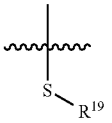

or

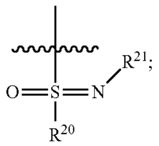

$R^{11}$, $R^{12}$, $R^{13}$, $R^{14}$, $R^{15}$, $R^{16}$, $R^{17}$, $R^{18}$, $R^{19}$ and $R^{20}$ are independently $C_{1-6}$ alkyl, $—OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, $C_{6-20}$ aryl substituted with one or more $R^{1-4}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-5}$, $C_{4-8}$ cycloalkenyl, $C_{4-8}$ cycloalkenyl substituted with one or more $R^{1-6}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-7}$;

$R^{21}$ is hydrogen or $C_{1-6}$ alkyl;

$R^{1-1}$, $R^{1-2}$, $R^{1-3}$, $R^{1-4}$, $R^{1-5}$, $R^{1-6}$ and $R^{1-7}$ are halogen, hydroxyl, cyano, $C_{1-6}$ alkyl, $C_{2-6}$ alkenyl, $C_{2-6}$ alkynyl, $—OC_{1-6}$ alkyl, $—SC_{1-6}$ alkyl, $—OC_{1-6}$ alkyl substituted with one or more $R^{1-1-1}$, $—SC_{1-6}$ alkyl substituted with one or more $R^{1-1-2}$, $—C(═O)R^{1a}$, $—NR^{1b1}R^{1b2}$, —C(═O)OR$^{1c}$, —C(═O)NR$^{1d1}$R$^{1d2}$, —S(O)$_2$NR$^{1e1}$R$^{1e2}$, —S(O)$_2$R$^{1f}$, C$_{3-10}$ cycloalkyl, C$_{3-10}$ cycloalkyl substituted with one or more R$^{1-1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more R$^{1-1-4}$, C$_{6-20}$ aryl, C$_{6-20}$ aryl substituted with one or more R$^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more R$^{1-1-6}$, C$_{4-8}$ cycloalkenyl, C$_{4-8}$ cycloalkenyl substituted with one or more R$^{1-1-7}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more R$^{1-1-8}$; provided that when multiple substituents are present, the substituents are the same or different;

R$^{1-1-1}$, R$^{1-1-2}$, R$^{1-1-3}$, R$^{1-1-4}$, R$^{1-1-5}$, R$^{1-1-6}$, R$^{1-1-7}$ and R$^{1-1-8}$ are independently azide, halogen, hydroxyl, cyano, oxo, C$_{1-6}$ alkyl, C$_{2-6}$ alkenyl, C$_{2-6}$ alkynyl, —OC$_{1-6}$ alkyl, —C(═O)R$^{11a}$, —NR$^{11b1}$R$^{11b2}$, —C(═O)OR$^{11c}$, —C(═O)NR$^{11d1}$R$^{11d2}$, —S(O)$_2$NR$^{11e1}$R$^{11e2}$, —S(O)$_2$R$^{11f}$, C$_{3-10}$ cycloalkyl, or, "4- to 12-membered heterocycloalkyl containing 1 to 3 heteroatoms independently selected from O, S and N"; provided that when multiple substituents are present, the substituents are the same or different;

R$^{1a}$, R$^{1b1}$, R$^{1b2}$, R$^{1c}$, R$^{1d1}$, R$^{1d2}$, R$^{1e1}$, R$^{1e2}$, R$^{1f}$, R$^{11a}$, R$^{11b1}$, R$^{11b2}$, R$^{11c}$, R$^{11d1}$, R$^{11d2}$, R$^{11e1}$, R$^{11e2}$, and R$^{11f}$ are independently hydrogen or C$_{1-6}$ alkyl;

R$^3$ is "5- to 6-membered heteroaryl containing 1 to 4 heteroatoms independently selected from O, S and N", or, "5- to 6-membered heteroaryl containing 1 to 4 heteroatoms independently selected from O, S and N" substituted with one or more R$^{3-1}$;

R$^{3-1}$ is halogen, hydroxyl, cyano, C$_{1-6}$ alkyl, C$_{1-6}$ alkyl substituted with one or more halogen, C$_{1-6}$ alkyl substituted with one or more —OC$_{1-6}$ alkyl, —OC$_{1-6}$ alkyl, —SC$_{1-6}$ alkyl, —OC$_{1-6}$ alkyl substituted with one or more halogen, or, —SC$_{1-6}$ alkyl substituted with one or more halogen; provided that when multiple substituents are present, the substituents are the same or different;

R$^4$ is hydrogen, halogen, C$_{1-6}$ alkyl, or, C$_{1-6}$ alkyl substituted with one or more R$^{4-1}$; R$^{4-1}$ is halogen, hydroxyl, C$_{3-12}$ cycloalkyl, —OC$_{1-6}$ alkyl or —SC$_{1-6}$ alkyl; provided that when multiple substituents are present, the substituents are the same or different;

R$^5$ is

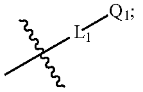

L$_1$ is a bond, C$_{1-6}$ alkylene or C$_{1-6}$ alkylene substituted with deuterium;

Q$_1$ is hydrogen, deuterium, halogen, cyano, C$_{2-6}$ alkenyl, C$_{2-6}$ alkynyl, hydroxyl, —OC$_{1-6}$ alkyl, —C(═O)R$^{5a}$, —NR$^{5b1}$R$^{5b2}$, —C(═O)OR$^{5c}$, —C(═O)NR$^{5d1}$R$^{5d2}$, —OC$_{1-6}$ alkyl substituted with one or more R$^{5-1}$, C$_{6-20}$ aryl, C$_{6-20}$ aryl substituted with one or more R$^{5-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more R$^{5-3}$, C$_{3-12}$ cycloalkyl, C$_{3-12}$ cycloalkyl substituted with one or more R$^{5-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more R$^{5-5}$, C$_{4-8}$ cycloalkenyl, C$_{4-8}$ cycloalkenyl substituted with one or more R$^{5-6}$, "4- to 8-membered heterocycloalkenyl containing 1 to 3 heteroatoms independently selected from O, S and N", "4- to 8-membered heterocycloalkenyl containing 1 to 3 heteroatoms independently selected from O, S and N" substituted with one or more R$^{5-7}$ or C$_{1-6}$ alkyl substituted with one or more R$^{5-8}$; provided that when multiple substituents are present, the substituents are the same or different;

R$^{5-1}$, R$^{5-2}$, R$^{5-3}$, R$^{5-4}$, R$^{5-5}$, R$^{5-6}$, R$^{5-7}$ and R$^{5-8}$ are independently halogen, hydroxyl, oxo, cyano, C$_{1-6}$ alkyl, C$_{1-6}$ alkyl substituted with one or more halogen, C$_{2-6}$ alkenyl, C$_{2-6}$ alkynyl, —OC$_{1-6}$ alkyl, —OC$_{1-6}$ alkyl substituted with one or more halogen, —C(═O)R$^{51a}$, —NR$^{51b1}$R$^{51b2}$, —C(═O)OR$^{51c}$ or —C(═O)NR$^{51d1}$R$^{51d2}$; provided that when multiple substituents are present, the substituents are the same or different;

R$^{5a}$, R$^{5b1}$, R$^{5b2}$, R$^{5c}$, R$^{5d1}$, R$^{5d2}$, R$^{51a}$, R$^{51b1}$, R$^{51b2}$, R$^{51c}$, R$^{51d1}$ and R$^{51d2}$ are independently hydrogen, C$_{1-6}$ alkyl, or C$_{1-6}$ alkyl substituted with one or more halogen;

or, R$^2$ and R$^5$ are connected together with the atoms to which they are attached independently form "5- to 12-membered heterocyclic olefin containing 1 to 3 heteroatoms independently selected from O, S and N";

or, R$^{a31}$ and R$^{a32}$, R$^{a51}$ and R$^{a52}$, R$^{2b1}$ and R$^{2b2}$, R$^{2d1}$ and R$^{2d2}$, R$^{22b1}$ and R$^{22b2}$, R$^{22d1}$ and R$^{22d2}$, R$^{22e1}$ and R$^{22e2}$, R$^{11b1}$ and R$^{1b2}$, R$^{1d1}$ and R$^{1d2}$, R$^{1e1}$ and R$^{1e2}$, R$^{11b1}$ and R$^{11b2}$, R$^{11d1}$ and R$^{11d2}$, R$^{11e1}$ and R$^{11e2}$, R$^{5b1}$ and R$^{5b2}$, R$^{5d1}$ and R$^{5d2}$, R$^{51b1}$ and R$^{51b2}$, R$^{51d1}$ and R$^{51d2}$ together with the N to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more R$^{1-2-1}$;

R$^{1-2-1}$ is independently hydrogen, C$_{1-6}$ alkyl, or C$_{1-6}$ alkyl substituted with one or more halogen;

the compound containing structure of a heteroaromatic ring represented by formula I is not one of the following compounds:

N-(1-Cyanocyclopropyl)-3-(5-(difluoromethyl)-1,3,4-thiadiazol-2-yl)-1-methyl-7-(4-(methylsulfonyl)piperazin-1-yl)-1H-indazole-5-sulfonamide;

N-(1-cyanocyclopropyl)-3-(5-(difluoromethyl)-1,3,4-thiadiazol-2-yl)-7-(4-(isopropylsulfonyl)piperazin-1-yl)-methyl-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-(2,2,2-trifluoroethyl)-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-methyl-1H-indazole-5-sulfonamide;

N-(1-Cyanocyclopropyl)-3-(5-(difluoromethyl)-1,3,4-thiadiazol-2-yl)-7-(4-(isopropylsulfonyl)piperazin-1-yl)-1-(2,2,2-trifluoroethyl)-1H-indazole-5-sulfonamide.

In a certain embodiment, with regard to the compound containing structure of a heteroaromatic ring represented by formula I, a pharmaceutically acceptable salt thereof, a stereoisomer thereof, an isomer thereof or an isotopic compound thereof, some groups are as defined as follows, and the unmentioned group definitions are as described in any one of the embodiments of the present disclosure (this content is hereinafter referred to simply as "in a certain embodiment").

In a certain embodiment, the compound containing structure of a heteroaromatic ring represented by formula I is shown as formula II:

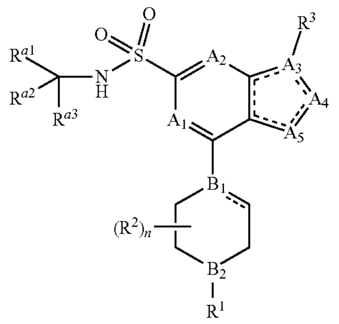

II

Wherein, is a single bond or a double bond; $B_1$ is N, C or CH, $B_2$ is N or CH, other group definitions are described as above.

In a certain embodiment, the compound containing structure of a heteroaromatic ring represented by formula I is shown as formula III:

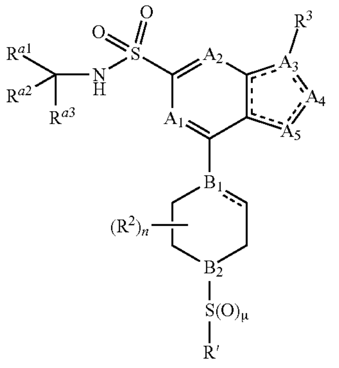

III

Wherein, is a single bond or a double bond; $B_1$ is N, C or CH, $B_2$ is N or CH, m is 0, 1 or 2;

R' is $R^{11}$, $NR^{12}R^{13}$, $R^{14}$ or $R^{19}$;

$R^{11}$, $R^{12}$, $R^{13}$, $R^{14}$ and $R^{19}$ as well as other group definitions are described as above.

In a certain embodiment, the compound containing structure of a heteroaromatic ring represented by formula I, a pharmaceutically acceptable salt thereof, a stereoisomer thereof, an isomer thereof or an isotopic compound thereof, wherein, the compound containing structure of a heteroaromatic ring represented by formula I is defined as solution 1, solution 2, solution 3 or solution 4:

solution 1:

is a single bond or a double bond;

Both rings of

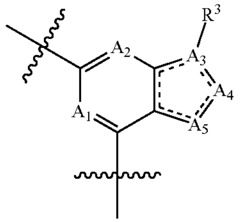

are aromatic;

$A_1$ and $A_2$ are independently N or $CR^{b1}$, $R^{b1}$ is hydrogen or halogen;

$A_3$ is C or N;

$A_4$ is N, $CR^4$ or $NR^4$;

$A_5$ is $NR^5$, N, $CR^5$, S or O;

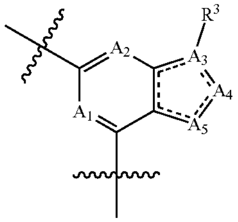

is

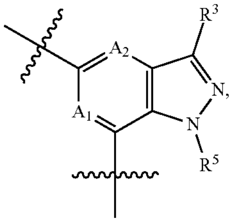

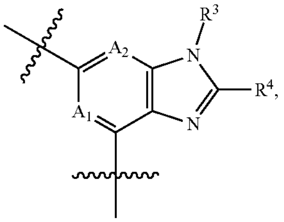

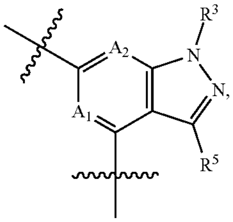

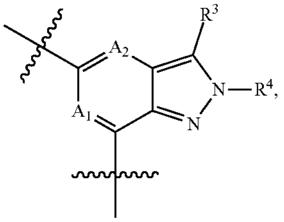

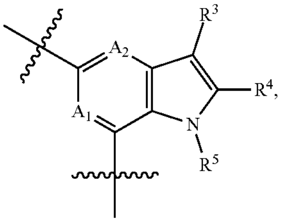

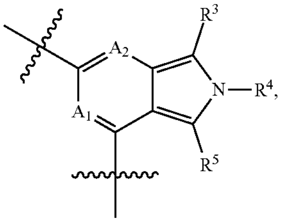

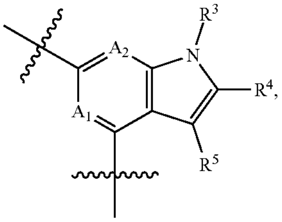

-continued

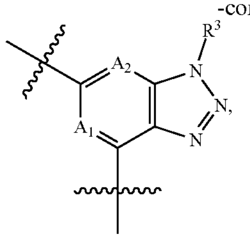, 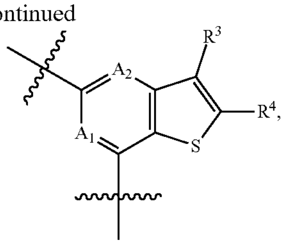, 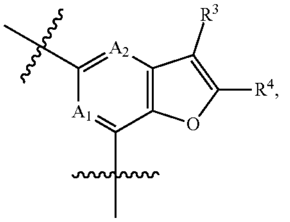, 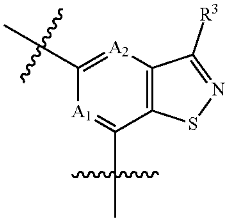 or 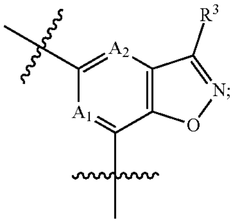;

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a-1}$, —C(═O)$R^{a-2}$, —$NR^{a-31}R^{a-32}$, —C(═O)$OR^{a-4}$, —C(═O)$NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

or, $R^{a2}$ and $R^{a3}$ together with the carbon atom to which they are attached form $C_{3-7}$ cycloalkane, $C_{3-7}$ cycloalkane substituted with one or more $R^{a2-1}$, 3- to 8-membered heterocycloalkyl containing 1 to 3 heteroatoms independently selected from O, S and N, or, "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, ═O, hydroxyl, $C_{1-6}$ alkyl, $C_{1-6}$ alkyl substituted with one or more halogen, —$OC_{1-6}$ alkyl, or, —$OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogen;

Ring Y is $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N";

n is 0, 1, 2, 3, 4, 5 or 6;

$R^2$ is halogen, hydroxyl, cyano, oxo, $C_{1-6}$ alkyl, $C_{1-6}$ alkyl substituted with one or more $R^{2-1}$, $C_{2-6}$ alkenyl, $C_{2-6}$ alkynyl, —$OC_{1-6}$ alkyl, —$SC_{1-6}$ alkyl, —$OC_{1-6}$ alkyl substituted with one or more $R^{2-2}$, —C(═O)$R^{2a}$, —$NR^{2b1}R^{2b2}$, —C(═O)$OR^{2c}$, —C(═O)$NR^{2d1}R^{2d2}$, $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N"; or, when n is 2, 3, 4, 5 or 6, two optional $R^2$ are connected, together with the atoms to which they are attached, independently form 3- to 8-membered carbon ring or "3- to 8-membered heterocycle containing 1 to 3 heteroatoms independently selected from O, S and N";

$R^{2-1}$ and $R^{2-2}$ are independently halogen, cyano, $C_{1-6}$ alkyl-O—, hydroxyl, —C(═O)$R^{22a}$, —$NR^{22b1}R^{22b2}$, —C(═O)$OR^{22c}$, —C(═O)$NR^{22d1}R^{22d2}$, —$S(O)_2NR^{22e1}R^{22e2}$ or —$S(O)_2R^{22f}$;

$R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$ and $R^{22f}$ are independently hydrogen, $C_{1-6}$ alkyl, or, $C_{1-6}$ alkyl substituted with one or more halogen;

$R^1$ is

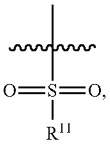, 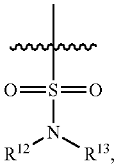, 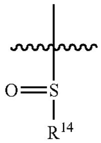, 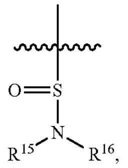, 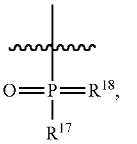, 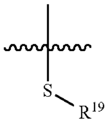 or 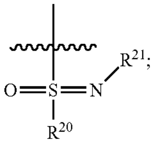;

$R^{11}$, $R^{12}$, $R^{13}$, $R^{14}$, $R^{15}$, $R^{16}$, $R^{17}$, $R^{18}$, $R^{19}$ and $R^{20}$ are independently $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, $C_{6-20}$ aryl substituted with one or more $R^{1-4}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-5}$, $C_{4-8}$ cycloalkenyl, $C_{4-8}$ cycloalkenyl substituted with one or more $R^{1-6}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-7}$;

$R^{21}$ is hydrogen or $C_{1-6}$ alkyl;

$R^{1-1}$, $R^{1-2}$, $R^{1-3}$, $R^{1-4}$, $R^{1-5}$, $R^{1-6}$ and $R^{1-7}$ are halogen, hydroxyl, cyano, $C_{1-6}$ alkyl, $C_{2-6}$ alkenyl, $C_{2-6}$ alkynyl, —$OC_{1-6}$ alkyl, —$SC_{1-6}$ alkyl, —$OC_{1-6}$ alkyl substituted with one or more $R^{1-1-1}$, —$SC_{1-6}$ alkyl substituted with one or more $R^{1-1-2}$, —C(═O)$R^{1a}$, —$NR^{1b1}R^{1b2}$, —C(═O)$OR^{1c}$, —C(═O)$NR^{1d1}R^{1d2}$, —$S(O)_2NR^{1e1}R^{1e2}$, —$S(O)_2R^{1f}$, $C_{3-10}$ cycloalkyl, $C_{3-10}$ cycloalkyl substituted with one or more $R^{1-1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{4-8}$ cycloalkenyl, $C_{4-8}$ cycloalkenyl substituted with one or more $R^{1-1-7}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently azide, halogen, hydroxyl, cyano, oxo, $C_{1-6}$ alkyl, $C_{2-6}$ alkenyl, $C_{2-6}$ alkynyl, —$OC_{1-6}$ alkyl, —C(═O)$R^{11a}$, —$NR^{11b1}R^{11b2}$, —C(═O)$OR^{11c}$, —C(═O)$NR^{11d1}R^{11d2}$, —$S(O)_2NR^{11e1}R^{11e2}$, —$S(O)_2R^{11f}$, $C_{3-10}$ cycloalkyl, or, "4- to 12-membered heterocycloalkyl containing 1 to 3 heteroatoms independently selected from O, S and N"; provided that when multiple substituents are present, the substituents are the same or different;

$R^{1a}$, $R^{1b1}$, $R^{1b2}$, $R^{1c}$, $R^{1d1}$, $R^{1d2}$, $R^{1e1}$, $R^{1e2}$, $R^{1f}$, $R^{11a}$, $R^{11b1}$, $R^{11b2}$, $R^{11c}$, $R^{11d1}$, $R^{11d2}$, $R^{11e1}$, $R^{11e2}$, and $R^{11f}$ are independently hydrogen or $C_{1-6}$ alkyl;

$R^3$ is "5- to 6-membered heteroaryl containing 1 to 4 heteroatoms independently selected from O, S and N", or, "5- to 6-membered heteroaryl containing 1 to 4 heteroatoms independently selected from O, S and N" substituted with one or more $R^{3-1}$;

$R^{3-1}$ is independently halogen, hydroxyl, cyano, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, —$SC_{1-6}$ alkyl, —$OC_{1-6}$ alkyl substituted with one or more halogen, or, —$SC_{1-6}$ alkyl substituted with one or more halogen; provided that when multiple substituents are present, the substituents are the same or different;

$R^4$ is hydrogen, halogen, $C_{1-6}$ alkyl, or, $C_{1-6}$ alkyl substituted with one or more $R^{4-1}$; $R^{4-1}$ is halogen, hydroxyl, —$OC_{1-6}$ alkyl or —$SC_{1-6}$ alkyl; provided that when multiple substituents are present, the substituents are the same or different;

$R^5$ is

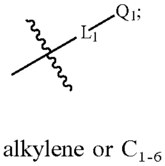

;

$L_1$ is a bond, $C_{1-6}$ alkylene or $C_{1-6}$ alkylene substituted with deuterium;

$Q_1$ is hydrogen, deuterium, halogen, cyano, $C_{2-6}$ alkenyl, $C_{2-6}$ alkynyl, hydroxyl, —$OC_{1-6}$ alkyl, —C(═O)$R^{5a}$, —$NR^{5b1}R^{5b2}$, —C(═O)$OR^{5c}$, —C(═O)$NR^{5d1}R^{5d2}$, —$OC_{1-6}$ alkyl substituted with one or more $R^{5-1}$, $C_{6-20}$ aryl, $C_{6-20}$ aryl substituted with one or more $R^{5-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-3}$, $C_{3-12}$ cycloalkyl, $C_{3-12}$ cycloalkyl substituted with one or more $R^{5-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-5}$, $C_{4-8}$ cycloalkenyl, $C_{4-8}$ cycloalkenyl substituted with one or more $R^{5-6}$, "4- to 8-membered heterocycloalkenyl containing 1 to 3 heteroatoms independently selected from O, S and N", or "4- to 8-membered heterocycloalkenyl containing 1 to 3 heteroatoms independently selected from O, S and N" substituted with one or more $R^{5-7}$; provided that when multiple substituents are present, the substituents are the same or different;

$R^{5-1}$, $R^{5-2}$, $R^{5-3}$, $R^{5-4}$, $R^{5-5}$, $R^{5-6}$ and $R^{5-7}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(═O)$R^{51a}$, —$NR^{51b1}R^{51b2}$, —C(═O)$OR^{51c}$ or —C(═O)$NR^{51d1}R^{51d2}$; provided that when multiple substituents are present, the substituents are the same or different;

$R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$ and $R^{51d2}$ are independently hydrogen, $C_{1-6}$ alkyl, or $C_{1-6}$ alkyl substituted with one or more halogen;

or, $R^2$ and $R^5$ are connected together with the atoms to which they are attached independently form "5- to 12-membered heterocyclic olefin containing 1 to 3 heteroatoms independently selected from O, S and N";

or, $R^{a31}$ and $R^{a32}$, $R^{a51}$ and $R^{a52}$, $R^{2b1}$ and $R^{2b2}$, $R^{2d1}$ and $R^{2d2}$, $R^{22b1}$ and $R^{22b2}$, $R^{22d1}$ and $R^{22d2}$, $R^{22e1}$ and $R^{22e2}$, $R^{1b1}$ and $R^{1b2}$, $R^{1d1}$ and $R^{1d2}$, $R^{1e1}$ and $R^{1e2}$, $R^{11b1}$ and $R^{11b2}$, $R^{11d1}$ and $R^{11d2}$, $R^{11e1}$ and $R^{11e2}$, $R^{5b1}$ and $R^{5b2}$, $R^{5d1}$ and $R^{5d2}$, $R^{51b1}$ and $R^{51b2}$, $R^{51d1}$ and $R^{51d2}$ together with the N to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-2-1}$;

$R^{1-2-1}$ is independently hydrogen, $C_{1-6}$ alkyl, or $C_{1-6}$ alkyl substituted with one or more halogen;

the compound containing structure of a heteroaromatic ring represented by formula I is not one of the following compounds:

N-(1-Cyanocyclopropyl)-3-(5-(difluoromethyl)-1,3,4-thiadiazol-2-yl)-1-methyl-7-(4-(methylsulfonyl)piperazin-1-yl)-1H-indazole-5-sulfonamide;

N-(1-cyanocyclopropyl)-3-(5-(difluoromethyl)-1,3,4-thiadiazol-2-yl)-7-(4-(isopropylsulfonyl)piperazin-1-yl)-methyl-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-(2,2,2-trifluoroethyl)-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-methyl-1H-indazole-5-sulfonamide;

N-(1-Cyanocyclopropyl)-3-(5-(difluoromethyl)-1,3,4-thiadiazol-2-yl)-7-(4-(isopropylsulfonyl)piperazin-1-yl)-1-(2,2,2-trifluoroethyl)-1H-indazole-5-sulfonamide.

Solution 2:

⌿⌿ is a single bond or a double bond;

$A_1$ and $A_2$ are independently N or $CR^{b1}R^{b1}$ is hydrogen or halogen;

$A_3$ is C or N;

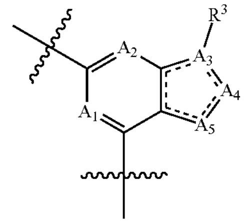
is
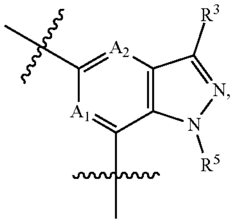
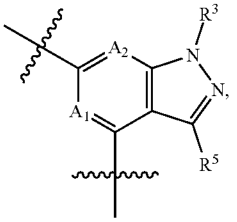
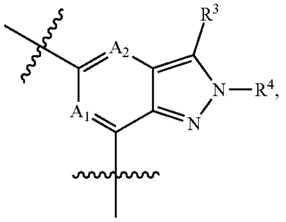
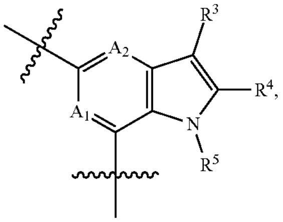
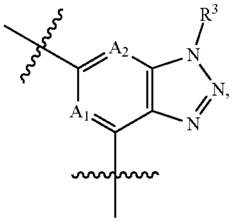
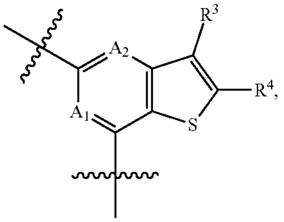
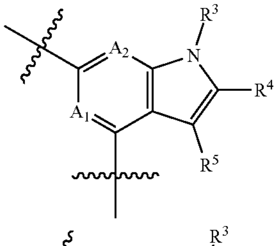
or
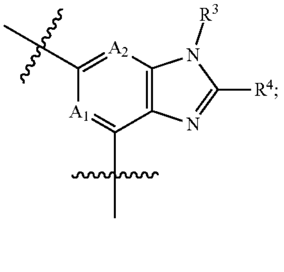

$R^4$ is hydrogen or $C_{1-6}$ alkyl substituted with one or more $R^{4-1}$; $R^{4-1}$ is $C_{3-12}$ cycloalkyl; provided that when multiple substituents are present, the substituents are the same or different;

$R^5$ is

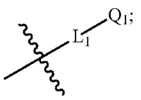

$L_1$ is a bond, $C_{1-6}$ alkylene or $C_{1-6}$ alkylene substituted with deuterium;

$Q_1$ is hydrogen, deuterium, halogen, —$OC_{1-6}$ alkyl, —$NR^{5b1}R^{5b2}$, —C(═O)$NR^{5d1}R^{5d2}$, —$C_{6-20}$ aryl, "5- to 12-membered heteroaryl containing 1 to 4 heteroatoms independently selected from O, S and N", $C_{3-12}$ cycloalkyl, $C_{1-6}$ alkyl substituted with one or more $R^{5-8}$ or "4- to 12-membered heterocycloalkyl containing 1 to 3 heteroatoms independently selected from O, S and N"; provided that when multiple substituents are present, the substituents are the same or different;

$R^{5b1}$, $R^{5b2}$, $R^{5d1}$ and $R^{5d2}$ are independently hydrogen or $C_{1-6}$ alkyl;

$R^{5-8}$ is independently halogen;

$R^{a1}$, $R^{a2}$ and $R^{a3}$ are independently cyano, $C_{1-6}$ alkyl, —C(═O)$NR^{a-51}R^{a-52}$, or, $C_{1-6}$ alkyl substituted with one or more $R^{a1-1}$, $R^{a1-1}$ is independently halogen;

or, $R^{a2}$ and $R^{a3}$ together with the carbon atom to which they are attached form $C_{3-7}$ cycloalkane; provided that when multiple substituents are present, the substituents are the same or different;

$R^{a-51}$ and $R^{a-52}$ are independently hydrogen;

Ring Y is "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, "5- to 6-membered heteroaryl containing 1 to 4 heteroatoms independently selected from O, S and N" fused with "5- to 6-membered heterocycloalkyl containing 1 to 3 heteroatoms independently selected from O, S and N", or, "4- to 8-membered heterocycloalkenyl containing 1 to 3 heteroatoms independently selected from O, S and N";

n is 0, 1 or 2;

$R^2$ is halogen, hydroxyl, cyano, $C_{1-6}$ alkyl, $C_{1-6}$ alkyl substituted with one or more $R^{2-1}$, —C(═O)$R^{2a}$, —C(═O)$OR^{2c}$ or —C(═O)$NR^{2d1}R^{2d2}$; or, when n is 2, two $R^2$ are connected, together with the atoms to which they are attached, independently form "3- to 8-membered heterocycle containing 1 to 3 heteroatoms independently selected from O, S and N";

$R^{2-1}$ is independently $C_{1-6}$ alkyl-O—, hydroxyl or —C(═O)$NR^{22d1}R^{22d2}$;

$R^{2a}$, $R^{2c}$, $R^{2d1}$, $R^{2d2}$, $R^{22b1}$ and $R^{22b2}$ are independently hydrogen or $C_{1-6}$ alkyl;

$R^1$ is

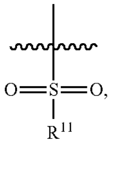
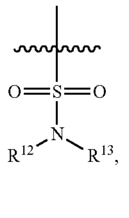
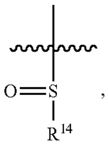
,

-continued

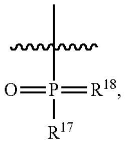

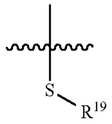

or

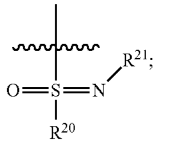

$R^{11}$, $R^{12}$, $R^{13}$, $R^{14}$, $R^{17}$, $R^{18}$, $R^{19}$ and $R^{20}$ are independently $C_{1-6}$ alkyl, $—OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, "5- to 12-membered heteroaryl containing 1 to 4 heteroatoms independently selected from O, S and N";

$R^{21}$ is hydrogen or $C_{1-6}$ alkyl;

$R^{1-1}$, $R^{1-2}$ and $R^{1-3}$ are $C_{1-6}$ alkyl or $—OC_{1-6}$ alkyl $R^3$ is "5- to 6-membered heteroaryl containing 1 to 4 heteroatoms independently selected from O, S and N" substituted with one or more $R^{3-1}$;

$R^{3-1}$ is independently $C_{1-6}$ alkyl or $C_{1-6}$ alkyl substituted with one or more halogen; provided that when multiple substituents are present, the substituents are the same or different;

the compound containing structure of a heteroaromatic ring represented by formula I is not one of the following compounds:

N-(1-Cyanocyclopropyl)-3-(5-(difluoromethyl)-1,3,4-thiadiazol-2-yl)-1-methyl-7-(4-(methylsulfonyl)piperazin-1-yl)-1H-indazole-5-sulfonamide;

N-(1-cyanocyclopropyl)-3-(5-(difluoromethyl)-1,3,4-thiadiazol-2-yl)-7-(4-(isopropylsulfonyl)piperazin-1-yl)-methyl-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-(2,2,2-trifluoroethyl)-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-methyl-1H-indazole-5-sulfonamide;

N-(1-Cyanocyclopropyl)-3-(5-(difluoromethyl)-1,3,4-thiadiazol-2-yl)-7-(4-(isopropylsulfonyl)piperazin-1-yl)-1-(2,2,2-trifluoroethyl)-1H-indazole-5-sulfonamide.

Solution 3:

the compound containing structure of a heteroaromatic ring represented by formula I is shown as formula III-1 or III-2:

III-1

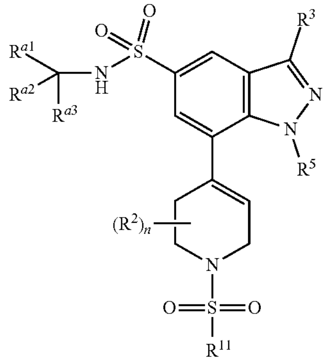

or

III-2

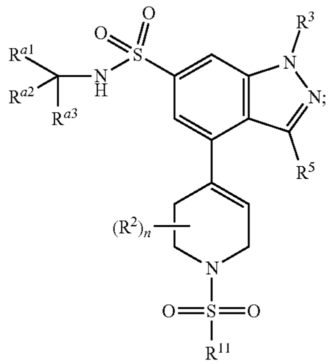

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a-1}$, $—C(═O)R^{a-2}$, $—NR^{a-31}R^{a-32}$, $—C(═O)OR^{a-4}$, $—C(═O)NR^{a-51}R^{a-52}$, or, $C_{1-6}$ alkyl substituted with one or more $R^{a1-1}$, $R^{a1-1}$ is halogen, hydroxyl or $—OC_{1-6}$ alkyl;

or, $R^{a2}$ and $R^{a3}$ together with the carbon atom to which they are attached form $C_{3-7}$ cycloalkane, $C_{3-7}$ cycloalkane substituted with one or more $R^{a2-1}$, 3- to 8-membered heterocycloalkyl containing 1 to 3 heteroatoms independently selected from O, S and N, or, "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, ═O, hydroxyl, $C_{1-6}$ alkyl, $C_{1-6}$ alkyl substituted with one or more halogen, $—OC_{1-6}$ alkyl, or, $—OC_{1-6}$ alkyl substituted with one or more halogen;

$R^{a1}$, $R^{a2}$, $R^{a31}$, $R^{a32}$, $R^{a4}$, $R^{a51}$ and $R^{a52}$ are independently hydrogen, $C_{1-6}$ alkyl, or, $C_{1-6}$ alkyl substituted with one or more halogen;

n is 0, 1, 2, 3, 4, 5 or 6;

$R^2$ is halogen, hydroxyl, cyano, oxo, $C_{1-6}$ alkyl, $C_{1-6}$ alkyl substituted with one or more $R^{2-1}$, $C_2$-6 alkenyl, $C_{2-6}$ alkynyl, $—OC_{1-6}$ alkyl, $—OC_{1-6}$ alkyl substituted with one or more $R^{2-2}$, $—C(═O)R^{2a}$, $—NR^{2b1}R^{2b2}$, $—C(═O)OR^{2c}$, $—C(═O)NR^{2a1}R^{2a2}$, $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N"; or, when n is 2, 3, 4, 5 or 6, two optional $R^2$ are connected, together with the atoms to which they are attached, independently form 3- to 8-membered carbon ring or "3- to 8-membered heterocycle containing 1 to 3 heteroatoms independently selected from O, S and N";

$R^{2-1}$ and $R^{2-2}$ are independently halogen, cyano, $C_{1-6}$ alkyl-O—, hydroxyl, —C(═O)$R^{22a}$, —$NR^{22b1}R^{22b2}$, —C(═O)$OR^{22c}$, —C(═O)$NR^{22d1}R^{22d2}$, —$S(O)_2NR^{22e1}R^{22e2}$ or —$S(O)_2R^{22f}$;

$R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$ and $R^{22f}$ are independently hydrogen, $C_{1-6}$ alkyl, or, $C_{1-6}$ alkyl substituted with one or more halogen;

$R^{11}$ is $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, $C_{6-20}$ aryl substituted with one or more $R^{1-4}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-5}$, $C_{4-8}$ cycloalkenyl, $C_{4-8}$ cycloalkenyl substituted with one or more $R^{1-6}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-7}$;

$R^{1-1}$, $R^{1-2}$, $R^{1-3}$, $R^{1-4}$, $R^{1-5}$, $R^{1-6}$ and $R^{1-7}$ are halogen, hydroxyl, cyano, $C_{1-6}$ alkyl, $C_{2-6}$ alkenyl, $C_{2-6}$ alkynyl, —$OC_{1-6}$ alkyl, —$SC_{1-6}$ alkyl, —$OC_{1-6}$ alkyl substituted with one or more $R^{1-1-1}$, —$SC_{1-6}$ alkyl substituted with one or more $R^{1-1-2}$, —C(═O)$R^{1a}$, —$NR^{1b1}R^{1b2}$, —C(═O)$OR^{1c}$, —C(═O)$NR^{1d1}R^{1d2}$, —$S(O)_2NR^{1e1}R^{1e2}$, —$S(O)_2R^{1f}$, $C_{3-10}$ cycloalkyl, $C_{3-10}$ cycloalkyl substituted with one or more $R^{1-13}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{4-8}$ cycloalkenyl, $C_{4-8}$ cycloalkenyl substituted with one or more $R^{1-1-7}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently azide, halogen, hydroxyl, cyano, oxo, $C_{1-6}$ alkyl, $C_{2-6}$ alkenyl, $C_{2-6}$ alkynyl, —$OC_{1-6}$ alkyl, —C(═O)$R^{11a}$, —$NR^{11b1}R^{11b2}$, —C(═O)$OR^{11c}$, —C(═O)$NR^{11d1}R^{11d2}$, —$S(O)_2NR^{1e1}R^{11e2}$, —$S(O)_2R^{11f}$, $C_{3-10}$ cycloalkyl, or, "4- to 12-membered heterocycloalkyl containing 1 to 3 heteroatoms independently selected from O, S and N"; provided that when multiple substituents are present, the substituents are the same or different;

$R^{1a}$, $R^{1b1}$, $R^{1b2}$, $R^{1c}$, $R^{1d1}$, $R^{1d2}$, $R^{1e1}$, $R^{1e2}$, $R^{1f}$, $R^{11a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen or $C_{1-6}$ alkyl;

$R^3$ is "5- to 6-membered heteroaryl containing 1 to 4 heteroatoms independently selected from O, S and N", or, "5- to 6-membered heteroaryl containing 1 to 4 heteroatoms independently selected from O, S and N" substituted with one or more $R^{3-1}$;

$R^{3-1}$ is independently halogen, hydroxyl, cyano, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, —$SC_{1-6}$ alkyl, —$OC_{1-6}$ alkyl substituted with one or more halogen, or, —$SC_{1-6}$ alkyl substituted with one or more halogen; provided that when multiple substituents are present, the substituents are the same or different;

$R^5$ is

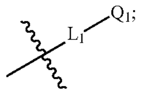

$L_1$ is a bond, $C_{1-6}$ alkylene or $C_{1-6}$ alkylene substituted with deuterium;

$Q_1$ is hydrogen, deuterium, halogen, cyano, $C_{2-6}$ alkenyl, $C_{2-6}$ alkynyl, hydroxyl, —$OC_{1-6}$ alkyl, —C(═O)$R^{5a}$, —$NR^{5b1}R^{5b2}$, —C(═O)$OR^{5c}$, —C(═O)$NR^{5d1}R^{5d2}$, —$OC_{1-6}$ alkyl substituted with one or more $R^{5-1}$, $C_{6-20}$ aryl, $C_{6-20}$ aryl substituted with one or more $R^{5-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-3}$, $C_{3-12}$ cycloalkyl, $C_{3-12}$ cycloalkyl substituted with one or more $R^{5-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-5}$, $C_{4-8}$ cycloalkenyl, $C_{4-8}$ cycloalkenyl substituted with one or more $R^{5-6}$, "4- to 8-membered heterocycloalkenyl containing 1 to 3 heteroatoms independently selected from O, S and N", "4- to 8-membered heterocycloalkenyl containing 1 to 3 heteroatoms independently selected from O, S and N" substituted with one or more $R^{5-7}$, or $C_{1-6}$ alkyl substituted with one or more $R^{5-8}$; provided that when multiple substituents are present, the substituents are the same or different;

$R^{5-1}$, $R^{5-2}$, $R^{5-3}$, $R^{5-4}$, $R^{5-5}$, $R^{5-6}$, $R^{5-7}$ and $R^{5-8}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(═O)$R^{51a}$, —$NR^{51b1}R^{51b2}$, —C(═O)$OR^{51c}$ or —C(═O)$NR^{51d1}R^{51d2}$; provided that when multiple substituents are present, the substituents are the same or different;

$R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$ and $R^{51d2}$ are independently hydrogen, $C_{1-6}$ alkyl, or $C_{1-6}$ alkyl substituted with one or more halogen;

or, $R^2$ and $R^5$ are connected together with the atoms to which they are attached independently form "5- to 12-membered heterocyclic olefin containing 1 to 3 heteroatoms independently selected from O, S and N";

or, $R^{a-31}$ and $R^{a-32}$, $R^{a-51}$ and $R^{a-52}$, $R^{2b1}$ and $R^{2b2}$, $R^{2d1}$ and $R^{2d2}$, $R^{22b1}$ and $R^{22b2}$, $R^{22d1}$ and $R^{22d2}$, $R^{22e1}$ and $R^{22e2}$, $R^{1b1}$ and $R^{1b2}$, $R^{1d1}$ and $R^{1d2}$, $R^{1e1}$ and $R^{1e2}$, $R^{11b1}$ and $R^{11b2}$, $R^{11d1}$ and $R^{11d2}$, $R^{11e1}$ and $R^{11e2}$, $R^{5b1}$ and $R^{5b2}$, $R^{5d1}$ and $R^{5d2}$, $R^{51b1}$ and $R^{51b2}$, $R^{51d1}$ and $R^{51d2}$ together with the N to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-2-1}$;

$R^{1-2-1}$ is independently hydrogen, $C_{1-6}$ alkyl, or $C_{1-6}$ alkyl substituted with one or more halogen.

Solution 4:

In the compound containing structure of a heteroaromatic ring represented by formula I, $A_1$ and $A_2$ are independently $CR^{b1}$, $R^{b1}$ is hydrogen;

$A_3$ is C or N;

$A_4$ is N, $CR^4$ or $NR^4$; $R^4$ is hydrogen;

$A_5$ is $NR^5$, $CR^5$ or S;

$R^{a1}$ is halogen, cyano, $C_{1-6}$ alkyl, —C(═O)$NR^{a-51}R^{a-52}$, or, $C_{1-6}$ alkyl substituted with one or more $R^{a1-1}$, $R^{a1-1}$ is independently halogen;

$R^{a2}$ and $R^{a3}$ together with the carbon atom to which they are attached form $C_{3-7}$ cycloalkane;

Ring Y is "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N";

n is 0, 1 or 2;

$R^2$ is hydroxyl, $C_{1-6}$ alkyl substituted with one or more $R^{2-1}$, —C(═O)$OR^{2c}$; or, when n is 2, two $R^2$ are connected, together with the atoms to which they are attached, independently form "3- to 8-membered heterocycle containing 1 to 3 heteroatoms independently selected from O, S and N";

$R^{2-1}$ is independently hydroxyl;

$R^{2c}$ is hydrogen;

$R^1$ is

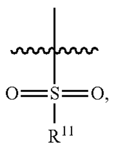
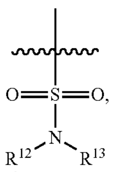
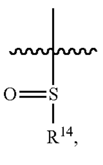
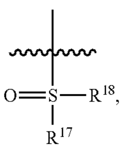
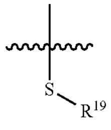
or
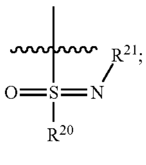

$R^{11}$, $R^{12}$, $R^{13}$, $R^{14}$, $R^{17}$, $R^{18}$, $R^{19}$ and $R^{20}$ are independently $C_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", or "4- to 12-membered heterocycloalkyl containing 1 to 3 heteroatoms independently selected from O, S and N" substituted with one or more $R^{1-3}$;

$R^{21}$ is hydrogen or $C_{1-6}$ alkyl;

$R^{1-1}$, $R^{1-2}$ and $R^{1-3}$ are independently $C_{1-6}$ alkyl or —$OC_{1-6}$ alkyl;

$R^3$ is "5- to 6-membered heteroaryl containing 1 to 4 heteroatoms independently selected from O, S and N" substituted with one or more $R^{3-1}$ $R^{3-1}$ is independently $C_{1-6}$ alkyl substituted with one or more halogen; provided that when multiple substituents are present, the substituents are the same or different;

$R^5$ is

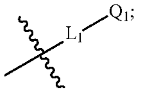

$L_1$ is a bond, $C_{1-6}$ alkylene or $C_{1-6}$ alkylene substituted with deuterium;

$Q_1$ is hydrogen, deuterium or —$OC_{1-6}$ alkyl.

In a certain embodiment, in the compound containing structure of a heteroaromatic ring represented by formula III-1, $R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a-1}$, —C(═O)$R^{a-2}$, —$NR^{a-31}R^{a-32}$, —C(═O)$OR^{a-4}$, —C(═O)$NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

or, $R^{a2}$ and $R^{a3}$ together with the carbon atom to which they are attached form $C_{3-7}$ cycloalkane, $C_{3-7}$ cycloalkane substituted with one or more $R^{a2-1}$, 3- to 8-membered heterocycloalkyl containing 1 to 3 heteroatoms independently selected from O, S and N, or, "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, ═O, hydroxyl, $C_{1-6}$ alkyl, $C_{1-6}$ alkyl substituted with one or more halogen, —$OC_{1-6}$ alkyl, or, —$OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogen;

n is 0, 1, 2, 3, 4, 5 or 6;

$R^2$ is independently halogen, hydroxyl, cyano, oxo, $C_{1-6}$ alkyl, $C_{1-6}$ alkyl substituted with one or more $R^{2-1}$, $C_{2-6}$ alkenyl, $C_{2-6}$ alkynyl, —$OC_{1-6}$ alkyl, —$OC_{1-6}$ alkyl substituted with one or more $R^{2-2}$, —C(═O)$R^{2a}$, —$NR^{2b1}R^{2b2}$, —C(═O)$OR^{2c}$, —C(═O)$NR^{2d1}R^{2d2}$, $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N"; or, when n is 2, 3, 4, 5 or 6, two optional $R^2$ are connected, together with the atoms to which they are attached, independently form 3- to 8-membered carbon ring or "3- to 8-membered heterocycle containing 1 to 3 heteroatoms independently selected from O, S and N";

$R^{2-1}$ and $R^{2-2}$ are independently halogen, cyano, $C_{1-6}$ alkyl-O—, hydroxyl, —C(=O)$R^{22a}$, —$NR^{22b1}R^{22b2}$, —C(=O)$OR^{22c}$, —C(=O)$NR^{22d1}R^{22d2}$, —$S(O)_2NR^{22e1}R^{22e2}$ or —$S(O)_2R^{22f}$;

$R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$ and $R^{22f}$ are independently hydrogen, $C_{1-6}$ alkyl, or, $C_{1-6}$ alkyl substituted with one or more halogen;

$R^{11}$ is independently $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, $C_{6-20}$ aryl substituted with one or more $R^{1-4}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-5}$, $C_{4-8}$ cycloalkenyl, $C_{4-8}$ cycloalkenyl substituted with one or more $R^{1-6}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-7}$;

$R^{1-1}$, $R^{1-2}$, $R^{1-3}$, $R^{1-4}$, $R^{1-5}$, $R^{1-6}$ and $R^{1-7}$ are halogen, hydroxyl, cyano, $C_{1-6}$ alkyl, $C_{2-6}$ alkenyl, $C_{2-6}$ alkynyl, —$OC_{1-6}$ alkyl, —$SC_{1-6}$ alkyl, —$OC_{1-6}$ alkyl substituted with one or more $R^{1-1-1}$, —$SC_{1-6}$ alkyl substituted with one or more $R^{1-1-2}$, —C(=O)$R^{1a}$, —$NR^{1b1}R^{1b2}$, —C(=O)$OR^{1c}$, —C(=O)$NR^{1d1}R^{1d2}$, —$S(O)_2NR^{1e1}R^{1e2}$, —$S(O)_2R^{1f}$, $C_{3-10}$ cycloalkyl, $C_{3-10}$ cycloalkyl substituted with one or more $R^{1-13}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{4-8}$ cycloalkenyl, $C_{4-8}$ cycloalkenyl substituted with one or more $R^{1-1-7}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently azide, halogen, hydroxyl, cyano, oxo, $C_{1-6}$ alkyl, $C_{2-6}$ alkenyl, $C_{2-6}$ alkynyl, —$OC_{1-6}$ alkyl, —C(=O)$R^{11a}$, —$NR^{11b1}R^{11b2}$, —C(=O)$OR^{11c}$, —C(=O)$NR^{11d1}R^{11d2}$, —$S(O)_2NR^{11e1}R^{11e2}$, —$S(O)_2R^{11f}$, $C_{3-10}$ cycloalkyl, or, "4- to 12-membered heterocycloalkyl containing 1 to 3 heteroatoms independently selected from O, S and N"; provided that when multiple substituents are present, the substituents are the same or different;

$R^{1a}$, $R^{1b1}$, $R^{1b2}$, $R^{1c}$, $R^{1d1}$, $R^{1d2}$, $R^{1e1}$, $R^{1e2}$, $R^{1f}$, $R^{11a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen or $C_{1-6}$ alkyl;

$R^3$ is "5- to 6-membered heteroaryl containing 1 to 4 heteroatoms independently selected from O, S and N", or, "5- to 6-membered heteroaryl containing 1 to 4 heteroatoms independently selected from O, S and N" substituted with one or more $R^{3-1}$;

$R^{3-1}$ is independently halogen, hydroxyl, cyano, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, —$SC_{1-6}$ alkyl, —$OC_{1-6}$ alkyl substituted with one or more halogen, or, —$SC_{1-6}$ alkyl substituted with one or more halogen; provided that when multiple substituents are present, the substituents are the same or different;

$R^5$ is

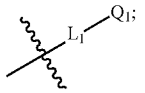

$L_1$ is a bond, $C_{1-6}$ alkylene or $C_{1-6}$ alkylene substituted with deuterium;

$Q_1$ is hydrogen, deuterium, halogen, cyano, $C_{2-6}$ alkenyl, $C_{2-6}$ alkynyl, hydroxyl, —$OC_{1-6}$ alkyl, —C(=O)$R^{5a}$, —$NR^{5b1}R^{5b2}$, —C(=O)$OR^{5c}$, —C(=O)$NR^{5d1}R^{5d2}$, —$OC_{1-6}$ alkyl substituted with one or more $R^{5-1}$, $C_{6-20}$ aryl, $C_{6-20}$ aryl substituted with one or more $R^{5-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-3}$, $C_{3-12}$ cycloalkyl, $C_{3-12}$ cycloalkyl substituted with one or more $R^{5-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-5}$, $C_{4-8}$ cycloalkenyl, $C_{4-8}$ cycloalkenyl substituted with one or more $R^{5-6}$, "4- to 8-membered heterocycloalkenyl containing 1 to 3 heteroatoms independently selected from O, S and N", or "4- to 8-membered heterocycloalkenyl containing 1 to 3 heteroatoms independently selected from O, S and N" substituted with one or more $R^{5-7}$; provided that when multiple substituents are present, the substituents are the same or different;

$R^{5-1}$, $R^{5-2}$, $R^{5-3}$, $R^{5-4}$, $R^{5-5}$, $R^{5-6}$ and $R^{5-7}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(=O)$R^{51a}$, —$NR^{51b1}R^{51b2}$, —C(=O)$OR^{51c}$ or —C(=O)$NR^{51d1}R^{51d2}$; provided that when multiple substituents are present, the substituents are the same or different;

$R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$ and $R^{51d2}$ are independently hydrogen, $C_{1-6}$ alkyl, or $C_{1-6}$ alkyl substituted with one or more halogen;

or, $R^2$ and $R^5$ are connected together with the atoms to which they are attached independently form "5- to 12-membered heterocyclic olefin containing 1 to 3 heteroatoms independently selected from O, S and N";

or, $R^{a31}$ and $R^{a32}$, $R^{a51}$ and $R^{a52}$, $R^{2b1}$ and $R^{2b2}$, $R^{2d1}$ and $R^{2d2}$, $R^{22b1}$ and $R^{22b2}$, $R^{22d1}$ and $R^{22d2}$, $R^{22e1}$ and $R^{22e2}$, $R^{1b1}$ and $R^{1b2}$, $R^{1d1}$ and $R^{1d2}$, $R^{1e1}$ and $R^{1e2}$, $R^{11b1}$ and $R^{11b2}$, $R^{11d1}$ and $R^{11d2}$, $R^{11e1}$ and $R^{11e2}$, $R^{5b1}$ and $R^{5b2}$, $R^{5d1}$ and $R^{5d2}$, $R^{51b1}$ and $R^{51b2}$, $R^{51d1}$ and $R^{51d2}$ together with the N to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-2-1}$;

$R^{1-2-1}$ is independently hydrogen, $C_{1-6}$ alkyl, or $C_{1-6}$ alkyl substituted with one or more halogen.

In a certain embodiment, In the compound containing structure of a heteroaromatic ring represented by formula III-1, $R^{a1}$, $R^{a2}$ and $R^{a3}$ are independently cyano, $C_{1-6}$ alkyl, —C(═O)NR$^{a-51}$R$^{a-52}$, or, $C_{1-6}$ alkyl substituted with one or more $R^{a1-1}$, $R^{a1-1}$ is independently halogen;

or, $R^{a2}$ and $R^{a3}$ together with the carbon atom to which they are attached form $C_{3-7}$ cycloalkane;

$R^{a-51}$ and $R^{a-52}$ are independently hydrogen;

n is 0, 1 or 2;

$R^2$ is halogen, cyano, $C_{1-6}$ alkyl, $C_{1-6}$ alkyl substituted with one or more $R^{2-1}$, —C(═O)R$^{2a}$, —C(═O)OR$^{2c}$ or —C(═O)NR$^{2d1}$R$^{2d2}$;

$R^{2-1}$ is independently $C_{1-6}$ alkyl-O—, hydroxyl or —C(═O)NR$^{22d1}$R$^{22d2}$;

$R^{2a}$, $R^{2c}$, $R^{2d1}$, $R^{2d2}$, $R^{22b1}$ and $R^{22b2}$ are independently hydrogen or $C_{1-6}$ alkyl;

$R^{11}$ is $C_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", or "4- to 12-membered heterocycloalkyl containing 1 to 3 heteroatoms independently selected from O, S and N" substituted with one or more $R^{1-3}$, $C_{6-20}$ aryl or "5- to 12-membered heteroaryl containing 1 to 4 heteroatoms independently selected from O, S and N";

$R^{1-1}$, $R^{1-2}$ and $R^{1-3}$ are independently $C_{1-6}$ alkyl or —O$C_{1-6}$ alkyl;

$R^3$ is "5- to 6-membered heteroaryl containing 1 to 4 heteroatoms independently selected from O, S and N" substituted with one or more $R^{3-1}$ $R^{3-1}$ is independently $C_{1-6}$ alkyl or $C_{1-6}$ alkyl substituted with one or more halogen; provided that when multiple substituents are present, the substituents are the same or different;

$R^5$ is

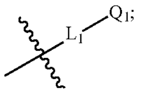

$L_1$ is a bond, $C_{1-6}$ alkylene or $C_{1-6}$ alkylene substituted with deuterium;

$Q_1$ is deuterium, —O$C_{1-6}$ alkyl, —NR$^{5b1}$R$^{5b2}$, —C(═O)NR$^{5d1}$R$^{5d2}$, $C_{6-20}$ aryl, "5- to 12-membered heteroaryl containing 1 to 4 heteroatoms independently selected from O, S and N", $C_{3-12}$ cycloalkyl, substituted with $R^{5-8}$ or "4- to 12-membered heterocycloalkyl containing 1 to 3 heteroatoms independently selected from O, S and N"; provided that when multiple substituents are present, the substituents are the same or different;

$R^{5-8}$ is independently halogen;

$R^{5b1}$, $R^{5b2}$, $R^{5d1}$ and $R^{5d2}$ are independently hydrogen or $C_{1-6}$ alkyl;

the compound containing structure of a heteroaromatic ring represented by formula I is not one of the following compounds:

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-(2,2,2-trifluoroethyl)-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-methyl-1H-indazole-5-sulfonamide.

When the definition of $R^{b1}$, $R^{a1}$, $R^{a2}$, $R^{a3}$, $R^{a1-1}$, $R^{a2-1}$, $R^{a2-2}$, $R^{a1}$, $R^{a2}$, $R^{a31}$, $R^{a32}$, $R^{a4}$, $R^{a51}$, $R^{a-52}$, $R^2$, $R^{2-1}$, $R^{2-2}$, $R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$, $R^{22}$, $R^{1-1}$, $R^{1-2}$, $R^{1-3}$, $R^{1-4}$, $R^{1-5}$, $R^{1-6}$, $R^{1-7}$, $R^{1-1-1}$, $R^{1-1-2}$, $R^{1-1-3}$, $R^{1-1-4}$, $R^{1-1-5}$, $R^{1-1-6}$, $R^{1-1-7}$, $R^{1-1-8}$, $R^{3-1}$, $R^4$, $R^{4-1}$, $Q_1$, $R^{5-1}$, $R^{5-2}$, $R^{5-3}$, $R^{5-4}$, $R^{5-5}$, $R^{5-6}$, $R^{5-7}$, $R^{5-8}$, $R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$, $R^{51d2}$ and $R^{1-2-1}$ refers to halogen, the halogen is fluorine, chlorine, bromine or iodine.

When the definition of $R^{a1}$, $R^{a2}$, $R^{a3}$, $R^{a2-1}$, $R^{a2-2}$, $R^{a1}$, $R^{a2}$, $R^{a31}$, $R^{a32}$, $R^{a4}$, $R^{a51}$, $R^{a52}$, $R^2$, $R^{2-1}$, $R^{2-2}$, $R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$, $R^{22f}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{1-1}$, $R^{1-2}$, $R^{1-3}$, $R^{1-4}$, $R^{1-5}$, $R^{1-6}$, $R^{1-7}$, $R^{1-1-1}$, $R^{1-1-2}$, $R^{1-1-3}$, $R^{1-1-4}$, $R^{1-1-5}$, $R^{1-1-6}$, $R^{1-1-7}$, $R^{1-1-8}$, $R^{1a}$, $R^{1b1}$, $R^{1b2}$, $R^{1c}$, $R^{1d1}$, $R^{1d2}$, $R^{1e1}$, $R^{1e2}$, $R^{1f}$, $R^{11a}$, $R^{11b1}$, $R^{11b2}$, $R^{1c}$, $R^{11d1}$, $R^{11d2}$, $R^{1e1}$, $R^{11e2}$, $R^{11f}$, $R^{3-1}$, $R^4$, $R^{4-1}$, $Q_1$, $R^{5-1}$, $R^{5-2}$, $R^{5-3}$, $R^{5-4}$, $R^{5-5}$, $R^{5-6}$, $R^{5-7}$, $R^{5-8}$, $R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$, $R^{51d2}$ and $R^{1-2-1}$ refers to $C_{1-6}$ alkyl, the $C_{1-6}$ alkyl is $C_{1-4}$ alkyl, for example, methyl, ethyl, n-propyl, isopropyl, n-butyl, sec-butyl, isobutyl or tert-butyl.

When the definition of $R^{4-1}$ and $Q_1$ refers to $C_{3-12}$ cycloalkyl, the $C_{3-12}$ cycloalkyl is $C_{3-6}$ cycloalkyl, for example, cyclohexyl, -cyclopentyl, cyclobutyl or cyclopropyl.

When $L_1$ is the $C_{1-6}$ alkylene or $C_{1-6}$ alkylene substituted with deuterium, the $C_{1-6}$ alkylene is —$CH_2$—, —$CH_2CH_2$—, —$CH_2CH_2CH_2$—, —$CH(CH_3)CH_2$—, —$CH_2CH_2CH_2CH_2$—, —$CH(CH_3)CH_2CH_2$—, —$CH_2CH(CH_3)CH_2$— or —$C(CH_3)_2CH_2$—.

When $L_1$ is $C_{1-6}$ alkylene substituted with deuterium, the $C_{1-6}$ alkylene substituted with deuterium is two or three hydrogen were substituted with deuterium.

When the definition of ring Y, $R^2$, $R^{11}$, $R^{12}$, $R^{13}$, $R^{14}$, $R^{15}$, $R^{16}$, $R^{17}$, $R^{18}$, $R^{19}$ and $R^{20}$, $R^{1-1}$, $R^{1-2}$, $R^{1-3}$, $R^{1-4}$, $R^{1-5}$, $R^{1-6}$, $R^{1-7}$ and $Q_1$ refers to $C_{6-20}$ aryl, the $C_{6-20}$ aryl is phenyl or naphthyl.

When the definition of ring Y, $R^2$, $R^{11}$, $R^{12}$, $R^{13}$, $R^{14}$, $R^{15}$, $R^{16}$, $R^{17}$, $R^{18}$, $R^{19}$, $R^{20}$, $R^{1-1}$, $R^{1-2}$, $R^{1-3}$, $R^{1-4}$, $R^{1-5}$, $R^{1-6}$, $R^{1-7}$, $R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ refers to $C_{3-10}$ cycloalkyl, the $C_{3-10}$ cycloalkyl is is $C_{3-6}$ cycloalkyl, for example, cyclohexyl, -cyclopentyl, cyclobutyl or cyclopropyl.

In a certain embodiment, $A_1$ and $A_2$ are independently $CR^{b1}$, $R^{b1}$ is hydrogen or halogen.

In a certain embodiment, $A_4$ is N or $CR^4$; $R^4$ is hydrogen or $C_{1-6}$ alkyl substituted with one or more $R^{4-1}$; $R^{4-1}$ is $C_{3-12}$ cycloalkyl.

In a certain embodiment, $A_5$ is N, $NR^5$, $CR^5$ or S.

In a certain embodiment, $R^5$ is

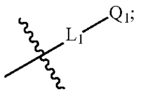

$L_1$ is a bond, $C_{1-6}$ alkylene or $C_{1-6}$ alkylene substituted with deuterium;

$Q_1$ is hydrogen, deuterium, halogen, —$OC_{1-6}$ alkyl, —$NR^{5b1}R^{5b2}$, —C(═O)$NR^{5d1}R^{5d2}$, —$C_{6-20}$ aryl, "5- to 12-membered heteroaryl containing 1 to 4 heteroatoms independently selected from O, S and N", $C_{3-12}$ cycloalkyl, $C_{1-6}$ alkyl substituted with one or more $R^{5-8}$ or "4- to 12-membered heterocycloalkyl containing 1 to 3 heteroatoms independently selected from O, S and N"; provided that when multiple substituents are present, the substituents are the same or different;

$R^{5b1}$, $R^{5b2}$, $R^{5d1}$ and $R^{5d2}$ are independently hydrogen or $C_{1-6}$ alkyl;

$R^{5-8}$ is independently halogen.

In a certain embodiment, $R^{a1}$ is cyano, $C_{1-6}$ alkyl, —C(═O)$NR^{a-51}R^{a-52}$, or, $C_{1-6}$ alkyl substituted with one or more $R^{a1}$, $R^{a1-1}$ is independently halogen.

In a certain embodiment, $R^{a2}$ and $R^{a3}$ together with the carbon atom to which they are attached form $C_{3-7}$ cycloalkane.

In a certain embodiment, $R^{a1}$ is cyano, $C_{1-6}$ alkyl, —C(═O)$NR^{a-51}R^{a-52}$, or, $C_{1-6}$ alkyl substituted with one or more $R^{a1}$, $R^{a1-1}$ is independently halogen, $R^{a2}$ and $R^{a3}$ together with the carbon atom to which they are attached form $C_{3-7}$ cycloalkane.

In a certain embodiment, $R^{a51}$ and $R^{a52}$ are independently hydrogen.

In a certain embodiment, ring Y is "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, "5- to 6-membered heteroaryl containing 1 to 4 heteroatoms independently selected from O, S and N" fused with "5- to 6-membered heterocycloalkyl containing 1 to 3 heteroatoms independently selected from O, S and N", or, "4- to 8-membered heterocycloalkenyl containing 1 to 3 heteroatoms independently selected from O, S and N".

In a certain embodiment, n is 0, 1 or 2.

In a certain embodiment, $R^2$ is independently halogen, hydroxyl, cyano, $C_{1-6}$ alkyl, $C_{1-6}$ alkyl substituted with one or more $R^{2-1}$, —C(═O)$R^{2a}$, —C(═O)$OR^{2c}$ or —C(═O)$NR^{2d1}R^{2d2}$; or, when n is 2, two $R^2$ are connected, together with the atoms to which they are attached, independently form "3- to 8-membered heterocycle containing 1 to 3 heteroatoms independently selected from O, S and N".

In a certain embodiment, $R^{2-1}$ is independently $C_{1-6}$ alkyl-O—, hydroxyl or —C(═O)$NR^{22d1}R^{22d2}$.

In a certain embodiment, $R^{2a}$, $R^{2c}$, $R^{2d1}$, $R^{2d2}$, $R^{22b1}$ and $R^{22b2}$ are independently hydrogen or $C_{1-6}$ alkyl.

In a certain embodiment, $R^1$ is

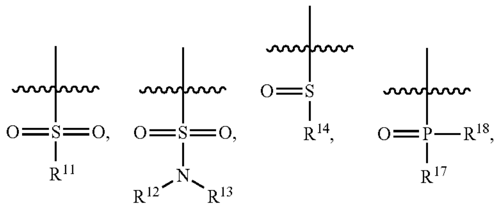

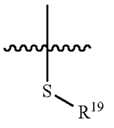 or 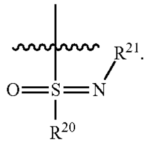

In a certain embodiment, $R^{11}$, $R^{12}$, $R^{13}$, $R^{14}$, $R^{17}$, $R^{18}$, $R^{19}$ and $R^{20}$ are independently $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, "5- to 12-membered heteroaryl containing 1 to 4 heteroatoms independently selected from O, S and N".

$R^{21}$ is hydrogen or $C_{1-6}$ alkyl.

$R^{1-1}$, $R^{1-2}$ and $R^{1-3}$ are $C_{1-6}$ alkyl or —$OC_{1-6}$ alkyl.

In a certain embodiment, when $R^1$ is

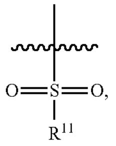

$R^{11}$ is $C_{1-6}$ alkyl, "4- to 12-membered heterocycloalkyl containing 1 to 3 heteroatoms independently selected from O, S and N", $C_{3-10}$ cycloalkyl, $C_{1-6}$ alkyl substituted with one or more $R^{1-1}$, $C_{3-10}$ cycloalkyl substituted with one or more $R^{1-2}$, "4- to 12-membered heterocycloalkyl containing 1 to 3 heteroatoms independently selected from O, S and N" substituted with one or more $R^{1-3}$, $C_{6-20}$ aryl or "5- to 12-membered heteroaryl containing 1 to 4 heteroatoms independently selected from O, S and N"; $R^{14}$ is —$OC_{1-6}$ alkyl; $R^{1-2}$ and $R^{1-3}$ are independently $C_{1-6}$ alkyl.

In a certain embodiment, when $R^1$ is

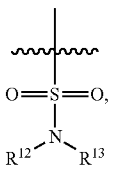

$R^{12}$ and $R^{13}$ are independently $C_{1-6}$ alkyl.

In a certain embodiment, when $R^1$ is

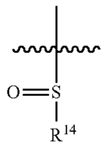
or
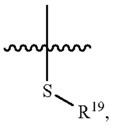

$R^{14}$ and $R^{19}$ are independently $C_{1-6}$ alkyl.

In a certain embodiment, when $R^1$ is

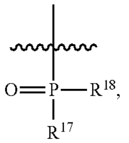

$R^{17}$ and $R^{18}$ are independently $C_{1-6}$ alkyl or $—OC_{1-6}$ alkyl.

In a certain embodiment, when $R^1$ is

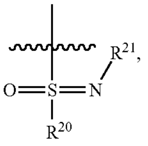

$R^{20}$ is $C_{1-6}$ alkyl.

In a certain embodiment, $R^3$ is "5- to 6-membered heteroaryl containing 1 to 4 heteroatoms independently selected from O, S and N" substituted with one or more $R^{3-1}$.

In a certain embodiment, $R^{3-1}$ is independently $C_{1-6}$ alkyl or $C_{1-6}$ alkyl substituted with one or more halogen; provided that when multiple substituents are present, the substituents are the same or different.

In a certain embodiment, when $Q_1$ is "5- to 12-membered heteroaryl containing 1 to 4 heteroatoms independently selected from O, S and N", the $Q_1$ is "5- to 6-membered heteroaryl containing 1 to 2 heteroatoms independently selected from N", for example, pyridinyl.

In a certain embodiment, when $Q_1$ is "4- to 12-membered heterocycloalkyl containing 1 to 3 heteroatoms independently selected from O, S and N", the $Q_1$ is "4- to 6-membered heterocycloalkyl containing 1 to 2 heteroatoms independently selected from O, S and N".

In a certain embodiment, when $Q_1$ is $C_{1-6}$ alkyl substituted with one or more $R^{5-8}$, the $Q_1$ is $C_{1-6}$ alkyl substituted with two or three $R^{5-8}$.

In a certain embodiment, when ring Y is "4- to 12-membered heterocycloalkyl containing 1 to 3 heteroatoms independently selected from O, S and N", the ring Y is "4- to 8-membered heterocycloalkyl containing 1 to 2 heteroatoms N", for example, 6-membered heterocycloalkyl containing 2 heteroatoms N.

In a certain embodiment, when ring Y is "5- to 12-membered heteroaryl containing 1 to 4 heteroatoms independently selected from O, S and N", the ring Y is "5- to 6-membered heteroaryl containing 1 to 2 heteroatoms independently selected from O and N", for example, pyridinyl or pyrimidinyl.

In a certain embodiment, when ring Y is $C_{4-8}$ cycloalkenyl, the ring Y is $C_{5-7}$ cycloalkenyl, for example, cyclohexenyl.

In a certain embodiment, when ring Y is "5- to 6-membered heteroaryl containing 1 to 4 heteroatoms independently selected from O, S and N" fused with "5- to 6-membered heterocycloalkyl containing 1 to 3 heteroatoms independently selected from O, S and N", the ring Y is "5- to 6-membered heteroaryl containing 1 to 2 heteroatoms N" fused with "5- to 6-membered heterocycloalkyl containing 1 heteroatom N".

In a certain embodiment, when ring Y is "4- to 8-membered heterocycloalkenyl containing 1 to 3 heteroatoms independently selected from O, S and N", the ring Y is "5- to 7-membered heterocycloalkenyl containing 1 to 3 heteroatoms independently selected from O and N", for example, 6-membered heterocycloalkenyl containing 1 to 3 heteroatoms N.

In a certain embodiment, when n is 2, two $R^2$ are connected, together with the atoms to which they are attached, independently form "3- to 8-membered heterocycle containing 1 to 3 heteroatoms independently selected from O, S and N", the "3- to 8-membered heterocycle containing 1 to 3 heteroatoms independently selected from O, S and N" is "3- to 6-membered heterocycle containing 1 to 2 heteroatoms independently selected from O, S and N".

In a certain embodiment, when $R^{11}$, $R^{12}$, $R^{13}$, $R^{14}$, $R^{17}$, $R^{18}$, $R^{19}$ and $R^{20}$ are independently "4- to 12-membered heterocycloalkyl containing 1 to 3 heteroatoms independently selected from O, S and N" or "4- to 12-membered heterocycloalkyl containing 1 to 3 heteroatoms independently selected from O, S and N" substituted with one or more $R^{1-3}$, the "4- to 12-membered heterocycloalkyl containing 1 to 3 heteroatoms independently selected from O, S and N" is "4- to 6-membered heterocycloalkyl containing 1 to 2 heteroatoms independently selected from O and N".

In a certain embodiment, when $R^{11}$, $R^{12}$, $R^{13}$, $R^{14}$, $R^{17}$, $R^{18}$, $R^{19}$ and $R^{20}$ are independently "5- to 12-membered heteroaryl containing 1 to 4 heteroatoms independently selected from O, S and N", the "5- to 12-membered heteroaryl containing 1 to 4 heteroatoms independently selected from O, S and N" is "5- to 6-membered heteroaryl containing 1 to 2 heteroatoms independently selected from O, S and N", for example, pyridinyl.

In a certain embodiment, when $R^3$ is "5- to 6-membered heteroaryl containing 1 to 4 heteroatoms independently selected from O, S and N" substituted with one or more $R^{3-1}$, the "5- to 6-membered heteroaryl containing 1 to 4 heteroatoms independently selected from O, S and N" is "5- to 6-membered heteroaryl containing 1 to 3 heteroatoms independently selected from O, S and N".

In a certain embodiment, when $R^{3-1}$ is $C_{1-6}$ alkyl substituted with one or more halogen, the $C_{1-6}$ alkyl substituted with one or more halogen is $C_{1-2}$ alkyl substituted with two or three halogen, for example, $—CHF_2$ or $—CF_3$.

When $R^{a2}$ and $R^{a3}$ together with the carbon atom to which they are attached form $C_{3-7}$ cycloalkane, the $C_{3-7}$ cycloalkane is $C_{3-6}$ cycloalkane, for example, cyclopropane, cyclobutane or cyclopentane.

In a certain embodiment,

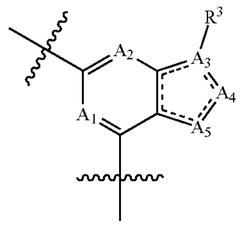
is

-continued
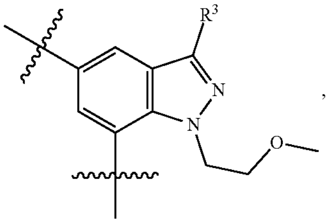
,
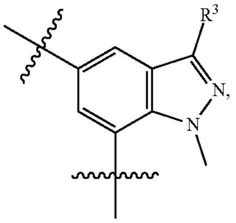
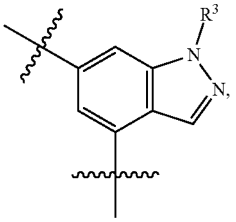
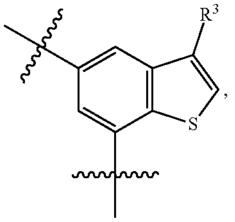
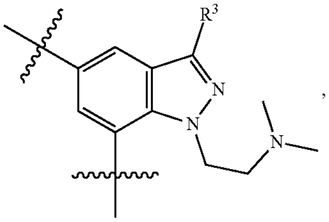
,
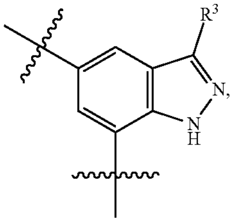
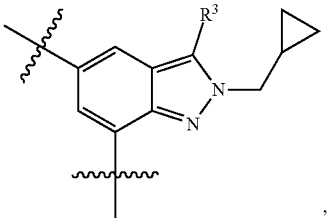
,
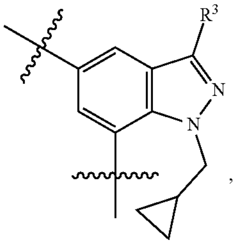
,
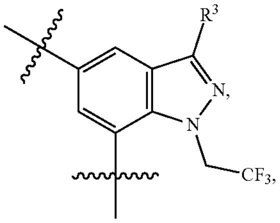
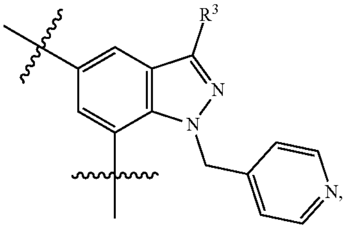
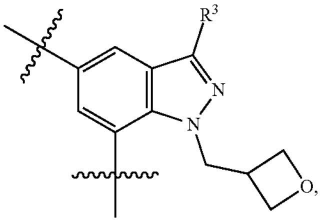
-continued
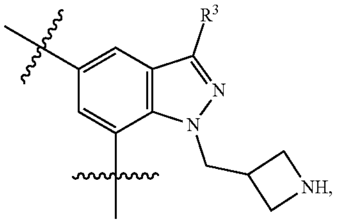
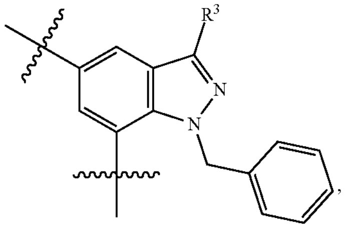
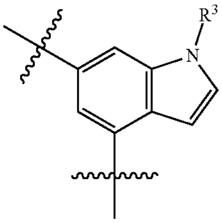
,
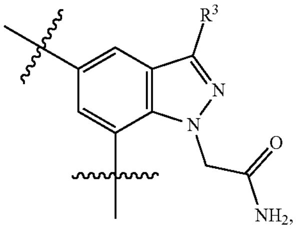
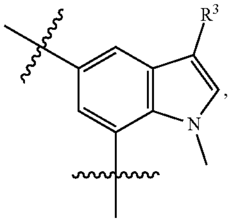
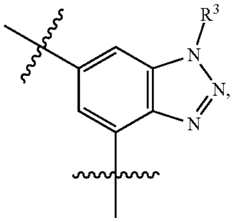
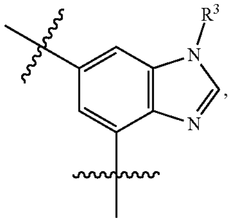
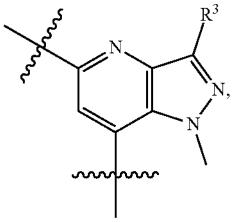
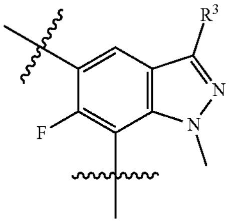
or
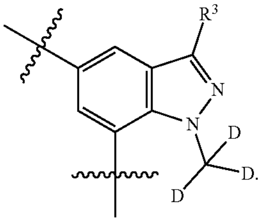

In a certain embodiment, $R^3$ is
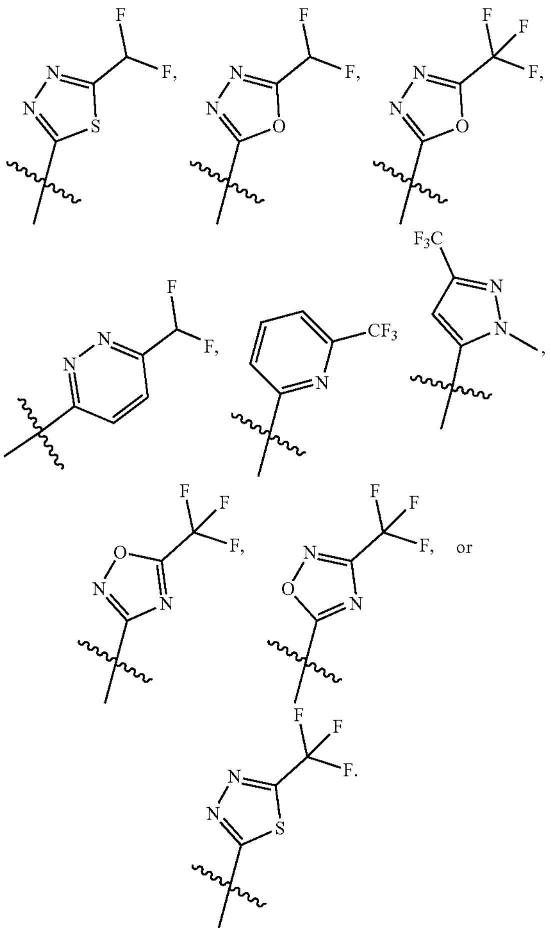
or
In a certain embodiment,
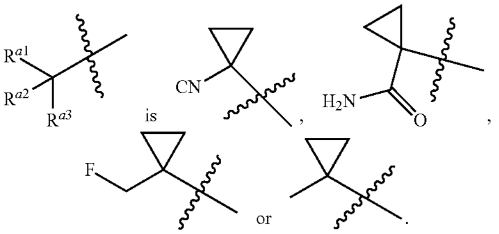
is ... or
In a certain embodiment, ring Y is
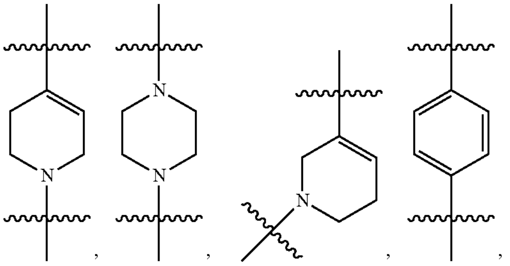
-continued
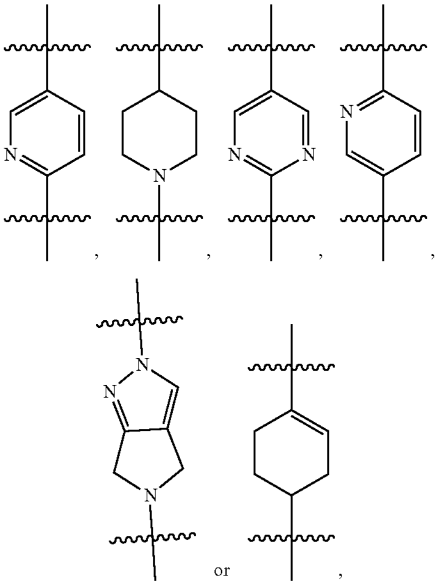
or
furthermore, the upper end is connected with the
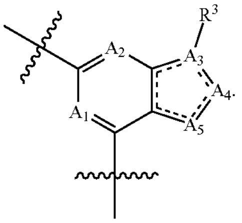
In a certain embodiment,
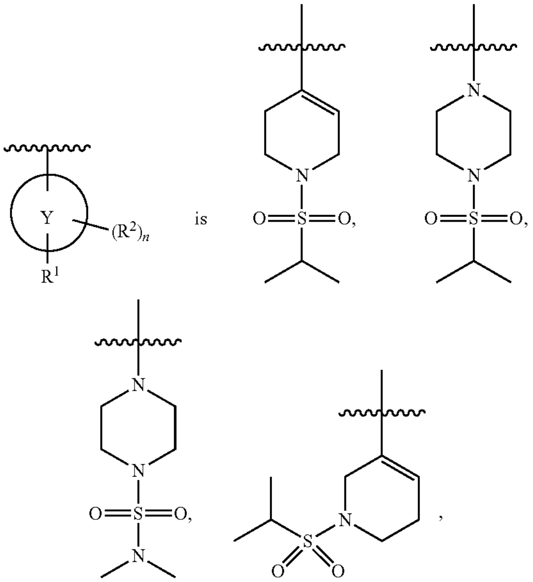
is -continued
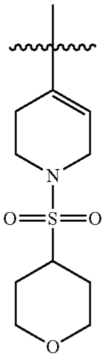,
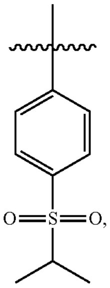
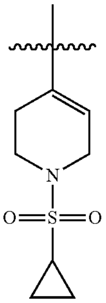,
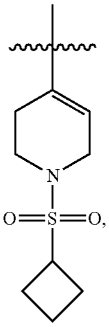
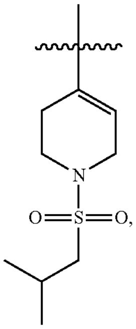
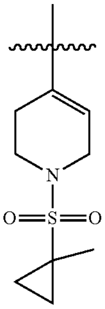,
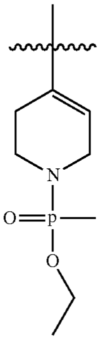,
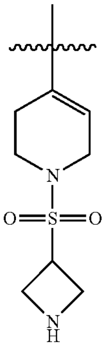,
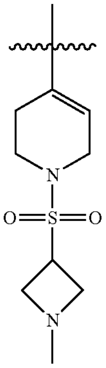,
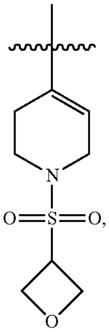
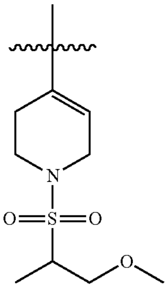,
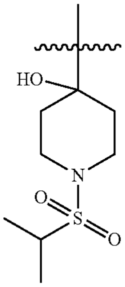,
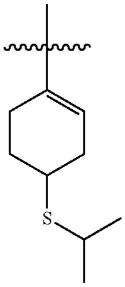,
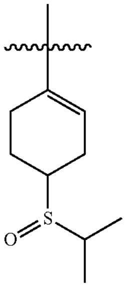,
-continued
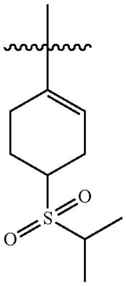,
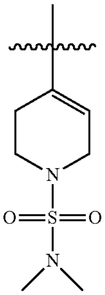,
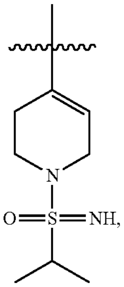
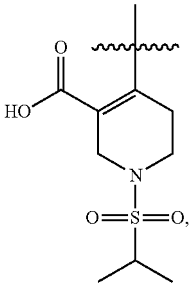
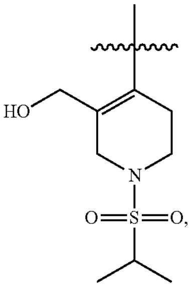
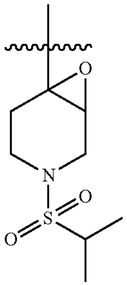,
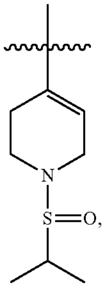
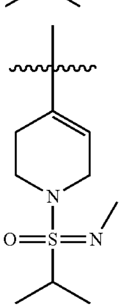,
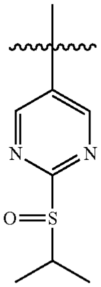,
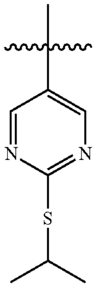,
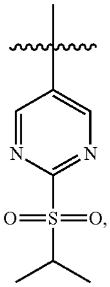
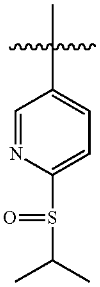
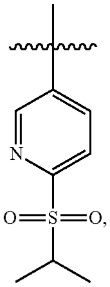
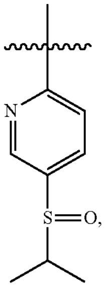

-continued
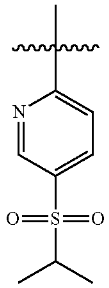
,
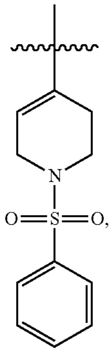
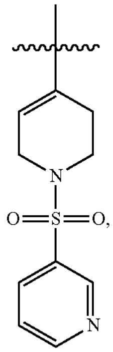
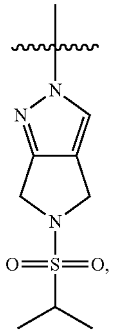
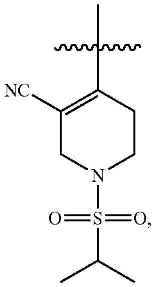
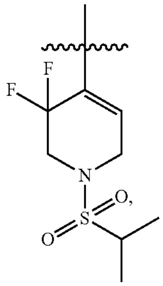
,
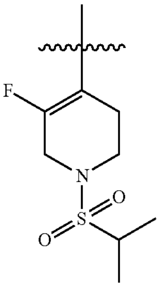
,
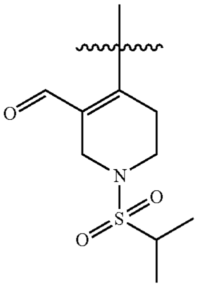
,
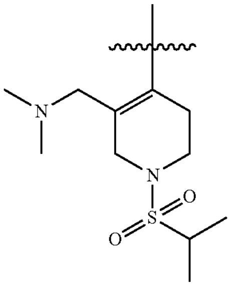
,
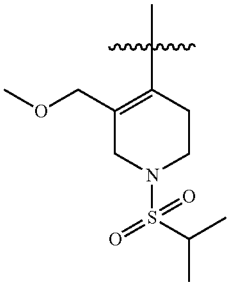
,
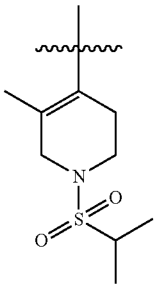
,
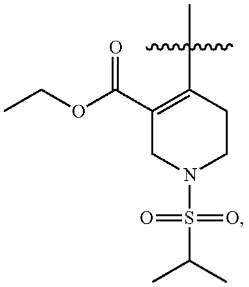
-continued
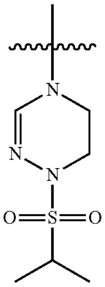
or
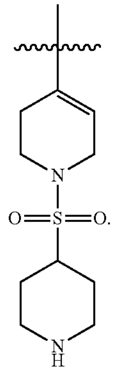
In a certain embodiment, the compound containing structure of a heteroaromatic ring represented by formula I as described above can be any one of the following structures:
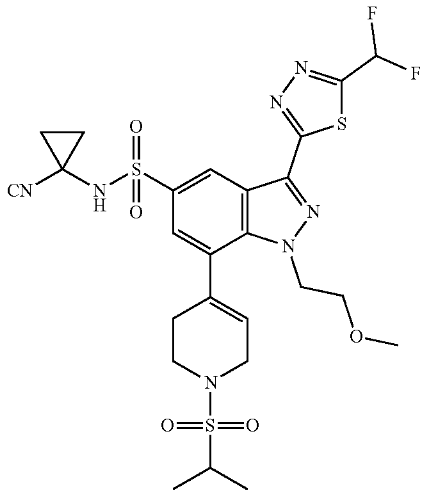
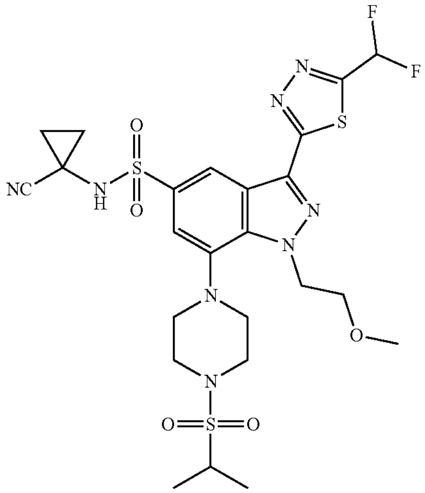

-continued
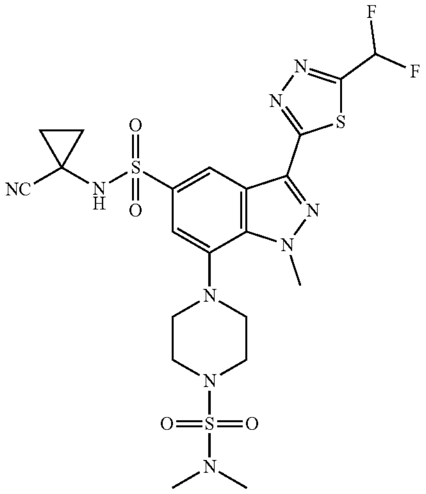
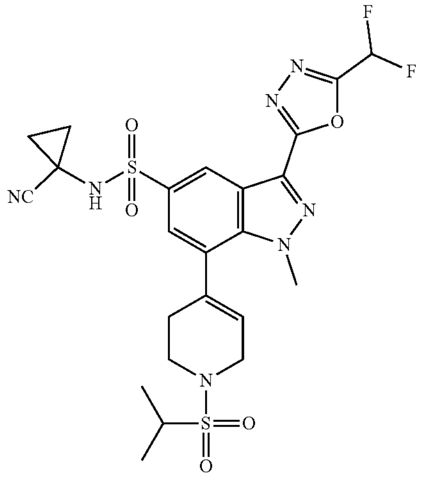
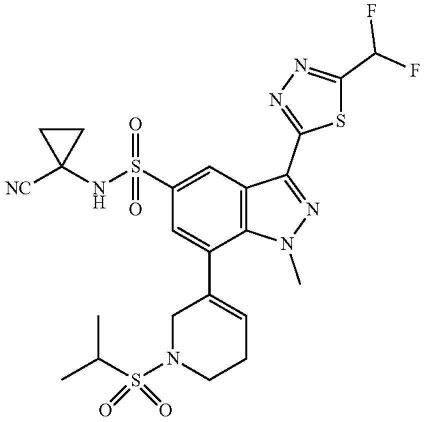
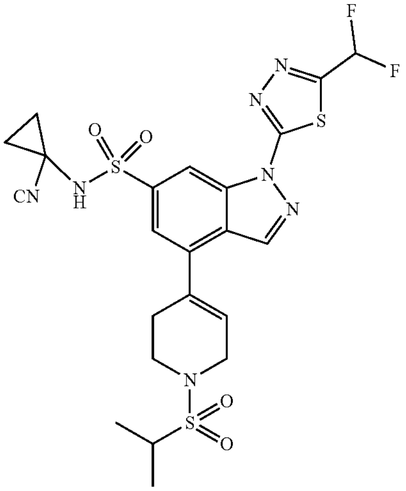
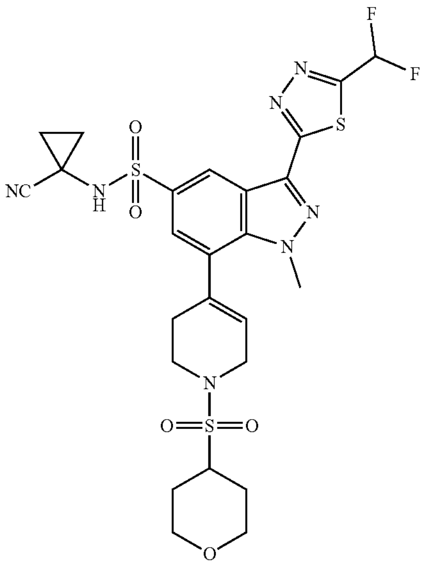
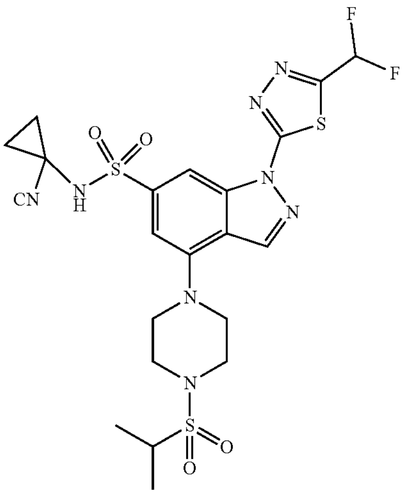

-continued
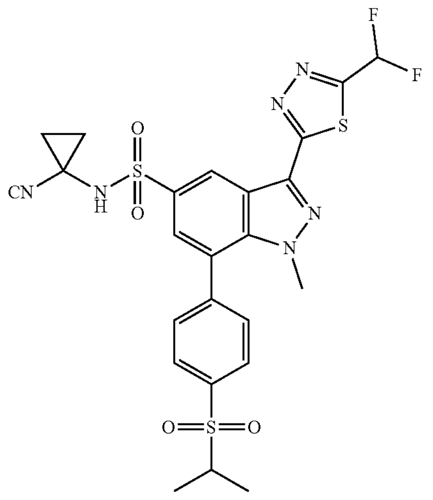
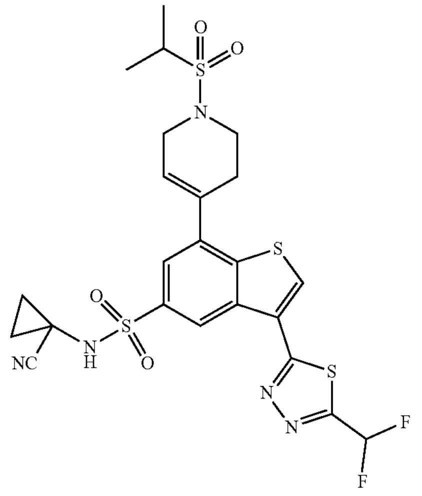
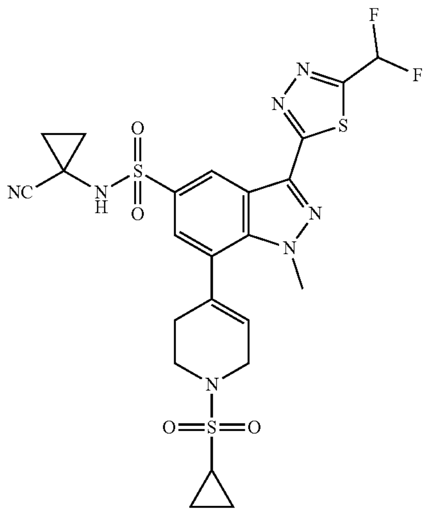
-continued
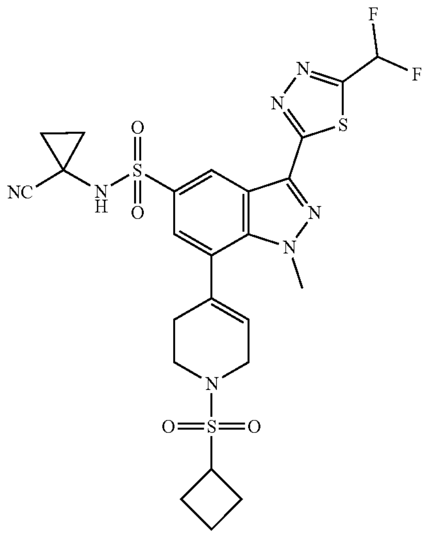
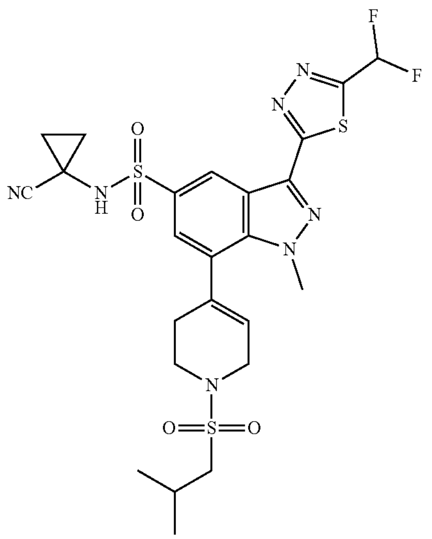
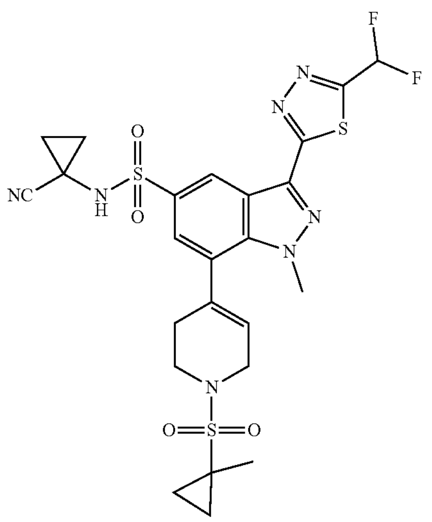

-continued
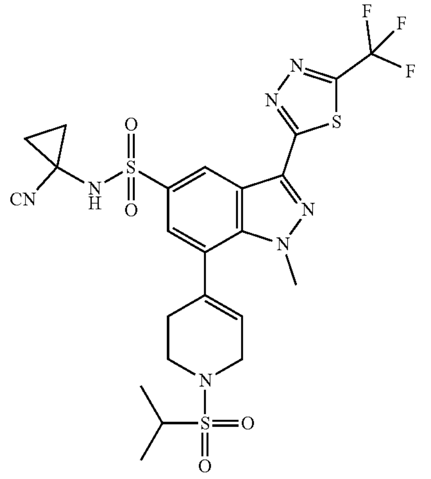
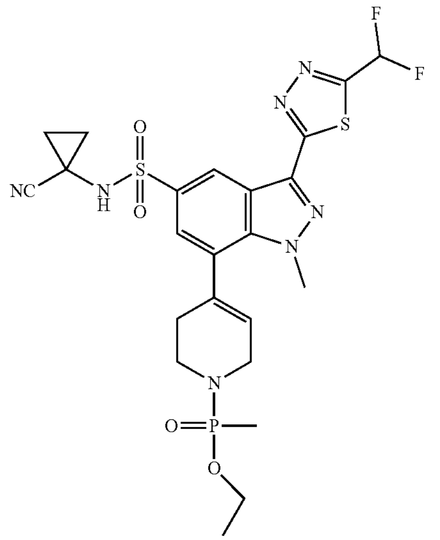
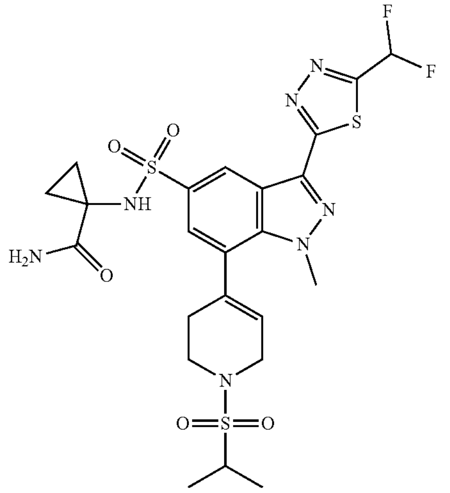
-continued
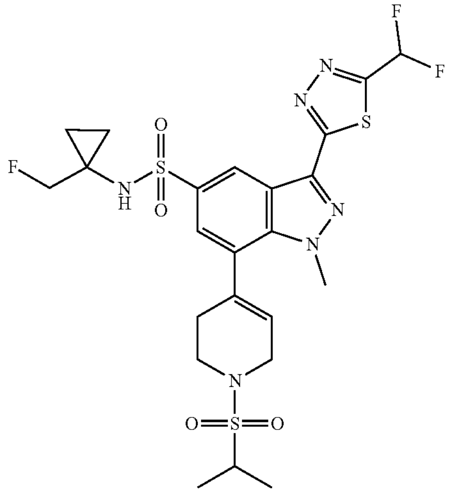
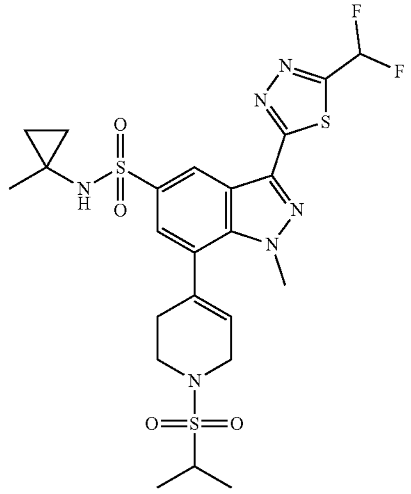
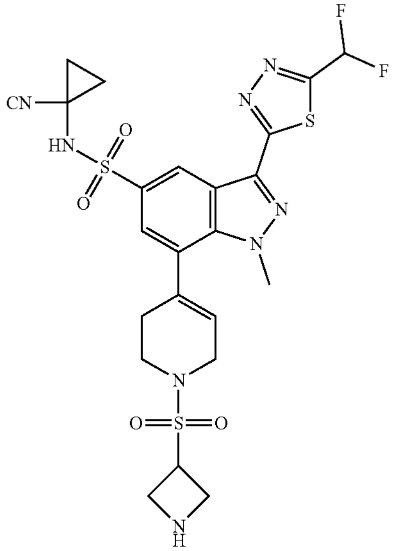

-continued
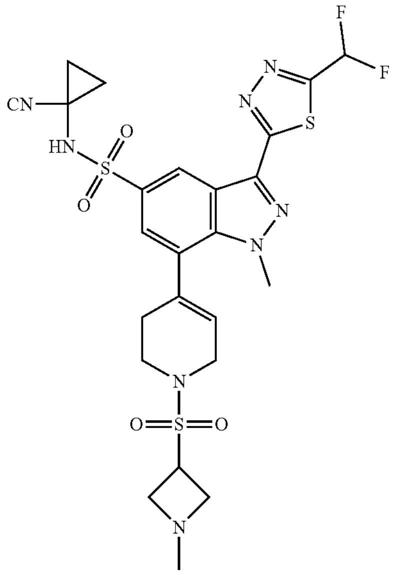
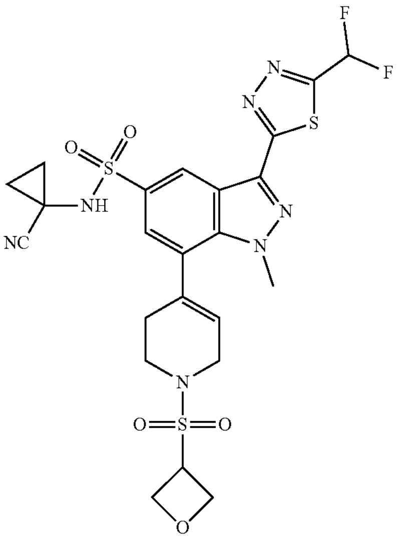
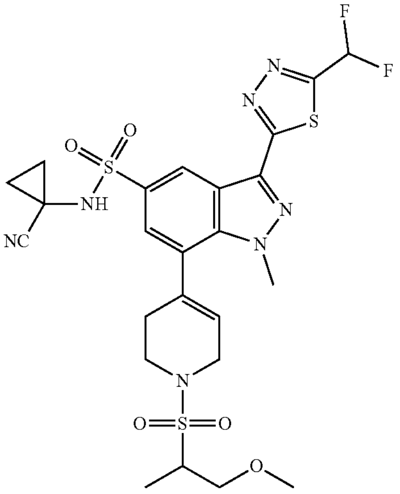
-continued
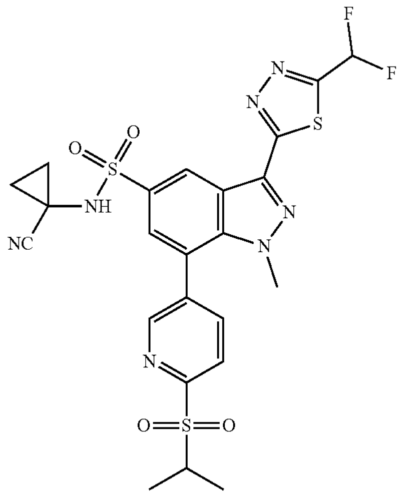
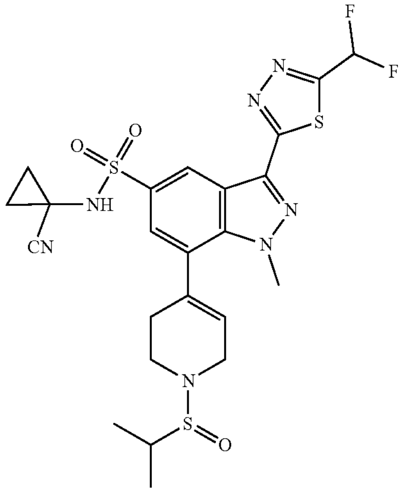
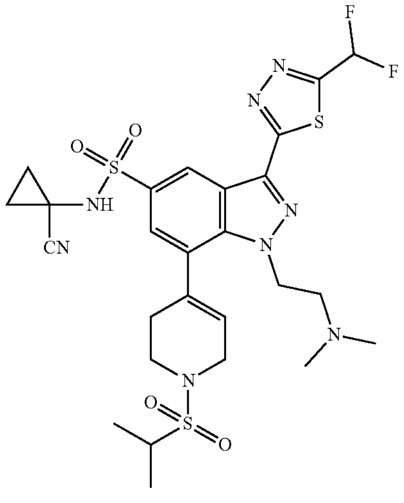

-continued
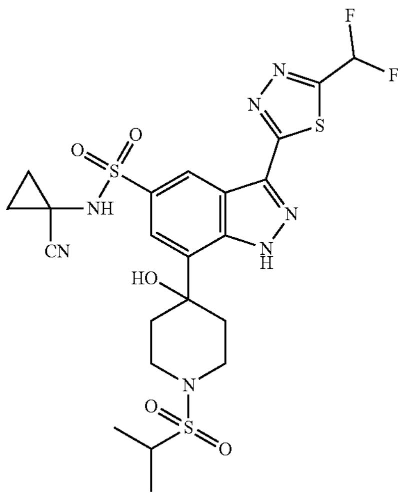
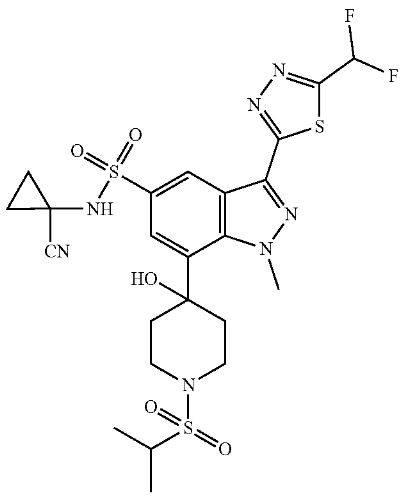
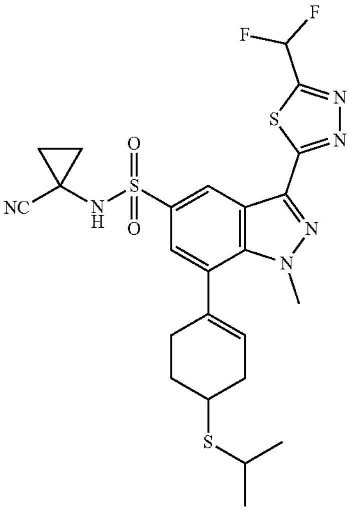
-continued
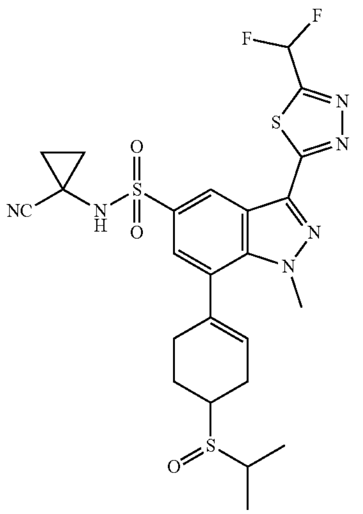
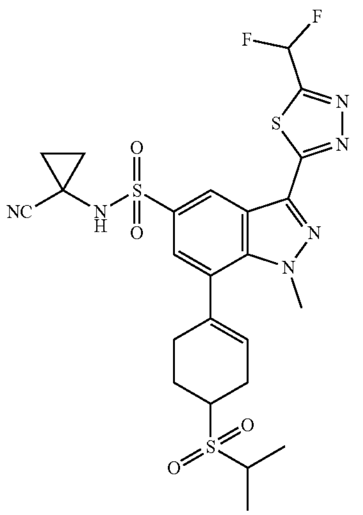
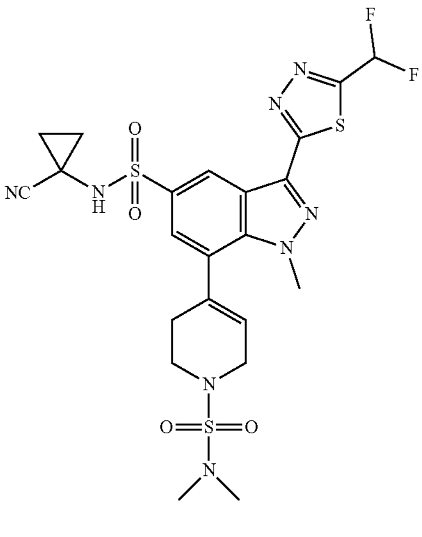

-continued
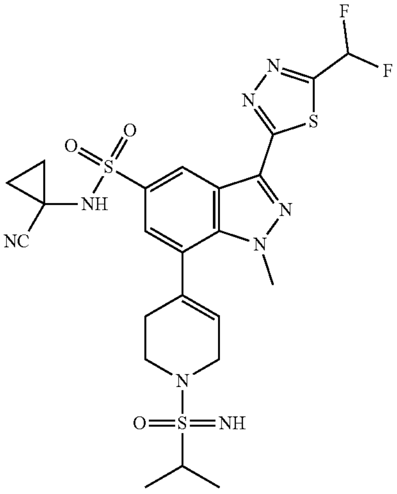
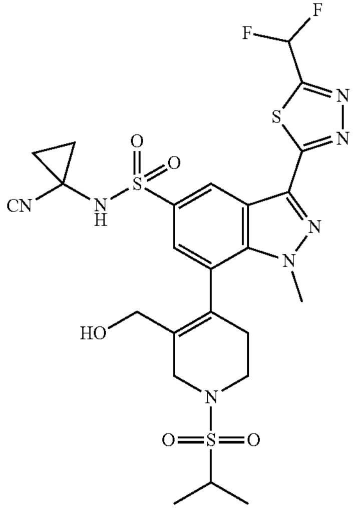
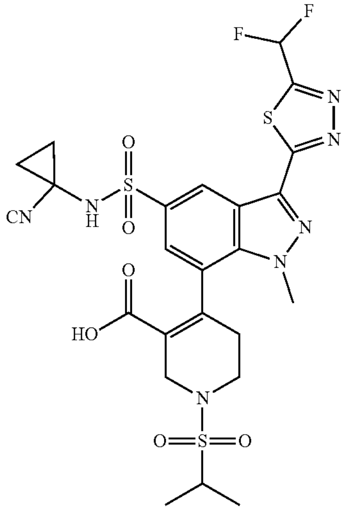
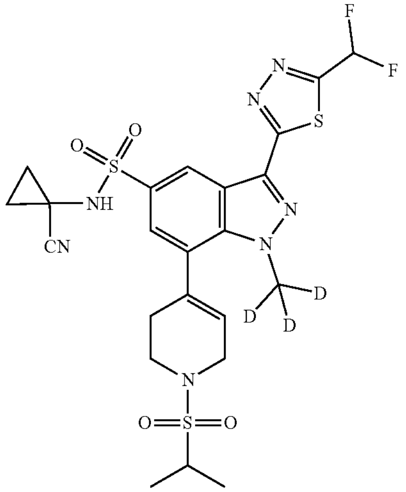
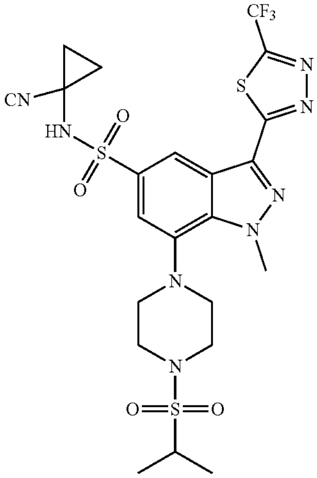
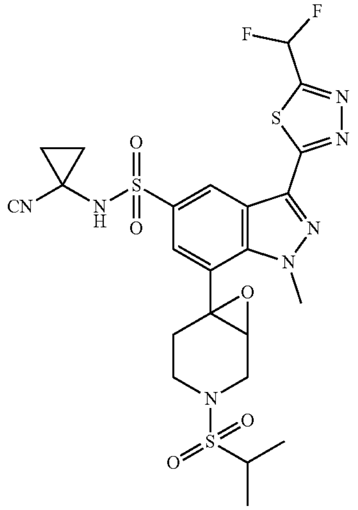

-continued
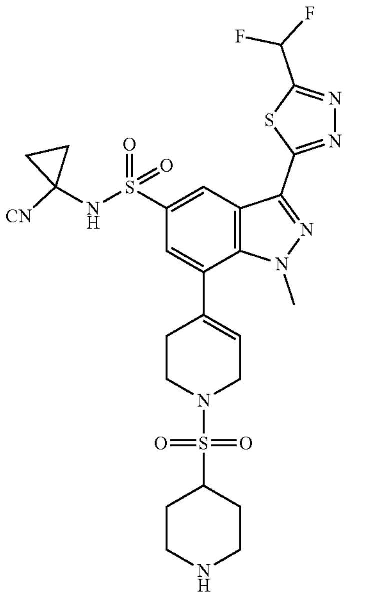
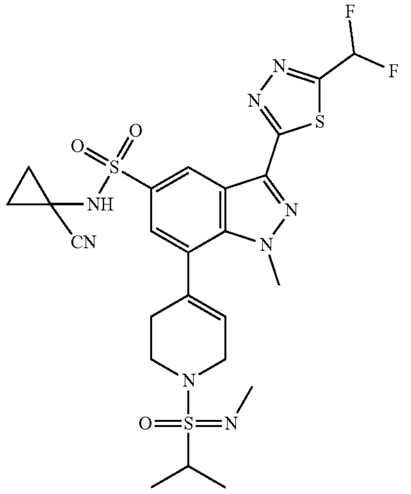
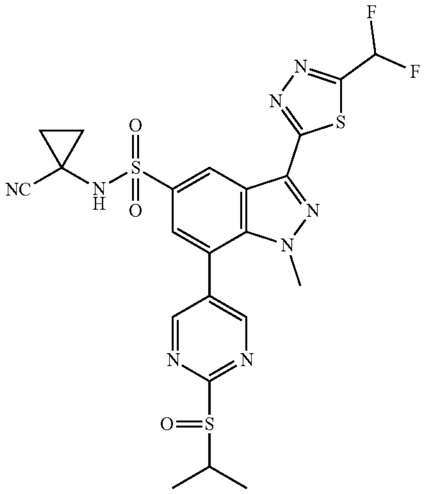
-continued
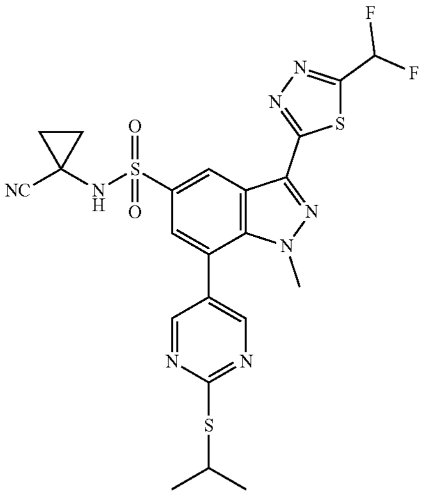
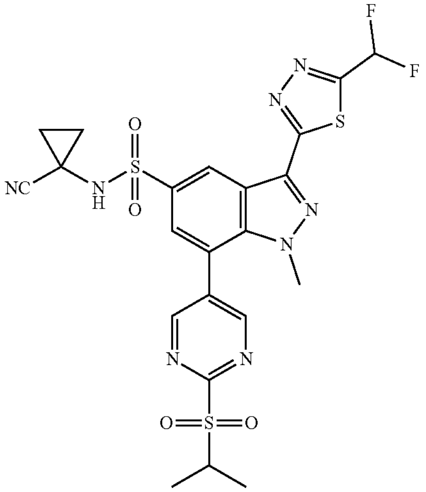
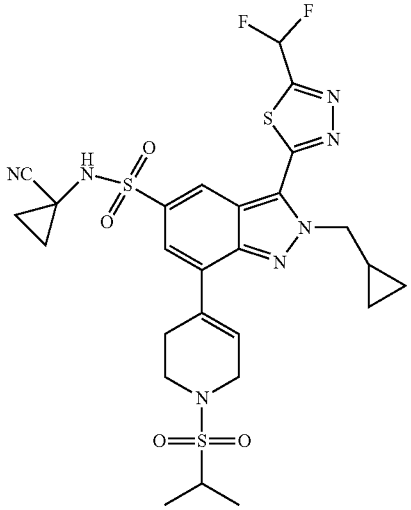

-continued
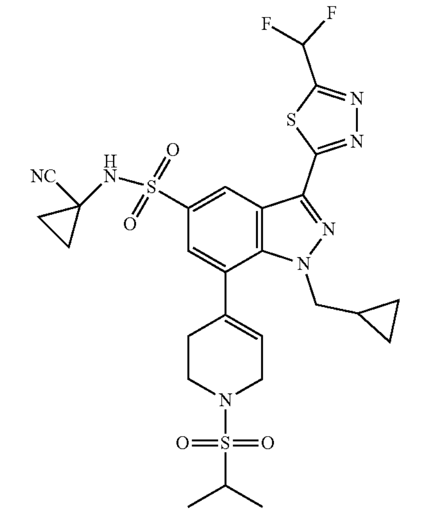
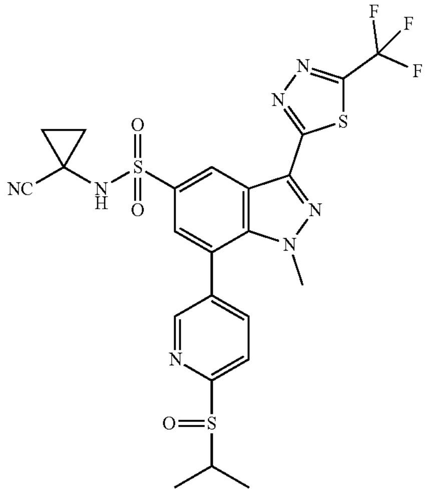
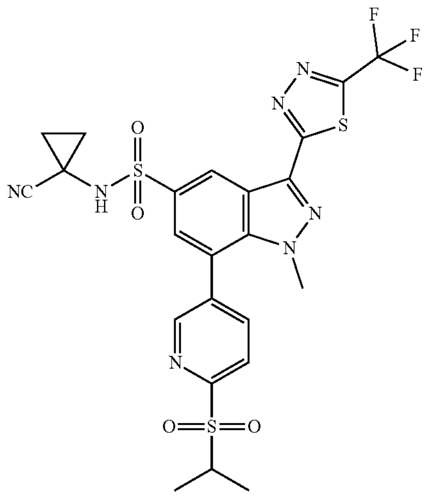
-continued
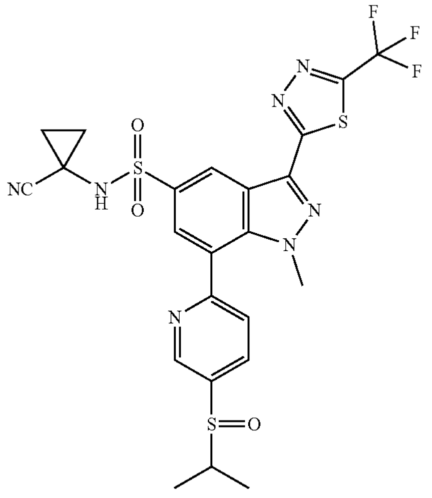
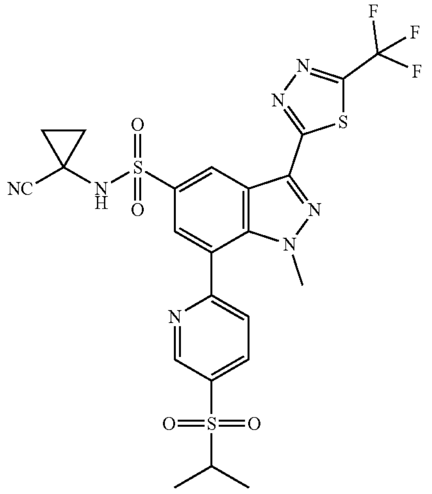
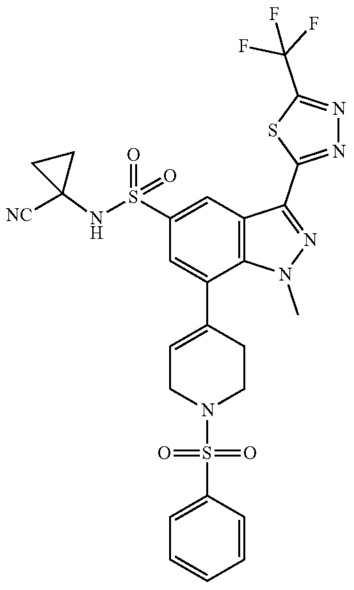

-continued
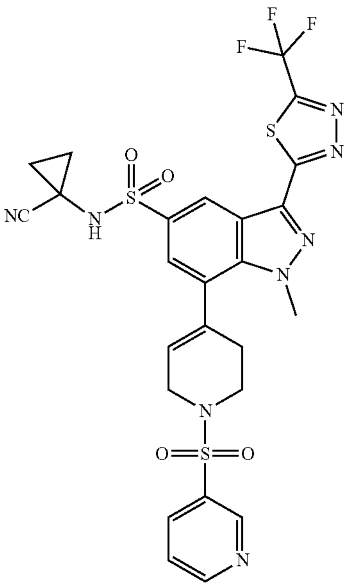
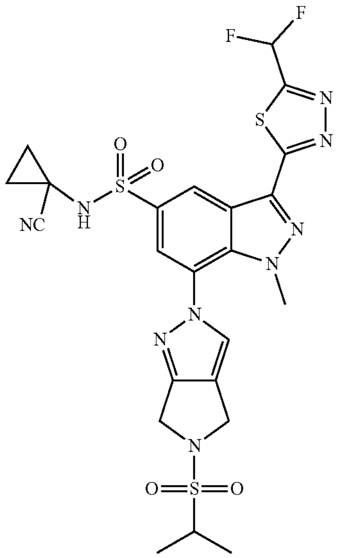
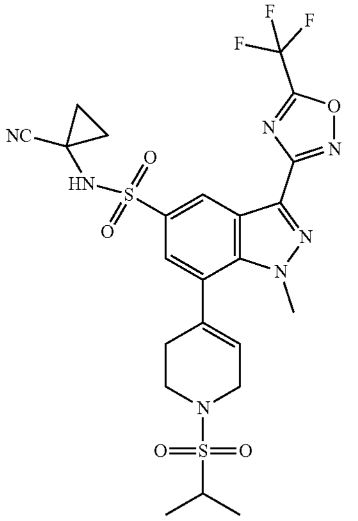
-continued
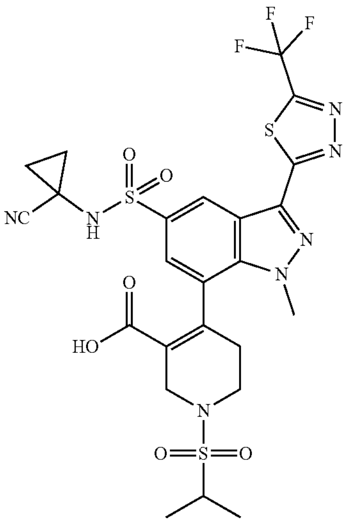
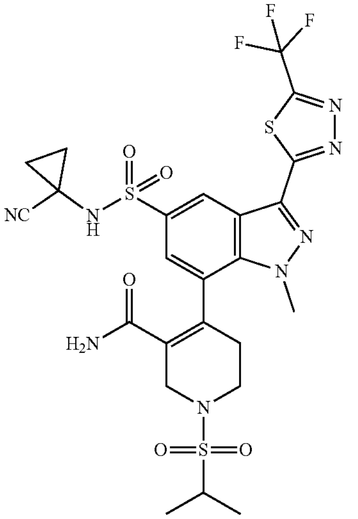
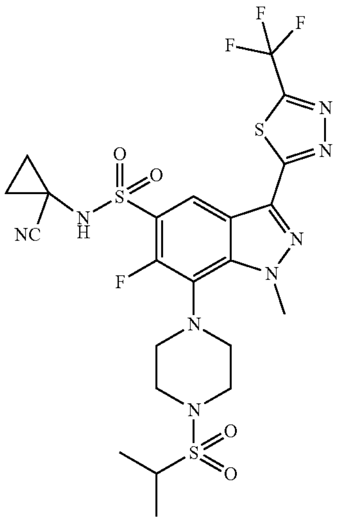

-continued
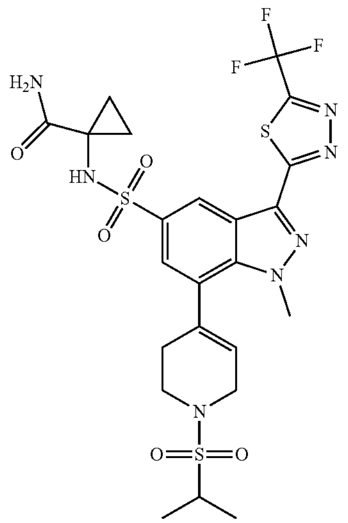
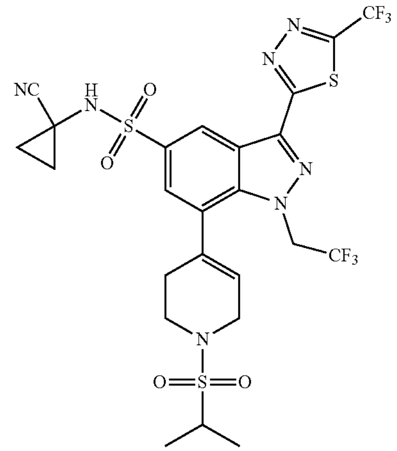
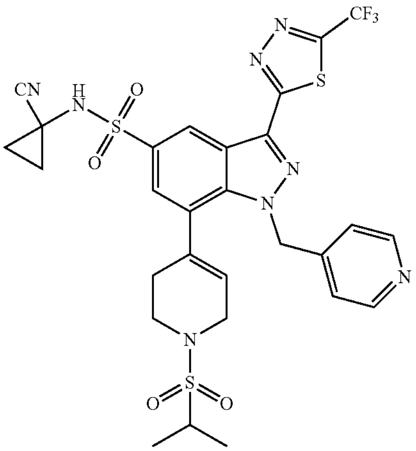
-continued
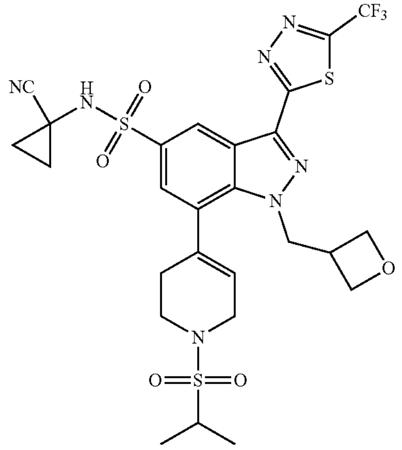
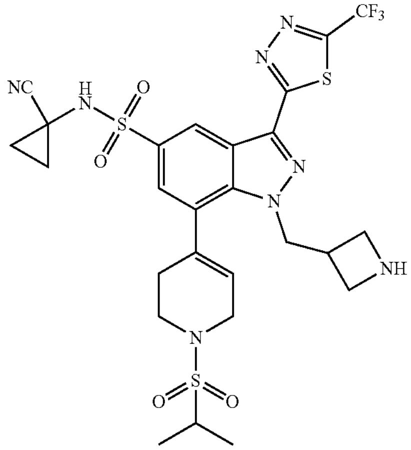
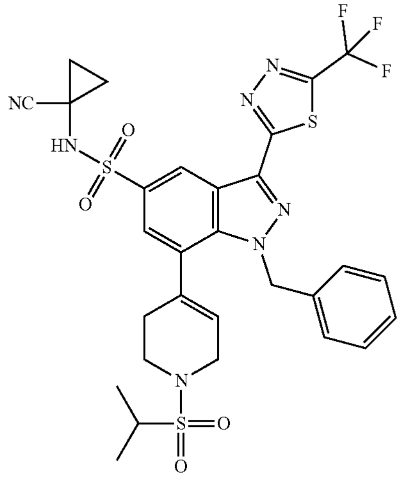

-continued
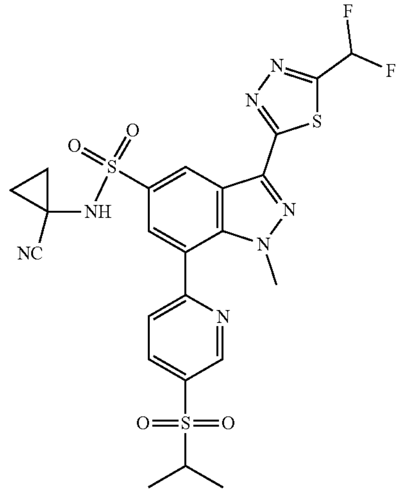
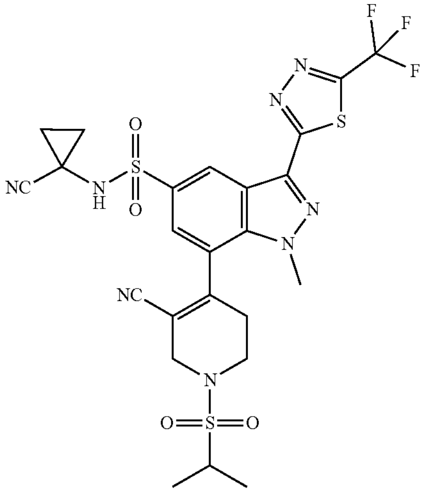
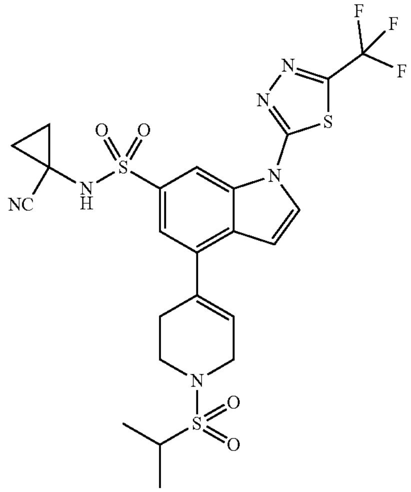
-continued
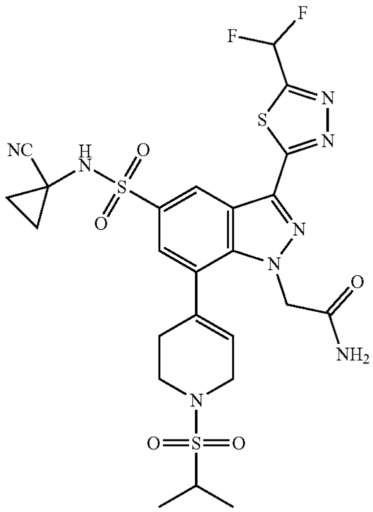
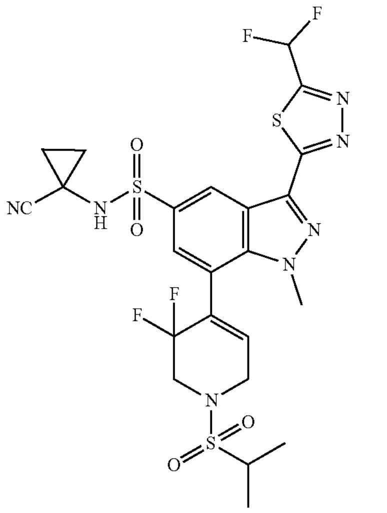
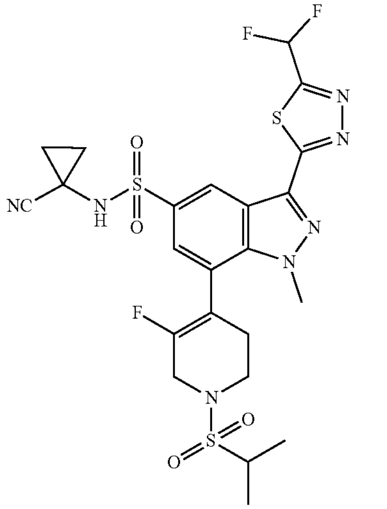

-continued
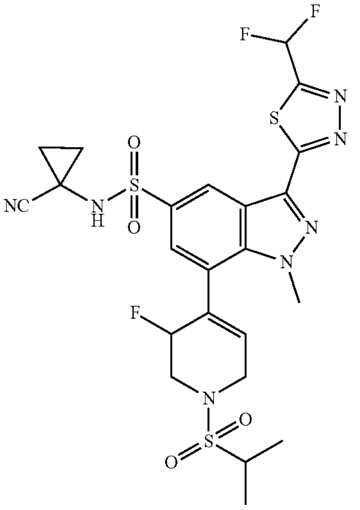
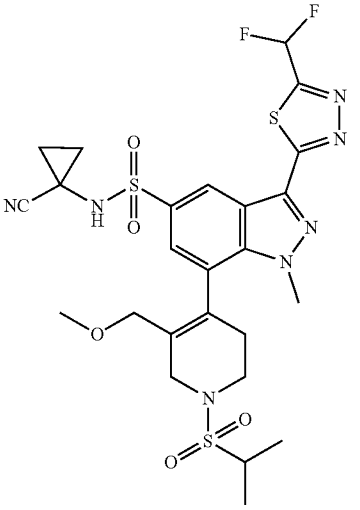
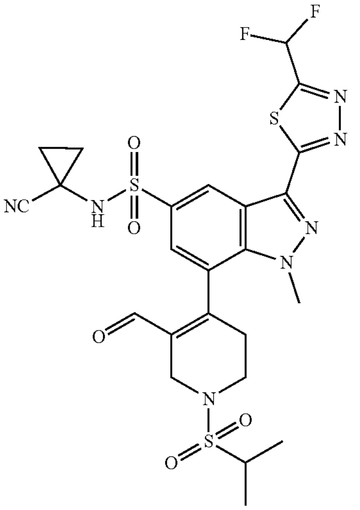
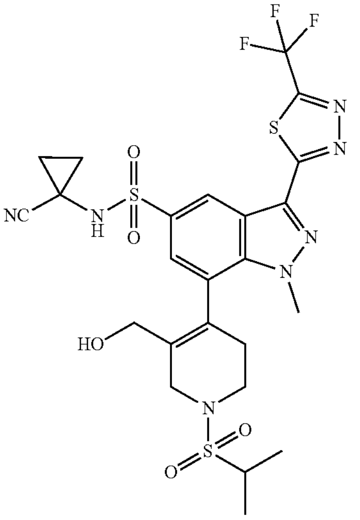
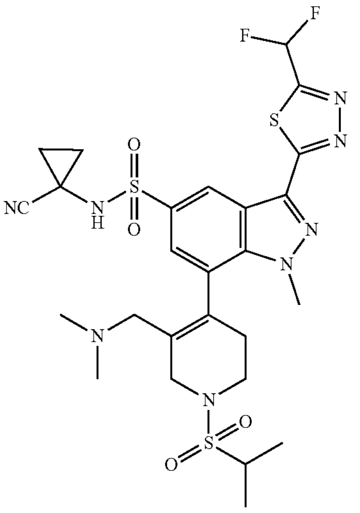
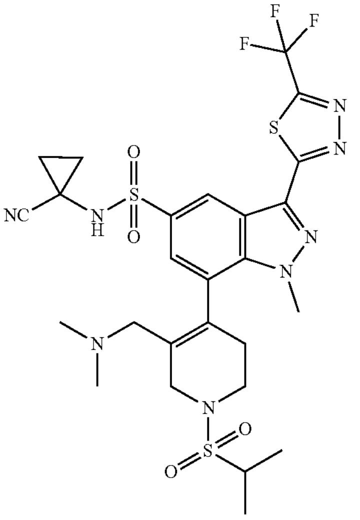

-continued
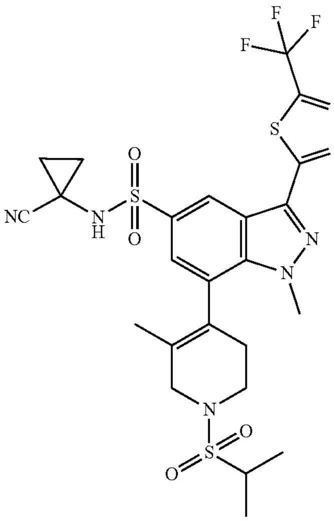
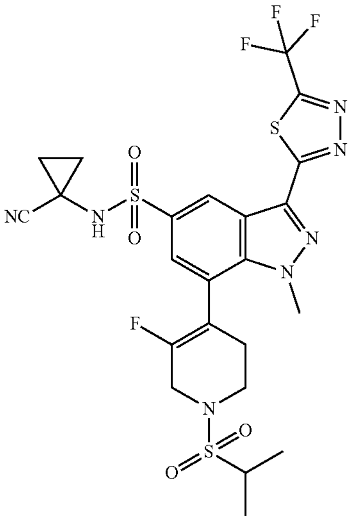
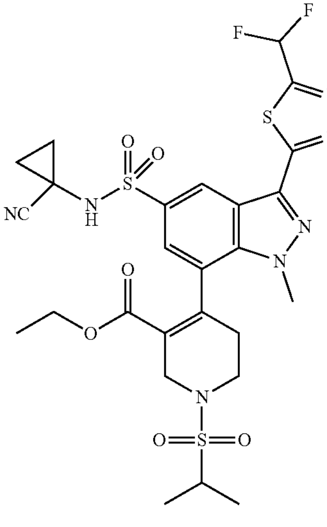
-continued
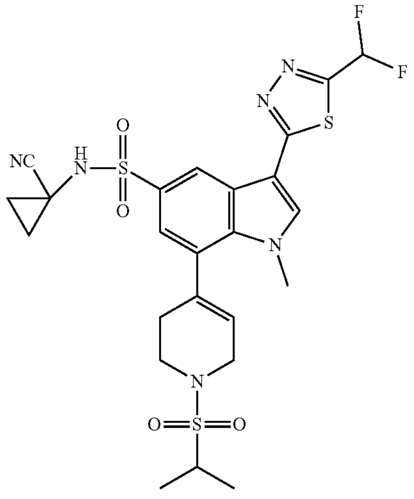
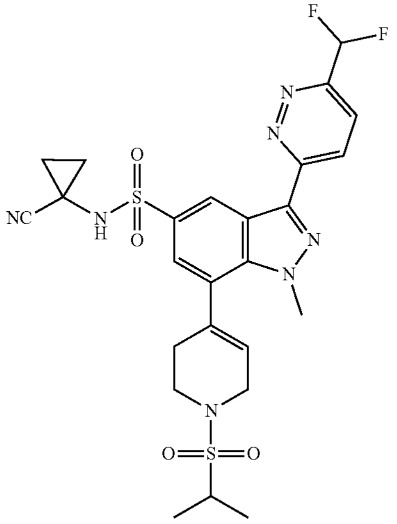
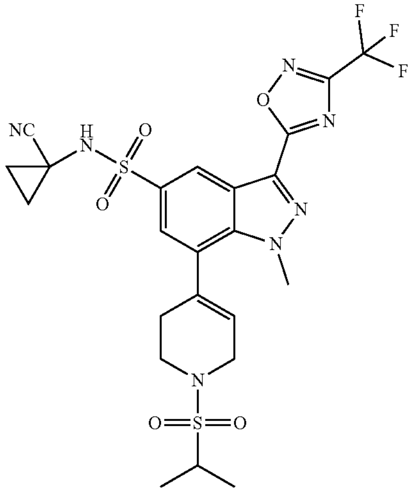

-continued
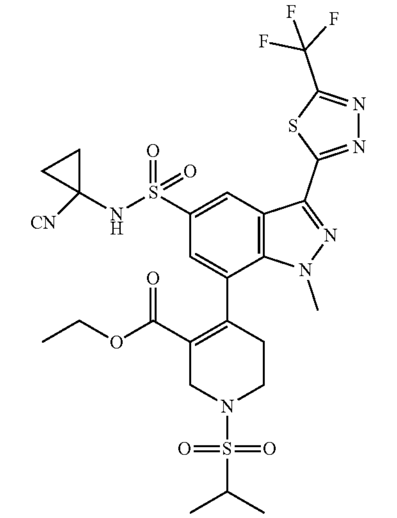
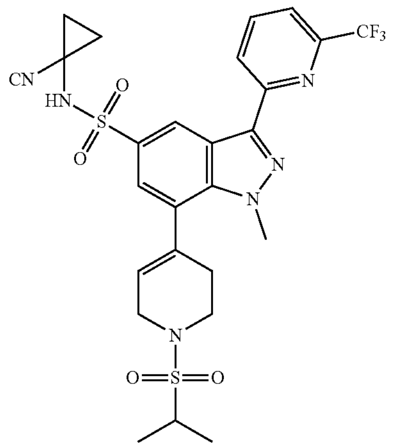
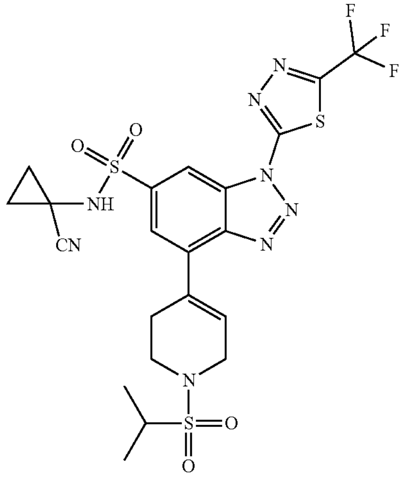
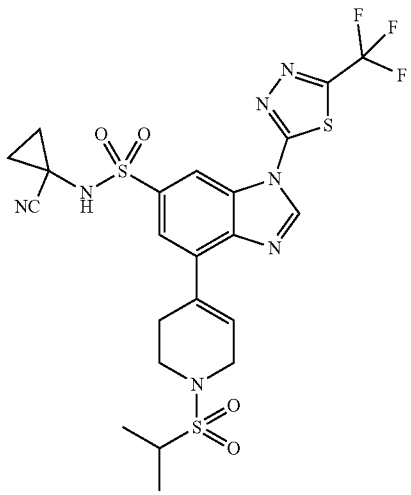
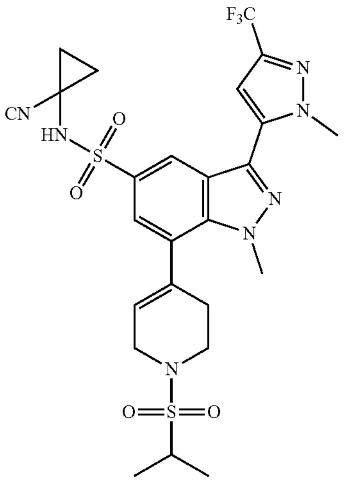
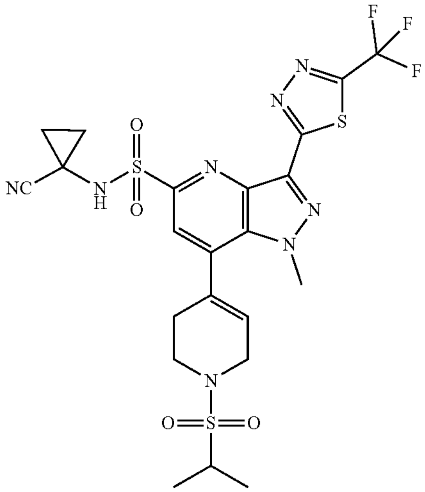
-continued -continued

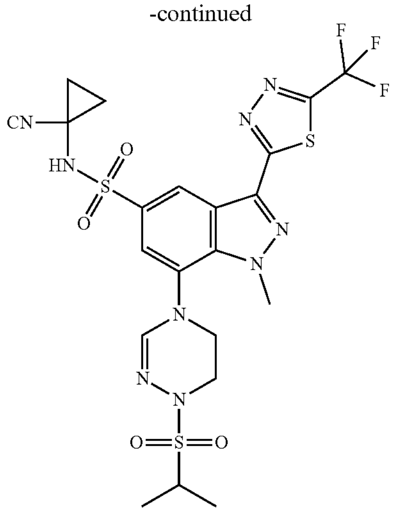

The present disclosure also provides a pharmaceutical composition comprising a substance A and a pharmaceutically acceptable excipient, wherein the substance A is a therapeutically effective amount of the compound containing structure of a heteroaromatic ring of formula I, the pharmaceutically acceptable salt thereof, the stereoisomer thereof, the tautomer thereof or the isotopically labeled compound thereof as described above.

The present disclosure also provides a method for inhibiting PARG in a subject in need thereof, comprising: administering a therapeutically effective amount of a substance A to the subject, wherein the substance A is the compound containing structure of a heteroaromatic ring of formula I, the pharmaceutically acceptable salt thereof, the stereoisomer thereof, the tautomer thereof or the isotopically labeled compound thereof as described above.

The present disclosure also provides a method for treating or preventing a PARG related disease in a subject in need thereof, comprising: administering an effective amount of a substance A, wherein the substance A is the compound containing structure of a heteroaromatic ring of formula I, the pharmaceutically acceptable salt thereof, the stereoisomer thereof, the tautomer thereof or the isotopically labeled compound thereof as described above.

In the method for treating or preventing an PARG related disease in a subject in need thereof, wherein the PARG related disease is cancer, the cancer is selected from the group consisting of colon cancer, appendicle cancer, pancreatic cancer, MYH-related polyposis, hematologic cancer, breast cancer, endometrial cancer, gallbladder cancer, bile duct cancer, prostate cancer, lung cancer, brain cancer, ovarian cancer, cervical cancer, testicular cancer, kidney cancer, head or neck cancer, bone cancer, skin cancer, rectal cancer, liver cancer, esophageal cancer, stomach cancer, thyroid cancer, bladder cancer, lymphoma, leukemia and melanoma.

The present disclosure also provides a method for treating or preventing a cancer, comprising: administering a therapeutically effective amount of a substance A to the subject, wherein the substance A is the compound containing structure of a heteroaromatic ring of formula I, the pharmaceutically acceptable salt thereof, the stereoisomer thereof, the tautomer thereof or the isotopically labeled compound thereof as described above; the cancer is selected from the group consisting of colon cancer, appendicle cancer, pancreatic cancer, MYH-related polyposis, hematologic cancer, breast cancer, endometrial cancer, gallbladder cancer, bile duct cancer, prostate cancer, lung cancer, brain cancer, ovarian cancer, cervical cancer, testicular cancer, kidney cancer, head or neck cancer, bone cancer, skin cancer, rectal cancer, liver cancer, esophageal cancer, stomach cancer, thyroid cancer, bladder cancer, lymphoma, leukemia and melanoma.

The term "pharmaceutically acceptable salt" refers to a salt prepared from compounds of the present disclosure with relatively non-toxic, pharmaceutically acceptable acids or bases. When compounds of the present disclosure contain relatively acidic functional groups, base addition salts can be obtained by contacting the neutral form of such compounds with a sufficient amount of pharmaceutically acceptable bases, either in pure solution or a suitable inert solvent. The pharmaceutically acceptable base addition salts include but are not limited to: lithium salt, sodium salt, potassium salt, calcium salt, aluminum salt, magnesium salt, zinc salt, bismuth salt, ammonium salt and diethanolamine salt. When compounds of the present disclosure contain relatively basic functional groups, acid addition salts can be obtained by contacting the neutral form of such compounds with a sufficient amount of pharmaceutically acceptable acids, either in pure solution or a suitable inert solvent. The pharmaceutically acceptable acids include inorganic acids, and the inorganic acids include but are not limited to: hydrochloric acid, hydrobromic acid, hydroiodic acid, nitric acid, carbonic acid, phosphoric acid, phosphorous acid and sulfuric acid. The pharmaceutically acceptable acids include organic acids, and the organic acids include but are not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acidic citric acid, oleic acid, tannic acid, pantothenic acid, hydrogen tartrate, ascorbic acid, gentisic acid, fumaric acid, gluconic acid, saccharic acid, formic acid, ethanesulfonic acid, pamoic acid (i.e., 4,4'-methylene-bis(3-hydroxy-2-naphthoic acid)) and amino acid (such as glutamic acid and arginine). When compounds of the present disclosure contain relatively acidic functional groups and relatively basic functional groups, such compounds can be converted into base addition salts or acid addition salts. For details, reference can be made to Berge et al., "Pharmaceutical Salts", Journal of Pharmaceutical Science 66: 1-19 (1977), or Handbook of Pharmaceutical Salts: Properties, Selection, and Use (P. Heinrich Stahl and Camille G. Wermuth, ed., Wiley-VCH, 2002).

In the present disclosure, when multiple substituents are present, the substituents are the same or different.

The term "stereoisomer" refers to an isomer in which the atoms or atomic groups in a molecule have the same interconnection order but different spatial arrangements, such as cis-trans isomers, optical isomers or atropisomers. These stereoisomers can be separated, purified and enriched by means of asymmetric synthesis methods or chiral separation methods (including but not limited to thin layer chromatography, rotation chromatography, column chromatography, gas chromatography and high-pressure liquid chromatography) or can also be obtained by means of chiral resolution via forming bonds (chemical bonding, etc.) or forming salts (physical bonding) with other chiral compounds, etc.

The term "tautomer" refers to a functional group isomer resulting from the rapid movement of an atom in two positions in a molecule. For example, acetone and 1-propene-2-ol can be converted into each other by the rapid movement of hydrogen atoms on oxygen and α-carbon.

The term "isotopic compound" refers to a compound in which one or more atoms are substituted with one or more atoms having a specific atomic mass or mass number. Examples of isotopes that can be incorporated into compounds of the present disclosure include, but are not limited to, isotopes of hydrogen, carbon, nitrogen, oxygen, fluorine, sulfur and chlorine (e.g., 2H, 3H, 13C, 14C, 15N, 180, 170, 18F, 35S and 36Cl). The isotopic compounds of the present disclosure can generally be prepared by substituting non-isotopically-labeled reagents with isotopically-labeled reagents according to the methods described herein.

The term "halogen" refers to fluorine, chlorine, bromine or iodine.

The term "alkyl" refers to a linear or branched alkyl group having a specified number of carbon atoms. Examples of alkyl include methyl, ethyl, n-propyl, isopropyl, n-butyl, tert-butyl, isobutyl, sec-butyl, n-pentyl, n-hexyl, n-heptyl, n-octyl, and the like.

The term "alkylene" refers to a linking group between two other species, which may be linear or branched. Examples include, but are not limited to, $—CH_2—$, $—CH_2CH_2—$, $—CH_2CH_2CH_2CH(CH_3)—$ and $—CH_2CH(CH_2CH_3)CH_2—$.

The terms "cycloalkyl" and "carbocyclic ring" refer to a saturated cyclic group consisting only of carbon atoms having a specified number of carbon atoms (e.g., $C_3$-$C_6$), which is a monocyclic, bridged or spiro ring. The cycloalkyl includes, but is not limited to, cyclopropyl, cyclobutyl, cyclopentyl, and cyclohexyl.

The term "aryl" refers to an aromatic group consisting of carbon atoms, each ring having aromaticity. For example, phenyl or naphthyl.

The term "heteroaryl" refers to a cyclic group having a specified number of ring atoms (e.g., 5-12 members), a specified number of heteroatoms (e.g., 1, 2, or 3) and specified heteroatom species (one or more of N, O and S), which is monocyclic or polycyclic, and has at least one aromatic ring (according to the Hückel's rule). Heteroaryls are linked to other fragments of the molecule through aromatic or non-aromatic rings. Heteroaryls include, but are not limited to, furyl, pyrrolyl, thienyl, pyrazolyl, imidazolyl, oxazolyl, thiazolyl, pyridinyl, pyrimidinyl, and indolyl.

The terms "heterocyclyl", "heterocycle" or "heterocycloalkyl" refer to a cyclic group having a specified number of ring atoms (e.g., 3-8 members), a specified number of heteroatoms (e.g., 1, 2, or 3) and specified heteroatom species (one or more of N, O and S), which is monocyclic, bridged, or spiro, and where each ring is saturated. Heterocycloalkyls include, but are not limited to, azetidinyl, tetrahydropyrrolyl, tetrahydrofuryl, morpholinyl, piperidinyl, and the like.

The term "hydroxyl" refers to a —OH group.

The term "cyano" refers to a —CN group.

The term "oxo" refers to a ═O group.

Substituted "$C_{x1}$-$C_{y1}$" groups with specified numbers of carbon atoms (x1 and y1 are integers), for example, "$C_{x1}$-$C_{y1}$" alkyl, "$C_{x1}$-$C_{y1}$" cycloalkyl, "$C_{x1}$-$C_{y1}$" cycloalkenyl, "$C_{x1}$-$C_{y1}$" alkoxyl, "$C_{x1}$-$C_{y1}$" alkenyl, "$C_{x1}$-$C_{y1}$" alkynyl, "$C_{x1}$-$C_{y1}$" aryl, "$C_{x1}$-$C_{y1}$" heteroaryl, or "$C_{x1}$-$C_{y1}$" heterocyclyl, all represent numbers of carbon atoms excluding substituents, e.g., a $C_1$-$C_6$ alkyl represents a $C_1$-$C_6$ alkyl excluding substituents.

The above preferred conditions may be combined arbitrarily to obtain preferred embodiments of the present disclosure without departing from the general knowledge in the art.

The reagents and starting materials used in the present disclosure are commercially available.

The positive/progressive effects of the present disclosure are as follows: the present disclosure provides a compound containing structure of heteroaromatic ring, pharmaceutical compositions thereof and applications thereof, and the compound containing structure of a heteroaromatic ring of formula I is expected to treat and/or prevent various PARG-related diseases.

DETAILED DESCRIPTION OF THE EMBODIMENTS

The present disclosure is further illustrated by the following examples, which are not intended to limit the present disclosure. Experimental procedures without specified conditions in the following examples were performed in accordance with conventional procedures and conditions, or in accordance with instructions.

In the present disclosure, room temperature refers to ambient temperature, or 10-35° C. Overnight refers to 8-15 hours. Reflux refers to the reflux temperature of a solvent at atmospheric pressure.

The solvents involved in the following embodiments are analytically pure or chromatographically pure. When the solvents involved in the following embodiments are mixed solvents, the solvents are in volume ratio unless otherwise indicated.

In the present disclosure, brine is referred as saturated sodium chloride solution.

The following is a list of abbreviations used in the examples:

| | |
|---|---|
| DCM | dichloromethane |
| DMF | N,N-dimethylformamide |
| EA | ethyl acetate |
| DMSO | Dimethyl sulfoxide |
| DMAP | 4-dimethylamino-pyridine |
| DIPEA | diisopropylethylamine |
| TEA | Triethylamine |
| TBSCl | t-Butyldimethylchlorosilane |
| TMS | Trimethylsilyl |
| NCS | N-Chlorosuccinimide |
| LHMDS | Lithium Hexamethyldisilazide |
| Oxone | Potassiumperoxomonosulfate |
| $Pd(dtbpf)Cl_2$ | 1,1'-Bis(di-tert-butylphosphino)ferrocene palladium dichloride |
| $Pd(Amphos)Cl_2$ | Bis(di-tert-butyl(4-dimethylaminophenyl)phosphine)dichloropalladium (II) |

-continued

| | |
|---|---|
| $Mn(TMHD)_3$ | Tris(2,2,6,6-tetramethyl-3,5-heptenoic acid) manganese |
| $Pd_2(dba)_3$ | tris(dibenzylideneacetone)dipalladium |
| m-CPBA | m-chloroperoxybenzoic acid |
| Xantphos | 4,5-Bis(diphenylphosphino)-9,9-dimethylxanthene |
| RuPhos | Dicyclohexyl(2',6'-diisopropoxy-[1,1'-biphenyl]-2-yl)phosphine |
| THF | Tetrahydrofuran |
| THP | 2-Tetrahydropyran |
| TFA | Trifluoroacetic acid |
| Ms | methylsulfonyl |
| Tf | Trifluoromethanesulfonyl |
| DBDMH | 1,3-Dibromo-5,5-Dimethylhydantoin |
| SEMCl | 2-(Trimethylsilyl)ethoxymethyl chloride |
| DHP | 3,4-Dihydro-2H-pyran |
| RuPhos Pd G3 | Methanesulfonato(2-dicyclohexylphosphino-2',6'-di-i-propoxy-1,1'-bipbenyl)(2'-amino-1,1'-biphenyl-2-yl)palladium(II) |
| NMM | 4-Methylmorpholine |
| $[Ir(COD)OMe]_2$ | (1,5-Cyclooctadiene)(methoxy)iridium(I) Dimer |
| Burgess reagent | Metbyl N-(triethylammoniumsulfonyl)carbamate |
| SelectFluor II | 1-Fluoro-4-methyl-1,4-diazabicyclo[2.2.2]octane-1,4-diium tetrafluoroborate |

Synthetic Route of Intermediate I-1

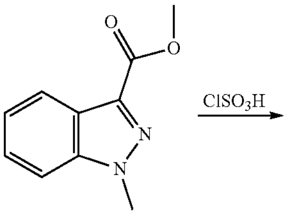

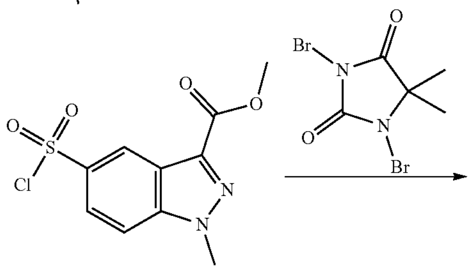

I-1-f

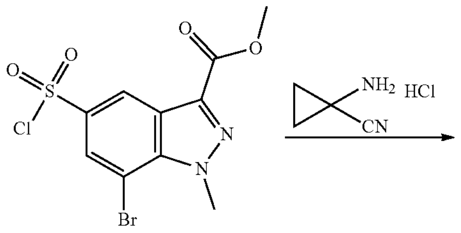

I-1-e

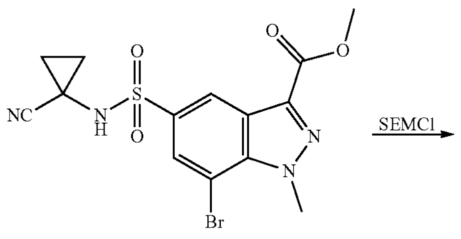

I-1-d

-continued

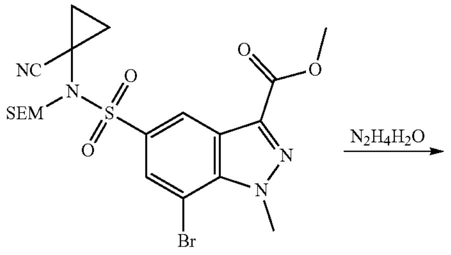

I-1-c

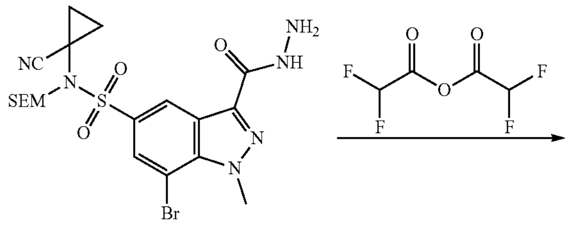

I-1-b

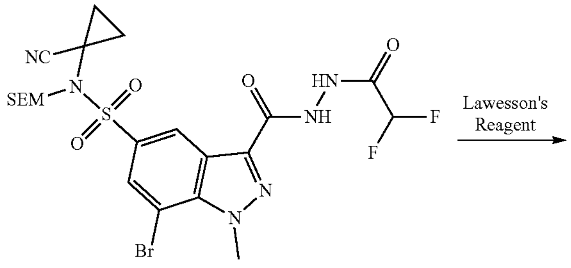

I-1-a

-continued

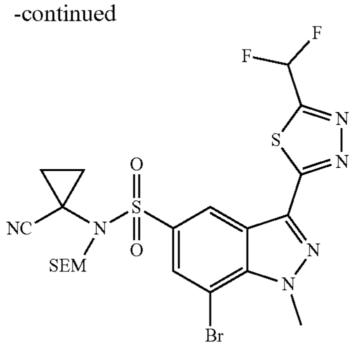

I-1

Synthesis of Compound I-1-f

A reaction flask charged with chlorosulfonic acid (30 mL) in an ice-cold water bath was added 1-methyl-3-methoxy-carbonylindazole (10 g, 52.58 mmol) in batches over a period of 10 min. The reaction was stirred at room temperature for 5 min. The reaction mixture was stirred at 65° C. for 18 h (with exhaust drying and absorption device). The reaction mixture was cooled to room temperature, then was added dropwise to 300 g of ice, extracted with ethyl acetate, washed with water and brine, dried over anhydrous sodium sulfate, filtered and the filtrate was evaporated to give I-1-f (13.5 g, 89%).

Synthesis of Compound J-1-e

A reaction flask charged with I-1-f (13.5 g, 46.76 mmol) and dichloromethane (135 mL) in an ice-cold water bath was added dibromohydantoin (13.37 g, 46.76 mmol). Trifluoromethanesulfonic acid (5 mL) was added dropwise to the above suspension. The reaction mixture was stirred in an ice-cold water bath for 10 minutes and then at room temperature for 1.5 hours. Trifluoromethanesulfonic acid (5 mL) was added dropwise to the suspension. Dichloromethane (60 mL) was added to the suspension. The reaction mixture was stirred at room temperature for 1.5 hours. Ice-cold water was added to the reaction mixture, extracted twice with ethyl acetate, washed twice with water, washed with brine, dried over anhydrous sodium sulfate, filtered, and the filtrate was evaporated to dryness and the residue was purified by column chromatography (mobile phase: petroleum ether/ethyl acetate 100:0 to 60:40) to obtain product I-1-e (10.1 g, 59%).

Synthesis of Compound I-1-d

A reaction flask charged with 1-amino-1-cyclopropanecarbonitrile hydrochloride (7.05 g, 59.46 mmol), pyridine (35 mL) and a small amount of 3A molecular sieve was stirred for 5 minutes in an ice-cold water bath. A solution of I-1-e (10.1 g, 27.48 mmol) in dried dichloromethane (70 mL) containing molecular sieves was added dropwise over 5 minutes in the ice-cold water bath. The resulting mixture was stirred in an ice-cold water bath for 10 minutes and then for 2 hours at room temperature. Removed the solvent by rotary evaporation. Ice-cold water and sodium bisulfate solid were added to adjust pH=6 to 7, followed by adding petroleum ether, filtered, and the filter cake was washed with sodium bisulfate, water, and petroleum ether. The aqueous phase was extracted with ethyl acetate, the extracted was washed with water, evaporated to dryness, slurried with ethyl acetate petroleum ether, the solids were combined and dried at vacuum to give I-1-d (11.3 g, 100%). LC-MS (ESI): m/z 412.9 $(M+H)^+$.

Synthesis of Compound I-1-c

A reaction flask charged with I-1-d (11.3 g, 27.34 mmol) and dichloromethane (150 mL) was added triethylamine (12.5 mL, 89.93 mmol) and stirred for 10 min, then in an ice-cold water bath, was added SEMCl (8.0 mL, 45.20 mmol) dropwise in an ice-cold water bath and stirred for 10 min. The resulting mixture was stirred for 1.5 hours in a room temperature in a water bath. The solvent was removed at room temperature, and the residue was added water and ethyl acetate and filtered after thorough stirring, the filtrate was partitioned, the aqueous phase was extracted once with ethyl acetate, the organic phases were combined, washed with water and brine, and evaporated to dryness to give I-1-c (14.8 g, 100%). LC-MS (ESI): m/z 560.1 $(M+NH_4)^+$.

Synthesis of Compound I-1-b

A reaction flask charged with I-1-c (14.8 g, 27.23 mmol), anhydrous ethanol (150 mL) and hydrazine hydrate (10 mL, 206.15 mmol) was stirred at 52° C. for 7 hours. The reaction mixture was cooled to room temperature, removed the solvent at room temperature, was added ice-cold water, extracted twice with ethyl acetate, washed with water and brine, dried over anhydrous sodium sulfate, filtered and the filtrate was evaporated to dryness to give I-1-b (14.5 g, 98%). LC-MS (ESI): m/z 1084.8 $(2M+H)^+$.

Synthesis of Compound I-1-a

A reaction flask charged with I-1-b (14.5 g, 26.68 mmol) and dichloromethane (150 mL) was added dropwise triethylamine (5.19 mL, 37.35 mmol) in an ice-cold water bath, then stirred for 5 minutes. Difluoroacetic anhydride (3.25 mL, 28.01 mmol) was added dropwise to the above mixture in an ice-cold water bath. The reaction mixture was stirred in an ice-cold water bath for 1 hour. Methanol (2.5 mL) was added and the mixture was stirred for 20 minutes from ice-cold water bath to room temperature. The solvent was removed at room temperature. Water and ethyl acetate were added into a reaction flask, partitioned, the aqueous phase was extracted once, and the organic phases were combined, washed with water and brine, dried over anhydrous sodium sulfate, filtered, and the filtrate was evaporated to dryness. The residue was purified by column chromatography (mobile phases: petroleum ether/ethyl acetate, 100/0 to 60/40) to give I-1-a (13.2 g, 80%). LC-MS (ESI): m/z 638.0 $(M+NH_4)^+$.

Synthesis of Compound I-1

A reaction flask charged with I-1-a (11.3 g, 18.18 mmol), Lawesson's reagent (17.75 g, 43.89 mmol) and THF (200 mL) was stirred at 80° C. directly under argon protection for 10 hours. Cooled to room temperature, it was removed solvent. The crude product was diluted with ethyl acetate/petroleum ether mixture, washed with aqueous sodium bicarbonate for three times, washed with brine, dried over anhydrous sodium sulfate, filtered and the filtrate was evaporated to obtain the crude product, which was added ammonia-methanol/methanol/dichloromethane (1:1:20) solution (200 mL) and stirred at room temperature for 2 hours. Evaporated to dryness and the residue was purified by column chromatography (mobile phase: petroleum ether/ethyl acetate, 100/0 to 70/30) to obtain I-1 (5.8 g, 51%). LC-MS (ESI): m/z 619.0 $(M+H)^+$.

Synthetic Route of Intermediate I-2

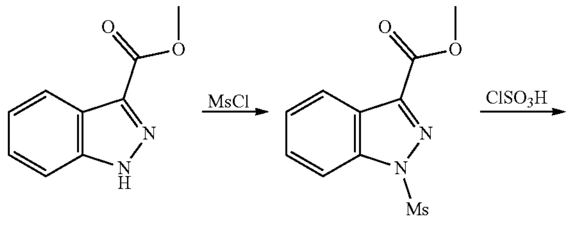

I-2-g

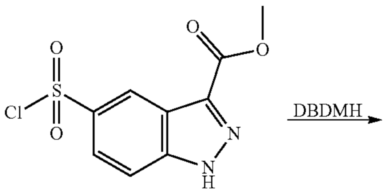

I-2-f

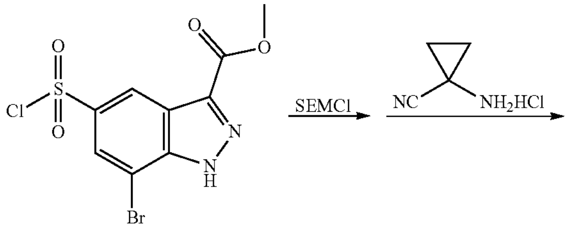

I-2-e

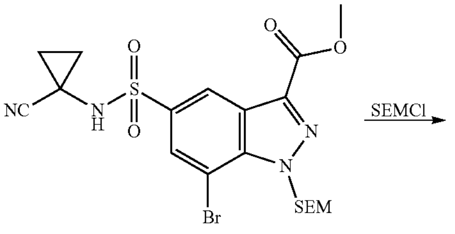

I-2-d

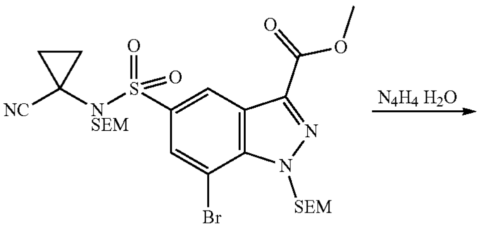

I-2-c

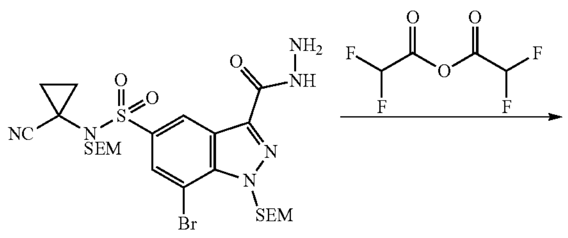

I-2-b

-continued

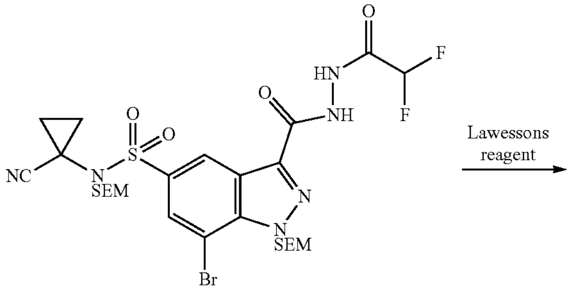

I-2-a

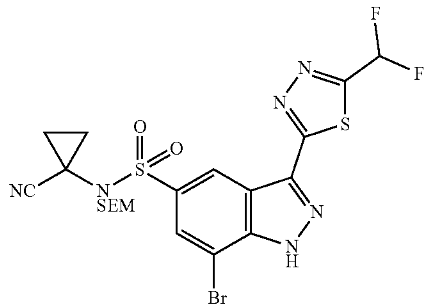

I-2

Synthesis of Compound I-2-g

Triethylamine (14.67 mL, 105.57 mmol) was added dropwise to a reaction flask charged with 3-methoxycarbonylindazole (12.4 g, 70.38 mmol) and dichloromethane (120 mL) in an ice-cold water bath and the mixture was stirred for 5 min. Then the mixture was added methanesulfonyl chloride (6.81 mL, 87.98 mmol) dropwise in an ice-cold water bath. After the dropwise addition, the reaction mixture was stirred in an ice-cold water bath for 1 hour. The organic phase was evaporated to dryness, and the residue was added water and petroleum ether, filtered, and the solid filter cake was washed with water, petroleum ether, dried by an oil pump, and then lyophilized to give I-2-g (16.4 g, 92%). LC-MS (ESI): m/z 254.9 $(M+H)^+$.

Synthesis of Compound I-2-f

I-2-g (16.4 g, 64.50 mmol) was added into a reaction flask charged with chlorosulfonic acid (33 mL) in an ice-cold water bath. The reaction mixture was stirred in an ice-cold water bath for 5 minutes and then at 65° C. for 5 hours. The reaction mixture was cooled to room temperature and added dropwise to 400 g of ice. The resulting mixture was extracted with ethyl acetate, the organic phase was washed with water, brine, dried over anhydrous sodium sulfate, filtered, and the filtrate was evaporated to give I-2-f (14.8 g, 84%).

Synthesis of Compound I-2-e

TMSOTf (18 mL, 117.67 mmol) was added dropwise to a reaction flask charged with I-2-f (14.8 g, 54.88 mmol) and dichloromethane (120 mL) in an ice-cold water bath. The mixture was stirred for 5 min, then was added dibromohydantoin (15.41 g, 53.88 mmol) and trifluoromethanesulfonic acid (7.5 mL, 84.76 mmol) in an ice-cold water bath. The reaction mixture was stirred at room temperature for 2 hours, then was added dichloromethane (150 mL) and trifluoromethanesulfonic acid (7.5 mL, 84.76 mmol) dropwise. The reaction mixture was stirred at room temperature for 5 hours, then was added ice-cold water, extracted twice with ethyl acetate, the organic phase was washed twice with water, washed with brine, dried over anhydrous sodium sulfate, filtered, and the filtrate was evaporated, and dried by an oil pump to give I-2-e (19.05 g, 98%).

Synthesis of Compound I-2-d

I-2-e (18.2 g, 51.47 mmol) and dichloromethane (200 mL) were added into a reaction flask. After stirred in an ice-cold water bath for 5 min, the above mixture was added SEMCl (9.11 mL, 51.48 mmol). After stirred in an ice-cold water bath for 5 minutes, the mixture was added triethylamine (7.16 mL, 51.48 mmol) dropwise over 15 minutes. The reaction mixture was stirred in an ice-cold water bath for 30 min to give a reaction mixture A. A second reaction vial charged with 1-amino-1-cyclopropanecarbonitrile hydrochloride (8.54 g, 72.07 mmol), pyridine (32 mL) and dichloromethane (60 mL) was stirred in an ice-cold water bath for 5 min, then was added the reaction mixture A by a double needle over 5 min in an ice-cold water bath. The resulting reaction mixture was stirred for 1 h in an ice-cold water bath, was added aqueous sodium bisulfate solution (10%) in an ice-cold water bath, partitioned, the aqueous phase was extracted with dichloromethane once, the organic phases were combined, washed with aqueous sodium bisulfate solution (5%), brine, dried over anhydrous sodium sulfate, filtered, and the filtrate was evaporated to give I-2-d (26 g, 95%). LC-MS (ESI): m/z 529.1 $(M+H)^+$.

Synthesis of Compound I-2-c

Triethylamine (13.0 mL, 93.53 mmol) was added into a reaction flask charged with I-2-d (24.8 g, 46.84 mmol) and dichloromethane (200 mL) in an ice-cold water bath, and the mixture was stirred for 5 min, then in an ice-cold water bath, the mixture was added SEMCl (9.6 mL, 54.24 mmol) dropwise. The mixture was stirred in an ice-cold water bath for 2 hours, then was added methanol (3 mL) and stirred in an ice-cold water bath for 5 min. The solvent was removed by concentration at reduced pressure at room temperature, the residue was diluted with ethyl acetate and petroleum ether, the organic phase was washed with 5% sodium bisulfate solution, washed with water and brine, dried over anhydrous sodium sulfate, filtered, and the filtrate was evaporated to dryness, and dried by an oil pump to give I-2-c (30 g, 97%). LC-MS (ESI): m/z 659.1 $(M+H)^+$.

Synthesis of Compound I-2-b

Hydrazine hydrate (13.5 mL, 278.31 mmol) was added into a reaction flask charged with I-2-c (30 g, 45.47 mmol) and anhydrous ethanol (180 mL) in a water bath at room temperature and the reaction mixture was stirred at 55° C. for 2 hours. Additional hydrazine hydrate (5.0 mL, 103.08 mmol) was added and the reaction mixture was stirred at 55° C. for 2 hours. The reaction mixture was cooled to room temperature, removed the solvent by concentration at reduced pressure at room temperature, and the residue was added water, extracted with ethyl acetate twice. The organic phases were washed with water once, washed with brine, dried over anhydrous sodium sulfate, filtered, and the filtrate was evaporated to dryness to obtain I-2-b (26 g, 87%). LC-MS (ESI): m/z 659.2 $(M+H)^+$.

Synthesis of Compound I-2-a

Triethylamine (8.0 mL, 57.56 mmol) was added into a reaction vial charged with I-2-b (26.0 g, 39.41 mmol) and dichloromethane (260 mL) in an ice-cold water bath. The reaction mixture was stirred in an ice-cold water bath for 5 min and then was added difluoroacetic anhydride (6.7 g, 38.50 mmol) dropwise over 15 min. The reaction mixture was stirred in an ice-cold water bath for 1 hour, was added a small amount of methanol and stirred in an ice-cold water bath for 5 minutes, then was added aqueous sodium bisulfate solution (5%), partitioned, and the aqueous phase was extracted with dichloromethane three times, the organic phases were combined, dried over anhydrous sodium sulfate, filtered, and the filtrate was evaporated to dryness, and the residue was purified by column chromatography (mobile phase: dichloromethane/methanol, 100/0 to 96.7/3.3) to obtain compound I-2-a (19.0 g, 65%). LC-MS (ESI): m/z 754.2 $(M+NH_4)^+$.

Synthesis of Compound I-2

A reaction flask charged with I-2-a (19 g, 25.75 mmol), anhydrous THF (190 mL) and Lawesson's reagent (35 g, 86.54 mmol) was stirred at 70° C. for 12 hours and at 75° C. for 4 hours. The reaction mixture was cooled to room temperature and was added ammonia in an ice-cold water bath and stirred for 5 minutes. The solvent was removed by concentration at reduced pressure, the residue was diluted with ethyl acetate and petroleum ether, the organic phase was washed with water, washed with ammonia (2%), the aqueous phase was back-extracted with ethyl acetate and petroleum ether (3:2) for 2 times, the combined organic phases were washed with brine, dried over anhydrous sodium sulfate, filtered, and the filtrate was evaporated to dryness. The residue purified by column chromatography (mobile phase: (petroleum ether/dichloromethane 5:1)/ethyl acetate, 100/0 to 75/25) to afford compound I-2 (6.3 g, 40%). LC-MS (ESI): m/z 605.0 $(M+H)^+$.

Synthetic Route of Intermediate I-3

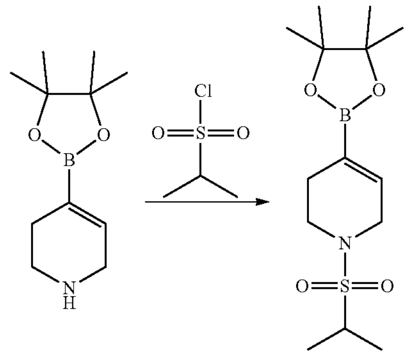

I-3

Synthesis of Compound I-3

Compound 1,2,3,6-tetrahydropyridine-4-boronic acid pinacol ester (200 mg, 0.96 mmol) was dissolved in dichloromethane (20 mL), to which was added triethylamine (194 mg, 1.92 mmol), and isopropylsulfonyl chloride (164 mg, 1.15 mmol) dropwise in an ice-cold water bath, and the reaction mixture was stirred at room temperature for 2 hours. The reaction mixture was added water (100 mL), extracted with dichloromethane (100 mL), the organic phase was washed with brine (100 mL), dried over sodium sulfate, filtered off the desiccant, and the filtrate was concentrated at reduced pressure to obtain the crude product, the crude product was purified by column chromatography (mobile phase, PE/EA 1/1) to obtain Compound I-3 (120 mg, 40%). LC-MS (ESI): m/z 316.2 $(M+H)^+$.

Synthetic Route of Compound I-4

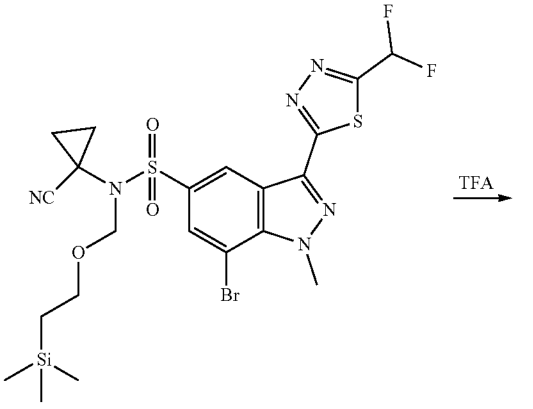

I-1

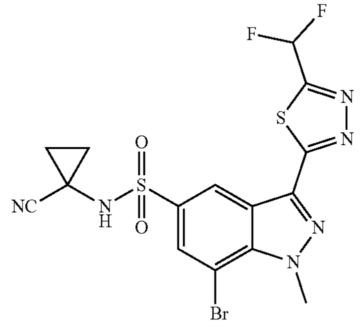

I-4

Synthesis of Compound I-4

A reaction flask charged with I-1 (80 mg, 0.13 mmol) and dichloromethane (5 mL) was added trifluoroacetic acid (1 mL) dropwise at room temperature. After the addition, the reaction mixture was stirred at room temperature for 4 hours. The reaction mixture was concentrated at room temperature to remove the solvent, and the residue was diluted with dichloromethane, washed with saturated sodium bicarbonate, washed with brine, dried over anhydrous sodium sulfate, filtered, and the filtrate was evaporated to dryness to obtain the crude product, which was purified by a flash column chromatography (mobile phase: ethyl acetate/(petroleum ether/dichloromethane 4:1), 0% to 100%) to obtain compound I-4 (50 mg, 79%). LC-MS (ESI): m/z 488.9 $[M+H]^+$.

Synthetic Route of Intermediate 1-5

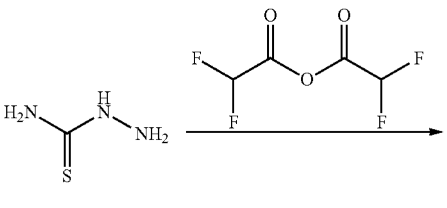

-continued

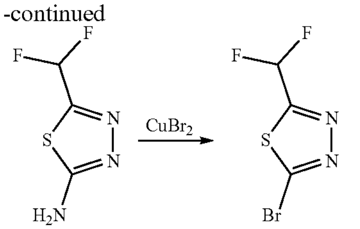

I-5-a I-5

Synthesis of Compound I-5-a

Thiosemicarbazone (3 g, 32.9 mmol) was added to difluoroacetic anhydride (8.6 g, 49.4 mol) in 4 batches in an ice-cold water bath. After the addition, the ice bath was removed, and the reaction mixture was stirred at 85° C. for 36 h. The reaction mixture was cooled to room temperature, after adjusted the pH to 7 to 8 with saturated sodium bicarbonate solution in an ice-cold water bath, some solid precipitated, filtered, and the solid was washed with water (5 mL), was added acetonitrile (10 mL), and the filtrate was concentrated to dryness by rotary evaporation at reduced pressure to obtain the product. The filtrate was extracted with DCM:MeOH=10:1 (100 mL) for 8 times, the organic phase was dried over sodium sulfate, filtered and the filtrate was concentrated at reduced pressure to obtain the crude product, which was purified by column chromatography ($SiO_2$, DCM:MeOH=10:1) to obtain the product. A total of compound I-5-a (1.6 g, 32%) was obtained. LC-MS (ESI): m/z 152.1 $(M+H)^+$; $^1$HNMR (400 MHz, DMSO-$d_6$): δ 7.77 (s, 2H), 7.24 (t, J=56.0 Hz, 1H).

Synthesis of Compound I-5

Compound I-5-a (400 mg, 2.65 mmol) was dissolved in anhydrous acetonitrile (20 mL), to which was added copper bromide (620.1 mg, 2.78 mmol). The mixture was added isoamyl nitrite (1.183 g, 5.3 mmol) dissolved in 1 mL of acetonitrile dropwise to after cooled down to 0° C. After addition, the reaction mixture was stirred at room temperature for 20 min and at 63° C. for 12 h. The reaction mixture was cooled to room temperature, filtered through celite, and the filtrate was concentrated by rotary evaporation at reduced pressure to obtain a concentrate, which was purified by column chromatography ($SiO_2$, petroleum ether:ethyl acetate=10:1) to give compound I-5 (370 mg, 65%). $^1$HNMR (400 MHz, DMSO-$d_6$): δ 7.59 (t, J=52.0 Hz, 1H).

Synthetic Route of Compound 1

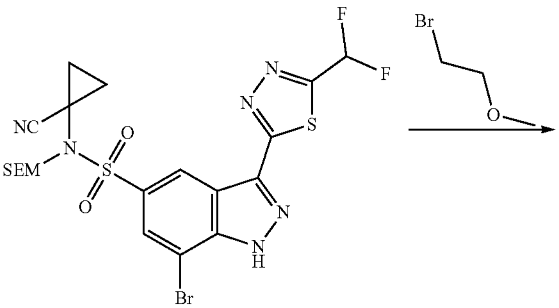

I-2

-continued

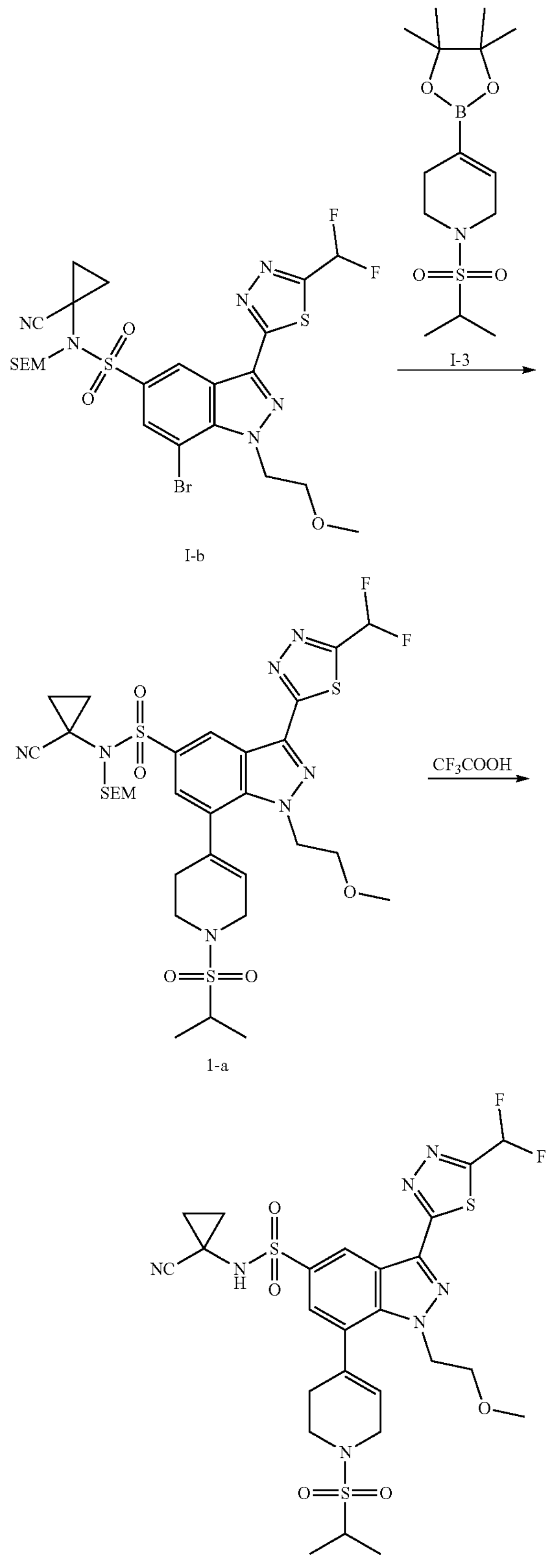

I-b 1-a

1

Synthesis of Compound 1-b

Cesium carbonate (162 mg, 0.50 mmol) and 2-bromoethyl methyl ether (69 mg, 0.50 mmol) were added to a mixture of compound I-2 (150 mg, 0.25 mmol) in N,N-dimethylformamide (6 mL), and the reaction mixture was stirred at 70° C. for 17 hours. Additional 2-Bromoethyl methyl ether (69 mg, 0.50 mmol) was added and continued stirring at 70° C. for 13 h. After cooled to room temperature, the reaction mixture was added water (500 mL) and extracted with ethyl acetate (200 mL). The organic phase was separated, washed twice with water (500 mL), washed with brine (50 mL), dried over anhydrous sodium sulfate, filtered off the desiccant, and the filtrate was concentrated at reduced pressure to obtain the crude product, which was purified by column chromatography (mobile phase, PE/EA 10/1) to obtain compound 1-b (80 mg, 48%).

Synthesis of Compound 1-a

Compound 1-b (70 mg, 0.11 mmol), I-3 (67 mg, 0.21 mmol), [1,1'-bis(diphenylphosphino)ferrocene]palladium dichloride (15 mg, 0.020 mmol) and potassium carbonate (44 mg, 0.32 mmol) were added to 1,4-dioxane (10 mL) and water (1 mL), the reaction mixture was degassed and purged with nitrogen for 3 times and then stirred at 100° C. for 3 h. The reaction mixture was filtered through celite, and the filtrate was added water (100 mL) and extracted with ethyl acetate (100 mL). The organic phase was washed with brine (100 mL), dried over anhydrous sodium sulfate, filtered, and the filtrate was concentrated at reduced pressure to obtain the crude product, which was purified by column chromatography (mobile phase, PE/EA 1/1) to obtain Compound 1-a (50 mg, 62%). LC-MS (ESI): m/z 772.2 $(M+H)^+$.

Synthesis of Compound 1

Compound 1-a (50 mg, 0.065 mmol) was dissolved in dichloromethane (6 mL), to which trifluoroacetic acid (2 mL) was added in an ice-cold water bath, and the reaction mixture was stirred at room temperature for 2 hours. The dichloromethane was removed by concentration at reduced pressure and the residue was adjusted to pH 7 to 8 with saturated sodium bicarbonate solution and extracted with ethyl acetate (50 mL). The organic phase was washed with brine (50 mL), dried over sodium sulfate, filtered off the desiccant, and the filtrate was concentrated at reduced pressure to obtain the crude product, which was purified by Prep-HPLC (basic conditions) to give Compound 1 (21 mg, 50%). LC-MS (ESI): m/z 642.1 $(M+H)^+$.

Synthetic Route of Compound 2

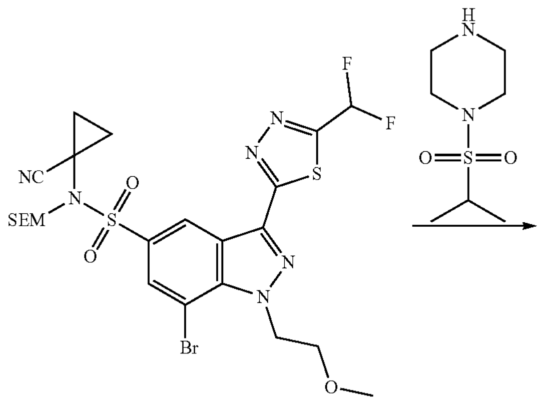

I-b

-continued

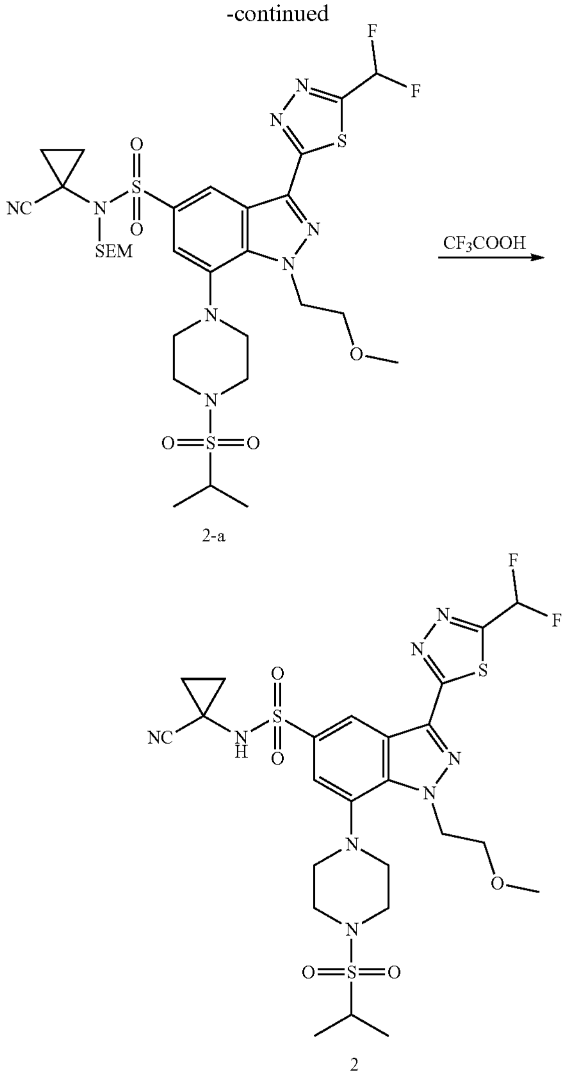

2-a

2

Synthesis of Compound 2-a

In a microwave tube, compound 1-b (75 mg, 0.11 mmol), 1-(isopropylsulfonyl)piperazine (43 mg, 0.22 mmol), [1,3-bis[2,6-bis(1-ethylpropyl)phenyl]-4,5-dichloro-1,3-dihydro-2H-imidazolylidene]dichloro(2-methylpyridine)palladium (10 mg, 0.012 mmol), 2-dicyclohexylphosphino-2',6'-diisopropoxy-1,1'-biphenyl (5 mg, 0.011 mmol) and cesium carbonate (74 mg, 0.23 mmol) were added into 1,4-dioxane (4 mL) and the resulting mixture was purged with nitrogen for 3 min, then sealed and heated at 80° C. with stirring for 14 hours. The reaction mixture was cooled to room temperature, filtered through celite, and the filtrate was concentrated at reduced pressure to obtain the crude product, which was purified by column chromatography (mobile phase, PE/BA 1/1) to give compound 2-a (40 mg, 45%). LC-MS (ESI): m/z 775.2 $(M+H)^+$.

Synthesis of Compound 2

Trifluoroacetic acid (1 mL) was added to a mixture of compound 2-a (40 mg, 0.052 mmol) in dichioromethane (3 mL) in an ice-cold waterbath, and the reaction mixture was stirred at room temperature for 2 h. The dichloromethane was removed by concentration at reduced pressure and the residue was adjusted to pH 7 to 8 with saturated sodium bicarbonate solution and extracted with ethyl acetate (50 mL). The organic phase was washed with brine (50 mL), dried over sodium sulfate, filtered off the desiccant, and the filtrate was concentrated at reduced pressure to obtain the crude product, which was purified by Prep-HPLC (basic conditions) to give Compound 2 (14 mg, 42%). LC-MS (ESI): m/z 645.1 (M+H)

Synthetic Route of Compound 3

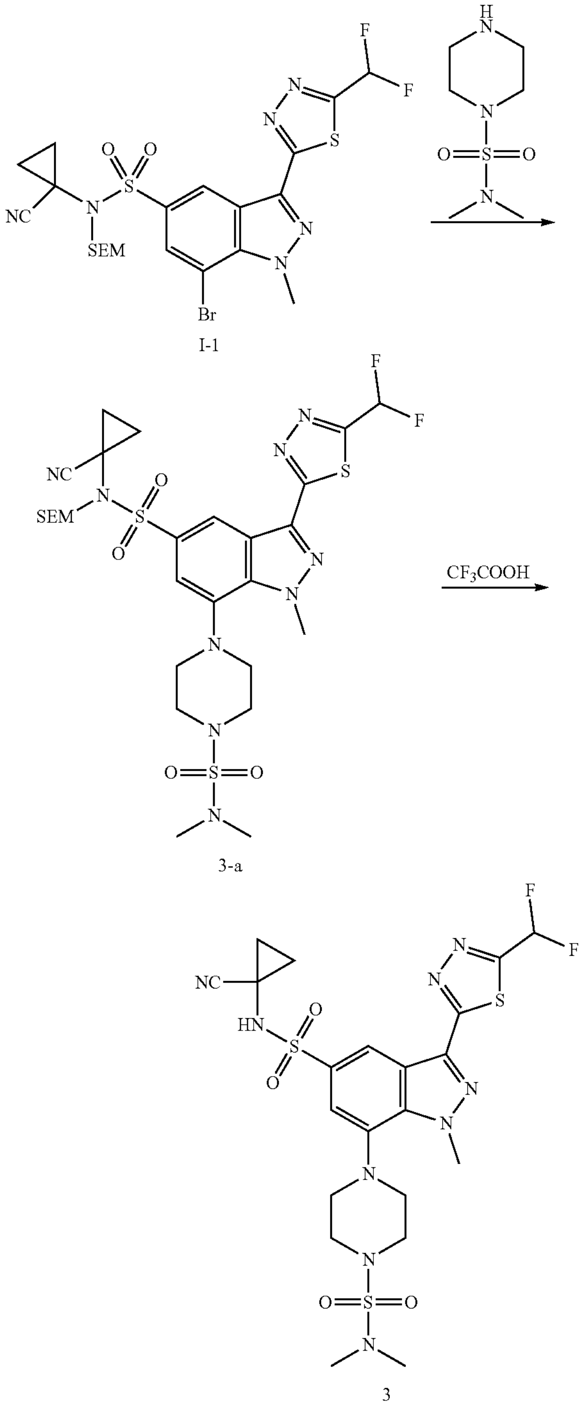

I-1

3-a

3

Synthesis of Compound 3-a

In a microwave tube, compound I-1 (100 mg, 0.16 mmol), N,N-dimethyl-1-piperazine sulfonamide (47 mg, 0.24 mmol), [1,3-bis[2,6-bis(1-ethylpropyl)phenyl]-4,5-dichloro-1,3-dihydro-2H-imidazol-2-ylidene]dichloro(2-methylpyridine)palladium (14 mg. 0.017 mmol), 2-dicyclohexylphosphino-2',6'-diisopropoxy-1,1'-biphenyl (8 mg, 0.017 mmol) and cesium carbonate (105 mg, 0.32 mmol) were added into 1,4-dioxane (4 mL), and the reaction mixture was sealed after purged with nitrogen for 3 min, then stirred for 14 hr at 80° C. The reaction mixture was cooled to room temperature, filtered through celite, and the filtrate was concentrated at reduced pressure to obtain the crude product, which was purified by column chromatography (mobile phase, PE/EA 1/1) to give compound 3-a (62 mg, 53%).

Synthesis of Compound 3

Trifluoroacetic acid (1 mL) was added to a solution of compound 3-a (60 mg, 0.082 mmol) in dichloromethane (3 mL) in an ice-cold water bath, and the reaction mixture was stirred at room temperature for 1.5 h. The dichloromethane was removed by concentration at reduced pressure and the residue was adjusted to pH 7 to 8 with saturated sodium bicarbonate solution and extracted with ethyl acetate (50 mL). The organic phase was washed with brine (50 mL), dried over sodium sulfate, filtered off the desiccant, and the filtrate was concentrated at reduced pressure to obtain the crude product, which was purified by Prep-HPLC (basic conditions) to give compound 3 (24 mg, 49%). LC-MS (ESI): m/z 602.1 $(M+H)^+$.

Synthetic Route of Compound 4

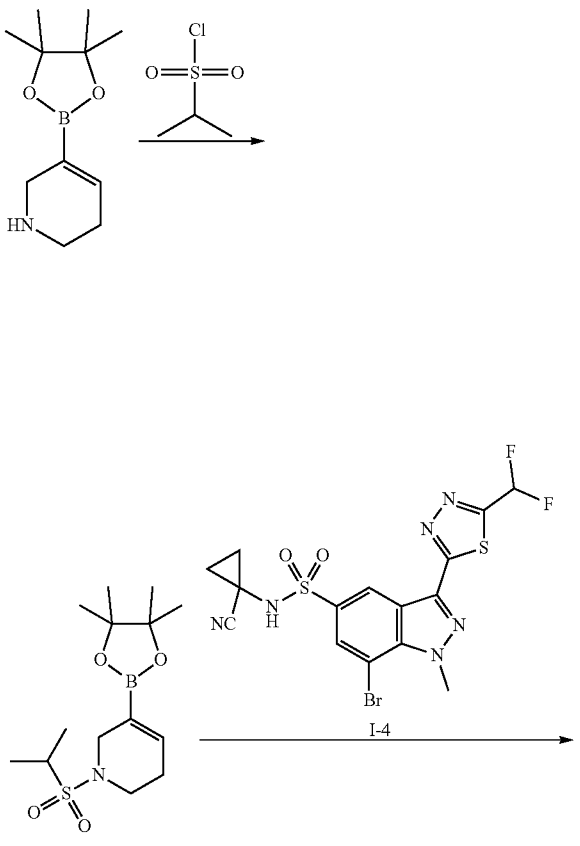

4-a

-continued

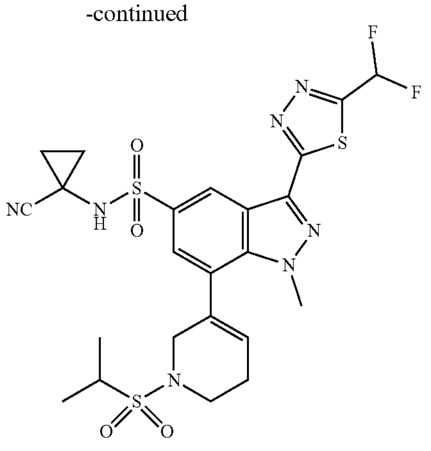

4

Synthesis of Compound 4-a

Compound 5-(4,4,5,5-tetramethyl-1,3,2-dioxaborolan-2-yl)-1,2,3,6-tetrahydropyridine hydrochloride (300 mg, 1.22 mmol) was dissolved in dichloromethane (15 mL), to which triethylamine (124 mg, 1.23 mmol) was added, and the mixture was stirred for 10 min at room temperature, and then was added triethylamine (185 mg, 1.83 mmol). The mixture was added isopropylsulfonyl chloride (209 mg, 1.47 mmol) dropwise in an ice-cold water bath. After addition, the reaction mixture was stirred at room temperature for 1 hour. The reaction mixture was concentrated, was added water (100 mL) and extracted with ethyl acetate (100 mL). The organic phase was washed with brine (100 mL), dried over sodium sulfate, filtered off the desiccant, and the filtrate was concentrated at reduced pressure to obtain the crude product, which was purified by column chromatography (mobile phase, PE/EA 1/1) to obtain compound 4-a (177 mg, 46%). LC-MS (ESI): m/z 315.8 $(M+H)^+$.

Synthesis of Compound 4

Compound I-4 (100 mg, 0.20 mmol), 4-a (97 mg, 0.31 mmol), [1,1'-bis(di-tert-butylphosphino)ferrocene]palladium dichloride (26 mg, 0.040 mmol), and cesium fluoride (93 mg, 0.61 mmol) were added into 1,4-dioxane (9 mL) and water (1 mL), the reaction mixture was degassed and purged with nitrogen 3 times and then stirred at 100° C. for 12 hours. The reaction mixture was cooled to room temperature and filtered through celite. Water (50 mL) was added to the filtrate and extracted with dichloromethane (50 mL). The organic phase was washed with brine (50 mL), dried over sodium sulfate, filtered off the desiccant, and the filtrate was concentrated at reduced pressure to obtain the crude product, which was purified by column chromatography (mobile phase, DCM/EA 3/1), and then purified by Prep-HPLC (basic conditions) to obtain compound 4 (53 mg, 43%). LC-MS (ESI): m/z 598.2 $(M+H)^+$.

Synthetic Route of Compound 5

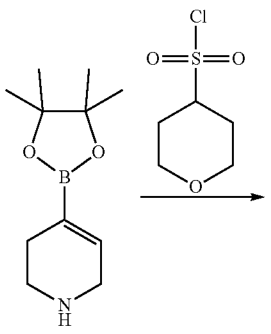

-continued

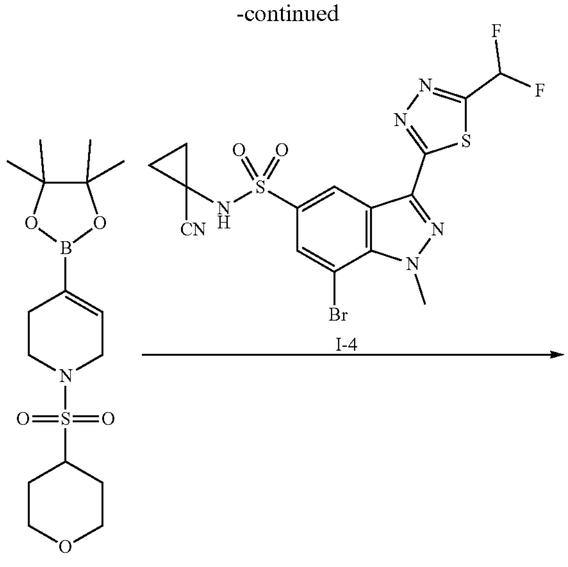

I-4

5-a

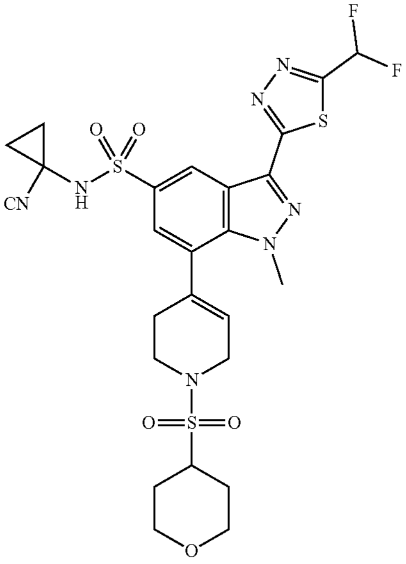

5

Synthesis of Compound 5-a

Compound 1,2,3,6-tetrahydropyridine-4-boronic acid pinacol ester (200 mg, 0.96 mmol) was dissolved in dichloromethane (10 mL), to which triethylamine (194 mg, 1.92 mmol) was added, and tetrahydropyran-4-sulfonyl chloride (184 mg, 1.15 mmol) was added dropwise in an ice-cold water bath. After addition, the reaction mixture was stirred at room temperature for 1 hour. The reaction mixture was concentrated and water (100 mL) was added to the residue and extracted with ethyl acetate (150 mL). The organic phase was washed with brine (100 mL), dried over sodium sulfate, filtered off the desiccant, and the filtrate was concentrated at reduced pressure to obtain the crude product, which was purified by column chromatography (mobile phase, DCM/MeOH 20/1) to obtain compound 5-a (230 mg, 67%). LC-MS (ESI): m/z 358.1 $(M+H)^+$.

Synthesis of Compound 5

Compound I-4 (100 mg, 0.20 mmol), 5-a (109 mg, 0.31 mmol), [1,1'-bis(di-tert-butylphosphino)ferrocene]palladium dichloride (26 mg, 0.040 mmol) and cesium fluoride (93 mg, 0.61 mmol) were added into 1,4-dioxane (9 mL) and water (1 mL). The reaction mixture was degassed and purged with nitrogen for 3 times, then stirred at 100° C. for 12 hours. The reaction mixture was filtered through celite, and the filtrate was added water (50 mL) to and extracted with dichloromethane (50 mL). The organic phase was washed with brine (50 mL), dried over sodium sulfate, filtered off the desiccant, and the filtrate was concentrated at reduced pressure to obtain the crude product, which was purified by column chromatography (mobile phase, DCM/EA 1/1), and then purified by Prep-HPLC (basic conditions) to obtain compound 5 (22 mg, 17%). LC-MS (ESI): m/z 640.2 $(M+H)^+$.

Synthetic Route of Compound 6

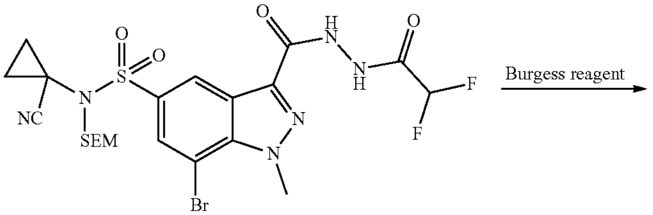

I-1-a

-continued

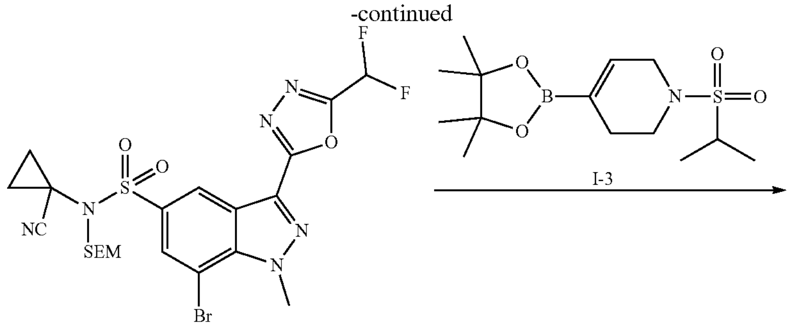

6-b

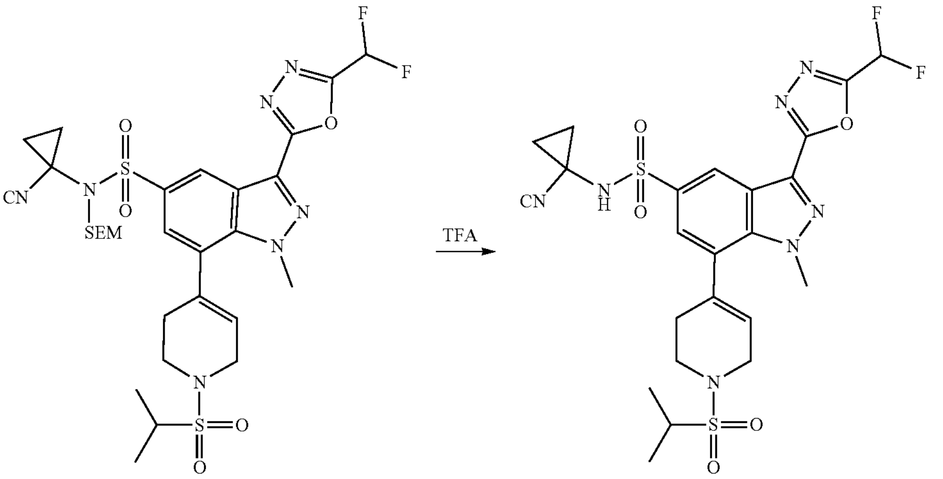

6-a 6

Synthesis of Compound 6-b

To a microwave tube were added I-1-a (600 mg, 0.97 mmol), anhydrous tetrahydrofuran (10 mL) and Burgess reagent (345 mg, 1.45 mmol). After addition, the microwave tube was sealed and heated at 80° C. with stirring overnight. The next day, the reaction mixture was cooled to room temperature, diluted with ethyl acetate, the organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to obtain compound 6-b (150 mg, 26%). LC-MS (ESI): m/z=603.0 $[M+H]^+$.

Synthesis of Compound 6-a

To a reaction vial were added 6-b (120 mg, 0.20 mmol), I-3 (94 mg, 0.30 mmol), [n-butylbis(1-adamantyl)phosphine](2-amino-1,1'-biphenyl-2-yl)palladium(II) (CAS No. 1651823-59-4) (15 mg, 0.020 mmol), potassium phosphate (127 mg. 0.60 mmol), tetrahydrofuran (10 mL) and $H_2O$ (2 mL). After degassed and purged with nitrogen for 3 times, the reaction mixture was stirred at 65° C. for 2 h. Upon completion, the reaction mixture was cooled to room temperature, concentrated at reduced pressure to remove the organic solvent, and the residue was diluted with ethyl acetate, and the organic phase was washed with water, brine, dried over anhydrous sodium sulfate, filtered, and the filtrate was evaporated to dryness to obtain the crude product, which was purified by a flash column chromatography (mobile phase: ethyl acetate/petroleum ether, 0% to 100%) to obtain compound 6-a (100 mg, 71%). LC-MS (ESI): m/z 712.1 $[M+H]^+$.

Synthesis of Compound 6

To a reaction vial were added 6-a (100 mg, 0.14 mmol) and dichloromethane (10 mL). Trifluoroacetic acid (3 mL) was added dropwise to the above mixture at room temperature. After the dropwise addition, the reaction mixture was stirred at room temperature for 4 h. The solvent was removed by concentration at reduced pressure at room temperature. The residue was diluted by adding ethyl acetate, and the organic phase was washed with saturated sodium bicarbonate, brine, dried over anhydrous sodium sulfate, filtered, and the filtrate was evaporated to obtain the crude product, which was purified by Prep-HPLC to give compound 6 (50 mg, 61%). LC-MS (ESI): m/z 582.1 $[M+H]^+$.

Synthetic Route of Compound 7
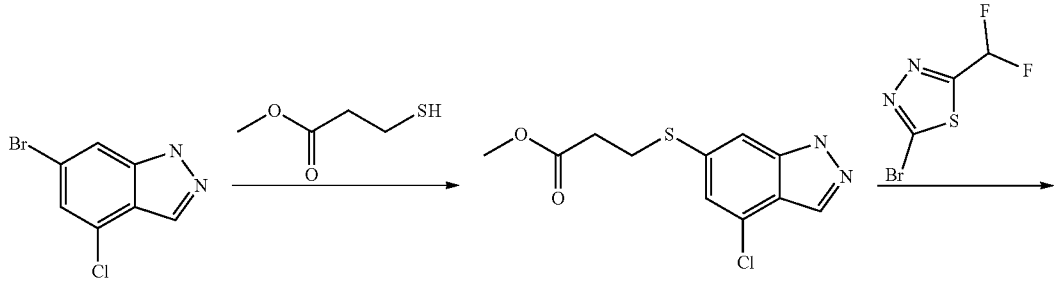
7-d
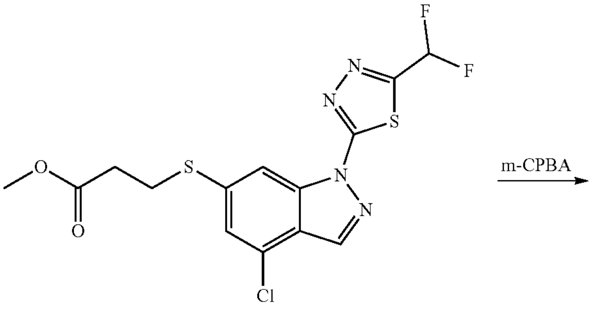
7-c
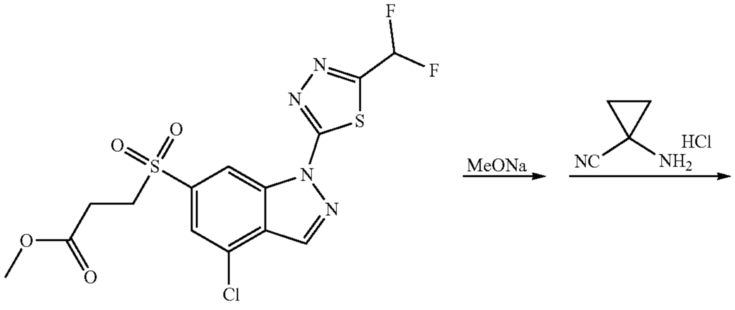
7-b
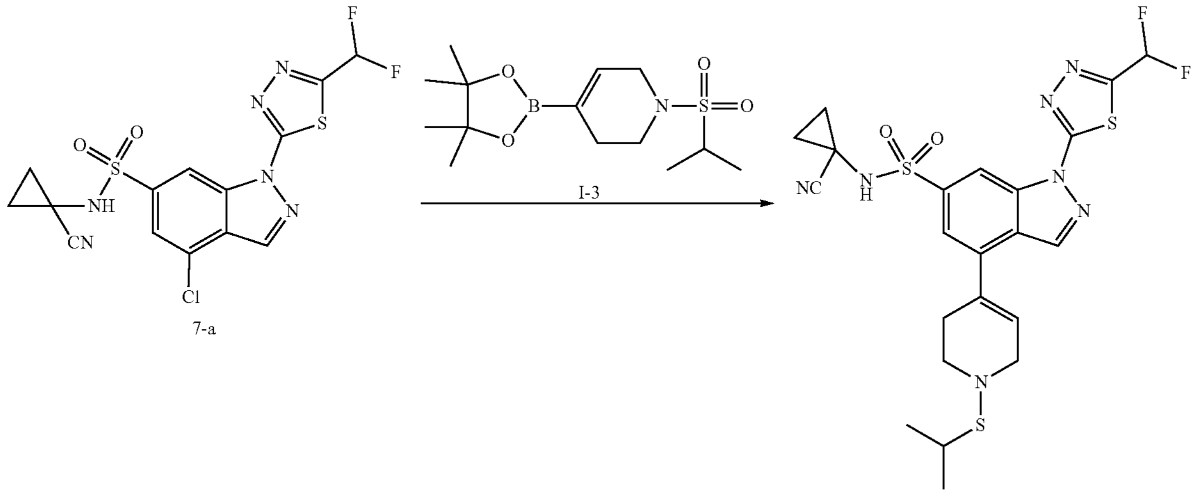
7-a
7
Synthesis of Compound 7-d
To a three-necked vial were added 6-bromo-4-chloro-1H-indazole (2.0 g, 8.64 mmol), Xantphos (500 mg, 0.86 mmol), 1,4-dioxane (50 mL), DIPEA (4.52 mL, 25.92 mmol), and methyl 3-mercaptopropionate (1.05 mL, 9.50 mmol). After degassed and purged with nitrogen for 2 times, the mixture was added $Pd_2(dba)_3$ (396 mg, 0.43 mmol), then degassed and purged with nitrogen for 3 times, and stirred at 90° C. for 2 hours. Upon completion, the reaction mixture was cooled to room temperature, concentrated at reduced pressure, and the crude product was purified by a flash column chromatography (mobile phase: ethyl acetate/petroleum ether, 0% to 100%) to obtain compound 7-d (2.2 g, 94%). LC-MS (ESI): m/z=271.1 [M+H]$^+$.

Synthesis of Compound 7-c

To a solution of 7-d (2.2 g, 8.13 mmol) in DMF (15 mL) was added 2-bromo-5-(difluoromethyl)-1,3,4-thiadiazole (1.92 g, 8.93 mmol) and cesium carbonate (3.18 g, 9.75 mmol) at room temperature. After addition, the reaction was stirred at room temperature overnight. Upon completion, the reaction mixture was quenched by slow addition of water, a white solid precipitated and was filtered. The filter cake was dissolved in ethyl acetate, the organic phase was washed with water, dried over anhydrous sodium sulfate and the filtrate was concentrated by filtration to give compound 7-c (2.4 g, 73%). LC-MS (ESI): m/z=404.9 [M+H]$^+$.

Synthesis of Compound 7-b

To a solution of 7-c (2.4 g, 5.93 mmol) in dichloromethane (100 mL) in an ice-cold water bath was added m-CPBA (3.2 g, 18.53 mmol). After addition, the reaction was kept at 0° C. and stirred for 1 hour. Upon completion, the solvent was removed by rotary evaporation at room temperature, diluted by adding ethyl acetate, washed with saturated sodium bicarbonate, washed with brine, dried over anhydrous sodium sulfate, filtered and the filtrate was evaporated to dryness. The crude product was purified by a flash column chromatography (mobile phase: ethyl acetate/petroleum ether, 0% to 100%) to give compound 7-b (1.6 g, 62%). LC-MS (ESI): m/z=437.0 [M+H]$^+$.

Synthesis of Compound 7-a

A reaction flask charged with 7-b (800 mg, 1.83 mmol), methanol (10 mL) and dichloromethane (10 mL) was cooled to 0° C. in an ice-cold water bath, then was added sodium methanol (297 mg, 5.49 mmol) and the reaction mixture was kept in an ice-cold water bath for 1 hour. The mixture was added 1-Amino-1-cyclopropanecarbonitrile hydrochloride (869 mg, 7.33 mmol) and stirred for 10 min, concentrated at room temperature to remove the solvent and dried at vacuum for 20 min. The residue was added DMF (8 mL) and a small amount of 3A molecular sieve, then stirred for 3 min in an ice-cold waterbath, was added triethylamine (0.51 mL, 3.66 mmol), 1-amino-1-cyclopropanecarbonitrile hydrochloride (217 mg, 1.83 mmol) and NCS (489 mg, 3.66 mmol). The resulting mixture was stirred in an ice-cold water bath for 1 hour, diluted with ethyl acetate, washed with sodium bisulfite solution, water and brine, dried over anhydrous sodium sulfate, filtered and the filtrate was evaporated to dryness. The crude was purified by a flash column chromatography (mobile phase: ethyl acetate/petroleum ether, 0% to 100%) to give 7-a (400 mg, 51%). LC-MS (ESI): m/z=430.9 [M+H]$^+$.

Synthesis of Compound 7

To a reaction flask were added 7-a (50 mg, 0.12 mmol), I-3 (55 mg, 0.17 mmol), tetrakis(triphenylphosphine)palladium (13 mg, 0.012 mmol), potassium acetate (34 mg, 0.35 mmol), 1,4-dioxane (2 mL) and $H_2O$ (2 mL). After degassed and purged with nitrogen for 3 times, the reaction mixture was stirred at 100° C. for 3 h. Upon completion, the reaction mixture was cooled to room temperature, concentrated at reduced pressure to remove the organic solvent, the residue was diluted with ethyl acetate, and the organic phase was washed with water, brine, dried over anhydrous sodium sulfate, filtered, and the filtrate was evaporated to obtain the crude. Compound 7 (18 mg, 27%) was obtained by Prep-HPLC purification. LC-MS (ESI): m/z 584.2 [M+H]$^+$.

Synthetic Route of Compound 8

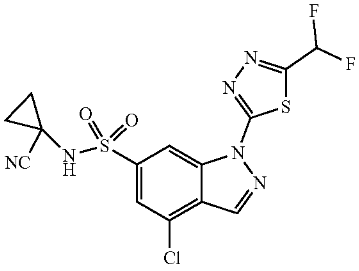

7-a

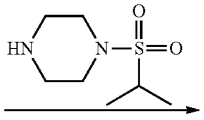

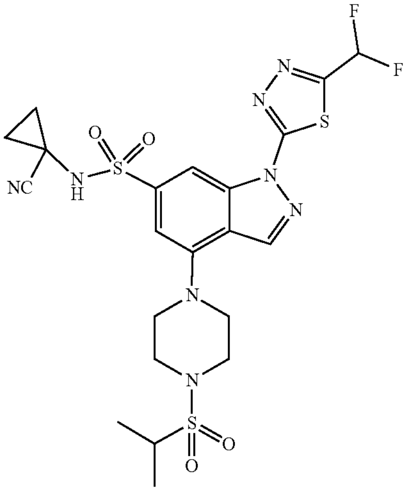

8

Synthesis of Compound 8

To a microwave tube were added 7-a (50 mg, 0.12 mmol), 1-(isopropylsulfonyl)piperazine (34 mg, 0.18 mmol), Ruphos (5 mg, 0.012 mmol), (SP-4-1)-[1,3-bis[2,6-bis(1-ethylpropyl)phenyl]-4,5-dichloro-1,3-dihydro-2H-imidazol-2-ylidene]dichloro(3-chloropyridine-KN)palladium (CAS: 1435347-24-2) (16 mg, 0.019 mmol), cesium carbonate (113 mg, 0.35 mmol) and 1,4-dioxane (3 mL). After degassed and purged with nitrogen for 3 times, the reaction mixture was sealed and heated at 75° C. overnight. Upon completion, it was cooled to room temperature, removed 1,4-dioxane, diluted by adding ethyl acetate, washed with water and brine, dried over anhydrous sodium sulfate, filtered and the filtrate was evaporated to obtain the crude product, which was purified by Prep-HPLC to give Compound 8 (30 mg, 44%). LC-MS (ESI): m/z 587.2 [M+H]$^+$.

Synthetic Route of Compound 9

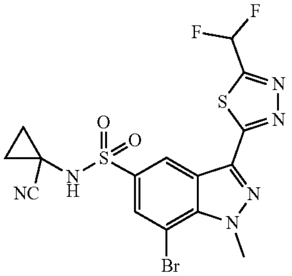

I-4

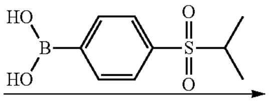

-continued

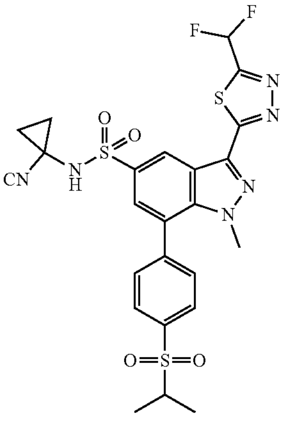

9

Synthesis of Compound 9

To a reaction vial were added I-4 (50 mg, 0.10 mmol), 4-isopropylsulfonylphenylboronic acid (47 mg, 0.20 mmol), [1,1'-bis(di-tert-butylphosphino)ferrocene]palladium dichloride (13 mg, 0.020 mmol), cesium fluoride (47 mg, 0.31 mmol), 1,4-dioxane (9 mL) and $H_2O$ (1 mL). After degassed and purged with nitrogen for 3 times, the reaction mixture was stirred at 100° C. for 5 hours. Upon completion, the reaction mixture was cooled to room temperature, concentrated at reduced pressure to remove the organic solvent, the residue was diluted by adding ethyl acetate, the organic phase was washed with water, brine, dried over anhydrous sodium sulfate, filtered and the filtrate was evaporated to obtain the crude product, which was purified by Prep-HPLC to obtain compound 9 (31 mg, 51%). LC-MS (ESI): m/z 593.1 [M+H]$^+$.

Synthetic Route of Compound 10

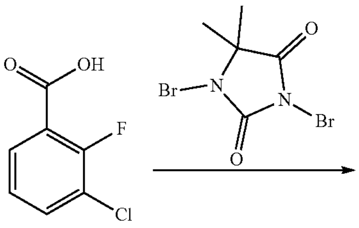

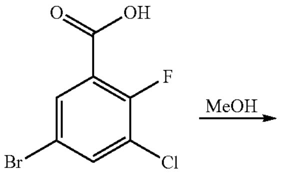

10-l

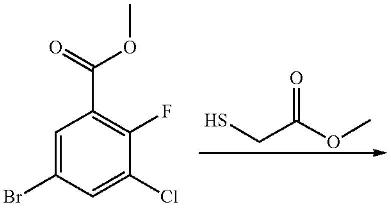

10-k

-continued

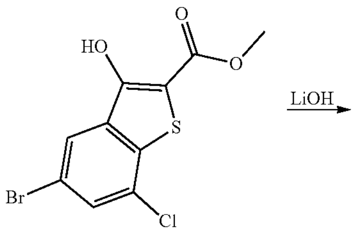

10-j

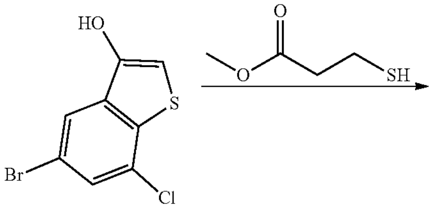

10-i

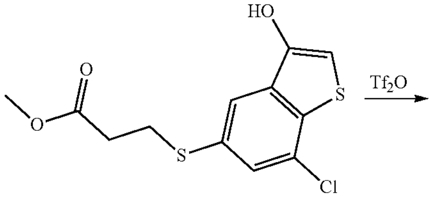

10-h

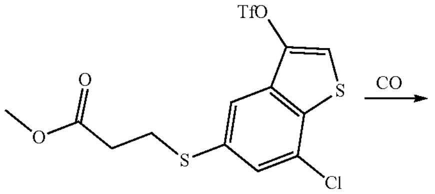

10-g

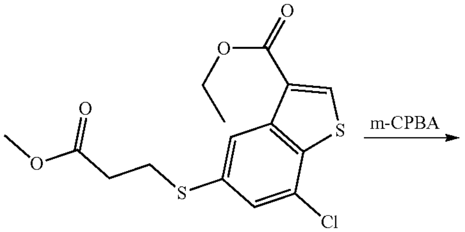

10-f

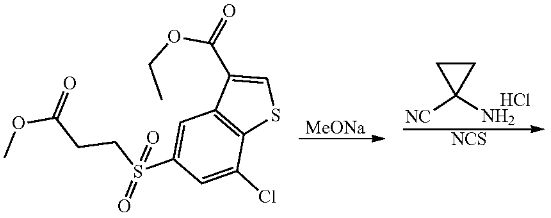

10-e

-continued

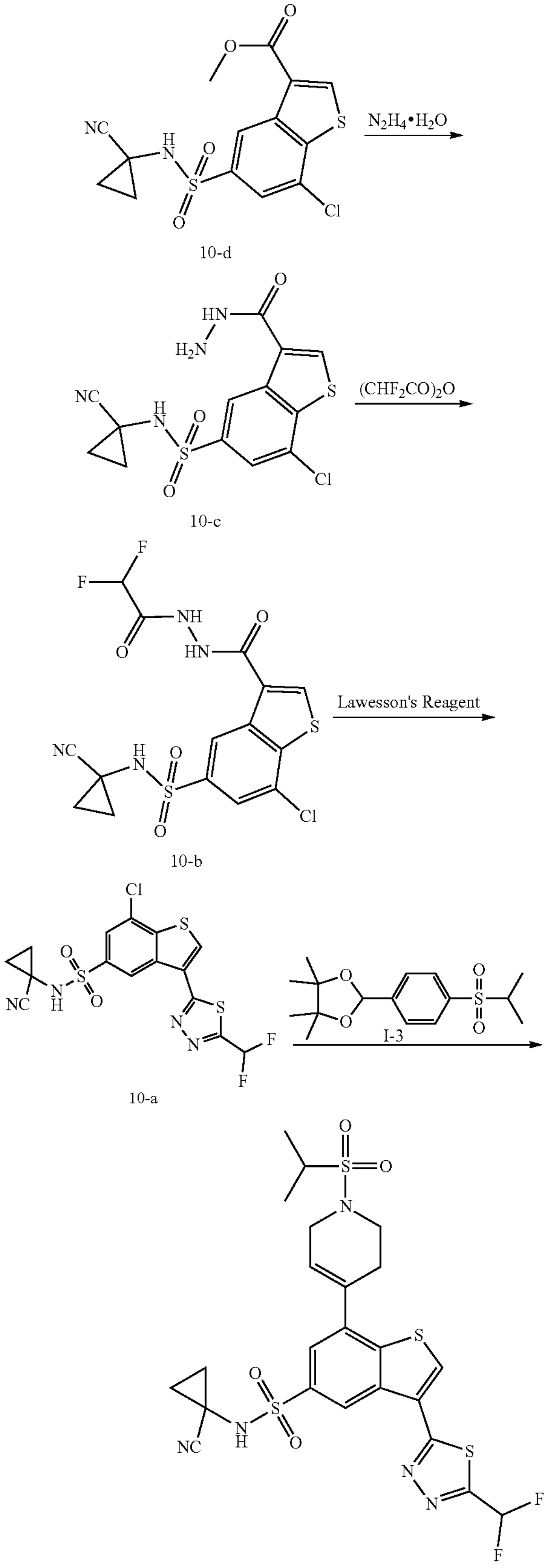

10-d 10-c 10-b 10-a

10

Synthesis of Compound 10-l

A reaction flask charged with 3-chloro-2-fluoro-benzoic acid (6.99 g, 40.04 mmol), dibromohydantoin (9.16 g, 32.04 mmol) and dichloromethane (80 mL) was added trifluoromethanesulfonic acid (5 mL) in an ice-cold water bath. The reaction mixture was stirred for 3 hours from ice-cold water bath to water bath. The reaction mixture was poured into ice-cold water, and was added ethyl acetate (80 mL), partitioned and the aqueous phase was extracted once with dichloromethane. The organic phase was washed twice with water, the organic phases were combined, washed once with aqueous sodium bisulfite, washed once with water, washed with brine, dried over anhydrous sodium sulfate, and filtered and the filtrate was evaporated to obtain 10-l (8.6 g, 85%). LC-MS (ESI): m/z 250.9 $(M-H)^-$.

Synthesis of Compound 10-k

A reaction flask charged with 10-l (8.6 g, 33.93 mmol) and methanol (70 mL) was added dichlorosulfoxide (6.5 mL) dropwise while stirring in an ice-cold water bath. The reaction mixture was stirred at 80° C. for 4 hours. The solvent was removed and the residue was dried by an oil pump for 1 h to give 10-k (9.0 g, 99%).

Synthesis of Compound 10-j

A reaction flask charged with 10-k (9.0 g, 33.65 mmol), anhydrous DMF (45 mL) and methyl mercaptoacetate (3.61 mL, 40.38 mmol) was added Lithium hydroxide (2.82 g, 117.77 mmol) under nitrogen protection in an ice-cod water bath. The reaction mixture was stirred at room temperature for 2 h and then poured into ice-cold water containing acetic acid (9 mL) and stirred for 2 min and filtered. The filter cake was dried at room temperature to give 10-j (10 g, 92%). LC-MS (ESI): m/z 321.0 $(M+H)^+$.

Synthesis of Compound 10-i

A reaction flask charged with 10-j (6 g, 18.66 mmol), DMSO (40 mL) and lithium hydroxide monohydrate (3.15 g, 75.07 mmol) was stirred at 80° C. for 2 hours. Supplemental lithium hydroxide monohydrate (0.95 g, 22.64 mmol) was added. The reaction mixture was stirred at 100° C. for 15 hours. Cooled to room temperature, the reaction mixture was added acetic acid (4.5 mL) dropwise (be careful of gas release), and stirred at room temperature for 1 hour then additional acetic acid (1.5 mL) was added dropwise to and continued stirring at room temperature for 1 hour. The reaction mixture was poured into ice-cold water (gas release), extracted twice with ethyl acetate, washed with brine, dried over anhydrous sodium sulfate, filtered and the filtrate was evaporated to give 10-i (4.0 g, 81%). LC-MS (ESI): m/z 260.8 $(M-H)^-$.

Synthesis of Compound 10-h

A reaction vial charged with 10-i (4.25 g, 16.13 mmol), $Pd_2(dba)_3$ (0.74 g, 0.81 mmol), Xantphos (0.93 g, 1.61 mmol), 1,4-dioxane (60 mL), DIPEA (8.6 mL, 48.57 mmol) and methyl 3-mercaptopropionate (1.89 mL, 16.93 mmol) was degassed and purged with nitrogen for three times, then was stirred at 90° C. for 6 hours. Cooled to room temperature, the reaction mixture was removed the solvent and the crude was purified by column chromatography (mobile phase: petroleum ether/ethyl acetate, 100/0 to 75/25) to give compound 10-h (3.5 g, 72%). LC-MS (ESI): m/z 301.0 $(M-H)^-$.

Synthesis of Compound 10-g

A reaction flask charged with 10-h (3.5 g, 11.56 mmol), dichloromethane (25 mL) and triethylamine (4.82 mL, 34.68 mmol) in an ice-salt bath was added trifluoromethanesulfonic anhydride (4.89 g, 17.34 mmol) dropwise. The reaction mixture was stirred in an ice-salt bath for 1 hour (ice basically melted). Aqueous sodium bicarbonate solution was added and stirred for 5 min, partitioned, concentrated to dryness by rotary evaporation and purified by column chromatography (mobile phase: petroleum ether/ethyl acetate, 100/0 to 90/10) to give compound 10-g (3.2 g, 64%).

Synthesis of Compound 10-f

A reaction flask charged with 10-g (3.0 g, 6.90 mmol), anhydrous DMF (15 mL), anhydrous ethanol (7.5 mL) (molecular sieve dried) and triethylamine (2.8 mL, 20.14 mmol) was added palladium acetate (0.090 g, 0.40 mmol) and 1,3-bis(diphenylphosphino)propane (0.38 g, 0.92 mmol). The reaction mixture was degassed and purged with carbon monoxide for 3 times, then stirred under carbon monoxide protection at 70-78° C. for 3 hours, then, stirred under carbon monoxide protection at 75° C. for 5 hours. The reaction mixture was cooled to room temperature, then removed part of the solvent. The residue was added ice-cold water and was extracted once with a mixture of ethyl acetate and petroleum ether. The organic phase was washed with water, brine, dried over anhydrous sodium sulfate, filtered and the filtrate was evaporated to dryness. The residue was purified by column chromatography (mobile phase: petroleum ether/ethyl acetate, 100/0 to 90/10) to give compound 10-f (1.05 g, 42%). LC-MS (ESI): m/z 359.0 $(M+H)^+$.

Synthesis of Compound 10-e

A reaction flask charged with 10-f (1.05 g, 2.93 mmol) and dichloromethane (20 mL) was added m-CPBA (1.26 g, 7.30 mmol) in an ice-cold water bath. The reaction mixture was stirred for in an ice-cold water bath 1.5 h. It was washed once with saturated sodium bicarbonate, dried over anhydrous sodium sulfate, filtered, and the filtrate was evaporated to dryness. The residue was purified by column chromatography (mobile phase: petroleum ether/ethyl acetate, 100/0 to 78/32) to give compound 10-e (1.1 g, 96%). LC-MS (ESI): m/z 391.1 $(M+H)^+$.

Synthesis of Compound 10-d

Sodium methanol (71 mg, 1.32 mmol) was added into a reaction vial charged with 10-e (166 mg, 0.43 mmol), methanol (10 mL) and dichloromethane (10 mL) in an ice-cold water bath. The reaction mixture was stirred for 1 hour in an ice-cold water bath, then was added 1-Amino-1-cyclopropanecarbonitrile hydrochloride (209 mg, 1.76 mmol) in an ice-cold water bath. The organic solvent was evacuated and dried by an oil pump for 30 minutes at room temperature. The residue was added 1-Amino-1-cyclopropanecarbonitrile hydrochloride (52 mg, 0.44 mmol) and DMF (10 mL), then was added triethylamine (0.12 mL, 0.88 mmol) and NCS (176 mg, 1.32 mmol) in an ice-cold water bath. The reaction mixture was stirred in an ice-cold water bath for 1 hour. The reaction mixture was added into ice-cold water and extracted with ethyl acetate (100 mL*3). The organic phase was washed with water and brine, dried over anhydrous sodium sulfate, concentrated, and purified by column chromatography (petroleum ether/ethyl acetate=3/1, 1/3) to give 10-d (153 mg, 97%).

Synthesis of Compound 10-c

A reaction vial charged with 10-d (153 mg, 0.41 mmol), ethanol (20 mL) and hydrazine hydrate (6 mL, 80.40 mmol) was stirred at 90° C. for 12 hours. The reaction mixture was concentrated to give 10-c (153 mg, 100%). LC-MS (ESI): m/z 370.9 $(M+H)^+$.

Synthesis of Compound 10-b

Difluoroacetic anhydride (84 mg, 0.49 mmol) was added dropwise to a reaction vial charged with 10-c (150 mg, 0.40 mmol), dichloromethane (20 mL) and triethylamine (0.08 mL, 0.61 mmol) in an ice-cold water bath. The reaction mixture was stirred for 1 hour in an ice-cold water bath, then was added methanol (1 mL). The organic solvent was concentrated at room temperature. The residue was purified by column chromatography (mobile phase: dichloromethane/methanol, 100/1 to 10/1) to afford 10-b (59 mg, 33%). LC-MS (ESI): m/z 446.9 $(M-H)^-$.

Synthesis of Compound 10-a

A reaction flask charged with 10-b (56 mg, 0.13 mmol), Lawesson's reagent (126 mg, 0.31 mmol) and 1,4-dioxane (10 mL) was stirred at 75° C. under nitrogen protection. The reaction mixture was concentrated, quenched with saturated sodium bicarbonate (10 mL) and extracted with ethyl acetate (20 mL*3). The organic phase was concentrated and purified by column chromatography (mobile phase: petroleum ether/ethyl acetate, 5/1 to 1/1) to give 10-a (19 mg, 34%). LC-MS (ESI): m/z 446.9 $(M+H)^+$.

Synthesis of Compound 10

To a microwave tube were added 10-a (16 mg, 0.04 mmol), 1,4-dioxane (5 mL), I-3 (16 mg, 0.05 mmol) and water (1 mL), dichlorodi-tert-butyl-(4-dimethylaminophenyl)phosphopalladium(II) (7 mg, 0.01 mmol) followed by potassium phosphate (20 mg, 0.09 mmol). The microwave tube was degassed and purged with nitrogen several times, then sealed and stirred at 110° C. for 11 hours. The reaction mixture was concentrated and purified by Prep-HPLC to give compound 10 (1 mg, 5%). LC-MS (ESI): m/z 600.1 $(M+H)^+$.

Synthetic Route of Compound 11

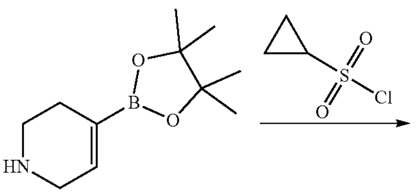

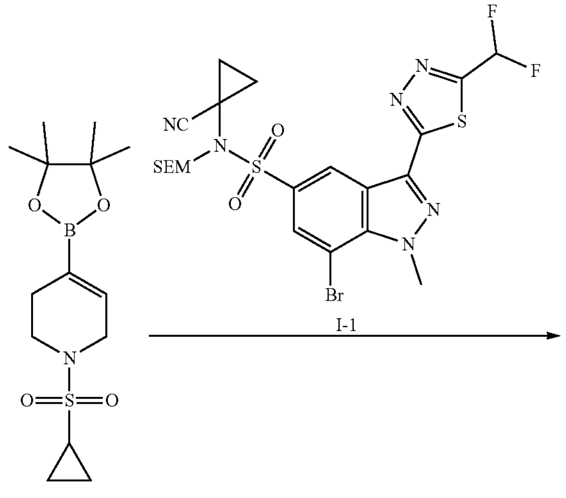

I-1

11-b

-continued

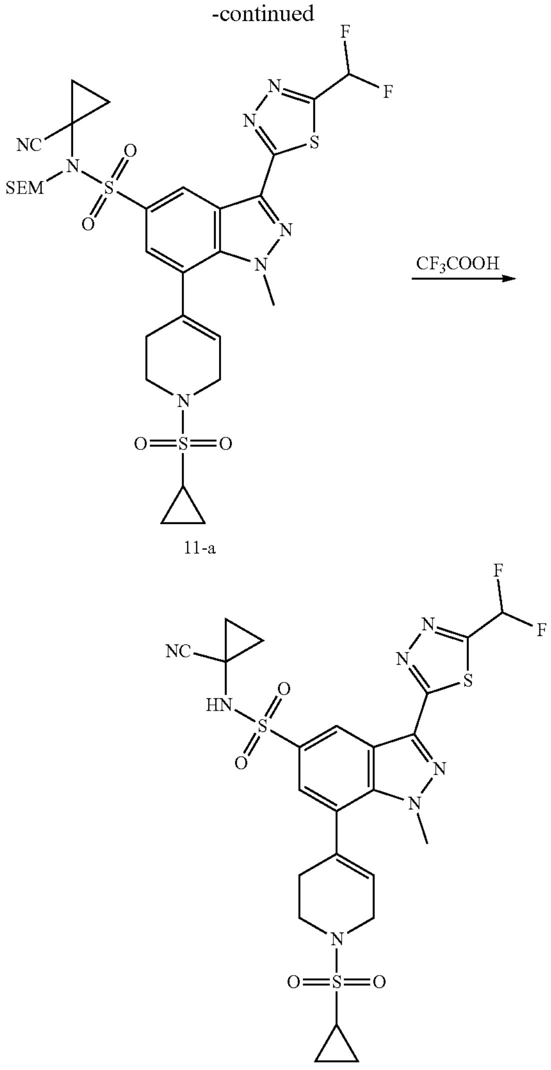

11-a

11

Synthesis of Compound 11-b 1,2,3,6-Tetrahydropyridine-4-boronic acid pinacol ester (220 mg, 1.05 mmol), triethylamine (320 mg, 3.16 mmol), and cyclopropylsulfonyl chloride (260 mg, 1.85 mmol) were added into dichloromethane (20 mL), and the mixture was stirred at room temperature for 3 hours. The reaction mixture was washed with saturated sodium bicarbonate (30 mL). The organic phase was concentrated to give compound 11-b (291 mg, 88%). LC-MS (ESI): m/z 314.0 $(M+H)^+$.

Synthesis of Compound 11-a 11-b (114 mg, 0.36 mmol), I-1 (150 mg, 0.24 mmol), potassium carbonate (100 mg, 0.72 mmol), $PdCl_2$(dppf) $\cdot CH_2Cl_2$ (20 mg, 0.02 mmol) were added into a reaction flask, followed by addition of 1,4-dioxane (30 mL) and water (6 mL). The reaction mixture was stirred at 90° C. under nitrogen protection for 12 hours. The reaction mixture was concentrated at reduced pressure and the residue was purified by column chromatography (PE/EA=3/1, 1/1) to afford compound 11-a (116 mg, 66%). LC-MS (ESI): m/z 726.0 $(M+H)^+$.

Synthesis of Compound 11

11-a (116 mg, 0.16 mmol) was added into a reaction flask, followed by dichloromethane (3 mL) and trifluoroacetic acid (1 mL). The reaction mixture was stirred at room temperature under nitrogen protection for 2 h. The reaction mixture was concentrated at reduced pressure by adding dichloromethane (3 mL) and trifluoroacetic acid (1 mL). The reaction mixture was concentrated at reduced pressure, then was added solid potassium carbonate (3 g) and water (10 mL), ethyl acetate (10 mL) and stirred at room temperature for 2 hours. Extracted with ethyl acetate (10 mL*3) to afford compound 11 (60.3 mg, 63%). LC-MS (ESI): m/z 596.2 $(M+H)^+$.

Synthesis of Compound 12

12

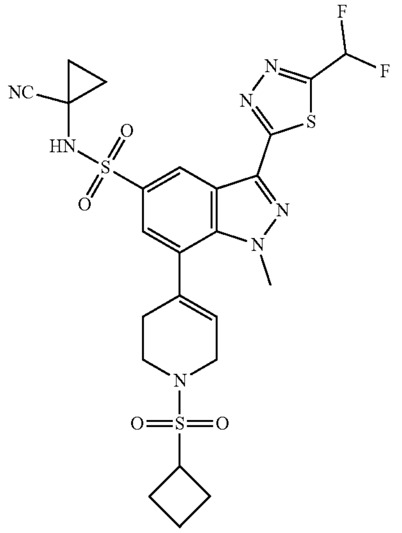

Referring to the synthesis of compound 11, compound 12 was synthesized using cyclobutylsulfonyl chloride instead of cyclopropylsulfonyl chloride. LC-MS (ESI): m/z 610.5 $(M+H)^+$.

Synthesis of Compound 13

13

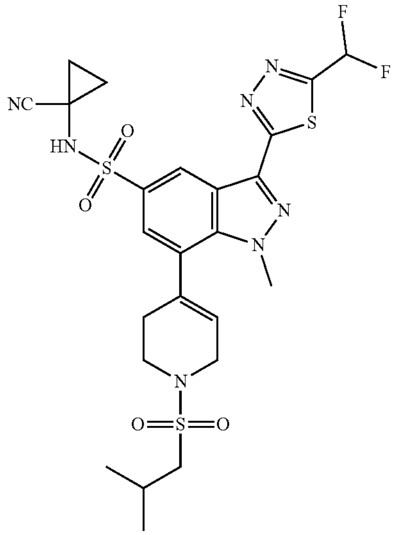

Referring to the synthesis of compound 11, compound 13 was synthesized using 2-methylpropanesulfonyl chloride instead of cyclopropanesulfonyl chloride. LC-MS (ESI): m/z 612.1 $(M+H)^+$.

Synthesis of Compound 14

14

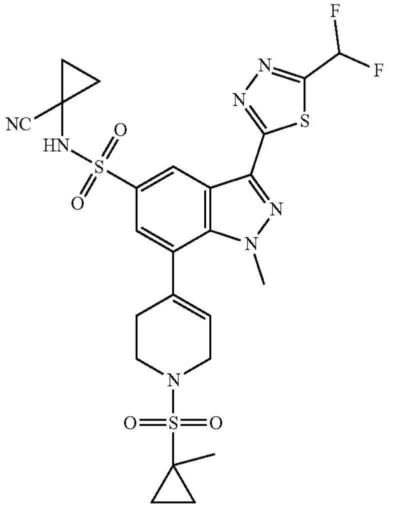

Referring to the synthesis of compound 11, compound 14 was synthesized using 1-methyl-cyclopropanesulfonyl chloride instead of cyclopropanesulfonyl chloride. LC-MS (ESI): m/z 610.5 $(M+H)^+$.

Synthetic Route of Compound 15

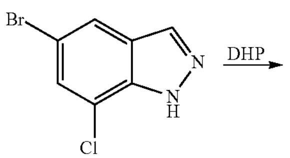

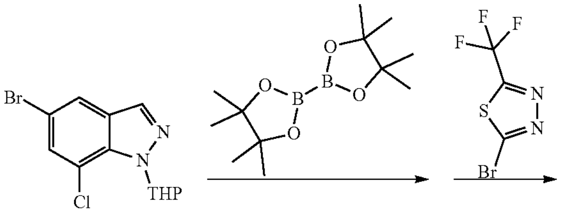

15-g

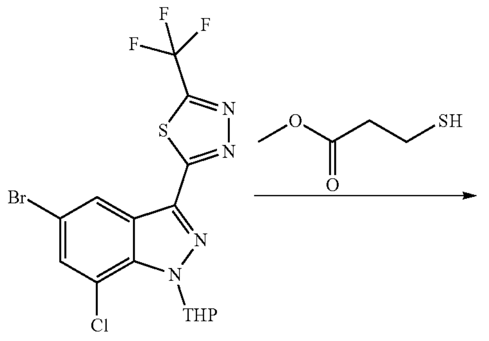

15-f

-continued

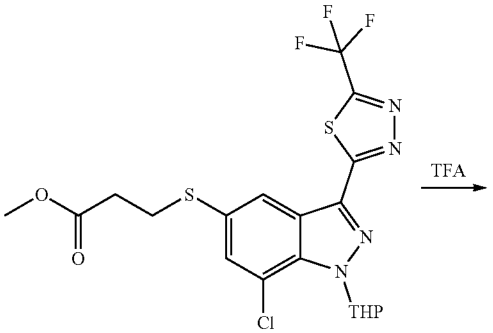

15-e

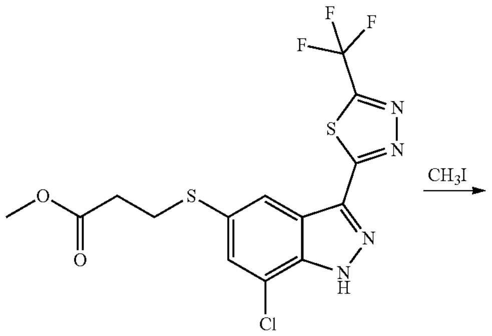

15-d

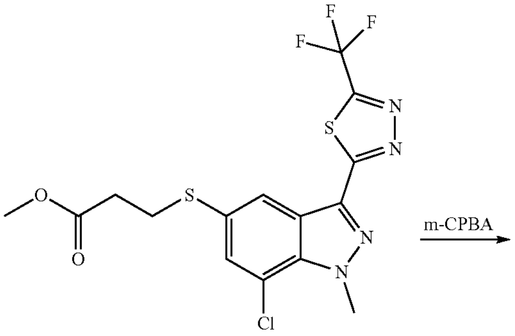

15-c

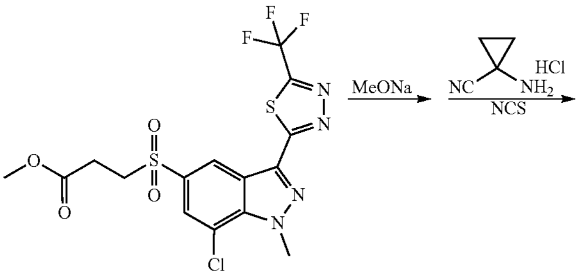

15-b

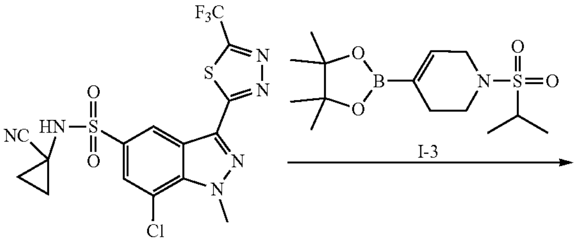

15-a

-continued

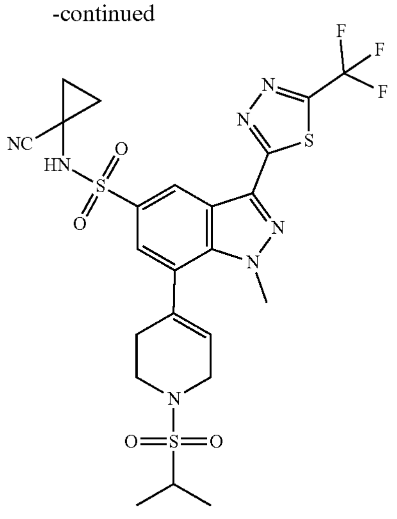

15

Synthesis of Compound 15-g

To a solution of compound 5-bromo-7-chloro-1H-indazole (2.0 g, 8.64 mmol) in 3,4-dihydro-2H-pyran (25 mL) was carefully added trifluoroacetic acid (0.066 mL, 0.86 mmol). After addition, the reaction was stirred at 90° C. for 3 hours. Upon completion, the reaction was cooled to room temperature, diluted with ethyl acetate, washed with saturated sodium bicarbonate, washed with brine, dried over anhydrous sodium sulfate, filtered, and the filtrate was concentrated to obtain the crude product, which was purified by a flash column chromatography (mobile phase: ethyl acetate/petroleum ether 0% to 50%) to give compound 15-g (2.5 g, 92%). LC-MS (ESI): m/z 314.9 $(M+H)^+$.

Synthesis of Compound 15-f

To a microwave tube was added methoxy(cyclooctadiene) iridium conjugate dimer (104 mg, 0.16 mmol), 4,4'-di-tert-butyl-2,2'-dipyridine (85 mg, 0.32 mmol), pinacol ester of bis(boronic acid) (603 mg, 2.38 mmol) and methyl tertiary-butyl ether (6 mL). After degassed and purged with nitrogen twice, the reaction mixture was stirred for 5 minutes at room temperature, then was added a solution of 15-g (0.5 g, 1.58 mmol) in methyl tert-butyl ether (6 mL), degassed and purged with nitrogen, sealed and stirred at 85° C. for 3.5 hours. The reaction mixture was evaporated to give intermediate borate.

The intermediate borate was dissolved in toluene (20 mL), followed by 2-bromo-5-(trifluoromethyl)-1,3,4-thiadiazole (556 mg, 2.38 mmol), palladium acetate (36 mg, 0.16 mmol), Xantphos (183 mg, 0.32 mmol), NMM (0.52 mL, 4.75 mmol) and water (10 mL). After degassed and purged with nitrogen for three times, the reaction mixture was stirred at 40° C. and for 18 h. The reaction mixture was then mixed with ethyl acetate (0.5 mL, 0.5 mmol). Upon completion, the reaction mixture was diluted with ethyl acetate, washed with water, washed with brine, dried over anhydrous sodium sulfate, filtered, and the filtrate was evaporated, and the residue was purified by column chromatography (mobile phases: ethyl acetate/petroleum ether 0% to 50%) to give compound 15-f (400 mg, 54%). LC-MS (ESI): m/z 466.9 $(M+H)^+$.

Synthesis of Compound 15-e

A reaction flask charged with 15-f (350 mg, 0.75 mmol), 1,4-dioxane (20 mL), Xantphos (43 mg, 0.075 mmol), DIPEA (0.39 mL, 2.25 mmol), and methyl 3-mercaptopropionate (0.099 mL, 0.90 mmol) was degassed and purged with nitrogen twice, then was added $Pd_2(dba)_3$ (34 mg, 0.037 mmol), then purged with nitrogen for 3 times. The reaction mixture was stirred at 85° C. for 2 hours. Upon completion, the reaction mixture was cooled to room temperature, evaporated to dryness, and purified by silica gel column chromatography (mobile phase: ethyl acetate/petroleum ether 0% to 50%) to afford compound 15-e (350 mg, 92%). LC-MS (ESI): m/z 507.0 $(M+H)^+$.

Synthesis of Compound 15-d

To a solution of 15-e (350 mg, 0.69 mmol) in dichloromethane (20 mL) was added TFA (5 mL) at room temperature. After addition, the reaction was stirred at room temperature overnight. Upon completion, the mixture was removed solvent by rotary evaporation at room temperature, diluted by addition of ethyl acetate, washed with saturated sodium bicarbonate, washed with brine, dried over anhydrous sodium sulfate, filtered, and the filtrate was evaporated to obtain compound 15-d (250 mg, 86%). LC-MS (ESI): m/z 423.0 $(M+H)^+$.

Synthesis of Compound 15-c

To a solution of 15-d (250 mg, 0.59 mmol) in DMF (5 mL) was added cesium carbonate (385 mg, 1.18 mmol) and iodomethane (0.096 mL, 1.18 mmol) at room temperature. After addition, the reaction was stirred at room temperature overnight. Upon completion, the reaction was diluted by adding ethyl acetate, washed with water and brine, dried over anhydrous sodium sulfate, filtered and the filtrate was evaporated to dryness. Purified by a flash column chromatography (mobile phase: ethyl acetate/petroleum ether 0% to 50%) and afforded compound 15-c (200 mg, 77%). LC-MS (ESI): m/z 437.4 $(M+H)^+$.

Synthesis of Compound 15-b

To a solution of 15-c (200 mg, 0.46 mmol) in dichloromethane (10 mL) was added m-CPBA (237 mg, 1.37 mmol) in an ice-cold water bath. After addition, the reaction was kept at 0° C. and stirred for 1 hour. Upon completion, the solvent was removed by rotary evaporation at room temperature. The residue was diluted by adding ethyl acetate, washed with saturated sodium bicarbonate, washed with brine, dried over anhydrous sodium sulfate, filtered and the filtrate was evaporated to dryness. The crude product was purified by a flash column chromatography (mobile phase: ethyl acetate/petroleum ether, 0% to 100%) to give compound 15-b (200 mg, 93%). LC-MS (ESI): m/z 469.0 $(M+H)^+$.

Synthesis of Compound 15-a

Sodium methanol (69 mg, 1.28 mmol) was added into a reaction flask charged with 15-b (200 mg, 0.43 mmol), methanol (10 mL) and dichloromethane (10 mL) in an ice-cold water bath. The reaction was stirred in an ice-cold water bath for 1 hour, then was added 1-amino-1-cyclopropanecarbonitrile hydrochloride (202 mg, 1.70 mmol) in an ice-cold water bath. The organic solvent was removed and the residue was dried by an oil pump for 30 minutes at room temperature. The residue was added 1-Amino-1-cyclopropanecarbonitrile hydrochloride (51 mg, 0.43 mmol) and DMF (10 mL). Then in an ice-cold water bath, the resulting mixture was added triethylamine (0.73 mL, 0.85 mmol) and NCS (171 mg, 1.28 mmol). The reaction mixture was stirred in an ice-cold water bath for 1 hour. The reaction mixture was added to ice-cold water and extracted twice with ethyl acetate. The organic phase was washed with water, brine, dried over anhydrous sodium sulfate, filtered and the filtrate was evaporated, and purified by column chromatography (PE/EA=3/1, 1/1) to give 15-a (103 mg, 52%). LC-MS (ESI): m/z 462.9 $(M+H)^+$.

Synthesis of Compound 15

15-a (46 mg, 0.10 mmol), I-3 (16 mg, 0.05 mmol), dichlorodi-tert-butyl-(4-dimethylaminophenyl)phosphopalladium(II) (18 mg, 0.03 mmol), potassium phosphate (20 mg, 0.09 mmol) were combined in a microwave tube, followed by addition of 1,4-dioxane (5 mL) and water (1 mL). The reaction mixture was protected by nitrogen, sealed and stirred at 110° C. for 11 hours. The reaction mixture was concentrated at reduced pressure and the residue was purified by Prep-HPLC to give compound 15 (15.9 mg, 76%). LC-MS (ESI): m/z 616.4 $(M+H)^+$; $^1$HNMR (400 MHz, DMSO-$d_6$): δ 8.86 (1H, d, J=2.0 Hz), 7.70 (1H, d, J=2.0 Hz), 6.00 (1H, s), 4.24 (3H, s), 4.07 (2H, d, J=2.4 Hz), 3.63 (2H, t, J=5.2 Hz), 3.42-3.54 (1H, m), 2.57 (2H, s), 1.40-1.47 (2H, m), 1.30-1.35 (2H, m), 1.30 (6H, d, J=6.8 Hz).

Synthetic Route of Compound 16

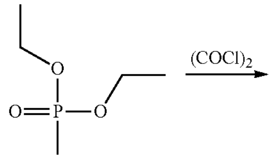

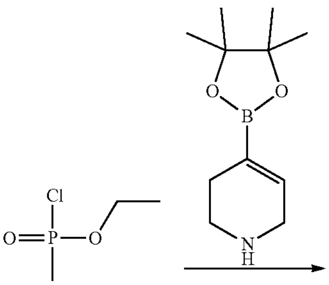

16-b

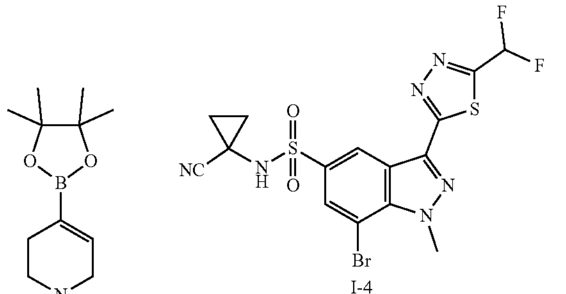

I-4

16-a

-continued

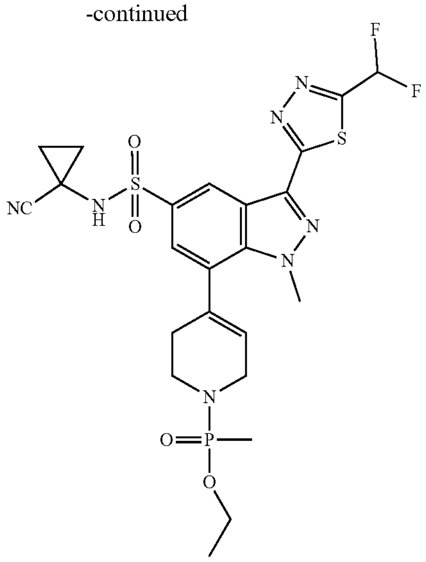

16

Synthesis of Compound 16-b

A reaction flask containing diethyl methylphosphate (850 mg, 5.59 mmol) and dichloromethane (4 mL) was stirred at 0° C. for 10 min, then was slow added oxalyl chloride (709.14 mg, 5.59 mmol) in dichloromethane (4 mL) dropwise. After addition, the reaction mixture was stirred at 0° C. under nitrogen protection, slowly warmed to room temperature and stirred for another 12 hours. The reaction mixture was directly used in the next reaction.

Synthesis of Compound 16-a

To a reaction flask were added 1,2,3,6-tetrahydropyridine-4-boronic acid pinacol ester (80 mg, 0.38 mmol), triethylamine (728 mg, 7.19 mmol) and dichloromethane (20 mL) and the resulting mixture was stirred at 0° C. for 10 min, then was slowly added 16-b (164 mg) dropwise to and stirred at 0° C. for 3 hours under nitrogen protection. The reaction mixture was washed with saturated sodium bisulfate (30 mL). Extracted with dichloromethane (10 mL*3). The organic phases were combined and the filtrate was concentrated to give compound 16-a (110 mg, 91%). LC-MS (ESI): m/z 316.2 $(M+H)^+$.

Synthesis of Compound 16

16-a (60 mg, 0.19 mmol), I-4 (40 mg, 0.08 mmol), dichlorodi-tert-butyl-(4-dimethylaminophenyl)phosphopalladium(II) (17 mg, 0.02 mmol) and potassium phosphate (52 mg, 0.25 mmol) were combined in a microwave tube, followed by addition of 1,4-dioxane (8 mL) and water (2 mL), the reaction was protected by nitrogen, sealed and stirred at 110° C. for 11 hours. The reaction mixture was concentrated at reduced pressure and the residue was purified by Prep-HPLC to give compound 16 (3.6 mg, 7%). LC-MS (ESI): m/z 598.1 $(M+H)^+$.

Synthetic Route of Compound 17

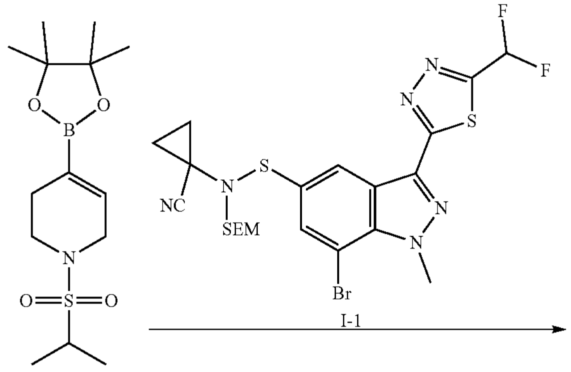

I-3

I-1

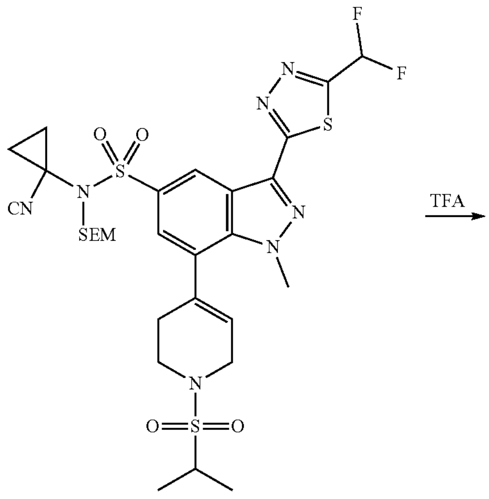

17-b

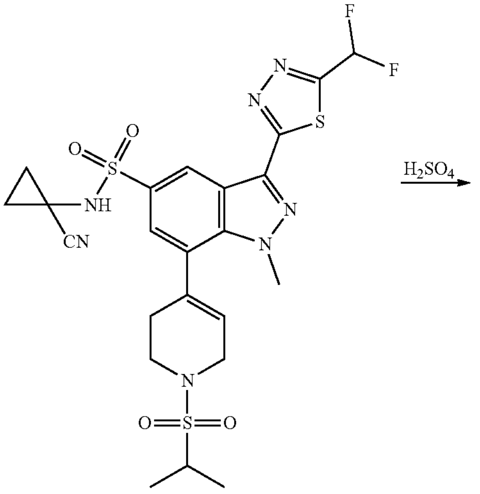

17-a

-continued

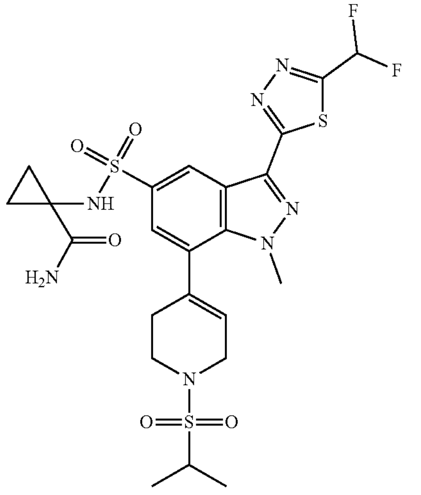

17

Synthesis of Compound 17-b

Compound I-1 (50 mg, 0.081 mmol), I-3 (51 mg, 0.16 mmol), [1,1'-bis(diphenylphosphino)ferrocene]palladium dichloride (12 mg, 0.016 mmol), and potassium carbonate (33 mg, 0.24 mmol) were added into 1,4-dioxane (10 mL) and water (1 mL). The reaction mixture was degassed and purged with nitrogen for 3 times and then stirred at 100° C. for 6 h. The reaction mixture was filtered through celite, and the filtrate was added water (100 mL), extracted with ethyl acetate (100 mL). The organic phase was washed with brine (100 mL), dried over sodium sulfate, filtered off the desiccant, and the filtrate was concentrated at reduced pressure to obtain the crude product, which was purified by column chromatography (mobile phase, PE/EA 1/1) to obtain compound 17-b (50 mg, 85%). LC-MS (ESI): m/z 728.2 $(M+H)^+$.

Synthesis of Compound 17-a

Trifluoroacetic acid (1.5 mL) was added to a solution of compound 17-b (50 mg, 0.069 mmol) in dichloromethane (4.5 mL) in an ice-cold water bath, and the reaction mixture was stirred at room temperature for 2 h. The dichloromethane was removed by concentration at reduced pressure and the residue was adjusted to pH 7 to 8 with saturated sodium bicarbonate solution and extracted with ethyl acetate (50 mL). The organic phase was washed with brine (50 mL), dried over sodium sulfate, filtered off the desiccant, and the filtrate was concentrated at reduced pressure to obtain the crude product, which was purified by Prep-HPLC (basic conditions) to give compound 17-a (33 mg, 80%). LC-MS (ESI): m/z 598.4 $(M+H)^+$.

Synthesis of Compound 17

A reaction flask charged with 17-a (50 mg, 0.08 mmol) and dichloromethane (8 mL) was stirred for 10 min in an ice-salt bath conditions, then was added concentrated sulfuric acid (1 mL). The reaction mixture was slowly warmed to room temperature and stirred for 3 hours. The reaction mixture was poured into ice-cold water (20 mL) and extracted with dichloromethane (20 mL). The organic phase was concentrated at reduced pressure and the residue was purified by Prep-HPLC to give compound 17 (22.7 mg, 44%). LC-MS (ESI): m/z 616.1 $(M+H)^+$.

Synthetic Route of Compound 18
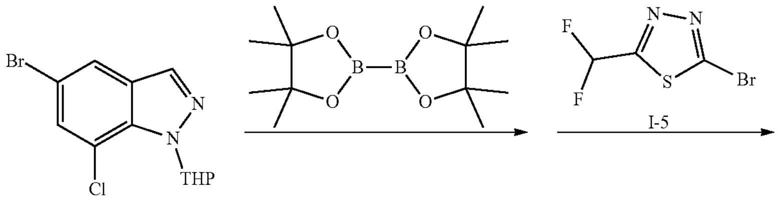
15-g
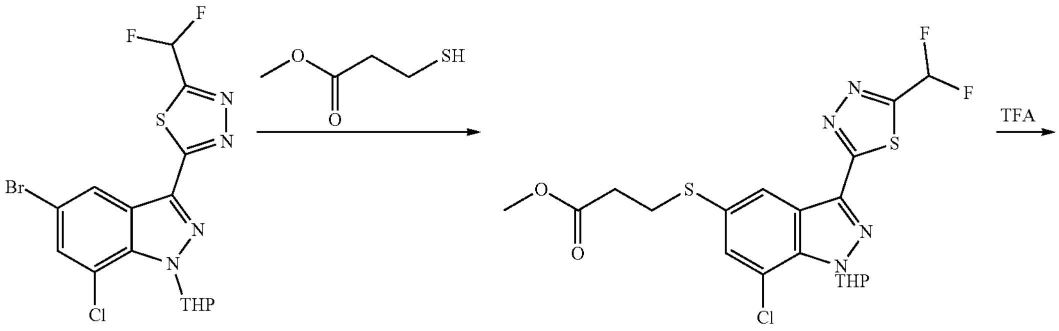
18-f 18-e
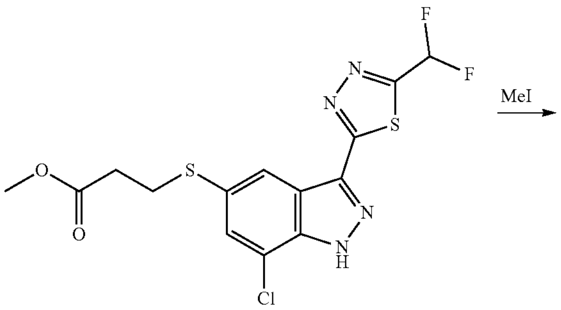
18-d
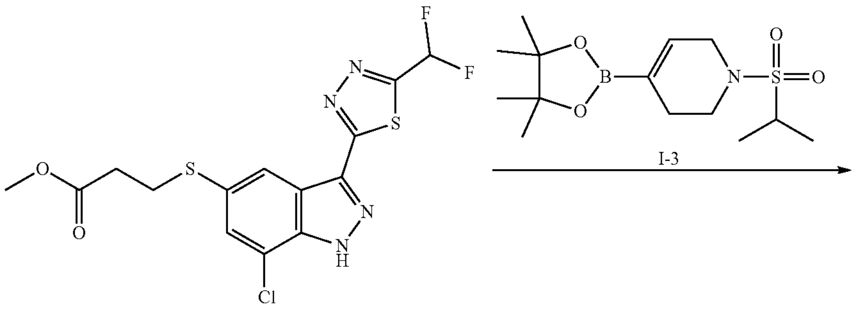
18-c -continued

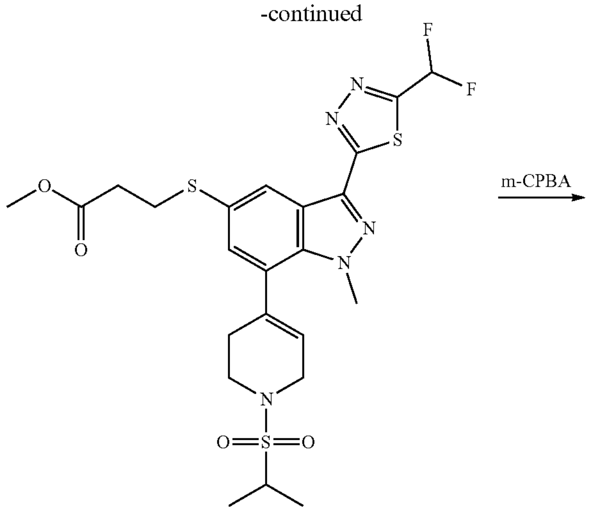

18-b

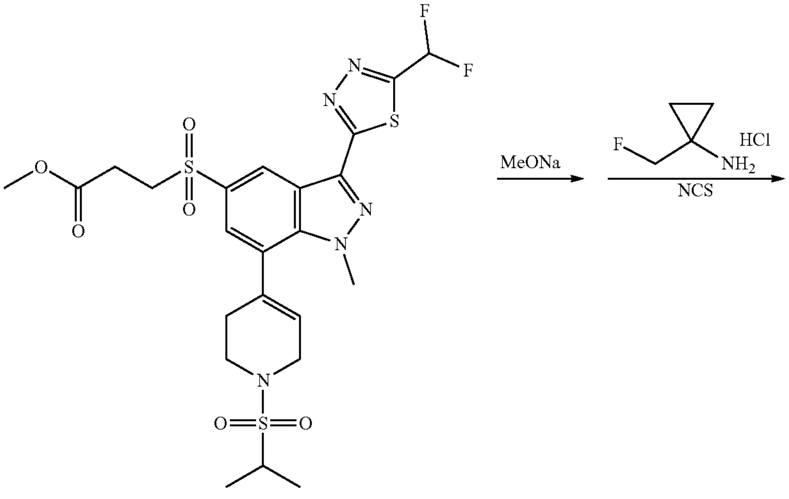

18-a

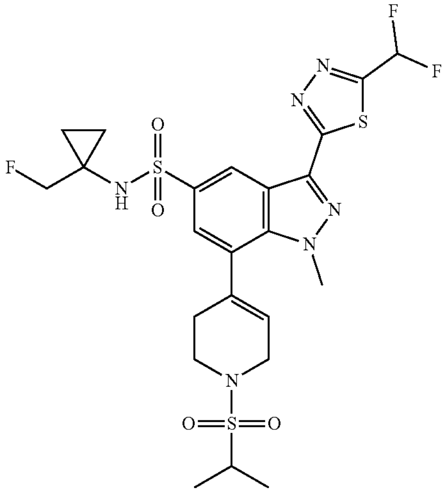

18

Synthesis of Compound 18-f

A sealed tube charged with pinacol ester of bis(boronic acid) (1.21 g, 4.75 mmol), 4,4'-di-tert-butyl-2,2'-dipyridine (208 mg, 0.32 mmol) and methyl tert-butyl ether (10 mL) was added methoxy(cyclooctadiene)iridium conjugate dimer (170 mg, 0.63 mmol) under nitrogen protection, then was degassed and purged with nitrogen for 2 times and stirred at room temperature for 10 minutes. The resulting mixture was added a solution of 15-g (1.0 g, 3.17 mmol) in methyl tert-butyl ether (10 mL), degassed and purged with nitrogen for three times and stirred at 85° C. for 3.5 hours. The reaction mixture was concentrated to obtain the crude borate ester.

The resulting crude borate ester was dissolved in toluene (20 mL) and water (10 mL) and was added I-5 (886 mg, 4.12 mmol), palladium acetate (71 mg, 0.32 mmol), Xantphos (367 mg, 0.63 mmol) and N-methylmorpholine (1.05 mL, 9.51 mmol). After degassed and purged with nitrogen twice, the reaction mixture was stirred at 40° C. for 18 hours. Upon completion, the reaction mixture was diluted with ethyl acetate, washed with water, washed with brine, dried over anhydrous sodium sulfate, filtered, concentrated, and purified by column chromatography (mobile phase: ethyl acetate/petroleum ether 0% to 50%) to give compound 18-f (1.0 g, 70%). LC-MS (ESI): m/z=449.0 $(M+H)^+$.

Synthesis of Compound 18-e

A reaction vial charged with 18-f (200 mg, 0.44 mmol), XANT PHOS (16 mg, 0.028 mmol), $Pd_2(dba)_3$ (11 mg, 0.01 mmol), 1,4-dioxane (4 mL), DIPEA (180 mg, 1.39 mmol) and methyl 3-mercaptopropionate (57 mg, 0.47 mmol) was degassed and purged with nitrogen twice, the reaction mixture was stirred at 85° C. for 2 hours. Cooled to room temperature. The reaction mixture was evaporated, diluted with ethyl acetate, washed with water and brine, dried over anhydrous sodium sulfate, filtered and the filtrate was evaporated to give compound 18-e (217 mg, 100%). LC-MS (ESI): m/z 489.0 $(M+H)^+$.

Synthesis of Compound 18-d

A reaction flask charged with 18-e (217 mg, 0.44 mmol) and dichloromethane (4.5 mL) was added trifluoroacetic acid (1.5 mL) dropwise in an ice-cold water bath. The reaction mixture was stirred at room temperature for 2 hours, then was removed solvent, diluted with ethyl acetate, washed with saturated sodium bicarbonate, washed with brine, dried over anhydrous sodium sulfate, filtered, and the filtrate was evaporated to give 18-d (179 mg, 100%). LC-MS (ESI): m/z 405.0 $(M+H)^+$.

Synthesis of Compound 18-c

A reaction flask charged with 18-d (171 mg, 0.42 mmol), DMF (4.2 mL) and cesium carbonate (360 mg, 1.10 mmol) was added iodomethane (0.042 mL, 0.68 mmol) dropwise in an ice-cold water bath. The reaction mixture was stirred at room temperature for 2 hours, then was added a small amount of methanol and ethyl acetate, concentrated by rotary evaporation for 5 minutes at room temperature. The reaction mixture was diluted by addition of ethyl acetate, washed with water and brine, dried over anhydrous sodium sulfate, and evaporated to dryness and the residue was purified by column chromatography (mobile phases: dichloromethane/methanol 100/0 to 96/4) to give 18-c (140 mg, 79%). LC-MS (ESI): m/z 419.0 $(M+H)^+$.

Synthesis of Compound 18-b

To a microwave tube were added 18-c (175 mg, 0.42 mmol), 1,4-dioxane (20 mL), I-3 (250 mg, 0.79 mmol), chloro(2-dicyclohexylphosphino-2',4',6'-triisopropyl-1,1'-biphenylyl)[2-(2'-amino-1,1'-biphenyl)]palladium(II) (44 mg, 0.06 mmol) and sodium carbonate (206 mg, 1.94 mmol). The microwave tube was degassed and purged with nitrogen, sealed, and stirred at 100° C. for 3 hours. The reaction mixture was concentrated and purified by column chromatography (PE/EA=5/1, 3/1) to give compound 18-b (176 mg, 74%). LC-MS (ESI): m/z 572.1 $(M+H)^+$.

Synthesis of Compound 18-a

A reaction vial charged with 18-b (179 mg, 0.31 mmol), dichloromethane (20 mL) and m-CPBA (159 mg, 0.78 mmol) was cooled in an ice-cold water bath and stirred for 3 hours. The reaction mixture was quenched with saturated aqueous sodium bicarbonate and extracted with dichloromethane (30 mL*2). The organic phase was concentrated and purified and the filtrate was concentrated by column chromatography (PE/EA=3/1, 1/3) to give compound 18-a (170 mg, 90%). LC-MS (ESI): m/z 604.1 $(M+H)^+$.

Synthesis of Compound 18

A reaction vial charged with 18-a (80 mg, 0.13 mmol), methanol (10 mL) and dichloromethane (10 mL) was added sodium methanol (21 mg, 0.40 mmol) in an ice-cold water bath. The reaction mixture was stirred in an ice-cold water bath for 1 hour, then was added 1-(fluoromethyl)cyclopropylamine hydrochloride (67 mg, 0.53 mmol) in an ice-cold water bath. The solvent was concentrated at room temperature and the residue was dried by an oil pump for 30 minutes. The residue was added 1-(fluoromethyl)cyclopropanamine hydrochloride (17 mg, 0.13 mmol) and DMF (10 mL), followed by addition of triethylamine (0.04 mL, 0.27 mmol) and NCS (53 mg, 0.40 mmol) in an ice-cold water bath. The reaction was stirred for 1 hour in an ice-cold water bath. The reaction mixture was added water (10 mL) and extracted with ethyl acetate (10 mL*3). The organic phase was concentrated and purified by Prep-HPLC to give 18 (19.3 mg, 24%). LC-MS (ESI): m/z 605.1 $(M+H)^+$.

Synthetic Route of Compound 19

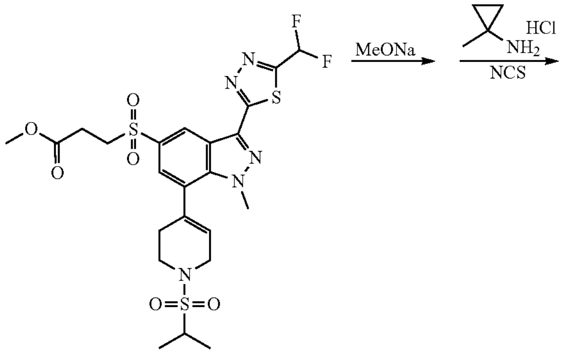

18-a

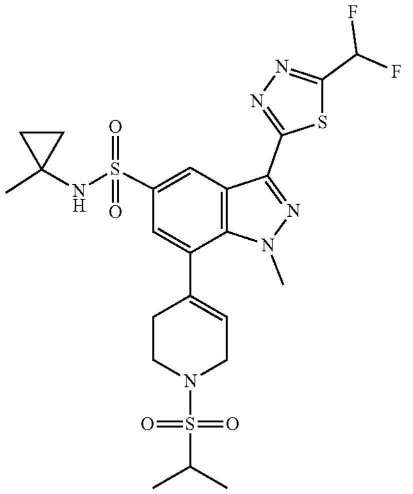

19

Synthesis of Compound 19

A reaction flask charged with 18-a (87 mg, 0.14 mmol), methanol (10 mL) and dichloromethane (10 mL) was added sodium methanolate (23 mg, 0.43 mmol) in an ice-cold water bath. The reaction mixture was stirred for 1 hour in an ice-cold water bath, then was added 1-methylcyclopropanamine hydrochloride (62 mg, 0.58 mmol). The solvent was concentrated at room temperature and the residue was dried by an oil pump for 30 minutes. The residue was added 1-Methylcyclopropanamine hydrochloride (16 mg, 0.14 mmol) and DMF (10 mL), followed by addition of triethylamine (0.04 mL, 0.29 mmol) and NCS (58 mg, 0.43 mmol) in an ice-cold water bath, then stirred in an ice-cold water bath for 1 hour. The reaction mixture was added water (10 mL) and extracted with ethyl acetate (10 mL*3). The organic phase was concentrated and purified by Prep-HPLC to give 19 (16.9 mg, 20%). LC-MS (ESI): m/z 587.1 $(M+H)^+$.

Synthetic Route of Compound 20

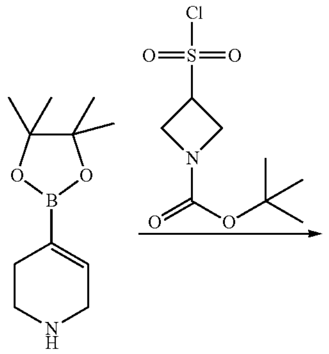

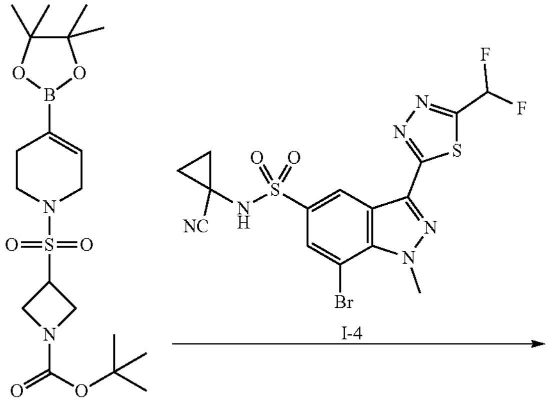

20-b

-continued

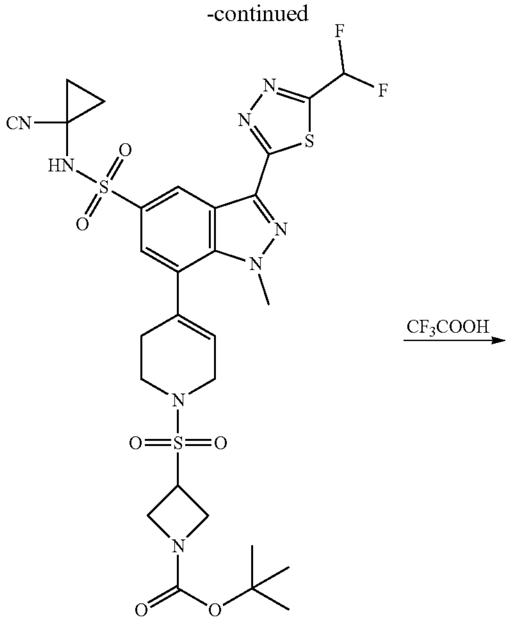

20-a

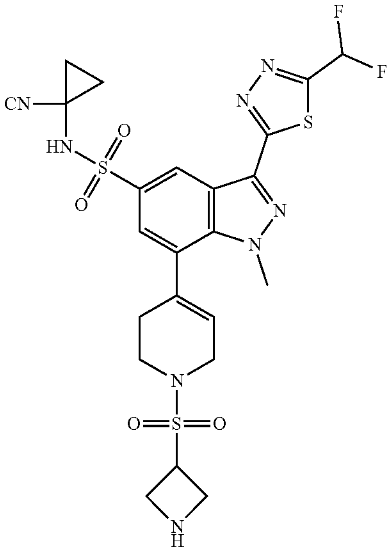

20

Synthesis of Compound 20-b

At room temperature, a solution of 1,2,3,6-tetrahydropyridine-4-boronic acid pinacol ester (105 mg, 0.50 mmol) and triethylamine (203 mg, 2.01 mmol) in dichloromethane (10 mL) in a reaction flask was slowly added N-Boc-azetidine-3-sulfonyl chloride (193 mg, 0.75 mmol) dropwise. After addition, the reaction mixture was stirred under nitrogen protection at room temperature for 1 hour. The reaction mixture was washed with saturated sodium bisulfate (30 mL) and the reaction mixture was concentrated to give compound 20-b (186 mg, 87%). LC-MS (ESI): m/z 446.1 $(M+NH_4)^+$.

Synthesis of Compound 20-a 20-b (180 mg, 0.42 mmol), I-4 (100 mg, 0.20 mmol), [1,1'-bis(di-tert-butylphosphino)ferrocene]palladium dichloride(II) (40 mg, 0.06 mmol), and cesium fluoride (93 mg, 0.61 mmol) were combined in a microwave tube, followed by addition of 1,4-dioxane (9 mL) and water (1 mL). Under nitrogen protection and sealed, the reaction mixture was stirred at 100° C. for 12 hours. The reaction mixture was concentrated at reduced pressure and the residue was purified by column chromatography (PE/EA=3/2, 1/3) to give compound 20-a (110 mg, 76%). LC-MS (ESI): m/z 711.1 $(M+H)^+$.

Synthesis of Compound 20

A mixture of compound 20-a (110 mg, 0.16 mmol), dichloromethane (10 mL) and trifluoroacetic acid (3 mL) was stirred at room temperature under nitrogen protection for 3 h. The mixture was concentrated at reduced pressure and the residue was purified by Prep-HPLC to give compound 20 (66.3 mg, 70%). LC-MS (ESI): m/z 611.1 $(M+H)^+$.

Synthetic Route of Compound 21

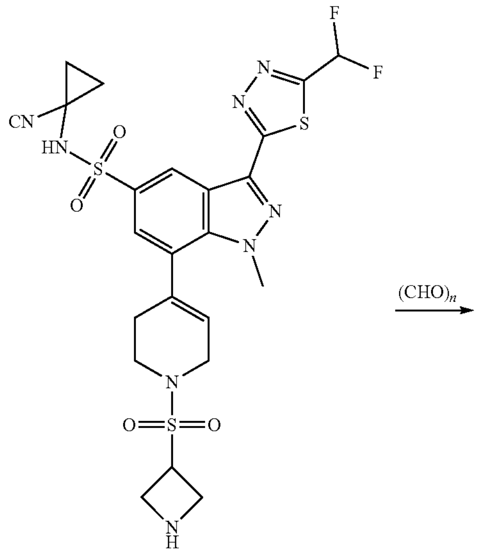

20

-continued

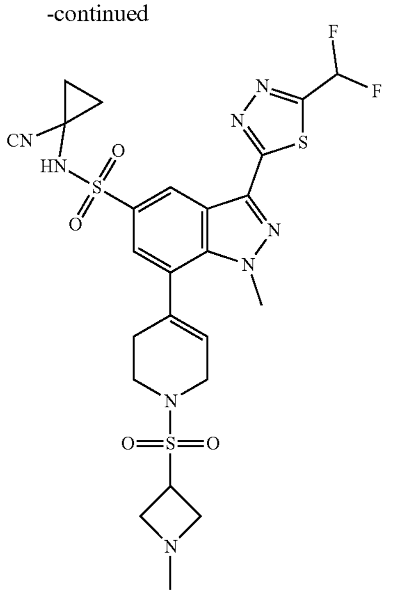

21

Synthesis of Compound 21

A reaction vial charged with 20 (49 mg, 0.08 mmol), paraformaldehyde (49 mg), sodium cyanoborohydride (15 mg, 0.24 mmol) and methanol (20 mL) and the mixture was stirred for 12 h at room temperature. The reaction mixture was concentrated and purified by Prep-HPLC to give compound 21 (9.3 mg, 19%). LC-MS (ESI): m/z 625.5 $(M+H)^+$.

Synthetic Route of Compound 22

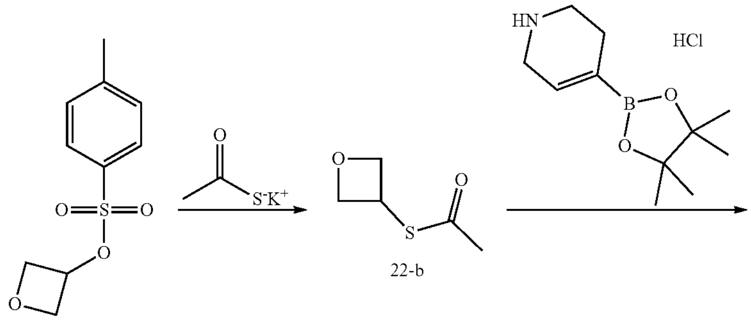

22-b

-continued

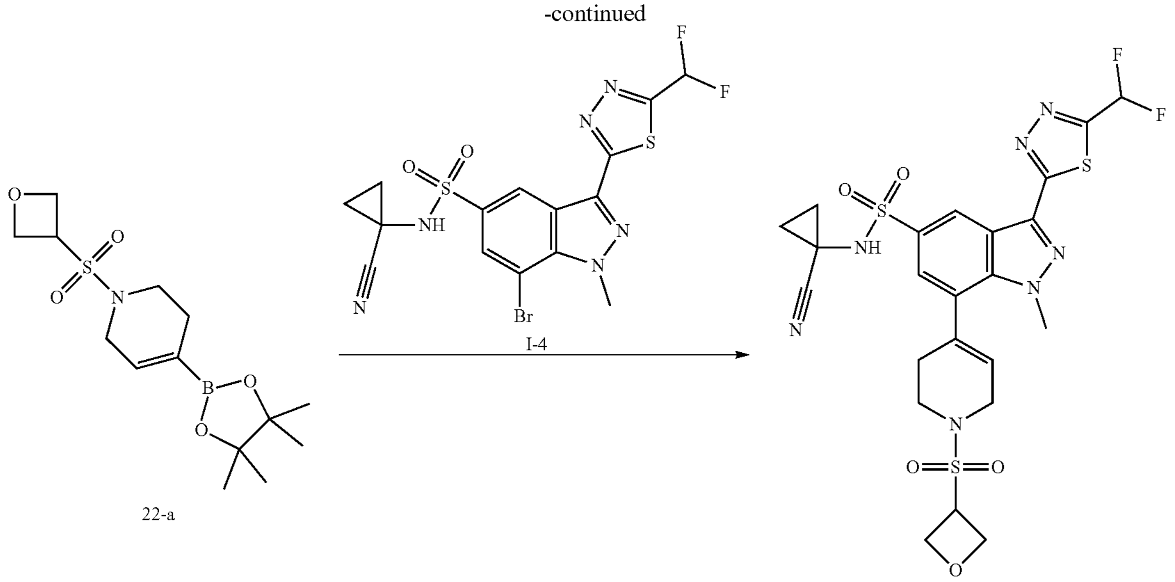

22-a

22

Synthesis of Compound 22-b

At room temperature, compound toluene-4-sulfonic acid oxetan-3-yl ester (5 g, 21.90 mmol) was dissolved in 50 mL of DMF and potassium thioacetate (7.57 g, 65.72 mmol) was added. The reaction mixture was stirred at 100° C. under nitrogen protection for 2 hours. The reaction mixture was cooled to room temperature, was added 2 00 mL of water and extracted with ethyl acetate (300 mL). The organic phase was washed with brine (200 mL*5), dried over anhydrous sodium sulfate, filtered, and the filtrate was concentrated at reduced pressure at room temperature. The crude product 22-b (2.9 g, 100%) was obtained. The crude product was directly used in the next reaction without further purification. LC-MS (ESI): m/z=133.0[M+H]$^+$.

Synthesis of Compound 22-a

2 M hydrochloric acid (5.67 mL, 11.35 mmol) was added to a solution of compound NCS (4.04 g, 30.26 mmol) in 30 mL of acetonitrile at room temperature and. Compound 22-b (1.00 g, 7.57 mmol) was then dissolved in acetonitrile (10 mL) and slowly added dropwise to the above mixture, after about 15 minutes of the dropwise addition, the reaction mixture was concentrated at reduced pressure at room temperature and the residue was dissolved in 100 mL of ether. The organic phase was washed sequentially with saturated sodium bicarbonate solution (100 mL*2), saturated sodium thiosulfate solution (100 mL*2), brine (100 mL), dried over anhydrous sodium sulfate, filtered, and the filtrate was concentrated at reduced pressure at room temperature, and the residue was dissolved in 5 mL of DCM to afford solution A. TEA (5.26 mL, 37.83 mmol) was added to a solution of compound 1,2,3,6-tetrahydropyridine-4-boronic acid pinacol ester hydrochloride (1.52 g, 6.19 mmol) in 50 mL of DCM in an ice-cold water bath. The reaction mixture was stirred for 10 min in an ice-cold water bath and then was added the solution A dropwise. Upon completion of the dropwise addition, the reaction mixture was stirred at room temperature for 30 min. The reaction mixture was added 100 mL of water, extracted with DCM (100 mL), the organic phase was washed sequentially with 10% sodium bisulfate solution (100 mL), saturated sodium bicarbonate solution (100 mL), dried over anhydrous sodium sulfate, filtered, and the filtrate was concentrated at reduced pressure to give compound 22-a (1.2 g). LC-MS (ESI): m/z=330.1 [M+H]$^+$.

Synthesis of Compound 22

Compound 22-a (101 mg, 0.31 mmol), 1,1'-di-tert-butylphosphino ferrocene palladium dichloride (27 mg, 0.041 mmol), cesium fluoride (93 mg, 0.61 mmol) and water (2 mL) were added to a solution of compound I-4 (100 mg, 0.20 mmol) in 1,4-dioxane (18 mL) at room temperature. The reaction mixture was stirred at 100° C. under nitrogen protection for 6 hours. The reaction mixture was cooled to room temperature, concentrated at reduced pressure. The residue was added 100 mL of water and extracted with DCM (100 mL*2). The organic phase was dried over anhydrous sodium sulfate, filtered, and the filtrate was concentrated at reduced pressure to obtain the crude product. The crude product was purified by Prep-HPLC (basic method, $NH_4HCO_3$) to give compound 22 (92 mg, 75%). LC-MS (ESI): m/z=612.2 [M+H]$^+$; $^1$HNMR (DMSO-$d_6$, 400 MHz): δ 8.79 (1H, d, J=2.0 Hz), 7.70 (1H, t, J=53.2 Hz), 7.63 (1H, d, J=1.6 Hz), 6.08 (1H, brs), 5.96-5.91 (1H, m), 4.96-4.83 (3H, m), 4.78 (2H, t, J=5.6 Hz), 4.20 (3H, s), 4.02-3.96 (2H, m), 3.55 (2H, t, J=5.2 Hz), 2.60-2.53 (2H, m), 1.28-1.21 (2H, m), 1.16-1.10 (2H, m).

Synthetic Route of Compound 23

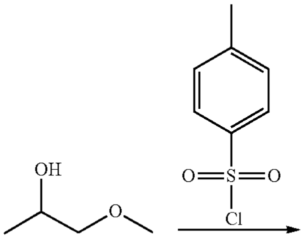

-continued

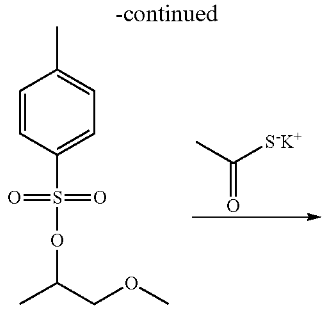

23-c

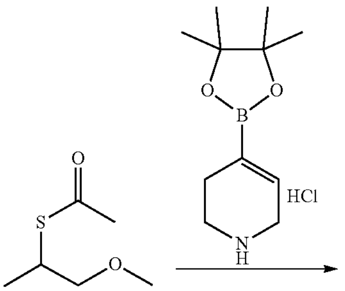

23-b

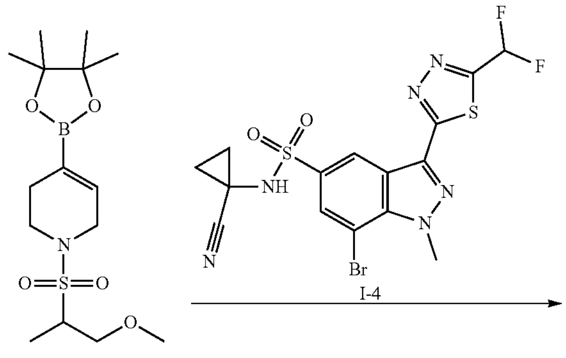

I-4

23-a

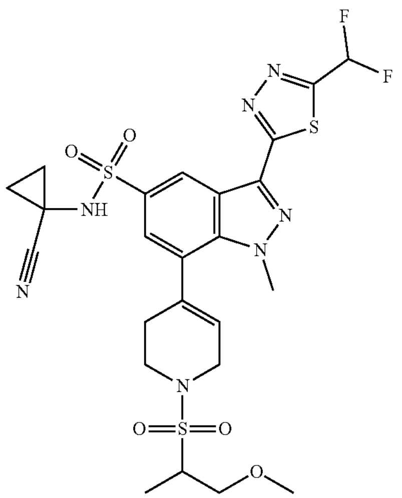

23

Synthesis of Compound 23-c p-toluenesulfonyl chloride (11.63 g, 61.03 mmol) was added to a solution of compound I-methoxy-2-propanol (5 g, 55.48 mmol) in 50 mL of DCM at room temperature and. The resulting mixture was added DMAP (0.68 g, 5.55 mmol) in an ice-cold water bath and TEA (11.57 mL, 83.22 mmol) dropwise. Upon completion of the dropwise addition, the reaction mixture was warmed to room temperature and stirred overnight. The reaction mixture was added 200 mL of water and extracted with DCM (200 mL). The organic phase was washed sequentially with 10% sodium bisulfate solution (200 mL), saturated sodium bicarbonate solution (200 mL), dried over anhydrous sodium sulfate, filtered, and the filtrate was concentrated at reduced pressure to give the crude product 23-c (13.5 g, 100%). The crude product was directly used in the next reaction without further purification. LC-MS (ESI): m/z=262.1[$M+NH_4]^+$.

Synthesis of Compound 23-b

Potassium thioacetate (7.07 g, 61.40 mmol) was added to a solution of compound 23-c (5 g, 20.47 mmol) in 50 mL of DMF at room temperature. The reaction mixture was stirred at 100° C. under nitrogen protection for 2 hours. The reaction mixture was cooled to room temperature, then was added 200 mL of water and extracted with ethyl acetate (200 mL). The organic phase was washed with brine (200 mL*5), dried over anhydrous sodium sulfate, filtered, and the filtrate was concentrated to dryness at reduced pressure at room temperature to give the crude product 23-b (3.4 g), which was used directly in the next reaction without further purification. LC-MS (ESI): m/z=149.1$[M+H]^+$.

Synthesis of Compound 23-a

2 M hydrochloric acid (5.06 mL, 10.12 mmol) was added to a solution of compound NCS (3.60 g, 26.99 mmol) in 30 mL of acetonitrile at room temperature and. Compound 23-b (1.00 g, 6.75 mmol) dissolved in acetonitrile (10 mL) was slowly added dropwise to the above mixture, after about 15 minutes of dropwise addition, the reaction mixture was concentrated at reduced pressure at room temperature and the residue was dissolved in 100 mL of ether. The organic phase was washed sequentially with saturated sodium bicarbonate solution (100 mL*2), saturated sodium thiosulfate solution (100 mL*2), brine (100 mL), dried over anhydrous sodium sulfate, filtered, and the filtrate was concentrated at reduced pressure at room temperature, and the residue was dissolved in 5 mL of DCM to give solution A. In an ice-cold water bath, a solution of compound 1,2,3,6-tetrahydropyridine-4-boronic acid pinacol ester hydrochloride (1.33 g, 5.40 mmol) in 30 mL of DCM was added TEA (4.69 mL, 33.73 mmol). The reaction mixture was stirred for 10 minutes in an ice-cold water bath and then was added the solution A dropwise. Upon completion of the dropwise addition, the reaction mixture was stirred for 30 minutes at room temperature, then was added 100 mL of water, extracted with DCM (100 mL), the organic phase was washed sequentially with 10% sodium bisulfate solution (100 mL*2), saturated sodium bicarbonate solution (100 mL), dried over anhydrous sodium sulfate, filtered, and the filtrate was concentrated at reduced pressure to give compound 23-a (1.7 g). LC-MS (ESI): m/z=345.8 $[M+H]^+$.

Synthesis of Compound 23

A solution of compound I-4 (200 mg, 0.41 mmol) dissolved in 36 mL of 1,4-dioxane at room temperature was added compound 23-a (212 mg, 0.61 mmol), 1,1'-di-tert-butylphosphinoferrocene palladium dichloride (53 mg, 0.082 mmol), cesium fluoride (186 mg, 1.23 mmol) and water (4 mL). The reaction mixture was stirred at 100° C. under nitrogen protection for 6 hours. The reaction mixture was cooled to room temperature, concentrated at reduced pressure. The residue was added 100 mL of water to and extracted with DCM (100 mL*2). The organic phase was dried over anhydrous sodium sulfate, filtered and the filtrate was concentrated at reduced pressure to give the crude product. The crude product was purified by Prep-HPLC (basic method, $NH_4HCO_3$) to give compound 23 (150 mg, 58%). LC-MS (ESI): m/z=628.2 $[M+H]^+$; $^1$HNMR (DMSO-$d_6$, 400 MHz): δ 9.05 (1H, brs), 8.87 (1H, d, J=2.0 Hz), 7.71 (1H, t, J=53.2 Hz), 7.69 (1H, d, J=1.6 Hz), 6.02-5.96 (1H, m), 4.23 (3H, s), 4.05 (2H, d, J=2.0 Hz), 3.70-3.56 (4H, m), 3.54-3.47 (1H, m), 3.32 (3H, s), 2.61-2.53 (2H, m), 1.47-1.39 (2H, m), 1.35-1.27 (5H, m).

Synthetic Route of Compound 24

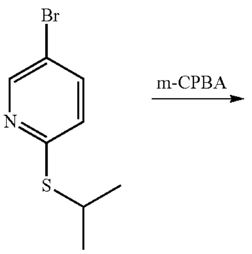

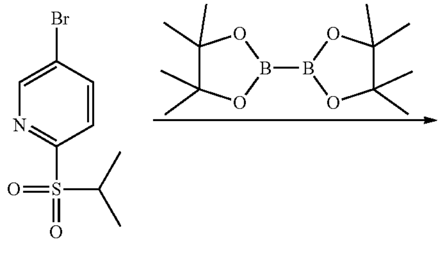

24-b

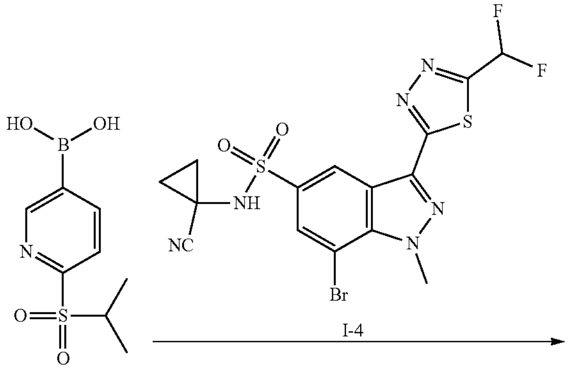

24-a

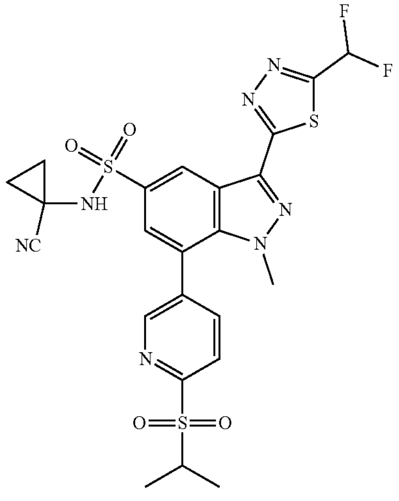

24

Synthesis of Compound 24-b

Compound 2-isopropylthio-5-bromopyridine (500 mg, 2.15 mmol) was dissolved in 10 mL of DCM at room temperature and m-CPBA (1.09 g, 5.39 mmol) was added in batches to the above mixture. The mixture was stirred at room temperature under nitrogen protection for 30 min, then was added 100 mL of saturated sodium bicarbonate solution and extracted with DCM (100 mL). The organic phase was washed sequentially with saturated sodium bicarbonate solution (100 mL), water (200 mL), dried over anhydrous sodium sulfate, filtered, and the filtrate was concentrated at reduced pressure to give the crude product 24-b (665 mg). The crude product was directly used in the next reaction without further purification. LC-MS (ESI): m/z=264.0$[M+H]^+$.

Synthesis of Compound 24-a

A solution of compound 24-b (120 mg, 0.45 mmol) dissolved in 10 mL of 1,4-dioxane at room temperature was sequentially added pinacol ester of bis(diphenylphosphino) ferrocene dichloropalladium(II) dichloromethane complex (37 mg, 0.045 mmol) and potassium acetate (223 mg (2.27 mmol). The reaction mixture was stirred at 80° C. under argon for 18 hours. The reaction mixture was cooled to room temperature and the filtrate was concentrated at reduced pressure. The residue was dissolved in 10 mL of DCM and the mixture was filtered through a short silica gel column (to 10 CM), the filtrate was discarded, the silica gel column was continued to be drenched with methanol (50 mL), the methanol filtrate was concentrated at reduced pressure, and the residue was dried at vacuum for 30 min to give the crude product 24-a (100 mg). The crude product was used directly in the next reaction without further purification. LC-MS (ESI): m/z=230.0$[M+H]^+$.

Synthesis of Compound 24

A solution of compound I-4 (50 mg, 0.10 mmol) dissolved in 18 mL of 1,4-dioxane at room temperature was added compound 24-a (47 mg, 0.20 mmol), 1,1'-di-tert-butylphosphinoferrocene palladium dichloride (13 mg, 0.020 mmol), cesium fluoride (47 mg, 0.31 mmol) and water (2 mL). The reaction mixture was stirred at 100° C. under nitrogen protection for 6 hours. The reaction mixture was cooled to room temperature, concentrated at reduced pressure. The residue was added 50 mL of water to and extracted with DCM (50 mL*2). The organic phase was dried over anhydrous sodium sulfate, filtered and the filtrate was concentrated at reduced pressure to give the crude product. The crude product was purified by Prep-HPLC (basic method, $NH_4HCO_3$) to give compound 24 (15.4 mg, 25%). LC-MS (ESI): m/z=594.1 $[M+H]^+$.

Synthetic Route of Compound 25

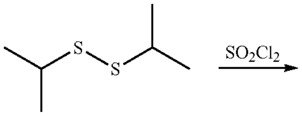

-continued

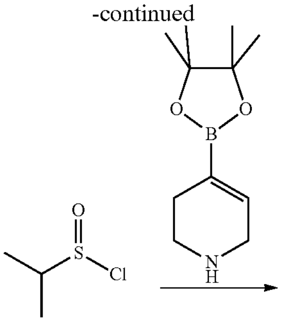

25-b

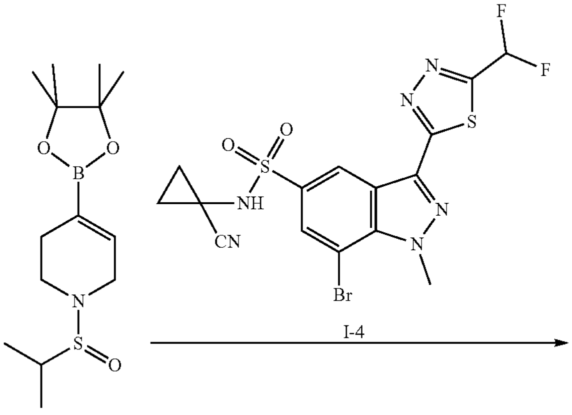

I-4

25-a

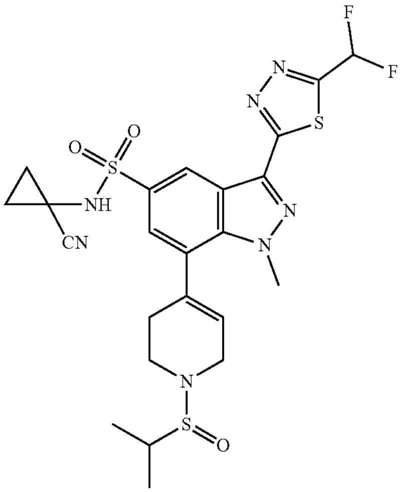

25

Synthesis of Compound 25-b

Isopropyl disulfide (606 mg, 4.03 mmol) and acetic acid (0.461 mL, 8.06 mmol) were added into a reaction flask. The mixture was stirred in an ice-salt bath for 5 min and then was added sulfuryl chloride (1632 mg, 12.10 mmol) dropwise over 10 min. The reaction mixture was stirred at −20° C. to room temperature for 3 hours, then at 35° C. for 1 hour. The solvent was removed by rotary evaporation at room temperature to give 25-b (900 mg, 88%).

Synthesis of Compound 25-a

In an ice-cold water bath, a reaction vial charged with 1,2,3,6-tetrahydropyridine-4-boronic acid pinacol ester (105 mg, 0.50 mmol), dichloromethane (5 mL) and triethylamine (0.275 mL, 1.98 mmol) was added 25-b (102 mg, 0.81 mmol) dropwise. The reaction mixture was stirred in an ice-cold water bath for 1 hour, then was placed in the lower level of the refrigerator overnight. The solvent was removed by rotary evaporation, diluted with ethyl acetate, washed with brine, dried over anhydrous sodium sulfate, filtered, and the filtrate was evaporated to give 25-a (120 mg, 80%). LC-MS (ESI): m/z 300.1 $(M+H)^+$.

Synthesis of Compound 25

A microwave tube charged with 25-a (120 mg, 0.40 mmol), I-4 (106 mg, 0.22 mmol), Pd(Amphos)$Cl_2$ (12 mg, 0.017 mmol), anhydrous potassium phosphate (136 mg, 0.64 mmol), 1,4-dioxane (2.5 mL) and water (0.5 mL) was degassed and purged with nitrogen for five times. The reaction mixture was stirred at 100° C. for 18 hours. The upper organic phase of the reaction mixture was concentrated to dryness by rotary evaporation and the residue was dissolved in DMF and purified by Prep-HPLC (ammonium bicarbonate) to give 25 (36.5 mg, 29%). LC-MS (ESI): m/z 582.1 $(M+H)^+$; $^1$HNMR (DMSO-$d_6$, 400 MHz) δ 9.13 (1H, bs), 8.86 (1H, d, J=1.2 Hz), 7.87-7.54 (2H, m), 6.00 (1H, s), 4.23 (3H, s), 3.95-3.78 (2H, m), 3.55-3.39 (2H, m), 3.11 (1H, p, J=6.8 Hz), 2.69-2.53 (2H, m), 1.46-1.38 (2H, m), 1.35-1.26 (2H, m), 1.24 (3H, d, J=6.8 Hz), 1.14 (3H, d, J=6.8 Hz).

Synthetic Route of Compound 26

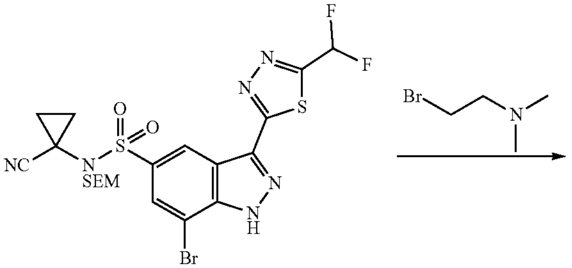

I-2

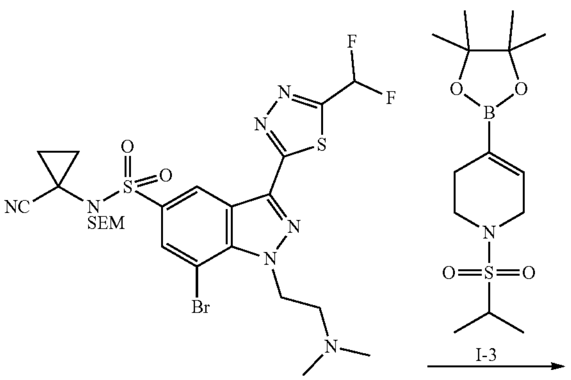

I-3

26-b

-continued

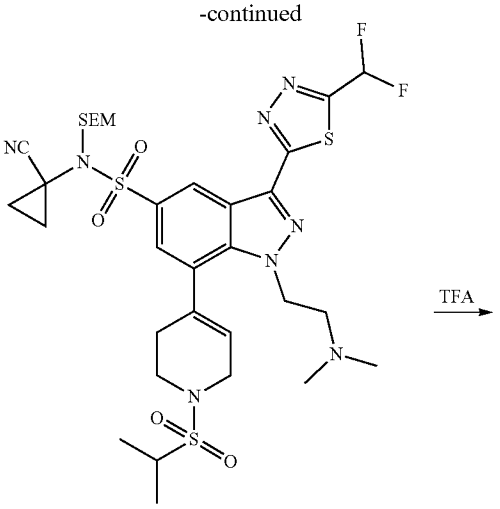

26-a

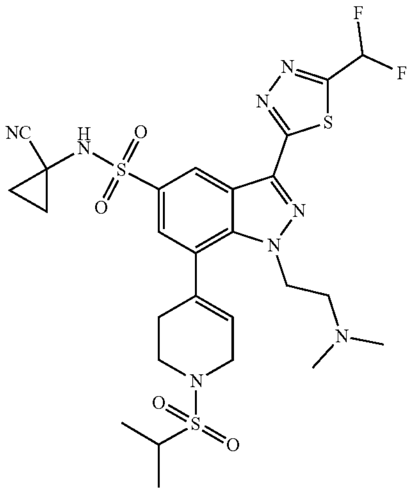

26

Synthesis of Compound 26-b

A microwave tube charged with I-2 (150 mg, 0.25 mmol), N, N-dimethylaminoethyl bromide hydrobromide (86 mg, 0.37 mmol), cesium carbonate (323 mg, 0.99 mmol) and DMF (2.5 mL) was sealed, and the reaction mixture was stirred at 70° C. for 18 hours, then continued stirring at 70° C. for 4 hours. The reaction mixture was cooled to room temperature, was added ice-cold water and extracted with ethyl acetate. The organic phase was washed with water, brine, dried over anhydrous sodium sulfate, filtered, and the filtrate was evaporated to give 26-b (125 mg, 74%). LC-MS (ESI): m/z 675.9 $(M+H)^+$.

Synthesis of Compound 26-a

A microwave tube charged with 26-b (125 mg, 0.18 mmol), 1-3 (80 mg, 0.25 mmol), Pd(dppf)$Cl_2$ (18 mg, 0.025 mmol), potassium carbonate (76 mg, 0.55 mmol), 1,4-dioxane (2.5 mL) and water (0.5 mL) was degassed and purged with nitrogen for four times, then sealed and stirred at 100° C. for 3 hours. Supplemental Pd(dppf)$Cl_2$ (18 mg, 0.025 mmol) was added, and the microwave tube was degassed and purged with nitrogen 4 times, then sealed and stirred at 100° C. for 18 hours. The reaction mixture was cooled, then was added ethyl acetate. The organic phase was washed with water, brine, dried over anhydrous sodium sulfate, filtered, and the filtrate was evaporated, and the crude product was purified by column chromatography (mobile phase: dichloromethane/methanol, 100/0 to 0/100) to obtain 26-a (120 mg, 85%). LC-MS (ESI): m/z 785.1 $(M+H)^+$.

Synthesis of Compound 26

A reaction flask charged with 26-a (120 mg, 0.15 mmol) and dichloromethane (2 mL) was added trifluoroacetic acid (0.7 mL) dropwise in an ice-cold water bath. After addition, the reaction mixture was warmed naturally to room temperature for 2 hours. The reaction mixture was concentrated to dryness by rotary evaporation. The residue was added saturated aqueous sodium bicarbonate, anhydrous potassium carbonate solid, extracted twice with ethyl acetate. The organic phases were combined, dried over anhydrous sodium sulfate, filtered, and the filtrate was evaporated, and the residue was purified by column chromatography (DCM/MeOH, 100/0 to 85/15) to obtain the crude product, which was purified by Prep-HPLC (Ammonium bicarbonate) to give 26 (22.2 mg, 23%). LC-MS (ESI): m/z 655.2 $(M+H)^+$; $^1$HNMR (DMSO-$d_6$, 400 MHz): δ 8.95 (1H, bs), 8.89 (1H, d, J=1.6 Hz), 7.85-7.56 (2H, m), 6.13-6.05 (1H, m), 4.63 (2H, t, J=6.8 Hz), 4.11-4.00 (2H, m), 3.63 (2H, t, J=5.2 Hz), 3.49 (1H, p, J=6.8 Hz), 2.73 (2H, t, J=6.4 Hz), 2.65-2.55 (2H, m), 2.13 (6H, s), 1.47-1.40 (2H, m), 1.38-1.30 (2H, m), 1.30 (6H, d, J=6.8 Hz).

Synthetic Route of Compounds 27&28

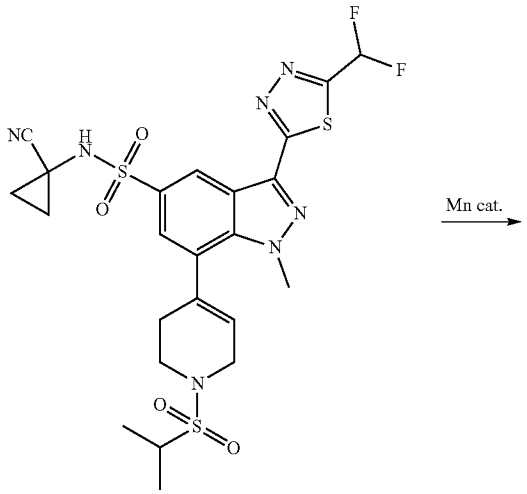

17-a

-continued

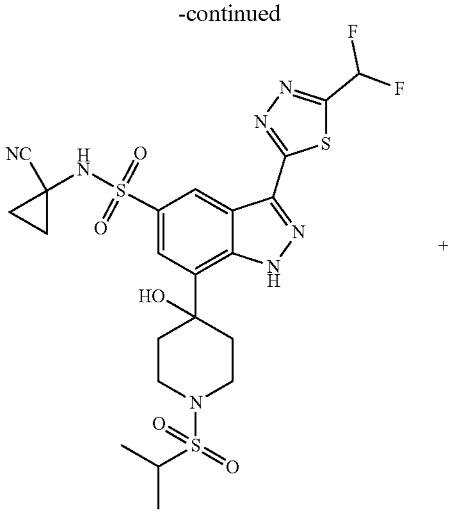

27

+

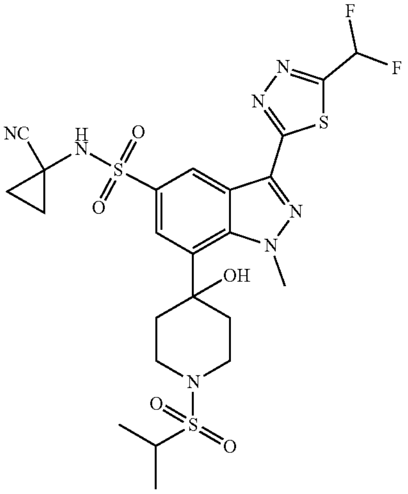

28

Synthesis of Compounds 27&28

A two-necked vial charged with 17-a (100 mg, 0.17 mmol) and $Mn(TMHD)_3$ (18 mg, 0.030 mmol) was added isopropanol (2 mL) and dichloromethane (1 mL) slowly along the walls of the vial under the protection of an air bulb in an ice-cold water bath, followed by dropwise addition of Phenylsilane (46 mg, 0.43 mmol). The reaction mixture was stirred at room temperature for 4 hours, then was added 10% aqueous sodium thiosulfate (2 mL) and the reaction mixture was stirred at room temperature for 2 hours. Ethyl acetate and brine were added, partitioned and the aqueous phase was extracted with ethyl acetate once. The organic phases were combined, dried over anhydrous sodium sulfate, filtered, and the filtrate was evaporated, and the crude was purified by Prep-HPLC (ammonium bicarbonate) to give 27 (14.8 mg, 14%) and 28 (21.8 mg, 21%).

Compound 27, LC-MS (ESI): m/z 602.1 $(M+H)^+$; $^1$HNMR (DMSO-$d_6$, 400 MHz): δ 8.73 (1H, s), 8.59 (2H, bs), 7.80-7.49 (2H, m), 6.19 (1H, s), 3.72-3.62 (2H, m), 3.45-3.41 (3H, m), 2.38-2.27 (2H, m), 1.94 (2H, d, J=12.8 Hz), 1.43-1.34 (2H, m), 1.28 (6H, d, J=6.8 Hz), 1.26-1.22 (2H, m).

Compound 28, LC-MS (ESI): m/z 616.1 $(M+H)^+$; $^1$HNMR (DMSO-$d_6$, 400 MHz): δ 8.97 (1H, d, J=1.6 Hz), 8.86 (1H, bs), 7.87 (1H, d, J=1.6 Hz), 7.71 (1H, t, J=53.2 Hz), 6.17 (1H, s), 4.67 (3H, s), 3.68 (2H, d, J=11.6 Hz), 3.52-3.40 (3H, m), 2.22 (2H, d, J=12.8 Hz), 2.15-2.01 (2H, m), 1.46-1.40 (2H, m), 1.35-1.30 (2H, m), 1.27 (6H, d, J=6.8 Hz).

Synthetic Route of Compound 29

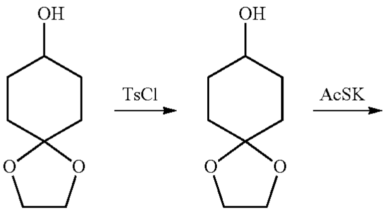

29-f

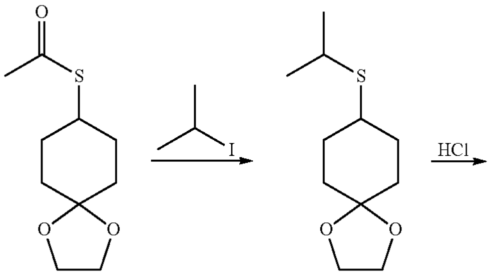

29-e 29-d

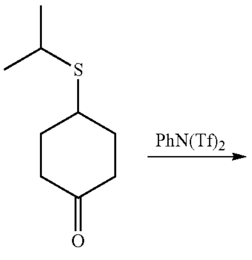

29-c

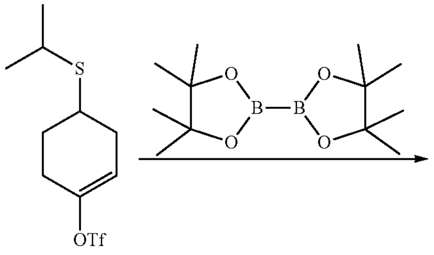

29-b

-continued

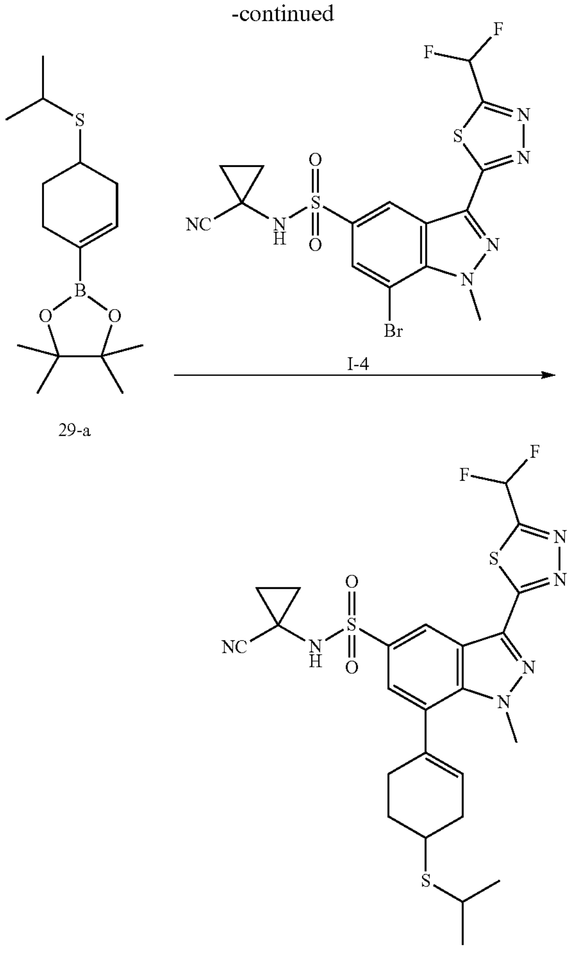

29-a

29

Synthesis of Compound 29-f

In an ice-cold water bath, a reaction flask charged with 4-Hydroxycyclohexanone ethylene glycol acetal (3.16 g, 19.97 mmol), DCM (50 mL) and triethylamine (8.33 mL, 59.92 mmol) was added TsCl (5.71 g, 29.95 mmol) and DMAP (0.24 g, 2.00 mmol). The reaction mixture was stirred in an ice-cold water bath for 10 min and at room temperature for 18 h. The solvent was removed and the residue was diluted with ethyl acetate and petroleum ether, washed with water and brine, dried over anhydrous sodium sulfate, filtered and the filtrate was evaporated to give 29-f (6.2 g, 99%).

Synthesis of Compound 29-e 29-f (1.2 g, 3.84 mmol), potassium thioacetate (0.71 g, 6.15 mmol) and DMF (10 mL) were added into a reaction flask. The reaction mixture was stirred at 80° C. for 7 hours. The reaction mixture was added ice-cold water and extracted twice with ethyl acetate. The organic phase was washed with brine, dried over anhydrous sodium sulfate, filtered, and the filtrate was evaporated to give 29-e (800 mg, 96%). LC-MS (ESI): m/z 217.0 $(M+H)^+$.

Synthesis of Compound 29-d

A reaction vial charged with 29-e (800 mg, 3.70 mmol), 2-iodopropane (0.94 mL, 9.41 mmol) and anhydrous ethanol (15 mL) was added potassium tert-butoxide (1060 mg, 9.45 mmol) in an ice-cold water bath. The reaction mixture was stirred on an ice-cold water bath for 10 min and then at room temperature overnight, then was removed solvent, added ethyl acetate and ice-cold water, partitioned, the aqueous phase was extracted once with ethyl acetate, the organic phases were combined, washed with brine, dried over anhydrous sodium sulfate, filtered, and the filtrate was evaporated, and the crude was purified by column chromatography (mobile phases: petroleum ether/ethyl acetate, 100/0 to 75/25) to give 29-d (600 mg, 75%).

Synthesis of Compound 29-c

A reaction vial charged with 29-d (600 mg, 2.77 mmol), tetrahydrofuran (10 mL) and aqueous hydrochloric acid (4 mL, 4 M). The reaction mixture was stirred at room temperature overnight, then was removed tetrahydrofuran at room temperature, added pure water and extracted twice with dichloromethane. The organic phases were combined, dried over anhydrous sodium sulfate, filtered and the filtrate was evaporated to give 29-c (470 mg, 98%).

Synthesis of Compound 29-b

LHMDS (1M in THF, 4.0 mL, 4.00 mmol) was added slowly dropwise to a reaction flask charged with 29-c (470 mg, 2.73 mmol) and anhydrous tetrahydrofuran (5 mL) at −78° C. The reaction mixture was stirred at −78° C. for 1 hour, then was added a solution of N-phenylbis(trifluoromethanesulfonyl)imide (1300 mg, 3.64 mmol) in anhydrous tetrahydrofuran (5 mL) slowly dropwise at −78° C. The reaction mixture was stirred at −78° C. to room temperature for 2 hours, then was placed in refrigerator overnight. The reaction mixture was added ethyl acetate and petroleum ether, washed twice with water, washed with 5% aqueous sodium bicarbonate, washed with brine, dried over anhydrous sodium sulfate, filtered, and the filtrate was evaporated to obtain 29-b (830 mg, 100%).

Synthesis of Compound 29-a

A solution of pinacol ester of bisboronic acid (860 mg, 3.39 mmol), $Pd(dppf)Cl_2$—$CH_2Cl_2$ (100 mg, 0.12 mmol), potassium acetate (800 mg, 8.15 mmol), and 29-b (830 mg, 2.73 mmol) in 1,4-dioxane (10 mL) in a microwave tube were degassed and purged with nitrogen for three times, then sealed, and stirred at 90° C. for 5 hours. The reaction mixture was cooled to room temperature, added ethyl acetate and petroleum ether, washed with water and brine, dried over anhydrous sodium sulfate, filtered, and the filtrate was evaporated, and the residue was purified by column chromatography (mobile phase: petroleum ether/ethyl acetate, 100/0 to 90/10) to obtain 29-a (440 mg, 57%).

Synthesis of Compound 29

A microwave tube charged with 29-a (153 mg, 0.54 mmol), I-4 (200 mg, 0.41 mmol), $Pd(dtbpf)Cl_2$ (28 mg, 0.043 mmol), cesium fluoride (180 mg, 1.19 mmol), 1,4-dioxane (8 mL) and water (2 mL) was degassed and purged with nitrogen for 3 times, then sealed and stirred at 100° C. for 3.5 hours. The reaction mixture was cooled to room temperature, was added supplemental $Pd(dtbpf)Cl_2$ (50 mg, 0.077 mmol), cesium fluoride (60 mg, 0.40 mmol) and 1,4-dioxane (2 mL). The reaction mixture was degassed and purged with nitrogen for 3 times, then sealed and stirred at 100° C. for 4 hours. The reaction mixture was cooled to room temperature, added into ice-cold water and extracted twice with ethyl acetate. The organic phases were combined, washed with brine, dried over anhydrous sodium sulfate, filtered, and the filtrate was evaporated, and purified by column chromatography (mobile phase: petroleum ether/ethyl acetate, 100/0 to 50/50) to obtain the crude product (130 mg). The crude (40 mg) was purified by Prep-HPLC (ammonium bicarbonate) to give 29 (18.5 mg, 8.0%). LC-MS (ESI): m/z 565.3 $(M+H)^+$; $^1$HNMR (DMSO-$d_6$, 400 MHz): δ 9.22 (1H, brs), 8.84 (1H, d, J=1.6 Hz), 7.87-7.52 (2H, m), 5.57-5.53 (1H, m), 4.24 (3H, s), 3.27-3.18 (1H, m), 3.13 (1H, h, J=6.8 Hz), 2.76-2.61 (1H, m), 2.50-2.47 (2H, m), 2.29-2.09 (2H, m), 1.89-1.75 (1H, m), 1.50-1.39 (2H, m), 1.33-1.29 (2H, m), 1.29-1.25 (6H, m).

Synthetic Route of Compounds 30&31

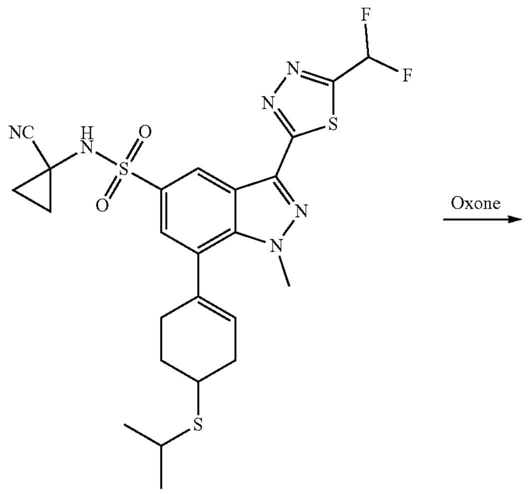

29

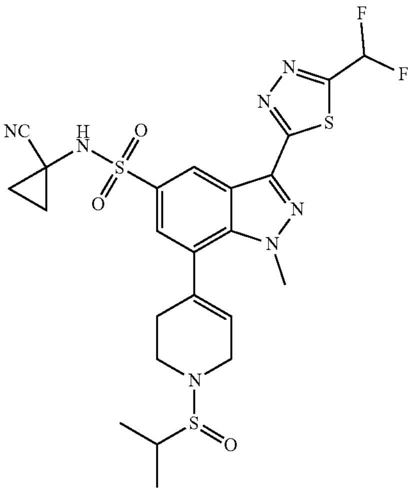

+

30

-continued

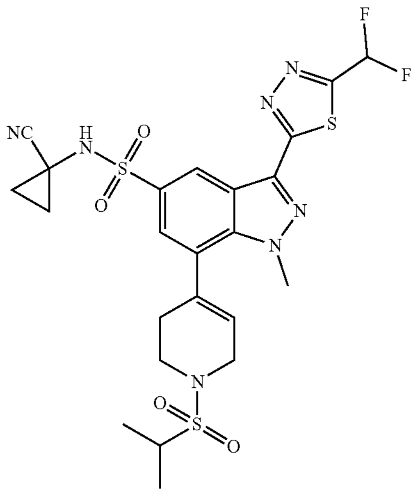

31

Synthesis of Compounds 30 and 31

In an ice-cold water bath, a reaction flask charged with 29 (85 mg, 0.15 mmol) and acetone (4 mL) was added a solution of oxone (60 mg, 0.098 mmol) in water (2 mL) dropwise. After addition, the reaction mixture was stirred in an ice-cold water bath for 1 hour and then stirred at room temperature for 1 hour. Supplemental oxone (5 mg, 0.008 mmol) was added and the reaction mixture was stirred at room temperature for 30 min. The reaction mixture was added ethyl acetate, washed with brine, dried over anhydrous sodium sulfate, filtered, and the filtrate was evaporated to dryness, and the residue was purified by Prep-HPLC purification (ammonium bicarbonate) to give 30 (25 mg, 29%) as a white solid and 31 (16 mg, 18%) as a white solid.

Compound 30, LC-MS (ESI): m/z 581.1 $(M+H)^+$; $^1$HNMR (DMSO-$d_6$, 400 MHz) δ 9.22 (1H, bs), 8.85 (1H, d, J=1.2 Hz), 7.88-7.51 (2H, m), 6.01-5.86 (1H, m), 4.23 (3H, s), 3.20-3.03 (2H, m), 2.98 (1H, p, J=6.8 Hz), 2.70-2.54 (2H, m), 2.38-2.07 (2H, m), 2.01-1.83 (1H, m), 1.48-1.38 (2H, m), 1.34-1.18 (8H, m).

Compound 31, LC-MS (ESI): m/z 597.1 $(M+H)^+$; $^1$HNMR (DMSO-$d_6$, 400 MHz) δ 9.16 (1H, bs), 8.86 (1H, d, J=1.2 Hz), 7.89-7.53 (2H, m), 5.99-5.85 (1H, m), 4.23 (3H, s), 3.79-3.65 (1H, m), 3.48 (1H, h, J=6.8 Hz), 2.72-2.53 (4H, m), 2.37-2.27 (1H, m), 2.00-1.83 (1H, m), 1.50-1.38 (2H, m), 1.35-1.25 (8H, m).

Synthetic Route of Compound 32

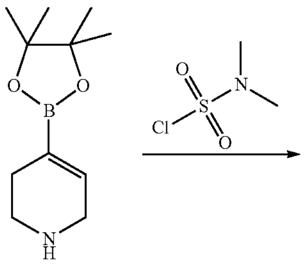

-continued

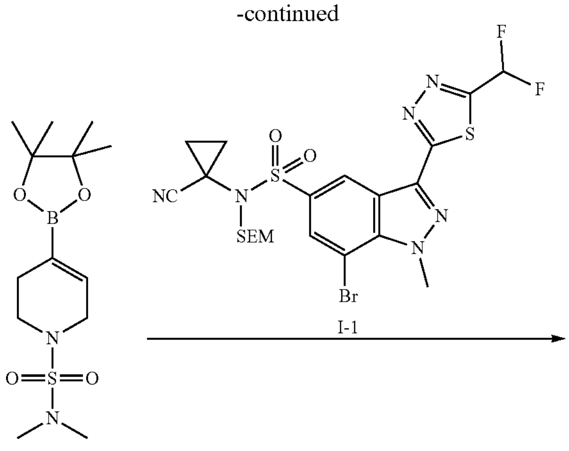

32-b

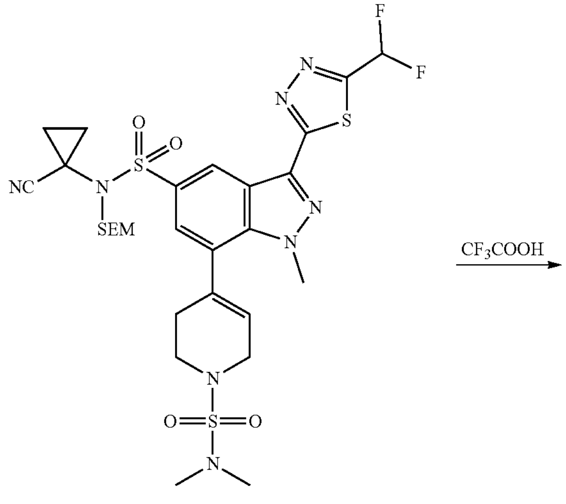

32-a

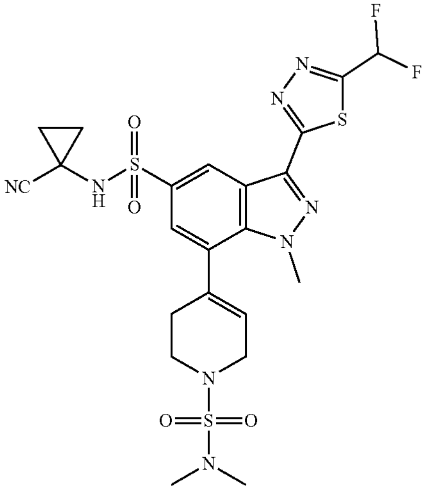

32

Synthesis of Compound 32-b 1,2,3,6-Tetrahydropyridine-4-boronic acid pinacol ester (80 mg, 0.38 mmol), triethylamine (728 mg, 7.19 mmol), and dimethylaminosulfonyl chloride (110 mg, 0.77 mmol), were added into dichloromethane (20 mL), and the mixture was stirred for 3 hours at room temperature. Washed with saturated sodium bicarbonate (30 mL) and the organic phase was concentrated to give compound 32-b (98 mg, 81%). LC-MS (ESI): m/z 317.0 (M+H)$^+$.

Synthesis of Compound 32-a 32-b (80 mg, 0.25 mmol), I-1 (46 mg, 0.07 mmol), potassium carbonate (124 mg, 0.90 mmol) and $PdCl_2$(dppf) $\cdot CH_2Cl_2$ (18 mg, 0.02 mmol) were combined in a microwave tube, followed by addition of 1,4-dioxane (4 mL) and water (1 mL). Under nitrogen protection, the reaction mixture was sealed and stirred at 90° C. for 12 hours. The reaction mixture was concentrated at reduced pressure and the residue was purified by column chromatography (PE/EA=3/1, 1/1) to give compound 32-a (41 mg, 76n). LC-MS (ESI): m/z 729.1 (M+H)$^+$.

Synthesis of Compound 32

32-a (41 mg, 0.06 mmol) was added into a reaction flask, followed by dichloromethane (3 mL) and trifluoroacetic acid (1 mL). Protected by nitrogen, the mixture was stirred at room temperature for 2 hours. The reaction mixture was concentrated at reduced pressure, and the residue was added supplemental solid potassium carbonate (3 g) and water (10 mL), followed by the addition of ethyl acetate (10 mL) to a reaction flask and the mixture was stirred at room temperature for 2 hours. The reaction mixture was extracted with ethyl acetate (10 mL*3) and purified by Prep-HPLC to afford compound 32 (18.3 mg, 54%). LC-MS (ESI): m/z 599.1 (M+H)$^+$.

Synthetic Route of Compound 33

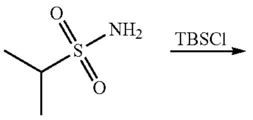

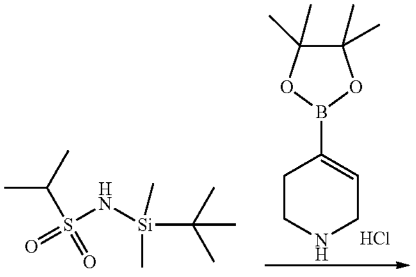

33-b

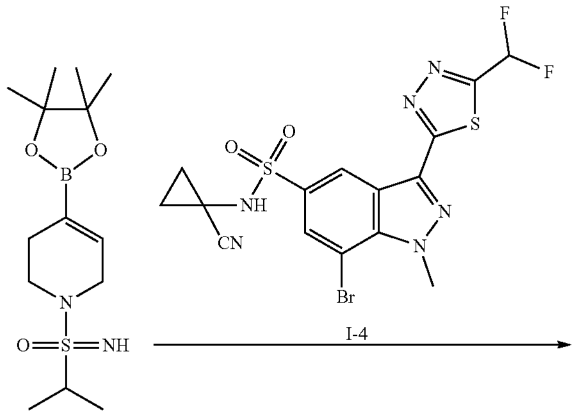

33-a

-continued

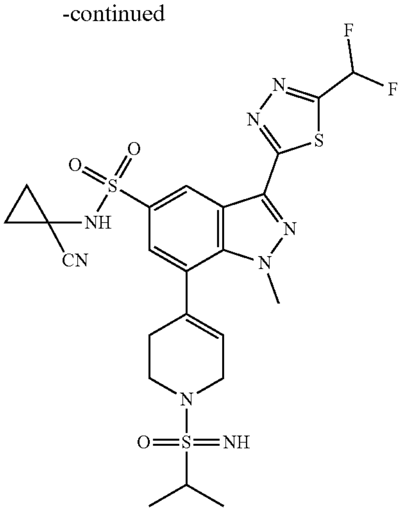

33

Synthesis of Compound 33-b

At room temperature, compound isopropylsulfonamide (1.0 g, 8.12 mmol) was dissolved in 15 mL of chloroform and tert-butyldimethylchlorosilane (1.84 g, 12.18 mmol) was added to the above mixture. The resulting mixture was cooled in an ice-cold water bath and was slowly added triethylamine (1.69 mL, 12.18 mmol) dropwise. Upon completion of the dropwise addition, the reaction mixture was warmed to room temperature and stirred overnight. The reaction mixture was concentrated at reduced pressure, and the residue was dissolved in 100 mL of ethyl acetate, washed sequentially with water (100 mL), brine (100 mL). The organic phase was dried over anhydrous sodium sulfate, filtered, and the filtrate was concentrated at reduced pressure to give compound 33-b (1.68 g, 87%). LC-MS (ESI): m/z=238.1[M+H]$^+$; $^1$HNMR (DMSO-$d_6$, 400 MHz) δ 6.75 (1H, s), 3.03-2.96 (1H, m), 1.21 (6H, d, J=6.8 Hz), 0.89 (9H, s), 0.14 (6H, s).

Synthesis of Compound 33-a

Compound dichlorotriphenylphosphorane (814 mg, 2.44 mmol) was dissolved in 10 mL of chloroform at room temperature, then in an ice-cold water bath, the mixture was added triethylamine (0.46 mL, 3.30 mmol) dropwise. Upon completion of the dropwise addition, the reaction mixture was warmed to room temperature and stirred for 10 min. The reaction mixture was cooled in an ice-cold water bath and was added a mixed solution of compound 33-b (600 mg, 2.53 mmol) in chloroform (5 mL) to the above reaction mixture and stirred in an ice-cold water bath for 20 minutes. A solution of compound 1,2,3,6-tetrahydropyridine-4-boronic acid pinacol ester hydrochloride (200 mg, 0.81 mmol) in chloroform (5 mL) and triethylamine (0.17 mL, 1.22 mmol) was added to the above reaction mixture in an ice-cold water bath, and after addition, the reaction mixture was warmed to room temperature and stirred overnight. The reaction mixture was concentrated at reduced pressure and the residue was purified by a flash column chromatography (DCM/MeOH=10:1) to give the crude compound 33-a (256 mg). The crude product was used directly in the next reaction without further purification. LC-MS (ESI): m/z=315.1[M+H]$^+$.

Synthesis of Compound 33

A solution of compound I-4 (100 mg, 0.20 mmol) in 36 mL of 1,4-dioxane at room temperature was added compound 33-a (96 mg, 0.31 mmol), 1,1'-di-tert-butylphosphinoferrocene palladium dichloride (27 mg, 0.041 mmol), cesium fluoride (93 mg, 0.61 mmol) and water (4 mL). The reaction mixture was stirred at 100° C. under nitrogen protection for 6 hours. The reaction mixture was cooled to room temperature, concentrated at reduced pressure, and the residue was added 100 mL of water and extracted with ethyl acetate (100 mL*2). The organic phase was dried over anhydrous sodium sulfate, filtered and the filtrate was concentrated at reduced pressure to give the crude product. The crude product was purified by Prep-HPLC (basic method, $NH_4HCO_3$) to give compound 33 (15 mg, 13%). LC-MS (ESI): m/z=597.2 [M+H]$^+$; $^1$HNMR ($CDCl_3$, 400 MHz) δ 9.05 (1H, d, J=2.0 Hz), 7.75 (1H, d, J=1.6 Hz), 7.10 (1H, t, J=54.0 Hz), 6.34 (1H, s), 5.99-5.93 (1H, m), 4.21 (3H, s), 4.18-4.12 (2H, m), 3.78-3.66 (2H, m), 3.42-3.31 (1H, m), 2.67-2.54 (2H, m), 1.67-1.60 (2H, m), 1.48-1.37 (8H, m).

Synthetic Route of Compound 34

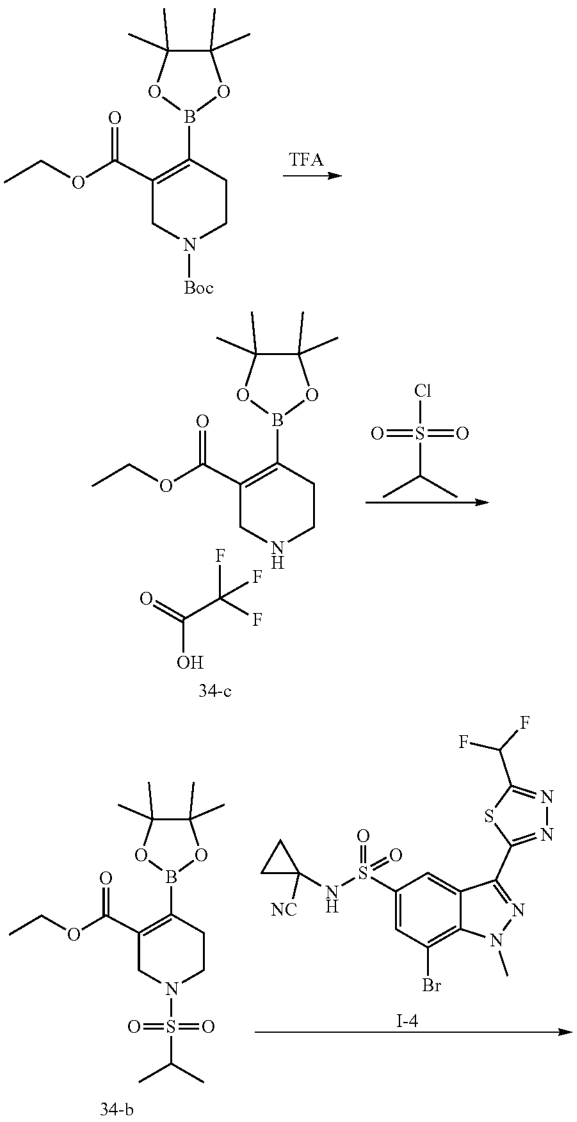

-continued

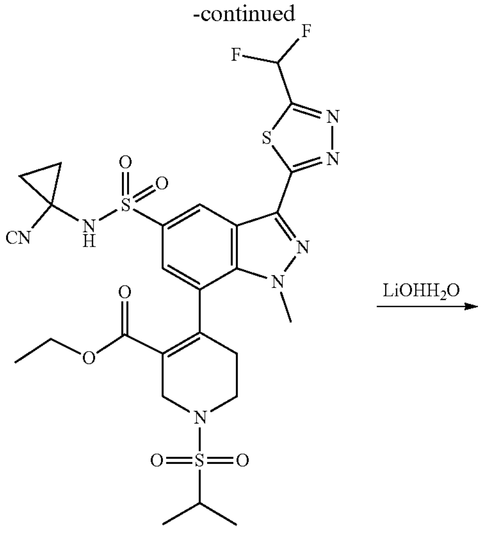

34-a

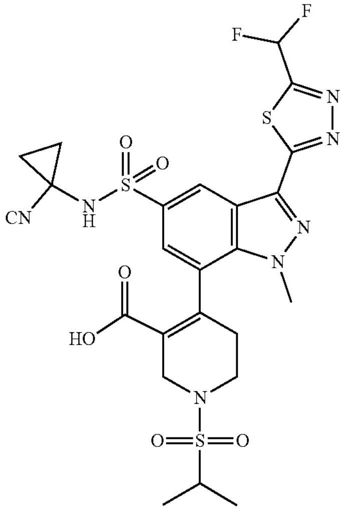

34

Synthesis of Compound 34-c

Trifluoroacetic acid (3 mL) was added dropwise to a reaction vial charged with ethyl N-Boc-1,2,5,6-tetrahydropyridine-4-boronic acid pinacol ester-3-carboxylate (300 mg, 0.79 mmol) and dichilоromethane (10 mL) at room temperature. Upon completion of the dropwise addition, the reaction mixture was stirred at room temperature for 4 hours. Upon completion, the solvent was removed by concentration at reduced pressure at room temperature to give the crude compound 34-c (300 mg, 96%). LC-MS (ESI): m/z 281.8 $[M+H]^+$.

Synthesis of Compound 34-b

In an ice-cold water bath, a reaction flask charged with 34-c (300 mg, 0.76 mmol), dichiloromethane (10 mL) and triethylamine (0.53 mL, 3.80 mmol) was added isopropylsulfonyl chloride (0.17 mL, 1.52 mmol) dropwise. Upon completion of the dropwise addition, the reaction mixture was stirred at room temperature for 2 hours. Upon completion, the reaction mixture was quenched with water, extracted with dichiloromethane, and the organic phase was washed with brine, dried over anhydrous sodium sulfate, and the filtrate was concentrated at reduced pressure to obtain the crude product, which was purified by a flash column chromatography (mobile phase: methanol/dichloromethane: 0% to 10%) to give compound 34-b (250 mg, 85%). LC-MS (ESI): m/z=388.4 $[M+H]^+$.

Synthesis of Compound 34-a

A reaction vial charged with I-4 (250 mg, 0.51 mmol), 34-b (238 mg, 0.61 mmol), [1,1'-bis(di-tert-butylphosphino) ferrocene]palladium dichloride (66 mg, 0.10 mmol), cesium fluoride (233 mg, 1.53 mmol), 1,4-dioxane (18 mL) and $H_2O$ (2 mL) was degassed and purged with nitrogen for 3 times, then stirred at 100° C. for 5 hours. Upon completion, the reaction mixture was cooled to room temperature, concentrated at reduced pressure to remove the organic solvent. The residue was diluted with ethyl acetate, and the organic phase was washed with water, brine, dried over anhydrous sodium sulfate, filtered, and the filtrate was concentrated at reduced pressure to obtain the crude product. The crude product was purified by a flash column chromatography (mobile phase: ethyl acetate/petroleum ether: 0% to 100%) to give compound 34-a (250 mg, 73%). LC-MS (ESI): m/z=670.5 [M+H]+.

Synthesis of Compound 34

34-a (100 mg, 0.15 mmol) was dissolved in THF (5 mL) and water (5 mL), then $LiOH \cdot H_2O$ (25 mg, 0.60 mmol) was added to the above mixture. After addition, the reaction mixture was stirred at room temperature for 4 hours. Upon completion, the reaction mixture was neutralized with diluted hydrochloric acid, concentrated at reduced pressure to remove the organic solvent, and the residue was extracted with ethyl acetate. The organic phase was washed with brine, dried over anhydrous sodium sulfate, filtered and the filtrate was concentrated at reduced pressure to obtain the crude product. The crude product was purified by Prep-HPLC to give compound 34 (35 mg, 37%). LC-MS (ESI): m/z 642.2 $[M+H]^+$; $^1$HNMR (DMSO-$d_6$, 400 MHz): δ 8.78 (1H, s), 7.71 (1H, t, J=53.2 Hz), 7.50 (1H, s), 4.17 (3H, s), 4.08-4.34 (2H, m), 3.58-3.69 (1H, m), 3.43-3.56 (2H, m), 2.49-2.59 (2H, m), 1.34-1.41 (2H, m), 1.30 (6H, dd, J=6.8, 1.2 Hz), 1.13-1.20 (2H, m).

Synthetic Route of Compound 35

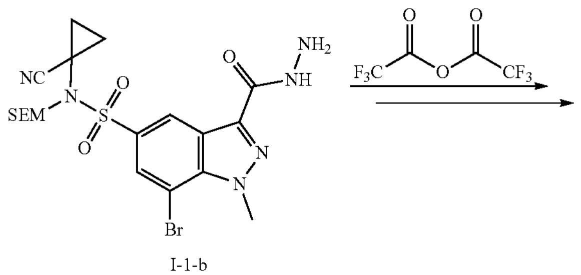

I-1-b

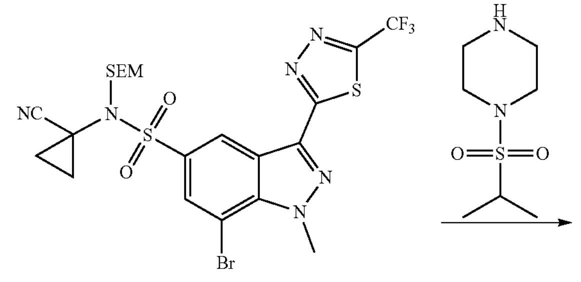

35-b

-continued

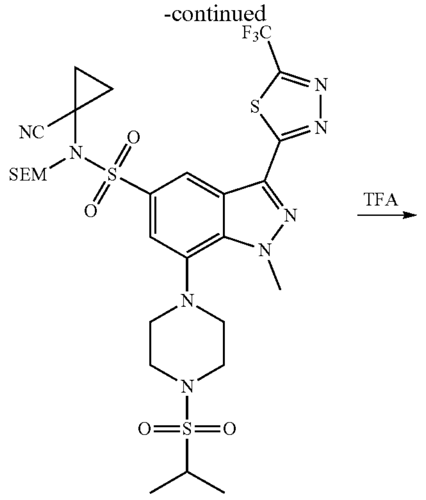

35-a

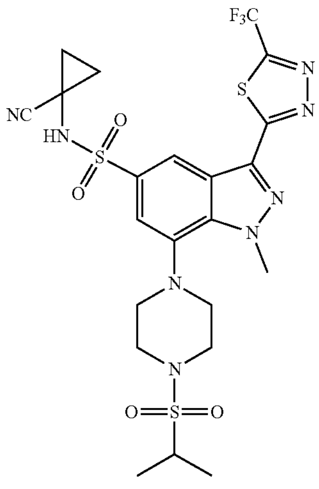

35

Synthesis of Compound 35-b

Referring to the Synthetic route of intermediate I-1, compound 35-b was obtained by using trifluoroacetic anhydride instead of difluoroacetic anhydride and using I-1-b as starting material.

Synthesis of Compound 35-a

A microwave tube charged with 35-b (50 mg, 0.08 mmol), 1-(isopropylsulfonyl)piperazine (30 mg, 0.16 mmol), Ruphos (4 mg, 0.008 mmol), cesium carbonate (77 mg, 0.24 mmol) and (SP-4-1)-[1,3-bis[2,6-bis(1-ethylpropyl)phenyl]-4,5-dichloro-1,3-dihydro-2H-imidazol-2-ylidene]dichloro (3-chloropyridine-KN)palladium (14 mg, 0.02 mmol) was degassed and purged with nitrogen for three times, then was added 1,4-dioxane (1.5 mL) and degassed and purged with for three more times, sealed. The reaction mixture was stirred at 88° C. for 12 hours. The reaction mixture was concentrated at reduced pressure, and the residue was extracted with dichloromethane (5 mL*2), filtered. The dichloromethane phase was concentrated at reduced pressure, and purified by column chromatography (methanol/dichloromethane=0/100; 1/10) to afford compound 35-a (28 mg, 48%). LC-MS (ESI): m/z 749.3 $(M+H)^+$.

Synthesis of Compound 35

35-a (28 mg, 0.04 mmol), dichloromethane (3 mL), trifluoroacetic acid (1 mL) were added into a reaction vial and the mixture was stirred at room temperature for 2 h under nitrogen protection. The reaction mixture was concentrated at reduced pressure, and the residue was added potassium carbonate (3 g), water (20 mL) and ethyl acetate (20 mL), and the mixture was stirred at room temperature for 2 hours. The mixture was extracted with ethyl acetate (20 mL*2), and the organic phase was concentrated at reduced pressure and the residue was purified by Prep-HPLC to give compound 35 (6.1 mg, 26%). LC-MS (ESI): m/z 619.2 $(M+H)^+$.

Synthetic Route of Compound 36

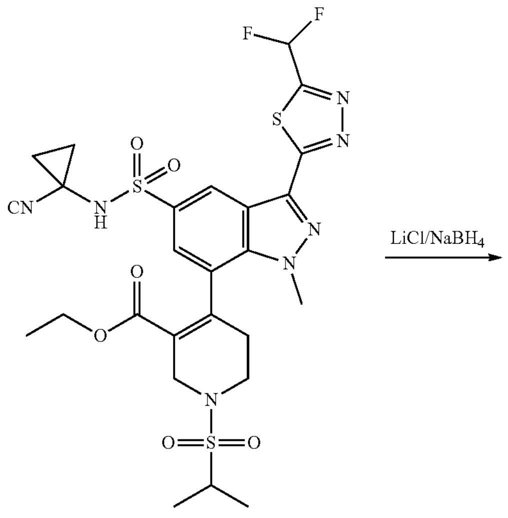

34-a

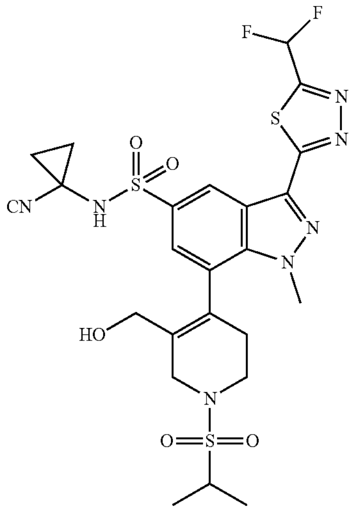

36

Synthesis of Compound 36

To a solution of 34-a (100 mg, 0.16 mmol) in THF (10 mL) and ethanol (5 mL) was added LiCl (63 mg, 1.49 mmol) and $NaBH_4$ (56 mg, 1.49 mmol) sequentially in an ice-cold water bath. After addition, the reaction mixture was warmed to room temperature and stirred for 10 min, then stirred at 50° C. for 4 h. Upon completion, the reaction mixture was cooled to room temperature and was quenched carefully by the addition of water. The residue was extracted with ethyl acetate, washed with brine, dried over anhydrous sodium sulfate, filtered and the filtrate was concentrated at reduced pressure to give the crude product. The crude was purified by Prep-HPLC to give compound 36 (15 mg, 15%). LC-MS (ESI): m/z 628.2 [M+H]$^+$.

Synthetic Route of Compound 37

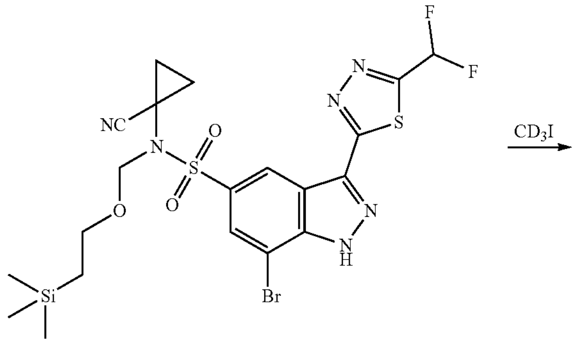

I-2

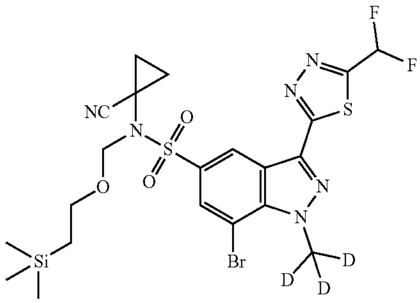

37-b

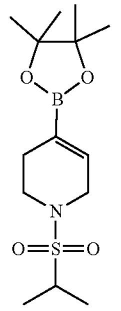

I-3

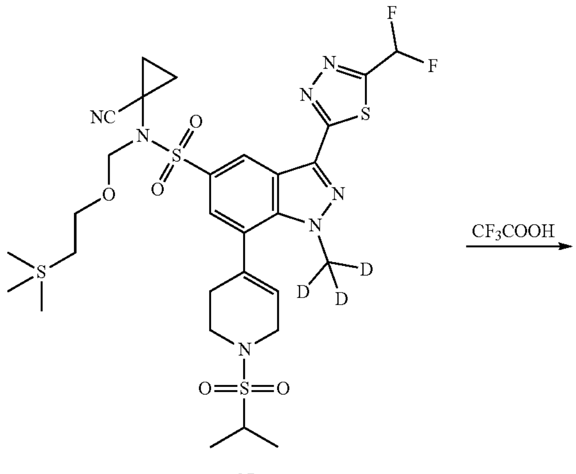

37-a

-continued

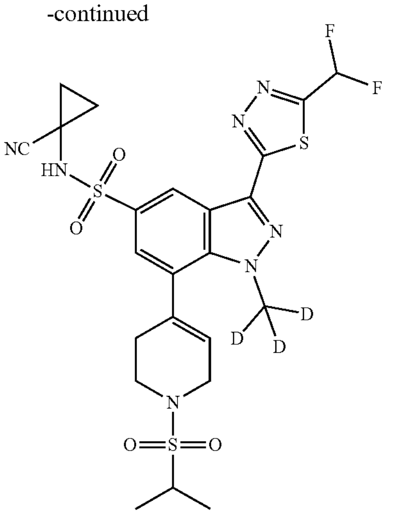

37

Synthesis of Compound 37-b

Potassium carbonate (650 mg, 4.70 mmol) was added to a solution of compound I-2 (950 mg, 1.57 mmol) in 20 mL of DMF at room temperature. Cooled in an ice-cold water bath, the mixture was added deuterated iodomethane (146 uL, 2.35 mmol) dropwise. Upon completion of the dropwise addition, the reaction mixture was continued stirring in an ice-cold water bath for 3 hours. The reaction mixture was added 100 mL of water, and the mixture was extracted with ethyl acetate (80 mL*2). The organic phase was washed with brine (100 mL*5), dried over anhydrous sodium sulfate, filtered, and the filtrate was concentrated at reduced pressure. The residue was purified by a flash column chromatography (PE/EA=2:1) to give compound 37-b (538 mg, 55%). LC-MS (ESI): m/z=622.0 [M+H]$^+$.

Synthesis of Compound 37-a

To a solution of compound 37-b (76 mg, 0.12 mmol) in 20 mL of 1,4-dioxane at room temperature was added water (2 mL), compound I-3 (50 mg, 0.16 mmol), [1,1-bis(diphenylphosphino)ferrocene]palladium dichloride (18 mg, 0.024 mmol) and potassium carbonate (51 mg, 0.37 mmoL), and the reaction mixture was stirred at 100° C. under nitrogen protection for 18 hours. The reaction mixture was cooled to room temperature, was added 50 mL of water, extracted with ethyl acetate (50 mL*2). The organic phase was dried over anhydrous sodium sulfate, filtered and the filtrate was concentrated at reduced pressure. The residue was purified by a flash column chromatography (PE/EA=1:1) to give compound 37-a (75 mg, 85%). LC-MS (ESI): m/z=731.1 [M+H]$^+$.

Synthesis of Compound 37

A solution of compound 37-a (75 mg, 0.10 mmoL) in 6 mL of dichloromethane at room temperature was added trifluoroacetic acid (2 mL), and the reaction mixture was stirred at room temperature under nitrogen protection for 1.5 h. The reaction mixture was concentrated at reduced pressure and the residue was suspended in 5 mL of saturated sodium bicarbonate, was added potassium carbonate (500 mg), and ethyl acetate (50 mL). The reaction mixture was stirred at room temperature for 30 min, then was added 50 mL of water and extracted with ethyl acetate (100 mL). The organic phase was dried over anhydrous sodium sulfate, filtered, and the filtrate was concentrated at reduced pressure, and the residue was purified by Prep-HPLC ($NH_4HCO_3$) to give the crude product. The crude product was further purified by prep-TLC (DCM/MeOH=40:1, 2 times) to give compound 37 (23.8 mg, 40%). LC-MS (ESI): m/z=601.1 $[M+H]^+$; $^1H$ NMR ($CDCl_3$, 400 MHz): δ 9.07 (1H, s), 7.75 (1H, s), 7.10 (1H, t, J=53.6 Hz), 6.04 (1H, s), 5.96 (1H, s), 4.12 (2H, s), 3.74-3.63 (2H, m), 3.33-3.26 (1H, m), 2.66-2.56 (2H, m), 1.68-1.61 (4H, m), 1.42 (6H, d, J=6.8 Hz).

Synthetic Route of Compound 38

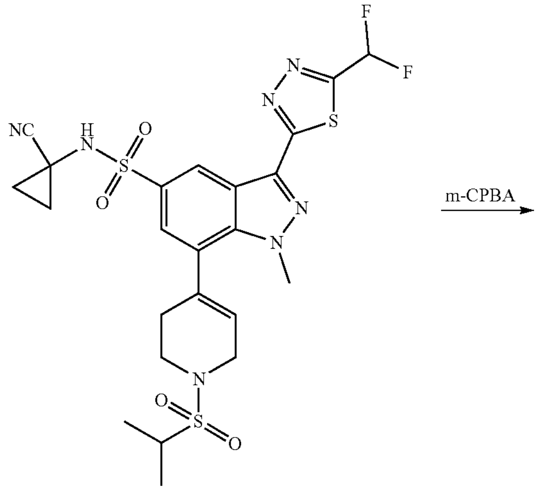

17-a

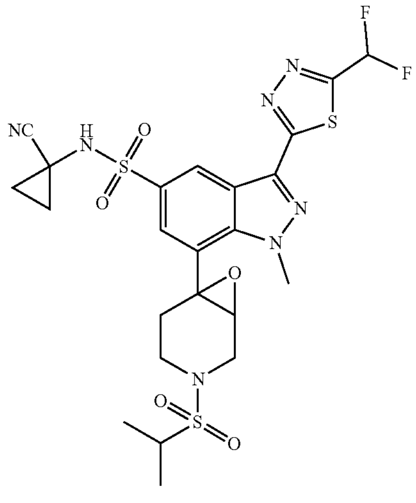

38

Synthesis of Compound 38

17-a (50 mg, 0.084 mmol) and dichloromethane (5 mL) were added into a reaction flask. m-CPBA (18 mg, 0.10 mmol) was added to the above mixture in an ice-cold water bath. The reaction mixture was stirred for 18 hours at room temperature. Supplemental m-CPBA (50 mg, 0.29 mmol) was added and continued stirring at room temperature for 48 hours. The solvent was removed and the residue was dissolved in ethyl acetate, added saturated aqueous sodium bicarbonate and anhydrous sodium sulfate solid. The liquid was partitioned, and the aqueous phase was extracted once with ethyl acetate. The organic phases were combined, dried over anhydrous sodium sulfate, filtered, and the filtrate was evaporated and the crude was purified by Prep-HPLC (ammonium bicarbonate) to give 38 (12 mg, 23%). LC-MS (ESI): m/z 614.1 $(M+H)^+$; $^1$HNMR (DMSO-$d_6$, 400 MHz): δ 8.92 (1H, bs), 8.91 (1H, s), 7.98 (1H, s), 7.71 (1H, t, J=53.2 Hz), 4.42 (3H, s), 4.16-4.01 (1H, m), 3.88 (1H, s), 3.79 (1H, d, J=14.4 Hz), 3.52-3.43 (2H, m), 3.33-3.26 (1H, m), 2.44-2.12 (2H, m), 1.47-1.38 (2H, m), 1.33-1.20 (8H, m).

Synthetic Route of Compound 39

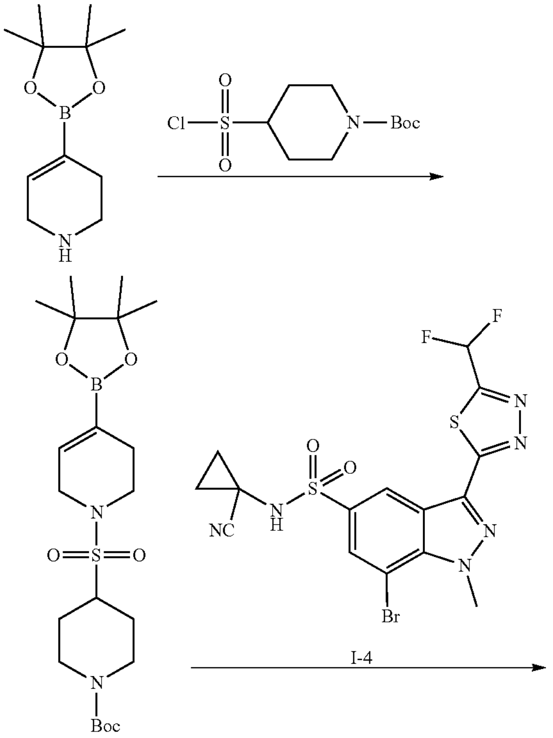

39-b

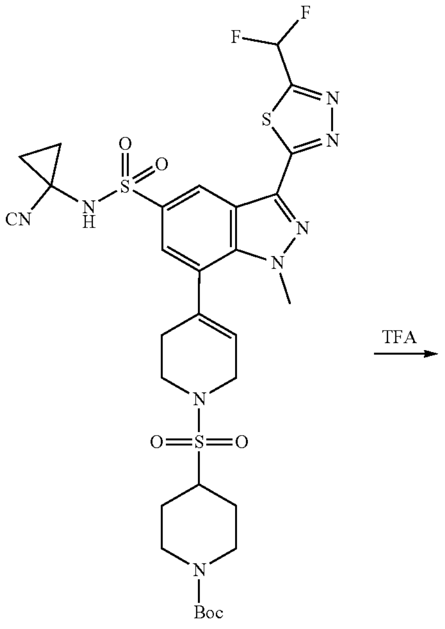

39-a

-continued

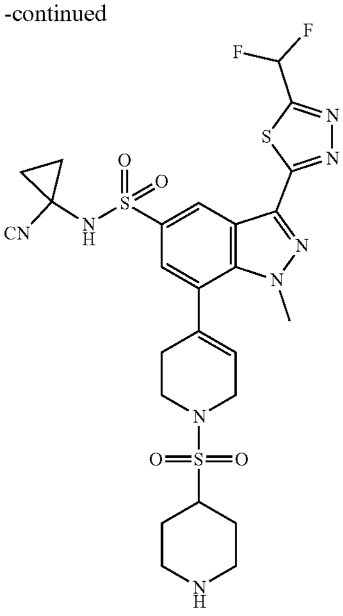

39

Synthesis of Compound 39-b

In an ice-cold water bath, a reaction flask charged with 1,2,3,6-tetrahydropyridine-4-boronic acid pinacol ester (250 mg, 1.20 mmol), dichloromethane (10 mL) and triethylamine (0.83 mL, 5.98 mmol) was added tert-butyl 4-chlorosulfonylpiperidine-1-carboxylate (0.39 mL, 1.79 mmol) dropwise. After the dropwise addition, the reaction mixture was stirred at room temperature for 2 hours. Upon completion, the reaction mixture was quenched with water, extracted with dichloromethane, and the organic phase was washed with brine, dried over anhydrous sodium sulfate, and the filtrate was concentrated at reduced pressure to give compound 39-b (500 mg, 92%). LC-MS (ESI): m/z=457.2 $[M+H]^+$.

Synthesis of Compound 39-a

A reaction flask charged with I-4 (50 mg, 0.10 mmol), 39-b (93 mg, 0.20 mmol), [1,1'-bis(di-tert-butylphosphino) ferrocene]palladium dichloride (13 mg, 0.020 mmol), cesium fluoride (47 mg, 0.31 mmol), 1,4-dioxane (9 mL) and $H_2O$ (1 mL) was degassed and purged with nitrogen for 3 times, and the reaction mixture was stirred at 100° C. for 5 hours. Upon completion, the reaction mixture was cooled to room temperature, concentrated at reduced pressure to remove the organic solvent. The residue was diluted by adding ethyl acetate to, and the organic phase was washed with water and brine, dried over anhydrous sodium sulfate, filtered and the filtrate was concentrated at reduced pressure to obtain the crude product. The crude product was purified by a flash column chromatography (mobile phase: ethyl acetate/petroleum ether: 0% to 100%) to obtain compound 39-a (50 mg, 66%). LC-MS (ESI): m/z=739.3 $[M+H]^+$.

Synthesis of Compound 39

A reaction vial charged with 39-a (50 mg, 0.068 mmol) and dichloromethane (10 mL) was added trifluoroacetic acid (3 mL) dropwise at room temperature. Upon completion of the dropwise addition, the reaction mixture was stirred at room temperature for 4 hours. Upon completion, the solvent was removed at reduced pressure at room temperature. The residue was diluted with ethyl acetate, and the organic phase was washed with saturated sodium bicarbonate, brine, dried over anhydrous sodium sulfate, filtered and the filtrate was evaporated to obtain the crude product, which was purified by Prep-HPLC to give compound 39 (25 mg, 58%). LC-MS (ESI): m/z 639.2 $[M+H]^+$.

Synthetic Route of Compound 40

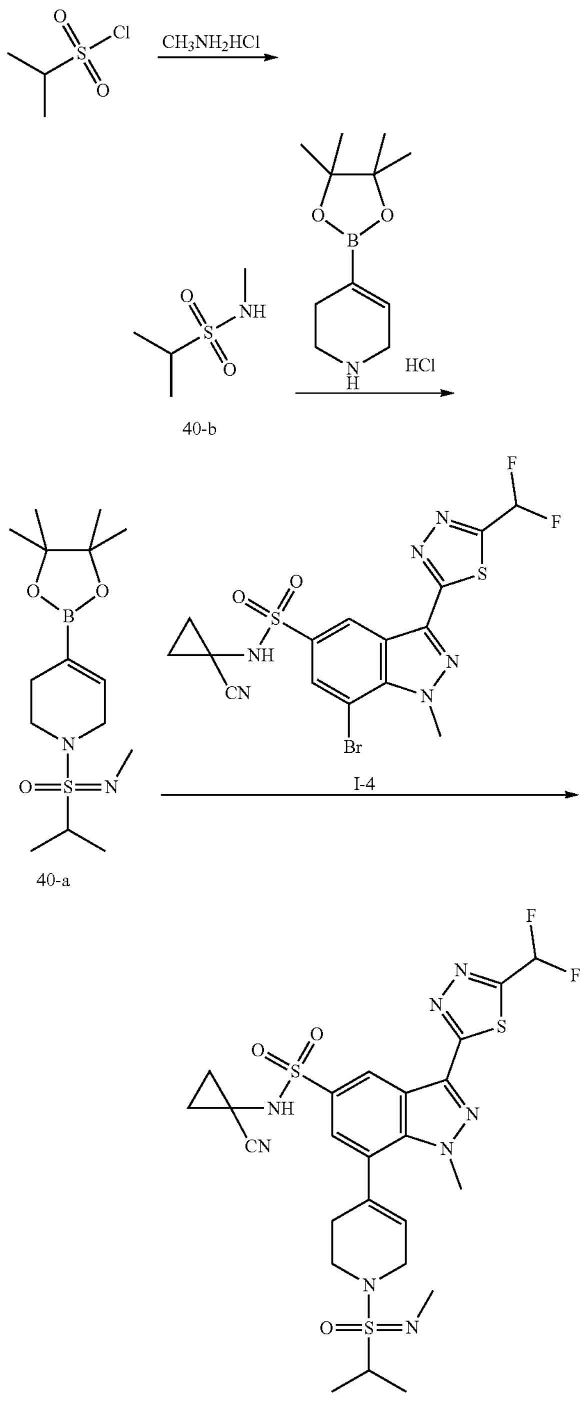

40-b 40-a

40

Synthesis of Compound 40-b

In an ice-cold water bath, a solution of isopropylsulfonyl chloride (1.0 g, 7.01 mmol) in 30 mL of dichloromethane was added methylamine hydrochloride (947 mg, 14.03 mmol). The mixture was stirred in an ice-cold water bath for 10 minutes, and then was slowly added triethylamine (4.87 mL, 35.06 mmol) dropwise. Upon completion of the dropwise addition, the reaction mixture was warmed to room temperature and stirred overnight. The reaction mixture was added 100 mL of water, extracted with dichloromethane (100 mL), and the organic phase was washed sequentially with 10% sodium bisulfate solution (100 mL), saturated sodium bicarbonate solution (100 mL), dried over anhydrous sodium sulfate, filtered, and the filtrate was concentrated at room temperature at reduced pressure to afford compound 40-b (208 mg, 22%). LC-MS (ESI): m/z=138.0 $[M+H]^+$.

Synthesis of Compound 40-a

Compound dichlorotriphenylphosphorane (488 mg, 1.47 mmol) was dissolved in 10 mL of chloroform at room temperature, then in an ice-cold water bath, the above mixture was added triethylamine (275 uL, 1.98 mmol) dropwise. Upon completion of the dropwise addition, the reaction mixture was warmed to room temperature and stirred for 10 min. The reaction mixture was cooled in an ice-cold water bath and was added a solution of compound 40-b (208 mg, 1.52 mmol) in chloroform (2 mL) and stirred in an ice-cold water bath for 20 minutes. A mixed solution of compound 1,2,3,6-tetrahydropyridine-4-boronic acid pinacol ester hydrochloride (120 mg, 0.49 mmol) in chloroform (5 mL) and triethylamine (102 uL, 0.73 mmol) was added to the above reaction mixture in an ice-cold water bath, and after addition, the reaction mixture was warmed to room temperature and stirred overnight. The reaction mixture was concentrated at reduced pressure and the residue was purified by a flash column chromatography (DCM/MeOH=10:1) to give the crude compound 40-a (160 mg). The crude product was used directly in the next step without further purification. LC-MS (ESI): m/z=329.2$[M+H]^+$.

Synthesis of Compound 40

Compound I-4 (100 mg, 0.20 mmol) was dissolved in 36 mL of 1,4-dioxane at room temperature and the above mixture was added compound 40-a (100 mg, 0.31 mmol), 1,1'-di-tert-butylphosphinoferrocene palladium dichloride (27 mg, 0.041 mmol), cesium fluoride (93 mg, 0.61 mmol), water (4 mL). The reaction mixture was stirred at 100° C. under nitrogen protection for 6 hours, then cooled to room temperature, concentrated at reduced pressure, and the residue was added 100 mL of water and extracted with ethyl acetate (100 mL*2). The organic phase was dried over anhydrous sodium sulfate, filtered and the filtrate was concentrated at reduced pressure to give the crude product. The crude product was purified by Prep-HPLC (basic method, $NH_4HCO_3$) to give compound 40 (3 mg, 2.4%). LC-MS (ESI): m/z=611.1 $[M+H]^+$.

Synthesis of Comparative Compound 1' comparative compound 1′

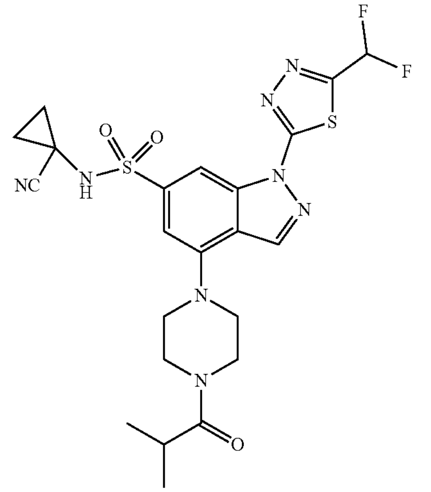

Comparative compound 1' was synthesized according to the method of WO2021055744A1.

Synthetic Route of Compound 41

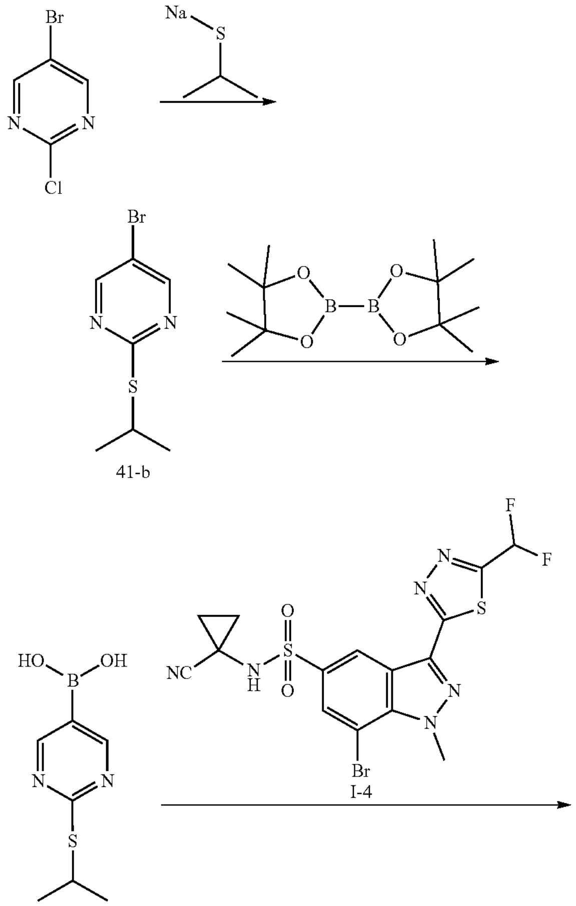

41-b

I-4

41-a

-continued

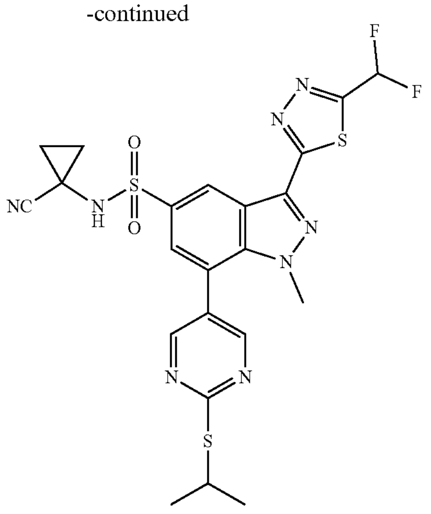

41

Synthesis of Compound 41-b

To a solution of compound 5-bromo-2-chloropyrimidine (1 g, 5.17 mmol) and sodium 2-propanethiol (760 mg, 7.74 mmol) in N,N-dimethylformamide (30 mL) was added potassium carbonate (1.43 g, 10.36 mmol). The reaction mixture was stirred at 50° C. for 2 hrs, then was added water (200 mL) and extracted with ethyl acetate (200 mL). The organic phase was washed with brine (200 mL), dried over sodium sulfate, filtered to remove the desiccant and the filtrate was concentrated at reduced pressure to obtain the crude product, which was purified by column chromatography (mobile phase, PE/EA 10/1) to obtain 41-b (1.12 g, 93%).

Synthesis of Compound 41-a

Compound 41-b (100 mg, 0.43 mmol) was dissolved in 1,4-dioxane (10 mL), to which were added bis(pinacolato) diboron (163 mg, 0.64 mmol), 1,1'-Bis(diphenylphosphino) ferrocene]dichloropalladium(II) (31 mg, 0.042 mmol) and potassium acetate (126 mg, 1.28 mmol). The reaction mixture was stirred at 85° C. under nitrogen protection for 12 hours, then was filtered through celite and the filtrate was concentrated at reduced pressure to give 41-a (80 mg, 94%). LC-MS (ESI): m/z 199.1 $(M+H)^+$.

Synthesis of Compound 41

Compound I-4 (200 mg, 0.41 mmol), 41-a (162 mg, 0.82 mmol), [1,1'-bis(di-tert-butylphosphino)ferrocene]palladium dichloride (53 mg, 0.082 mmol) and cesium fluoride (186 mg, 1.22 mmol) were added to 1,4-dioxane (27 mL) and water (3 mL) and the reaction mixture was degassed and purged with nitrogen for 3 times and then stirred at 100° C. for 6 hours. The reaction mixture was filtered through celite, and the filtrate was added water (100 mL), extracted with dichloromethane (100 mL). The organic phase was washed with brine (100 mL), dried over sodium sulfate, filtered off the desiccant and the filtrate was concentrated at reduced pressure to obtain the crude product, which was purified by column chromatography (mobile phase, PE/EA 1/1), and then part of the product was purified by Prep-HPLC (basic conditions) to obtain compound 41 (25 mg, 11%). LC-MS (ESI): m/z 563.2 $(M+H)^+$.

Synthetic Route of Compound 42

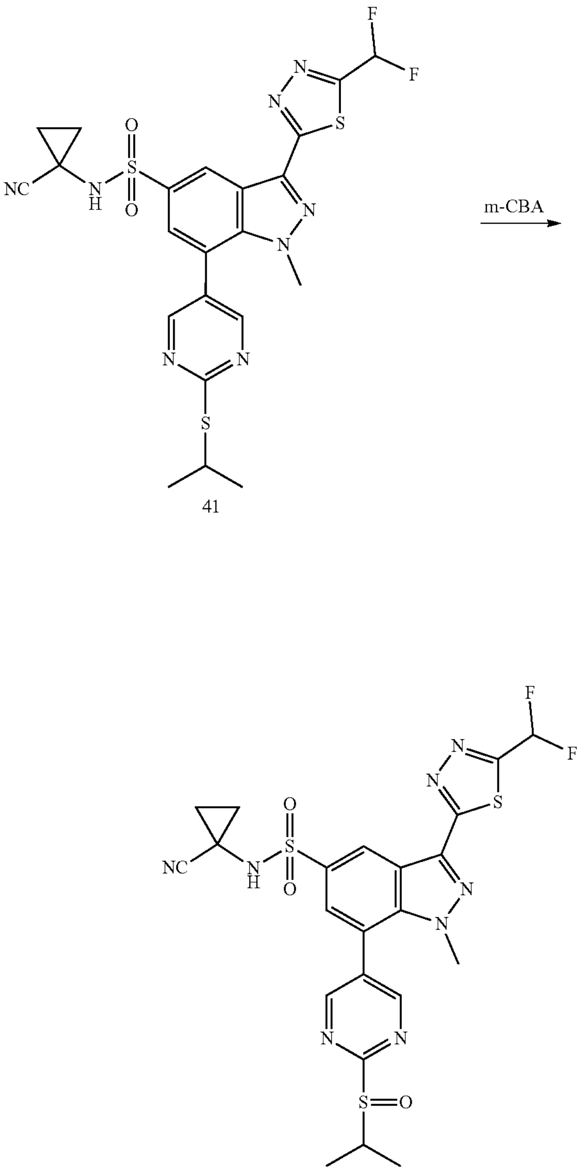

41

42

Synthesis of Compound 42

Compound 41 (50 mg, 0.089 mmol) was dissolved in dichloromethane (6 mL), to which m-chloroperoxybenzoic acid (20 mg, 0.12 mmol) was added, and the reaction mixture was stirred at room temperature for 2 h. After stirred for 2 h, the reaction mixture was added saturated sodium bicarbonate solution (10 mL), and the mixture was extracted with dichloromethane (50 mL), and the crude was obtained by concentration at reduced pressure, and the crude was purified by Prep-HPLC (basic conditions) to give compound 42 (13 mg, 25%). LC-MS (ESI): m/z 579.1 $(M+H)^+$.

Synthetic Route of Compound 43

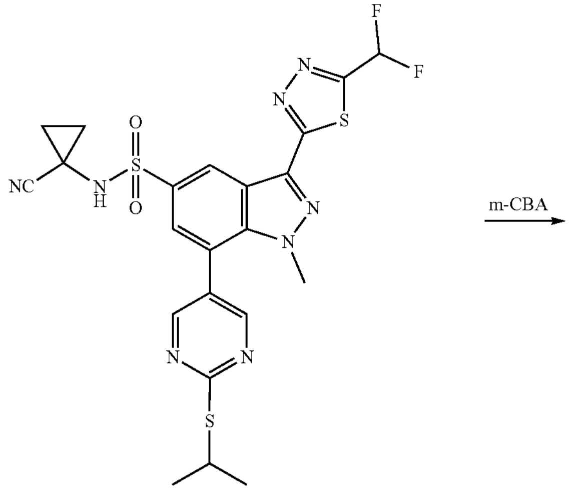

41

-continued

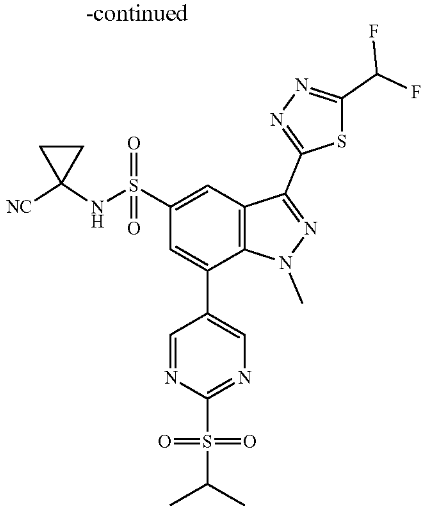

43

Synthesis of Compound 43

Compound 41 (100 mg, 0.18 mmol) was dissolved in dichloromethane (10 mL), to which m-chloroperoxybenzoic acid (90 mg, 0.52 mmol) was added, and the reaction mixture was stirred at room temperature for 2 h. After stirred for 2 h, the reaction mixture was added saturated sodium bicarbonate solution (50 mL), extracted with dichloromethane (50 mL), and the crude was obtained by concentration at reduced pressure, purified by Prep-HPLC (basic conditions) to give compound 43 (32 mg, 30%). LC-MS (ESI): m/z 595.1 $(M+H)^+$.

Synthetic Route of Compounds 44 and 45

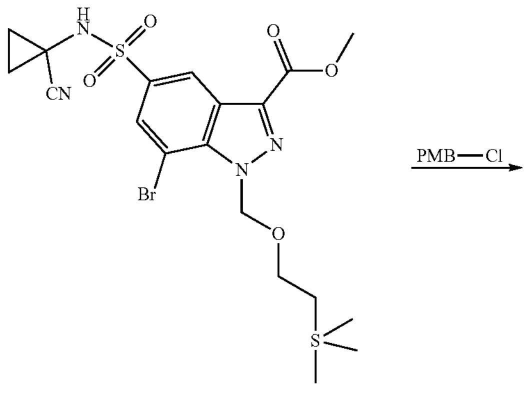

I-2-d

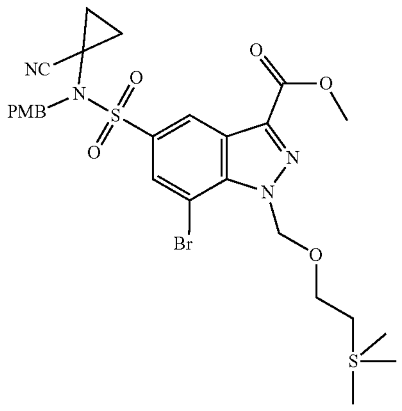

44-f-1

+

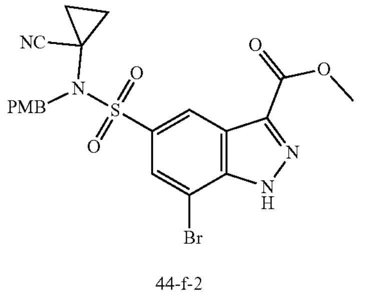

44-f-2

-continued
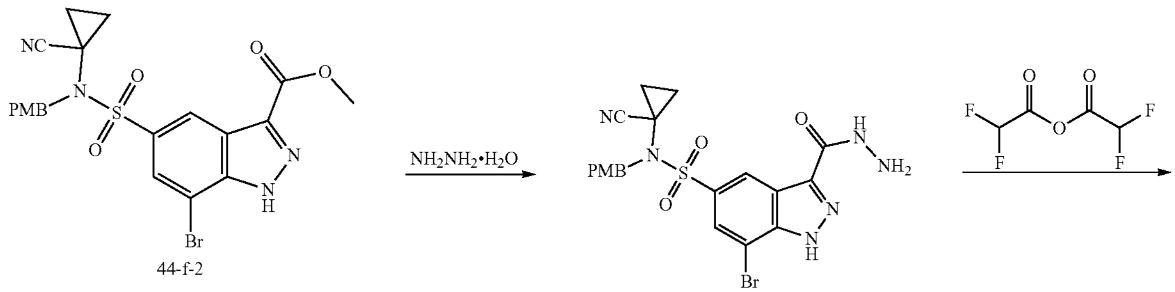
44-f-2 44-e
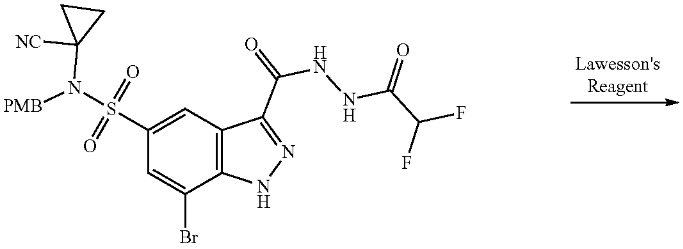
44-d
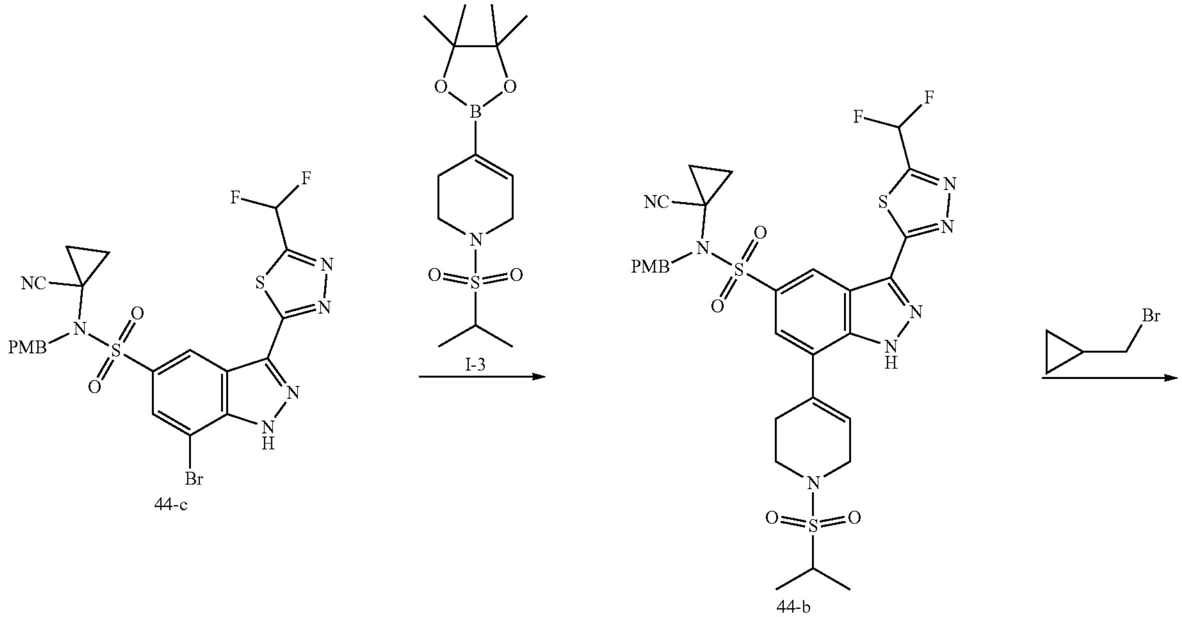
44-c 44-b

-continued

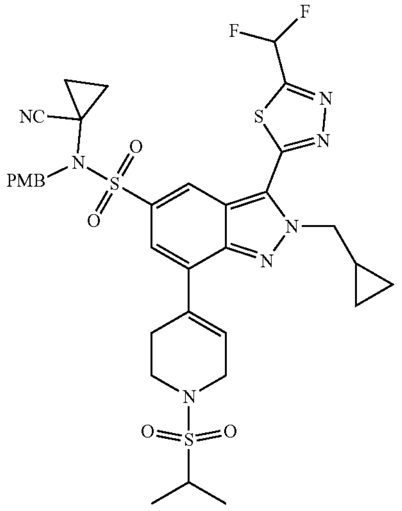

+

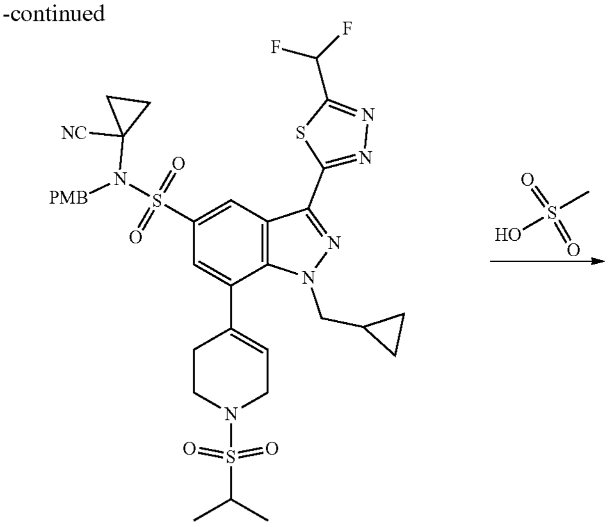

44-a

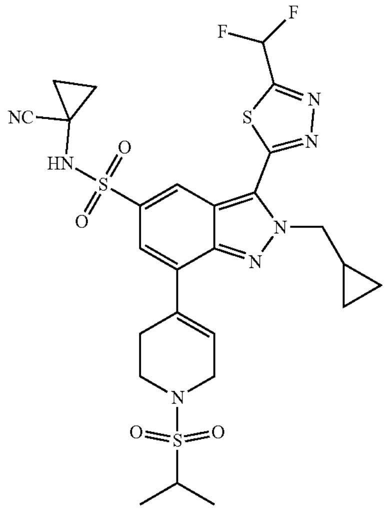

44

+

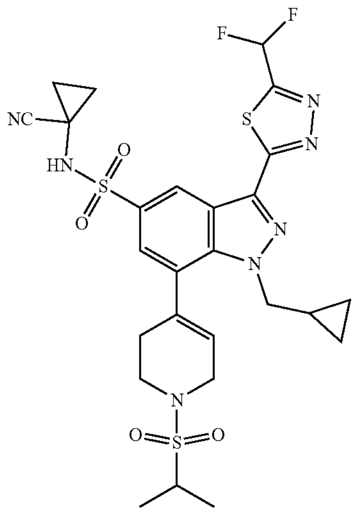

45

Synthesis of Compound 44-f-2

Potassium carbonate (3.26 g, 23.59 mmol) was added to a solution of compound J-2-d (5.0 g, 9.44 mmol) in DMIF (20 mL) at room temperature, the mixture was cooled in an ice-cold water bath and was added 4-methoxybenzyl chloride (1.93 mL, 14.17 mmol) dropwise. After the dropwise addition, the reaction mixture was stirred at room temperature overnight. The reaction mixture was added 100 mL of water, then extracted with ethyl acetate (100 mL*2). The organic phase was washed with brine (100 mL*5), dried over anhydrous sodium sulfate, filtered, and the filtrate was concentrated at reduced pressure, and the residue was purified by a flash column chromatography (PE/EA=1:1 to EA) to afford compound 44-f-1 (2.0 g, 33%), LC-MS (ESI): m/z=649.1 $[M+H]^+$; compound 44-f-2 (3.0 g, 61%). LC-MS (ESI): m/z=519.1 $[M+H]^+$.

Synthesis of Compound 44-e

At room temperature, compound 44-f-2 (3.0 g, 5.78 mmol) was dissolved in 30 mL of ethanol and hydrazine hydrate (3.0 mL, 59.93 mmol) was added. The reaction mixture was stirred under nitrogen protection at 60° C. for 3 hrs and then cooled to room temperature, concentrated at reduced pressure and the residue was dried at vacuum for 1 hr to give compound 44-e (3.0 g, 100%). LC-MS (ESI): m/z=519.0 $[M+H]^+$.

Synthesis of Compound 44-d

Compound 44-e (1.0 g, 1.93 mmol) was dissolved in 15 mL of DCM at room temperature and in an ice-cold water bath, triethylamine (0.80 mL, 5.78 mmol) was added and the reaction mixture was stirred in an ice-cold water bath for 10 min, then was added difluoroacetic anhydride (0.55 mL, 4.43 mmol) dropwise in an ice-cold water bath until the reaction mixture was clarified. After the dropwise addition, the reaction mixture was continued stirring in an ice-cold water bath for 30 minutes, then was added 5 mL of methanol and continued stirring for 10 minutes at the same temperature. The reaction mixture was concentrated at reduced pressure, and the residue was dissolved in 100 mL of ethyl acetate. The organic phase was washed sequentially with 10% $NaHSO_4$ solution (100 mL), saturated sodium bicarbonate solution (100 mL), brine (100 mL), dried over anhydrous sodium sulfate, filtered, and the filtrate was concentrated at reduced pressure to afford compound 44-d (1.15 g, 100%). LC-MS (ESI): m/z=597.1 $[M+H]^+$.

Synthesis of Compound 44-c

Compound 44-d (1.15 g, 1.93 mmol) was dissolved in 20 mL of anhydrous THF at room temperature, and Lawesson's reagent (1.95 g, 4.81 mmol) was added. The reaction mixture was stirred at 80° C. under nitrogen protection for 5 h. The reaction mixture was cooled to room temperature, concentrated at reduced pressure, and the residue was dissolved in 100 mL of ethyl acetate. The organic phase was washed sequentially with saturated sodium bicarbonate solution (100 mL), 10% $NaHSO_4$ solution (100 mL), brine (100 mL), dried over anhydrous sodium sulfate, filtered, the filtrate was concentrated at reduced pressure, and the residue was purified by a flash column chromatography (PE/EA=1:1) to obtain the crude product. The crude product was suspended in methyl tert-butyl ether (15 mL) and dispersed by ultrasonication for 5 min. The mixture was filtered, and the filter cake was washed with methyl tert-butyl ether (5 mL). The filter cake was collected and dried over vacuum for 1 h to obtain compound 44-c (330 mg, 29%). LC-MS (ESI): m/z=595.1 $[M+H]^+$.

Synthesis of Compound 44-b

Compound 44-c (110 mg, 0.18 mmol) was dissolved in 36 mL of 1,4-dioxane at room temperature and was added compound I-3 (87 mg, 0.28 mmol), 1,1'-di-tert-butylphosphinoferrocene palladium dichloride (24 mg, 0.037 mmol), cesium fluoride (84 mg, 0.55 mmol) and water (4 mL). The reaction mixture was stirred at 100° C. under nitrogen protection for 18 hours. The reaction mixture was cooled to room temperature, concentrated at reduced pressure, and the residue was added 100 mL of water to and extracted with DCM (100 mL*2). The organic phase was dried over anhydrous sodium sulfate, filtered, and the filtrate was concentrated at reduced pressure to obtain the crude product. The crude product was purified by a flash column chromatography (PE/EA=1:1) to give compound 44-b (110 mg, 87%). LC-MS (ESI): m/z=704.3 $[M+H]^+$.

Synthesis of Compound 44-a

Compound 44-b (58 mg, 0.082 mmol) was dissolved in 2 mL of DMF in a microwave tube at room temperature, then was added potassium carbonate (36 mg, 0.26 mmol), potassium iodide (2.7 mg, 0.016 mmol), and bromomethyl cyclopropane (24 uL, 0.25 mmol) sequentially and the reaction mixture was stirred at 50° C. overnight. The reaction mixture was cooled to room temperature, quenched by adding 50 mL of water, then extracted with ethyl acetate (50 mL*2). The organic phase was washed with brine (50 mL*3), dried over anhydrous sodium sulfate, filtered, and the filtrate was concentrated at reduced pressure to obtain the crude product. The crude product was purified by a flash column chromatography (PE/EA=1:1) to give compound 44-a (39 mg, 63%, mixture of two isomers). LC-MS (ESI): m/z=758.3$[M+H]^+$.

Synthesis of Compounds 44 and 45

Compound 44-a (35 mg, 0.046 mmol) was dissolved in 2 mL of DCM at room temperature and methanesulfonic acid (150 uL, 2.31 mmol) was added in an ice-cold water bath. The reaction mixture was warmed to room temperature and stirred for 3 hours. The reaction mixture was added 50 mL of DCM, washed with saturated sodium bicarbonate solution (50 mL), dried over anhydrous sodium sulfate, filtered, and the filtrate was concentrated at reduced pressure to give the crude product. The crude product was purified by PREP-HPLC (basic method, $NH_4HCO_3$) to afford compound 44 (1.5 mg, 5%), LC-MS (ESI): m/z=638.2$[M+H]^+$; compound 45 (9.1 mg, 31%). LC-MS (ESI): m/z=638.2$[M+H]^+$.

Synthetic Route of Compound 46

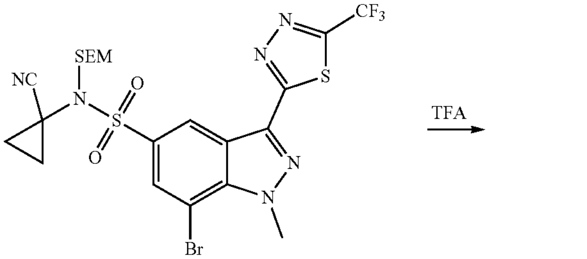

35-b

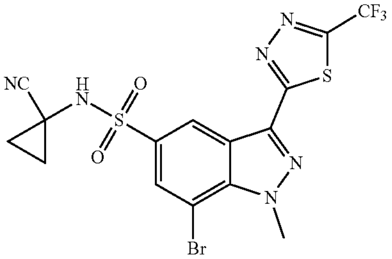

I-6

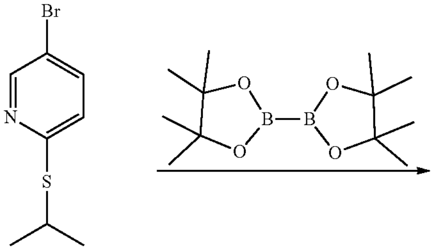

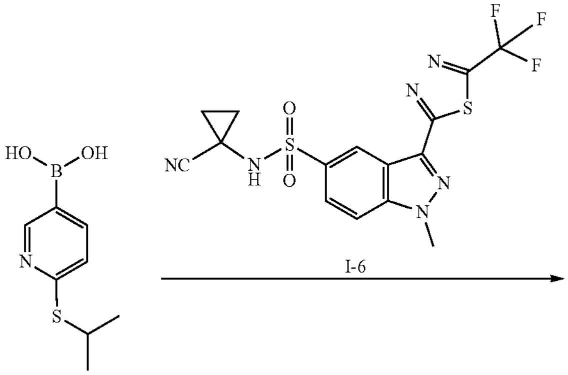

46-b

-continued

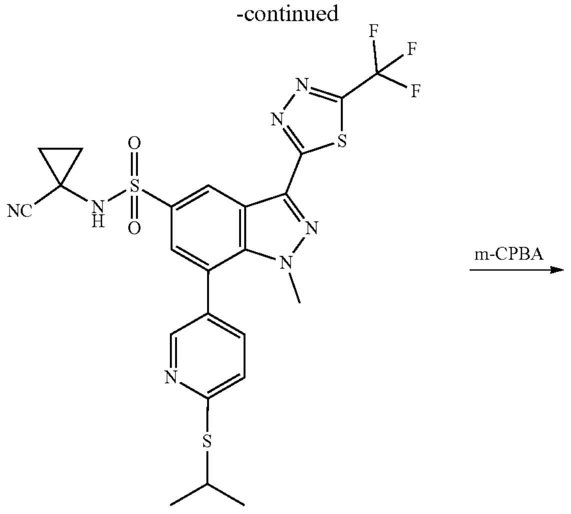

46-a

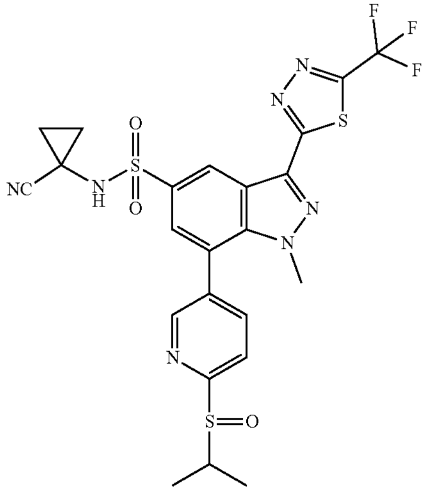

46

Synthesis of Compound I-6

A reaction flask charged with 35-b (88 mg, 0.14 mmol) and dichloromethane (5 mL) was added trifluoroacetic acid (1 mL) and water (0.1 mL) dropwise at room temperature. After addition, the reaction mixture was stirred at room temperature for 3 hours, then was concentrated at room temperature to remove the solvent. The residue was diluted with dichloromethane, washed with saturated sodium bicarbonate, washed with brine, dried over anhydrous sodium sulfate, filtered, and evaporated to dryness to obtain the crude product. The crude was purified by a flash column chromatography (mobile phase: petroleum ether/ethyl acetate, 0% to 100%) to obtain compound I-6 (56 mg, 80%). LC-MS (ESI): m/z 506.9 $[M+H]^+$.

Synthesis of Compound 46-b

Compound 5-bromo-2-(isopropylthio) pyridine (200 mg, 0.86 mmol) was dissolved in 1,4-dioxane (20 mL), to which was added bis(pinacolato)diboron (328 mg, 1.29 mmol), 1,1'-Bis(diphenylphosphino)ferrocene]dichloropalladium (II) (63 mg, 0.086 mmol), potassium acetate (254 mg, 2.59 mmol), and the reaction mixture was stirred at 95° C. under nitrogen protection for 6 hours. The reaction mixture was filtered through celite and the filtrate was concentrated at reduced pressure to give 46-b (169 mg, 99%). LC-MS (ESI): m/z 198.1 $(M+H)^+$.

Synthesis of Compound 46-a

Compound I-6 (200 mg, 0.39 mmol), 46-b (155 mg, 0.79 mmol), [1,1'-bis(di-tert-butylphosphino)ferrocene]palladium dichloride (51 mg, 0.079 mmol), and cesium fluoride (180 mg, 1.18 mmol) were added into 1,4-dioxane (27 mL) and water (3 mL) and the reaction mixture was degassed and purged with nitrogen for 3 times and then stirred at 100° C. for 6 hours. The reaction mixture was filtered through celite, the filtrate was added water (100 mL) and extracted with dichloromethane (100 mL). The organic phase was washed with brine (100 mL), dried over sodium sulfate, filtered off the desiccant and the filtrate was concentrated at reduced pressure to obtain the crude product, which was purified by column chromatography (mobile phase, PE/EA 1/1) to give compound 46-a (170 mg, 74%).

Synthesis of Compound 46

Compound 46-a (86 mg, 0.15 mmol) was dissolved in dichloromethane (8 mL), to which m-chloroperoxybenzoic acid (30 mg, 0.17 mmol) was added, and the reaction mixture was stirred at room temperature for 2 h. After stirred for 2 h, the reaction mixture was added saturated sodium bicarbonate solution (50 mL), and was extracted with dichloromethane (50 mL), and the crude was concentrated at reduced pressure to obtain the crude product, which was prepared by Prep-HPLC (basic conditions) to give compound 46 (57 mg, 65%). LC-MS (ESI): m/z 596.2 $(M+H)^+$.

Synthetic Route of Compound 47

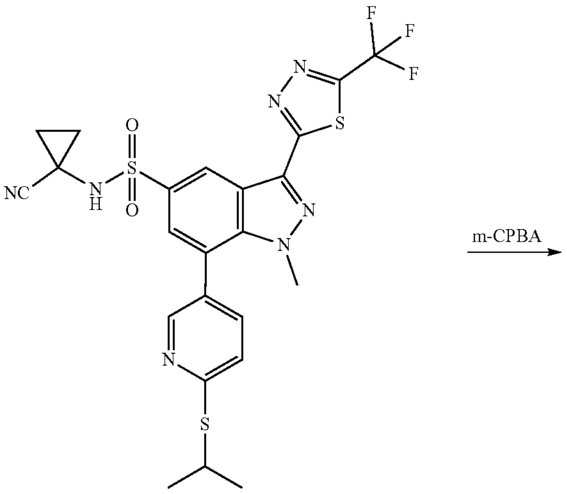

46-a

-continued

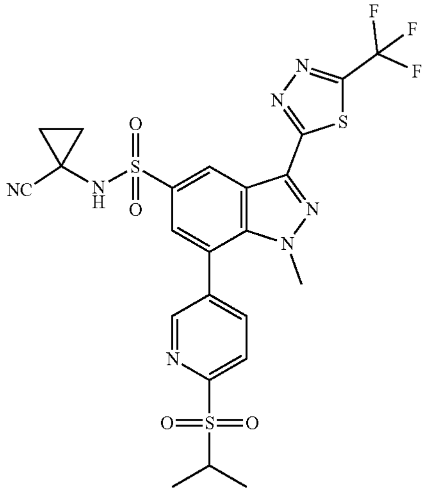

47

Synthesis of Compound 47

Compound 46-a (86 mg, 0.15 mmol) was dissolved in dichloromethane (8 mL), to which m-chloroperoxybenzoic acid (90 mg, 0.52 mmol) was added, and the reaction mixture was stirred at room temperature for 2 h. After stirred for 2 h, the reaction mixture was added saturated sodium bicarbonate solution (50 mL), extracted with dichloromethane (50 mL), and the crude was concentrated at reduced pressure to obtain the crude product, which was purified by Prep-HPLC (basic conditions) to give compound 47 (60 mg, 66%). LC-MS (ESI): m/z 612.2 $(M+H)^+$.

Synthetic Route of Compound 48

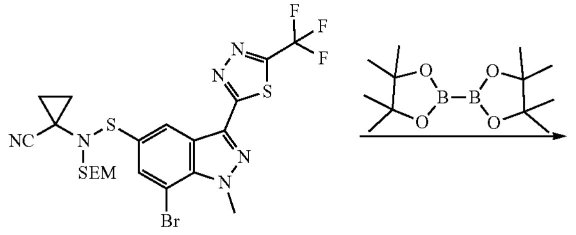

35-b

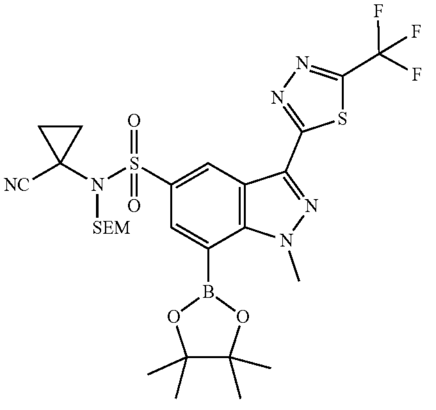

48-d

-continued

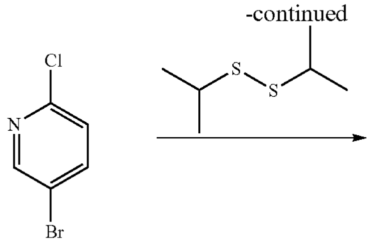

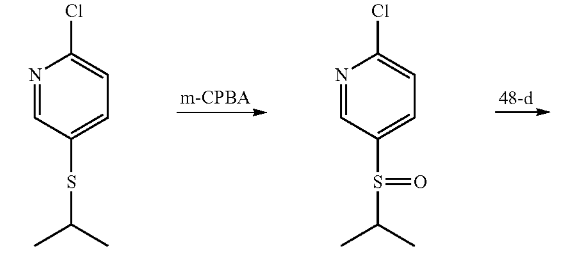

48-c 48-b

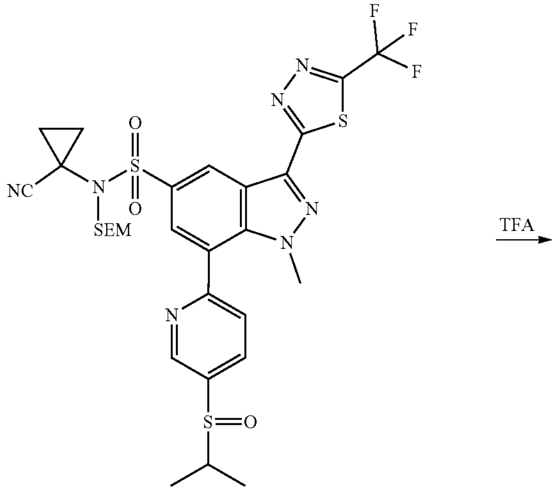

48-a

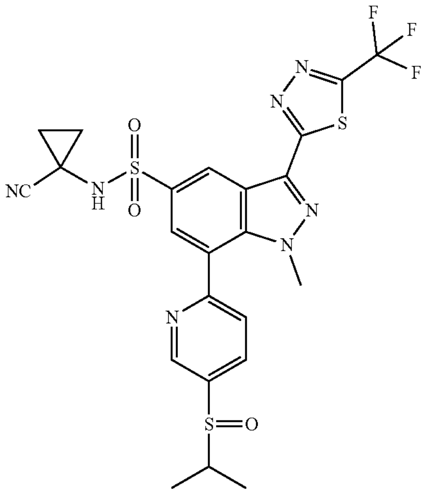

48

Synthesis of Compound 48-d

Compound 35-b (200 mg, 0.31 mmol) was dissolved in toluene (6 mL), to which were added pinacol ester of bis-boronic acid (199 mg, 0.78 mmol), chloro(2-dicyclohexylphosphino-2',4',6'-triisopropyl-1,1'-biphenyl)[2-(2'-amino-1,1'-biphenyl)]palladium(II) (25 mg. 0.32 mmol), 2-dicyclohexylphosphino-2',4',6'-triisopropylbiphenyl (30 mg, 0.063 mmol), potassium acetate (92 mg, 0.94 mmol), and the reaction mixture was stirred for 8 h at 65° C. after degassed and purged with nitrogen for three times. The reaction mixture was filtered through celite, and the filtrate was added water (50 mL), extracted with ethyl acetate (50 mL). The organic phase was washed with brine (50 mL), dried over sodium sulfate, filtered off the desiccant, and the filtrate was concentrated at reduced pressure to obtain 48-d (200 mg, 93%).

Synthesis of Compound 48-c

Compound 5-bromo-2-chloropyridine (3000 mg, 15.59 mmol) was dissolved in 30 mL of anhydrous THF under nitrogen protection at room temperature. The mixture was cooled at −78° C. and was added n-BuLi (7.5 mL, 18.71 mmol, 2.5 M) dropwise. After the addition, the mixture was stirred under nitrogen protection at −78° C. for 30 min, then was added isopropyl disulfide (2.98 mL, 18.71 mmol) dropwise. After the addition, the reaction mixture was stirred under nitrogen protection at room temperature for 1 hr. At room temperature, 100 mL of saturated ammonium chloride solution was slowly added to the reaction mixture, then the mixture was extracted with ethyl acetate (100 mL). The organic phase was washed with brine (100 mL), dried over anhydrous sodium sulfate, filtered, and the filtrate was concentrated at reduced pressure, and the residue was purified by a flash column chromatography (PE/EA=10:1) to give compound 48-c (750 mg, 26%). LC-MS (ESI): m/z=188.1 $[M+H]^+$.

Synthesis of Compound 48-b

Compound 48-c (446 mg, 2.38 mmol) was dissolved in dichloromethane (15 mL), to which m-chloroperoxybenzoic acid (473 mg, 2.74 mmol) was added, and the reaction mixture was stirred for 2 h at room temperature, then was added saturated sodium bicarbonate solution (50 mL), and extracted with dichloromethane (100 mL). The organic phase was washed with brine (50 mL), dried over sodium sulfate, filtered off the desiccant, and the filtrate was concentrated at reduced pressure to obtain the crude product, which was purified by column chromatography (mobile phase, PE/EA 1/1) to obtain compound 48-b (299 mg, 62%). LC-MS (ESI): m/z 204.1 $(M+H)^+$.

Synthesis of Compound 48-a

Compounds 48-b (60 mg, 0.29 mmol), 48-d (200 mg, 0.29 mmol), [1,1'-bis(di-tert-butylphosphino)ferrocene]palladium dichloride (38 mg, 0.059 mmol), and cesium fluoride (133 mg, 0.88 mmol) were added to 1,4-dioxane (9 mL) and water (1 mL). The reaction mixture was degassed and purged with nitrogen for three times and then stirred at 75° C. for 3 h. The reaction mixture was filtered through celite, and the filtrate was added water (50 mL), extracted with ethyl acetate (50 mL). The organic phase was washed with brine (50 mL), dried over sodium sulfate, filtered off the desiccant, and the filtrate was concentrated at reduced pressure to obtain the crude product, which was purified by column chromatography (mobile phase, PE/EA 1/2) to obtain compound 48-a (40 mg, 19%). LC-MS (ESI): m/z 726.2 $(M+H)^+$.

Synthesis of Compound 48

Compound 48-a (40 mg, 0.055 mmol) was dissolved in dichloromethane (3 mL), to which trifluoroacetic acid (1 mL) was added, and the reaction mixture was stirred at room temperature for 2 hours. The dichloromethane was removed by concentration at reduced pressure and the residue was adjusted to pH 7 to 8 with saturated sodium bicarbonate solution and the mixture was extracted with ethyl acetate (50 mL). The organic phase was washed with brine (50 mL), dried over sodium sulfate, filtered off the desiccant, and the filtrate was concentrated at reduced pressure to obtain the crude product, which was purified by Prep-HPLC (basic conditions) to give compound 48 (12 mg, 36%). LC-MS (ESI): m/z 596.2 $(M+H)^+$.

Synthetic Route of Compound 49

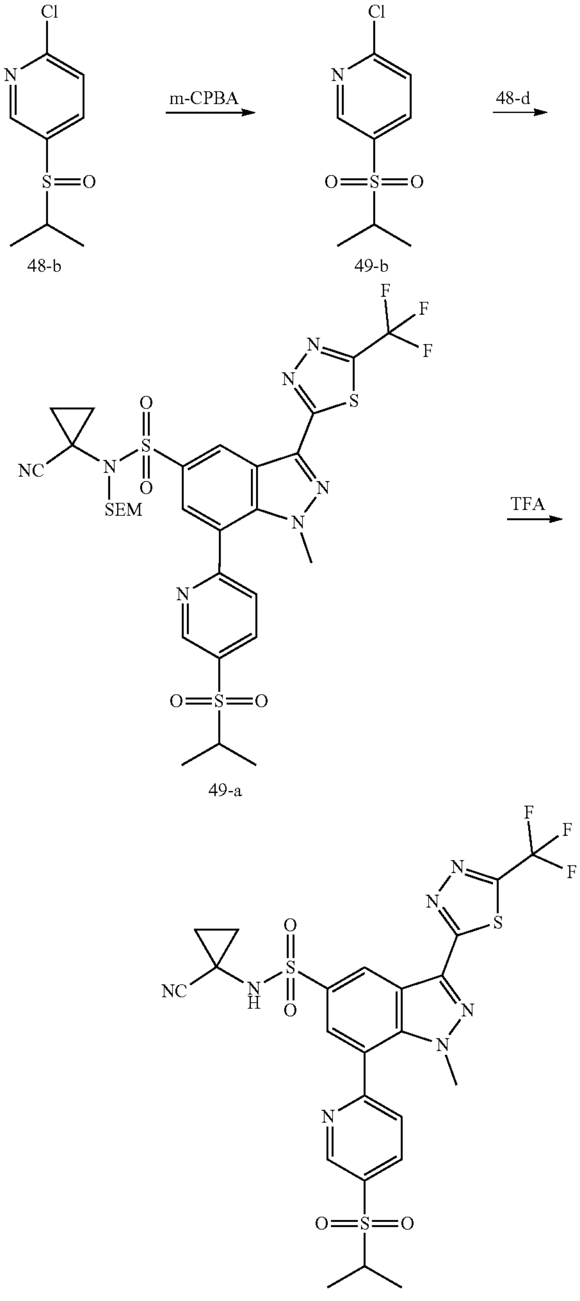

48-b 49-b 49-a

49

Synthesis of Compound 49-b

Compound 48-b (200 mg, 0.98 mmol) was dissolved in dichloromethane (10 mL), to which m-chloroperoxybenzoic acid (498 mg, 2.89 mmol) was added, and the reaction mixture was stirred at room temperature for 2 h. The reaction mixture was added saturated sodium bicarbonate solution (50 mL), extracted with dichloromethane. The organic phase was washed with brine (50 mL), dried over sodium sulfate, filtered off the desiccant, and the filtrate was concentrated at reduced pressure to obtain the crude product, which was purified by column chromatography (mobile phase, PE/EA 3/1) to obtain compound 49-b (200 mg, 93%). LC-MS (ESI): m/z 220.1 $(M+H)^+$.

Synthesis of Compound 49-a

Compounds 49-b (64 mg, 0.29 mmol), 48-d (200 mg, 0.29 mmol), [1,1'-bis(di-tert-butylphosphino)ferrocene]palladium dichloride (38 mg, 0.059 mmol), and cesium fluoride (133 mg, 0.88 mmol) were added to 1,4-dioxane (9 mL) and water (1 mL) and the reaction mixture was degassed and purged with nitrogen for 3 times, then stirred at 73° C. for 3 hours. The reaction mixture was filtered through celite, and water (50 mL) was added to the filtrate and extracted with ethyl acetate (50 mL). The organic phase was washed with brine (50 mL), dried over sodium sulfate, filtered off the desiccant, and the filtrate was concentrated at reduced pressure to obtain the crude product, which was purified by column chromatography (mobile phase, PE/EA 1/1) to obtain compound 49-a (55 mg, 25%). LC-MS (ESI): m/z 742.3 $(M+H)^+$.

Synthesis of Compound 49

Compound 49-a (55 mg, 0.074 mmol) was dissolved in dichloromethane (3 mL), to which trifluoroacetic acid (1 mL) was added, and the reaction mixture was stirred at room temperature for 2 hours. Dichloromethane was removed by concentration at reduced pressure and the residue was adjusted to pH 7 to 8 with saturated sodium bicarbonate solution and extracted with ethyl acetate (50 mL). The organic phase was washed with brine (50 mL), dried over sodium sulfate, filtered off the desiccant, and the filtrate was concentrated at reduced pressure to obtain the crude product, which was purified by Prep-HPLC (basic conditions) to give compound 49 (18 mg, 39%). LC-MS (ESI): m/z 612.2 $(M+H)^+$.

Synthetic Route of Compound 50

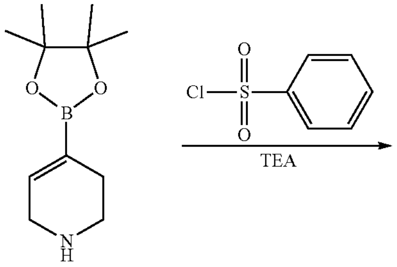

-continued

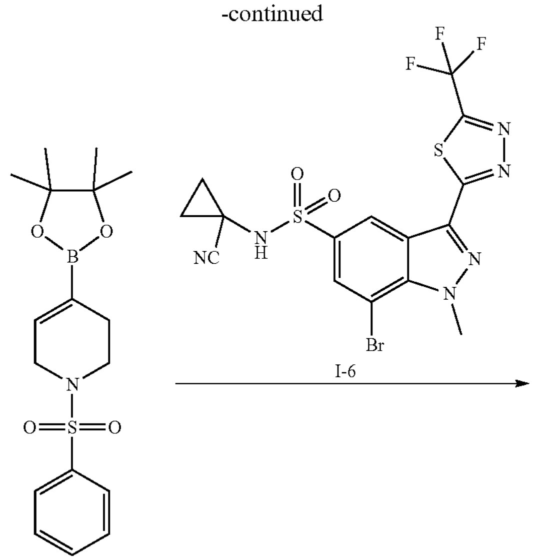

50-a

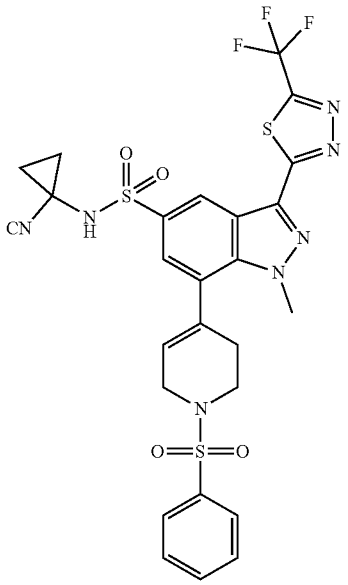

50

Synthesis of Compound 50-a 1,2,3,6-tetrahydropyridine-4-boronic acid pinacol ester (209 mg, 1.00 mmol), dichloromethane (10 mL) and triethylamine (0.70 mL, 5.00 mmol) were combined in a reaction flask in an ice-cold water bath, followed by dropwise addition of benzenesulfonyl chloride (0.19 mL, 1.50 mmol). After the dropwise addition, the reaction mixture was stirred at room temperature for 2 hours. Upon completion, the reaction mixture was quenched with water, extracted with dichloromethane, the organic phase was washed with brine, dried over anhydrous sodium sulfate and the filtrate was concentrated at reduced pressure to obtain the crude product. The crude product was purified by a flash column chromatography (mobile phase: ethyl acetate/petroleum ether: 0% to 100%) to give compound 50-a (200 mg, 57%). LC-MS (ESI): m/z=350.0 $[M+H]^+$.

Synthesis of Compound 50

To a reaction vial were added I-6 (50 mg, 0.099 mmol), 50-a (52 mg, 0.15 mmol), [1,1'-bis(di-tert-butylphosphino) ferrocene]palladium dichloride (13 mg, 0.020 mmol), cesium fluoride (45 mg, 0.30 mmol), 1,4-dioxane (9 mL) and $H_2O$ (1 mL). After degassed and purged with nitrogen for 3 times, the reaction mixture was stirred at 100° C. for 5 hours. Upon completion, the reaction mixture was cooled to room temperature, concentrated at reduced pressure to remove the organic solvent, the residue was diluted with ethyl acetate, and the organic phase was washed with water, brine, dried over anhydrous sodium sulfate, filtered, and the filtrate was concentrated at reduced pressure to obtain the crude product. The crude product was purified by a flash column chromatography (mobile phase: ethyl acetate/petroleum ether: 0% to 100%) to give compound 50 (30 mg, 47%). LC-MS (ESI): m/z=650.0 $[M+H]^+$.

Synthetic Route of Compound 51

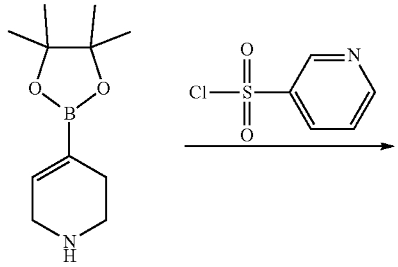

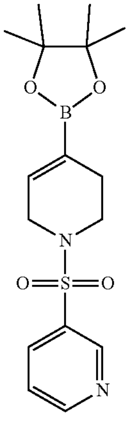

51-a

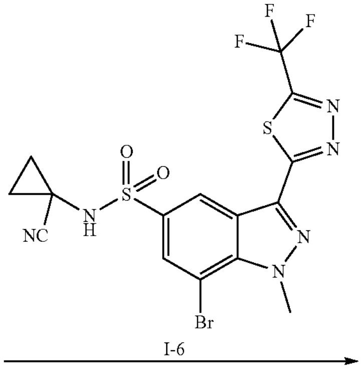

I-6

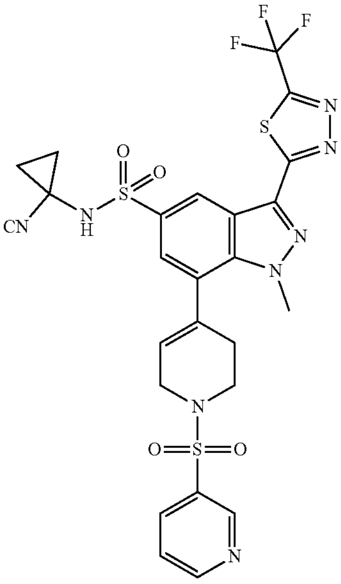

51

Synthesis of Compound 51-a 1,2,3,6-tetrahydropyridine-4-boronic acid pinacol ester (209 mg, 1.00 mmol), dichloromethane (10 mL), and triethylamine (0.70 mL, 5.00 mmol) were added into a reaction flask in an ice-cold water bath, followed by the dropwise addition of 3-pyridinesulfonyl chloride (0.18 mL, 1.50 mmol). After the dropwise addition, the reaction mixture was stirred at room temperature for 2 hours. Upon completion, the reaction mixture was quenched with water, extracted with dichloromethane, the organic phase was washed with brine, dried over anhydrous sodium sulfate, and the filtrate was concentrated at reduced pressure to give the crude compound 51-a (100 mg, 29%). LC-MS (ESI): m/z=351.2 $[M+H]^+$.

Synthesis of Compound 51

To a reaction vial were added I-6 (50 mg, 0.099 mmol), 51-a (52 mg, 0.15 mmol), [1,1'-bis(di-tert-butylphosphino)ferrocene]palladium dichloride (13 mg, 0.020 mmol), cesium fluoride (45 mg, 0.30 mmol), 1,4-dioxane (9 mL) and $H_2O$ (1 mL). After degassed and purged with nitrogen for 3 times, the reaction mixture was stirred at 100° C. for 4 hours. Upon completion, the reaction mixture was cooled to room temperature, concentrated at reduced pressure to remove the organic solvent. The residue was diluted with ethyl acetate, and the organic phase was washed with water, brine, dried over anhydrous sodium sulfate, filtered, and the filtrate was concentrated at reduced pressure to obtain the crude product, which was purified by Prep-HPLC to afford compound 51 (25 mg, 39%). LC-MS (ESI): m/z=651.2 $[M+H]^+$.

Synthetic Route of Compound 52

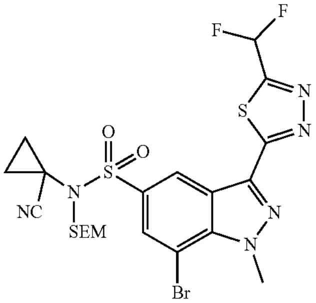

I-1

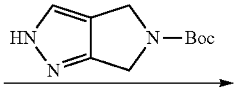

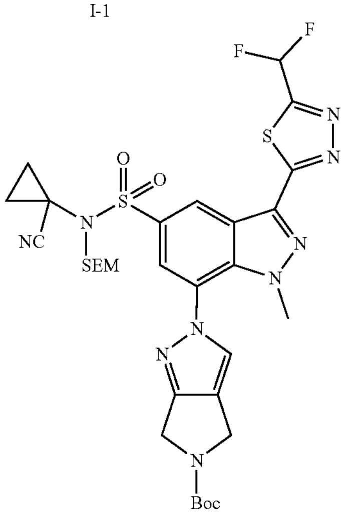

52-b

-continued

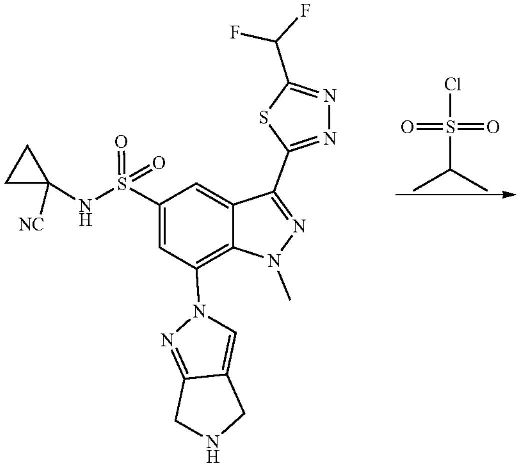

52-a

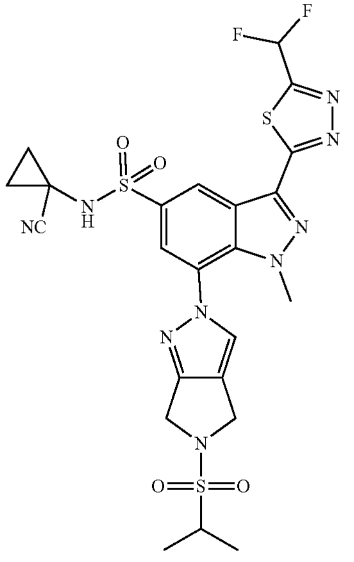

52

Synthesis of Compound 52-b

To a microwave tube were added I-1 (200 mg, 0.32 mmol), tert-butyl 2,6-dihydropyrrolo[3,4-c]pyrazole-5(4H)-carboxylate (135 mg, 0.65 mmol), t-BuXPhosPd-G3 (26 mg, 0.032 mmol), t-BuXphos (27 mg, 0.065 mmol), cesium carbonate (263 mg, 0.81 mmol) and 1,4-dioxane (8 mL). After degassed and purged with nitrogen for 3 times, the reaction mixture was stirred at 75° C. overnight. Upon completion, the reaction mixture was cooled to room temperature, concentrated at reduced pressure to remove the organic solvent. The residue was diluted by adding ethyl acetate, and the organic phase was washed with water, brine, dried over anhydrous sodium sulfate, filtered and the filtrate was concentrated at reduced pressure to obtain the crude product. The crude product was purified by a flash column chromatography (mobile phase: ethyl acetate/petroleum ether: 0% to 100%) to give compound 52-b (50 mg, 21%). LC-MS (ESI): m/z=748.3 $[M+H]^+$.

Synthesis of Compound 52-a

A reaction vial charged with 52-b (50 mg, 0.067 mmol) and dichloromethane (10 mL) was added trifluoroacetic acid (3 mL) dropwise at room temperature. After the dropwise addition, the reaction mixture was stirred at room temperature for 4 hours. Upon completion, the solvent was removed by concentration at reduced pressure at room temperature. The residue was diluted with ethyl acetate, and the organic phase was washed with saturated sodium bicarbonate, brine, dried over anhydrous sodium sulfate, filtered and evaporated to obtain the crude product, which was purified by Prep-HPLC to give compound 52-a (22 mg, 64%). LC-MS (ESI): m/z 518.1 $[M+H]^+$.

Synthesis of Compound 52

52-a (15 mg, 0.029 mmol), dichloromethane (10 mL) and triethylamine (20 μL, 0.15 mmol) were added into a reaction flask in an ice-cold water bath, followed by dropwise addition of isopropylsulfonyl chloride (4 μL, 0.035 mmol). After the dropwise addition, the reaction mixture was stirred at room temperature for 2 hours. Upon completion, the reaction mixture was quenched with water, extracted with dichloromethane, and the organic phase was washed with brine, dried over anhydrous sodium sulfate, and the filtrate was concentrated at reduced pressure to obtain the crude product, which was purified by Prep-HPLC to afford compound 52 (5 mg, 28%). LC-MS (ESI): m/z 624.1 $[M+H]^+$.

Synthetic Route of Compound 53

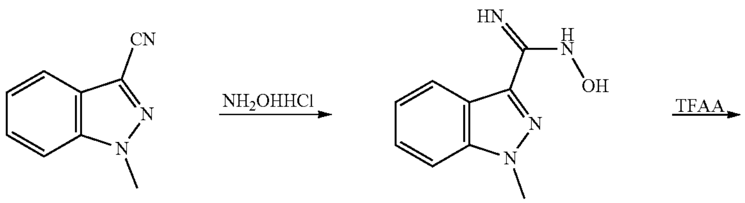

53-d

-continued

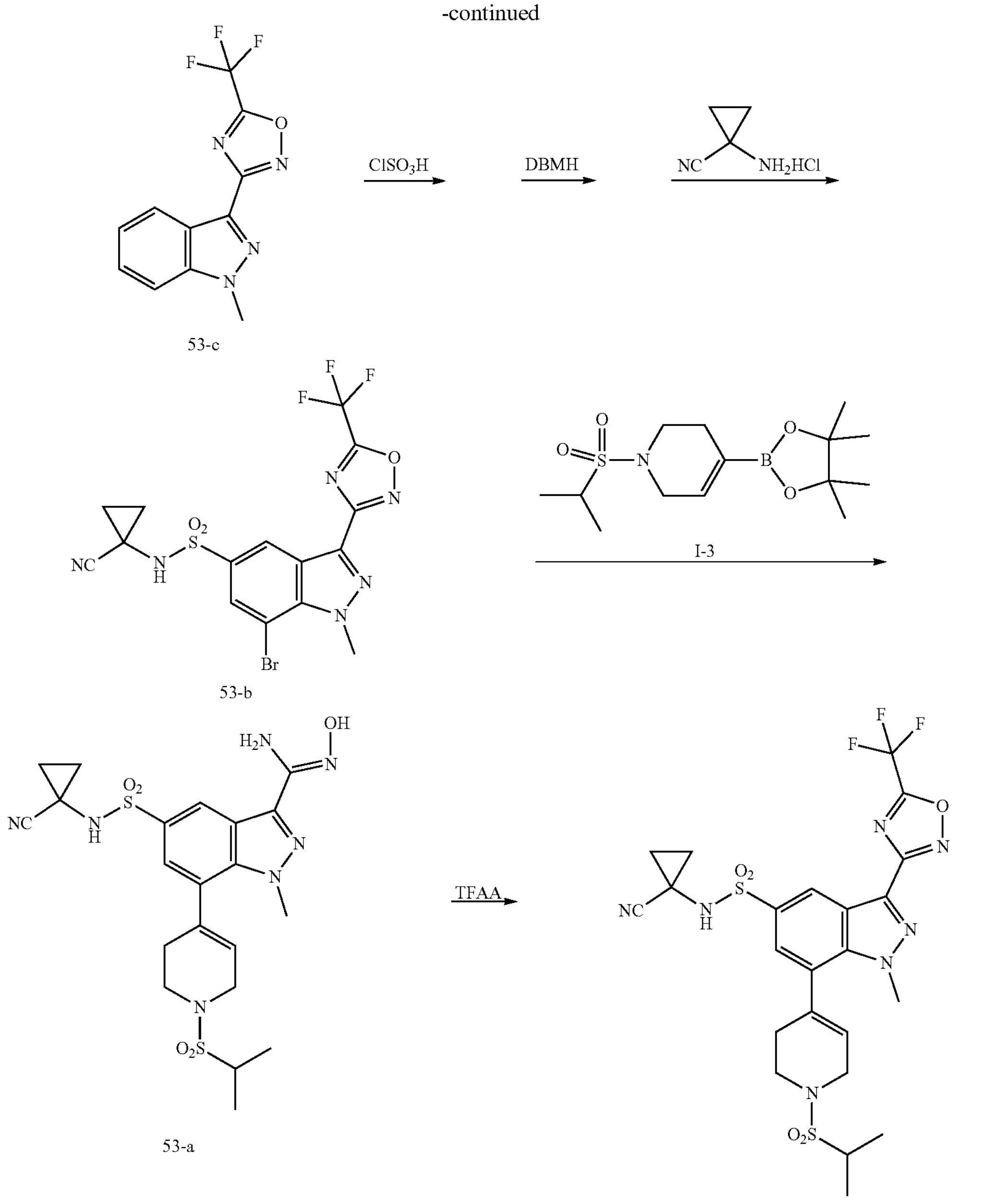

53-c 53-b 53-a

53

Synthesis of Compound 53-d

To a reaction flask were added 1-methyl-1H-indazole-3-carbonitrile (1.00 g, 6.36 mmol), hydroxylamine hydrochloride (0.88 g, 12.72 mmol), anhydrous potassium carbonate (1.76 g, 12.72 mmol) and anhydrous ethanol (30 mL). The reaction mixture was stirred at 80° C. for 15 hours. The reaction mixture was cooled to room temperature, removed the solvent, and the residue was diluted with ethyl acetate, washed with brine, dried over anhydrous sodium sulfate, filtered, and evaporated to give 53-d (1.2 g, 99%). LC-MS (ESI): m/z 191.2 $(M+H)^+$.

Synthesis of Compound 53-c

A reaction flask charged with 53-d (1.2 g, 6.31 mmol) and anhydrous tetrahydrofuran (20 mL) was added pyridine (1.53 mL, 18.93 mmol) and trifluoroacetic anhydride (1.32 mL, 9.46 mmol) dropwise in an ice-cold water bath. The reaction mixture was stirred for 30 min in an ice-cold water bath and then stirred for 2 h at room temperature. Pyridine (0.5 mL, 6.18 mmol) and trifluoroacetic anhydride (0.5 mL, 3.60 mmol) were added and the reaction mixture was stirred at room temperature for 1 hour. The solvent was removed, and the crude product was diluted with ethyl acetate, washed twice with water, washed with brine, dried over anhydrous sodium sulfate, filtered, and evaporated to obtain 53-c (1.61 g, 95%). LC-MS (ESI): m/z 269.1 $(M+H)^+$.

Synthesis of Compound 53-b 53-c (101 mg, 0.38 mmol) was added into a reaction flask and chlorosulfonic acid (1 mL) was added dropwise in a water bath. The reaction mixture was stirred at 65° C. for 6 hours, then cooled to room temperature, was added into ice-cold water and extracted with ethyl acetate. The organic phase was washed with water, brine, dried over anhydrous sodium sulfate, filtered and evaporated to obtain a solid crude product. The crude product in a reaction flask was added anhydrous dichloromethane (5 mL) and dibromohydantoin (118 mg, 0.41 mmol) in an ice-cold water bath. Trifluoromethanesulfonic acid (0.1 mL, 1.13 mmol) was added dropwise (8 drops) after stirred for 5 min in an ice-cold water bath. After addition, the reaction mixture was stirred for 3 hours in an ice-cold water bath. Ice-cold water was added to the reaction mixture, the solution was partitioned and the aqueous phase was extracted with dichloromethane once. The organic phases were combined, washed with brine, dried over anhydrous sodium sulfate, filtered, and the filtrate was evaporated to obtain the crude product, which was dissolved in dichloromethane to obtain Solution A. Another reaction flask charged with 1-amino-1-cyclopropylcyanide hydrochloride (89 mg, 0.75 mmol) was added pyridine (0.5 mL) and anhydrous dichloromethane (5 mL) in an ice-cold water bath, and stirred in an ice-cold water bath for 5 min, then was added the Solution A dropwise. After addition, the reaction mixture was stirred in an ice-cold water bath for 5 minutes and then stirred at room temperature for 2 hours. Removed the solvent to dryness, and the resulting crude product was diluted with ethyl acetate, was added brine and a small amount of sodium bisulfate. The liquid was partitioned, and the aqueous phase was extracted twice with ethyl acetate/tetrahydrofuran. The organic phases were combined, dried over anhydrous sodium sulfate, filtered, and evaporated to give 53-b (185 mg, 100%). LC-MS (ESI): m/z 491.0 $(M+H)^+$.

Synthesis of Compound 53-a

A solution of 53-b (185 mg, 0.38 mmol), I-3 (180 mg, 0.57 mmol), $Pd(dtbpf)Cl_2$ (20 mg, 0.031 mmol), 1,4-dioxane (20 mL) and a solution of cesium fluoride (720 mg, 4.74 mmol) in water (4 mL) were combined in a reaction flask. The reaction mixture was stirred at 100° C. for 2 h under nitrogen protection, supplemented with $Pd(dtbpf)Cl_2$ (20 mg, 0.031 mmol), and continued stirring at 100° C. for 2 h under nitrogen protection, supplemented with 1-3 (90 mg, 0.29 mmol) and anhydrous potassium phosphate (60 mg, 0.28 mmol). The reaction mixture was stirred at 100° C. for 4 h under nitrogen protection. Cooled to room temperature, the reaction mixture was added $Pd(dtbpf)Cl_2$ (20 mg, 0.031 mmol). The reaction mixture was stirred at 100° C. for 5 h under nitrogen protection. The reaction mixture was cooled to room temperature. The aqueous phase was separated, and a small amount of brine was added to 1,4-dioxane phase, and the aqueous phase was separated again. The aqueous phase was combined and extracted twice with ethyl acetate. The 1,4-dioxane phase was combined with the ethyl acetate extract, evaporated to dryness, and the crude was purified by Prep-HPLC (C8, 10 mM aqueous ammonium bicarbonate, acetonitrile) to give 53-a (90 mg, 46%). LC-MS (ESI): m/z 522.2 $(M+H)^+$.

Synthesis of Compound 53

A reaction flask charged with 53-a (90 mg, 0.17 mmol) and tetrahydrofuran (5 mL) was added pyridine (0.18 mL, 2.21 mmol) in an ice-cold water bath and trifluoroacetic anhydride (0.15 mL, 0.52 mmol) dropwise. The reaction mixture was stirred in an ice-cold bath for 15 minutes and then at room temperature for 4 hours. The solvent was removed, and the residue was diluted with ethyl acetate, washed with brine, dried over anhydrous sodium sulfate, filtered, and the filtrate was evaporated to dryness, and purified by Prep-HPLC (ammonium bicarbonate) to give 53 (10.1 mg, 9.7% yield). LC-MS (ESI): m/z 600.2 $(M+H)^+$; $^1$HNMR (DMSO-$d_6$, 400 MHz): δ 8.61 (1H, d, J=1.6 Hz), 7.67 (1H, d, J=1.2 Hz), 6.02-5.96 (1H, m), 4.25 (3H, s), 4.10-4.03 (2H, m), 3.63 (2H, t, J=5.6 Hz), 3.47 (1H, p, J=6.8 Hz), 2.60-2.54 (2H, m), 1.40-1.34 (2H, m), 1.30 (6H, d, J=6.8 Hz), 1.27-1.22 (2H, m).

Synthetic Route of Compound 54

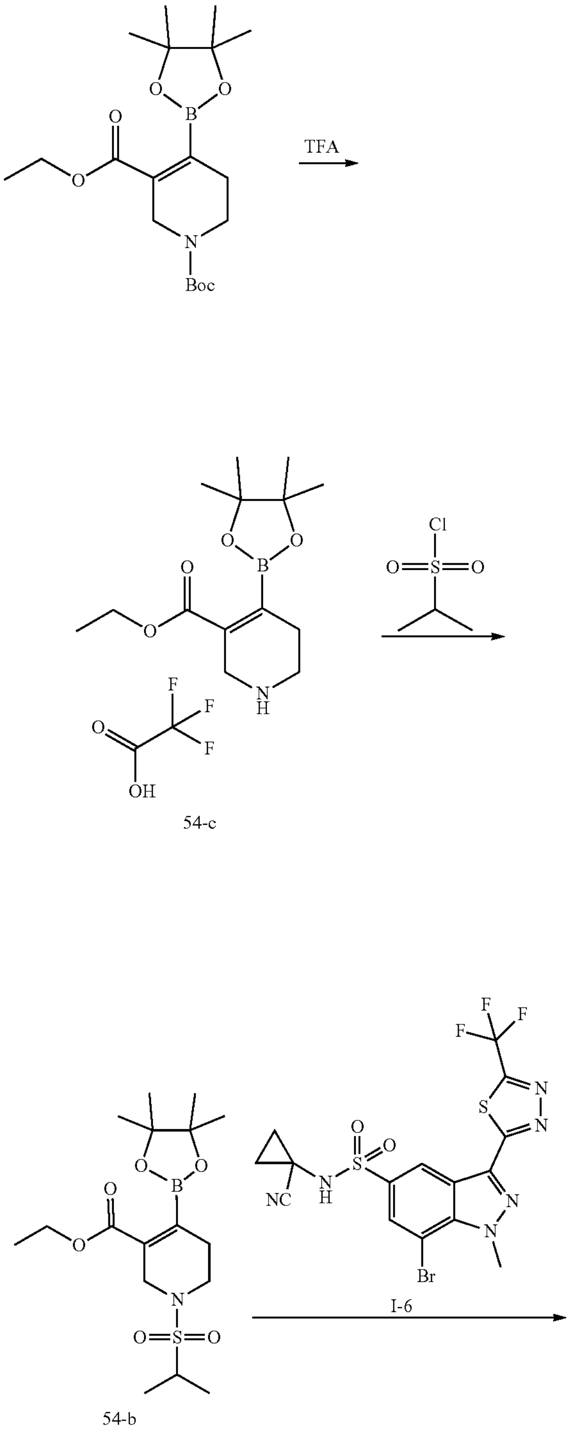

54-c 54-b

-continued

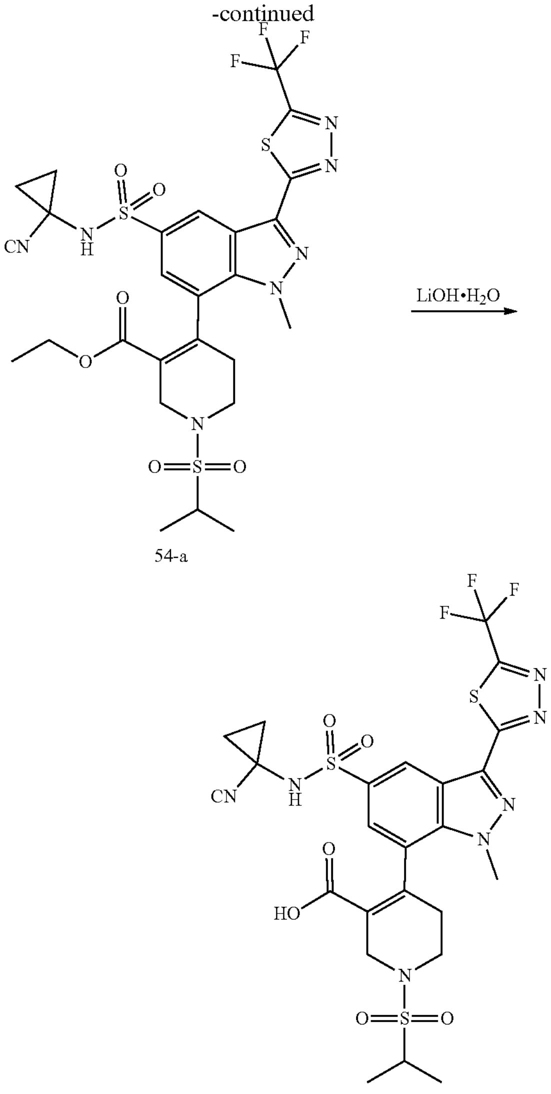

54-a

54

Synthesis of Compound 54-c

A reaction vial charged with ethyl N-Boc-1,2,5,6-tetrahydropyridine-4-boronic acid pinacol ester-3-carboxylate (300 mg, 0.79 mmol) and dichloromethane (10 mL) were added trifluoroacetic acid (3 mL) dropwise at room temperature. After finished the dropwise addition, the reaction mixture was stirred at room temperature for 4 hours. Upon completion, the solvent was removed by concentration at reduced pressure at room temperature to obtain crude compound 54-c (300 mg).

Synthesis of Compound 54-b

A reaction flask charged with 54-c (300 mg, 0.76 mmol), methylene chloride (10 mL) and triethylamine (0.53 mL, 3.80 mmol) in an ice-cold water bath was added isopropylsulfonyl chloride (0.17 mL, 1.52 mmol) dropwise. After the dropwise addition, the reaction mixture was stirred at room temperature for 2 hours. Upon completion, the reaction mixture was quenched with water, extracted with dichloromethane, and the organic phase was washed with brine, dried over anhydrous sodium sulfate, and the filtrate was concentrated at reduced pressure to obtain the crude product. The crude product was purified by a flash column chromatography (mobile phase: methanol/dichloromethane: 0% to 10%) to give compound 54-b (250 mg, 85%). LC-MS (ESI): m/z=388.4 $[M+H]^+$.

Synthesis of Compound 54-a

A reaction vial charged with I-6 (200 mg, 0.39 mmol), 54-b (183 mg, 0.47 mmol), [1,1'-bis(di-tert-butylphosphino) ferrocene]palladium dichloride (51 mg, 0.079 mmol), cesium fluoride (180 mg, 1.18 mmol), 1,4-dioxane (18 mL) and $H_2O$ (2 mL) was degassed and purged with nitrogen for 3 times, and the reaction mixture was stirred at 100° C. for 5 hours. Upon completion, the reaction mixture was cooled to room temperature, concentrated at reduced pressure to remove the organic solvent. The residue was diluted with ethyl acetate, and the organic phase was washed with water, brine, dried over anhydrous sodium sulfate, filtered, and the filtrate was concentrated at reduced pressure to obtain the crude product. The crude product was purified by a flash column chromatography (mobile phase: ethyl acetate/petroleum ether: 0% to 100%) to give compound 54-a (200 mg, 74%). LC-MS (ESI): m/z=688.2 $[M+H]^+$.

Synthesis of Compound 54

A solution of 54-a (200 mg, 0.29 mmol) dissolved in THF (30 mL) and water (8 mL), was added $LiOH \cdot H_2O$ (122 mg, 2.91 mmol). After addition, the reaction mixture was stirred at room temperature for 4 hours. Upon completion, the reaction mixture was neutralized with diluted hydrochloric acid, concentrated at reduced pressure to remove the organic solvent. The residue was extracted with ethyl acetate, and the organic phase was washed with brine, dried over anhydrous sodium sulfate, filtered and the filtrate was concentrated at reduced pressure to obtain the crude product. The crude was purified by Prep-HPLC to give compound 54 (100 mg, 52%). LC-MS (ESI): m/z 660.1 $[M+H]^+$.

Synthetic Route of Compound 55

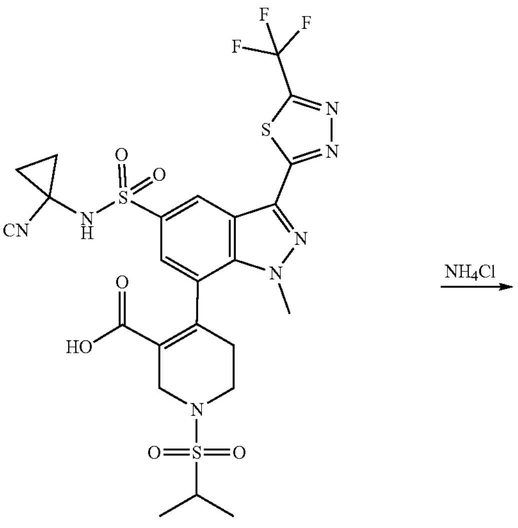

54

-continued

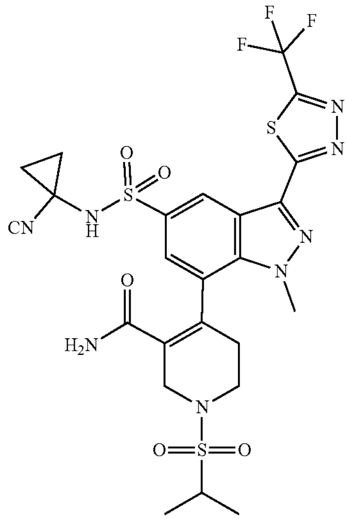

55

Synthesis of Compound 55

A reaction flask charged with 54 (50 mg, 0.076 mmol), ammonium chloride (41 mg, 0.76 mmol). DMF (5 mL), and DIPEA (0.066 mL, 0.38 mmol), followed by the slow addition of HATU (58 mg, 0.015 mmol) in an ice-cold water bath. After addition, the reaction mixture was warmed to room temperature and stirred overnight. On the next day, the reaction mixture was quenched with water, and the aqueous phase was extracted with ethyl acetate, the organic phase was washed with brine, dried over anhydrous sodium sulfate and the filtrate was concentrated. The crude was purified by Prep-HPLC to give compound 55 (10 mg, 20%). LC-MS (ESI): m/z 659.1 [M+H]$^+$.

Synthetic Route of Compound 56

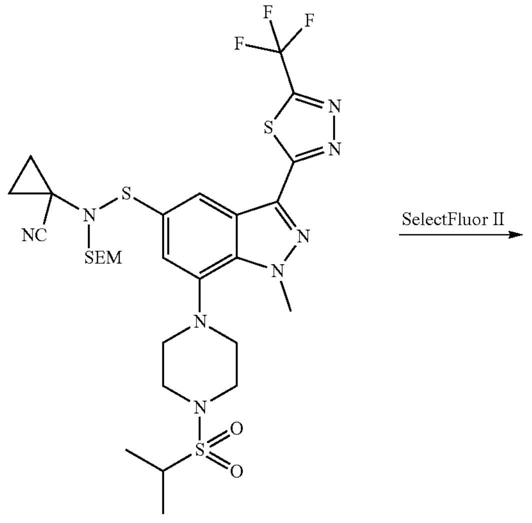

35-a

-continued

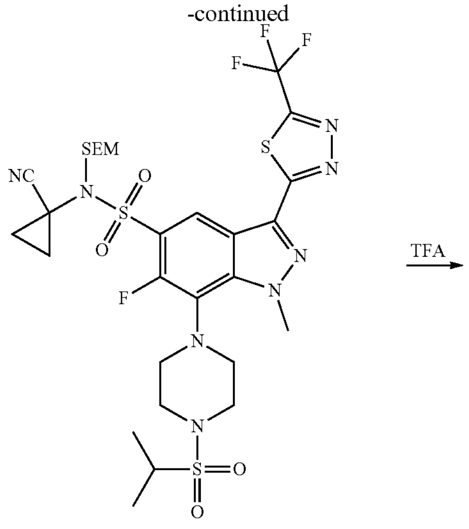

56-a

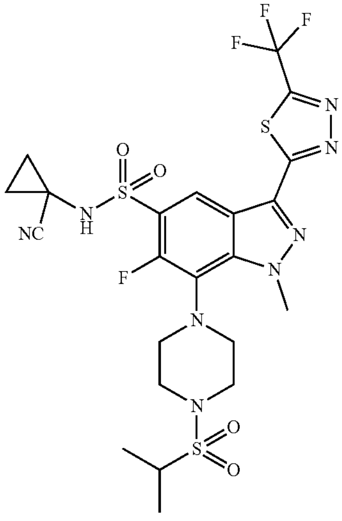

56

Synthesis of Compound 56-a

To a solution of 35-a (150 mg, 0.20 mmol) in acetonitrile (10 mL) was added SelectFluor II (256 mg, 0.80 mmol) and AcOH (0.2 mL). The reaction mixture was stirred at 50° C. overnight. On the next day, the reaction mixture was cooled to room temperature and the organic solvent was removed at low temperature at reduced pressure. The crude product was extracted with ethyl acetate, and the organic phase was washed with water, brine, dried over anhydrous sodium sulfate, filtered and evaporated to obtain the crude product, which was purified by a flash column chromatography (mobile phase: ethyl acetate/petroleum ether, 0% to 100%) to obtain compound 56-a (30 mg, 20%). LC-MS (ESI): m/z 767.1 [M+H]$^+$.

Synthesis of Compound 56

A reaction vial charged with 56-a (30 mg, 0.039 mmol), dichloromethane (5 mL) was added trifluoroacetic acid (1 mL) dropwise at room temperature. After the dropwise addition, the reaction mixture was stirred at room temperature for 4 hours. The solvent was removed by concentration at reduced pressure at room temperature, and the residue was diluted with dichloromethane. The organic phase was washed with saturated sodium bicarbonate, brine, dried over anhydrous sodium sulfate, filtered and the filtrate was concentrated at reduced pressure to obtain the crude product, which was purified by Prep-HPLC to give compound 56 (15 mg, 60%). LC-MS (ESI): m/z 637.2 $[M+H]^+$.

Synthetic Route of Compound 57

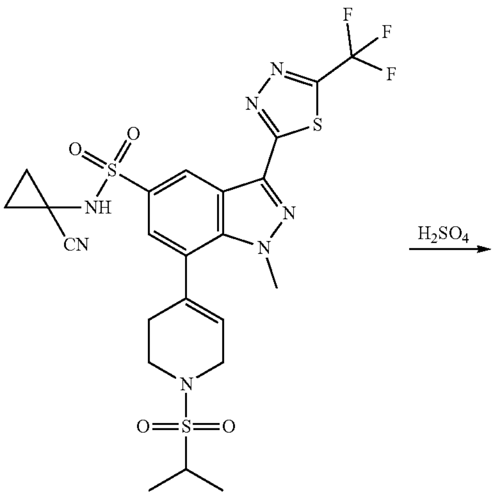

35

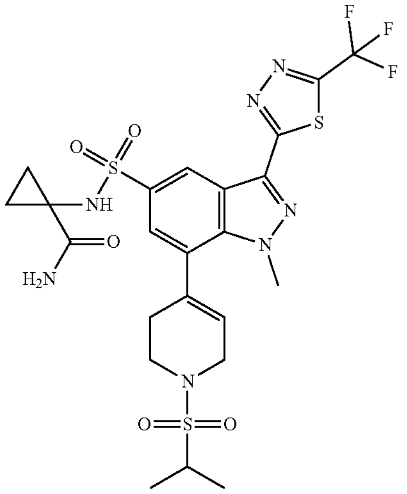

57

Synthesis of Compound 57

To a reaction flask charged with 35 (50 mg, 0.08 mmol) and dichloromethane (8 mL) was slowly added concentrated sulfuric acid (1 mL). The reaction mixture was stirred at room temperature for 3 hours, then was poured into ice-cold water (20 mL). The aqueous phase was extracted with dichloromethane (20 mL) and the organic phase was concentrated under reduced pressure and purified by Prep-HPLC to give compound 57 (23.3 mg, 45%). LC-MS (ESI): m/z 634.2 $(M+H)^+$. $^1H$ NMR (400 MHz, DMSO-$d_6$): δ 9.01 (1H, s), 8.86 (1H, s), 7.90 (1H, s), 5.71 (1H, s), 4.26 (3H, s), 4.02 (2H, d, J=2.0 Hz), 3.54 (2H, t, J=5.2 Hz), 3.40-3.51 (1H, m), 2.46 (2H, s), 1.39-1.47 (2H, m), 1.30 (6H, d, J=6.8 Hz), 1.15-1.21 (2H, m).

Synthetic Route of Compound 58

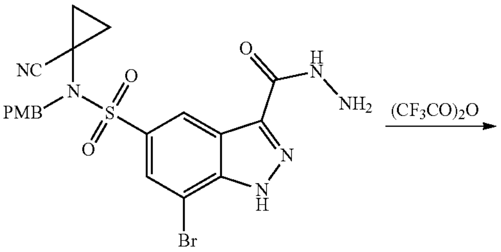

44-e

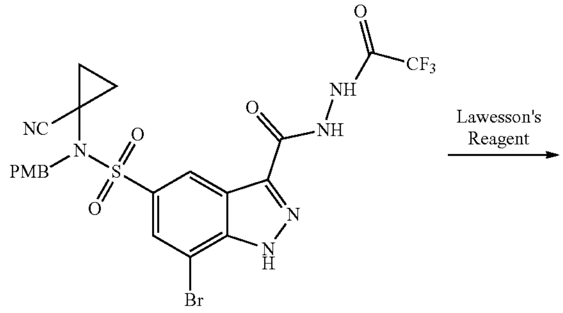

58-d

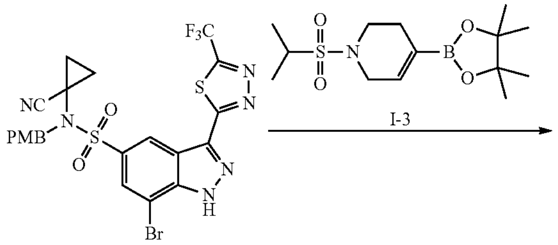

58-c

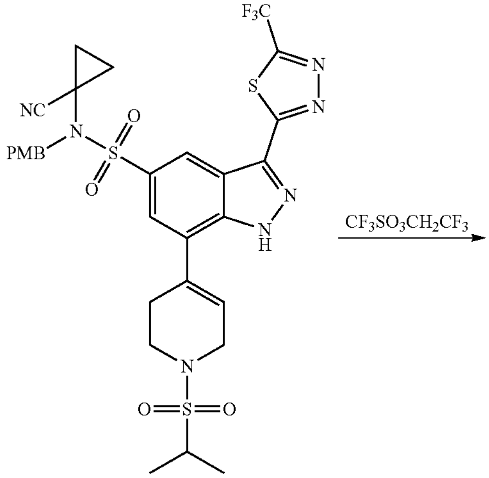

58-b

-continued

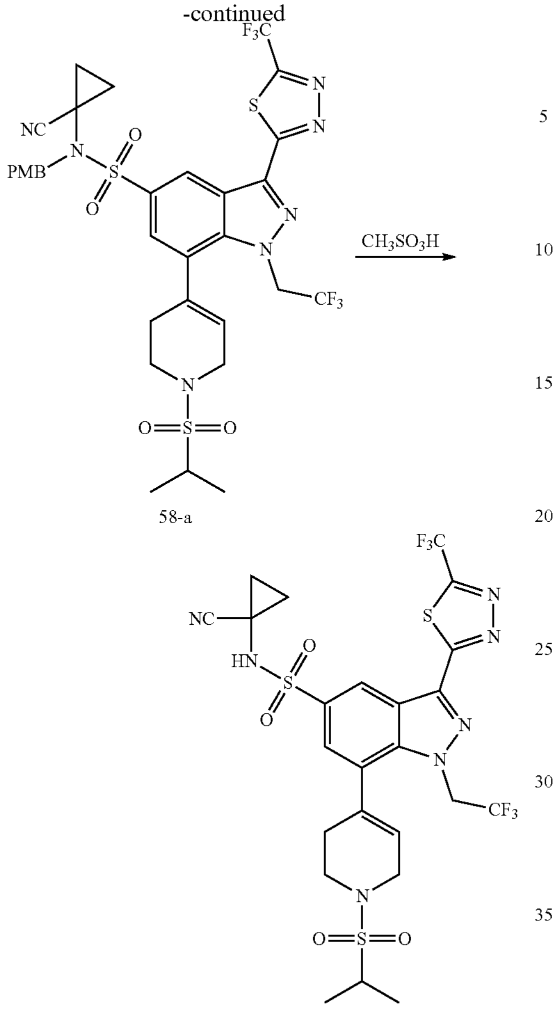

58-a

58

Synthesis of Compound 58-d

A reaction flask charged with 44-e (980 mg, 1.89 mmol), triethylamine (477 mg, 4.72 mmol) and dichloromethane (60 mL) was stirred in an ice-cold water bath for 10 minutes, then was slowly added trifluoroacetic anhydride (475 mg, 2.26 mmol) dropwise. After addition, the reaction mixture was stirred under nitrogen protection in an ice-cold water bath for 3 hours. The reaction mixture was washed with saturated sodium bisulfate (40 mL*2), washed once with water (30 mL), and the organic phase was concentrated to give compound 58-d (1100 mg, 95%). LC-MS (ESI): m/z 632.1 $(M+NH_4)^+$.

Synthesis of Compound 58-c

A reaction vial charged with 58-d (1100 mg, 1.79 mmol), Lawesson's reagent (1807 mg, 4.47 mmol) and tetrahydrofuran (100 mL) was stirred at 85° C. under nitrogen protection for 5 hours. The reaction mixture was concentrated. The residue was added toluene (70 mL), sodium carbonate (7.5 g) and water (75 mL). The mixture was stirred at room temperature for 2 hours. The liquid was partitioned, and the organic phase was concentrated. The residue was purified by column chromatography (petroleum ether/ethyl acetate=100/0; 100/70) to afford compound 58-c (241 mg, 22%). LC-MS (ESI): m/z 613.1 $(M+H)^+$.

Synthesis of Compound 58-b

A reaction flask charged with I-3 (280 mg, 0.89 mmol), 58-c (241 mg, 0.39 mmol), [1,1'-bis(di-tert-butylphosphino) ferrocene]palladium(II) dichloride (II) (63 mg, 0.10 mmol), cesium fluoride (179 mg, 1.18 mmol), 1,4-dioxane (90 mL) and water (10 mL), and then degassed and purged with nitrogen for three times. The reaction mixture was stirred at 100° C. for 12 hours. The reaction mixture was concentrated at reduced pressure, and the residue was washed with ethyl acetate (10 mL*3). The organic phase was concentrated at reduced pressure, and the residue was purified by column chromatography (petroleum ether/ethyl acetate=100/0, 10/20) to afford compound 58-b (240 mg, 84%). LC-MS (ESI): m/z 722.3 $(M+H)^+$.

Synthesis of Compound 58-a

A reaction vial charged with 58-b (45 mg, 0.06 mmol), trifluoroethyl trifluoromethanesulfonate (43 mg, 0.19 mmol), cesium carbonate (220 mg, 0.68 mmol), and N,N-dimethylformamide (4 mL) was stirred at room temperature for 8 h. The reaction mixture was quenched with water (20 mL). The aqueous phase was extracted with ethyl acetate (15 mL*2), and the organic phase was concentrated at reduced pressure and the residue was purified by column chromatography (petroleum ether/ethyl acetate=2/1) to give compound 58-a (12 mg, 24%). LC-MS (ESI): m/z 804.3 $(M+H)^+$.

Synthesis of Compound 58

A reaction vial charged with 58-a (12 mg, 0.015 mmol), methanesulfonic acid (120 mg, 1.25 mmol), dichloromethane (8 mL) was stirred at room temperature for 3 hours. The reaction mixture was quenched with saturated sodium bicarbonate (10 mL), the aqueous phase was extracted with dichloromethane (10 mL*2), and the organic phase was concentrated at reduced pressure and the residue was purified by Prep-HPLC to give compound 58 (2.9 mg, 28%). LC-MS (ESI): m/z 684.1 $(M+H)^+$.

Synthesis of Compound 59

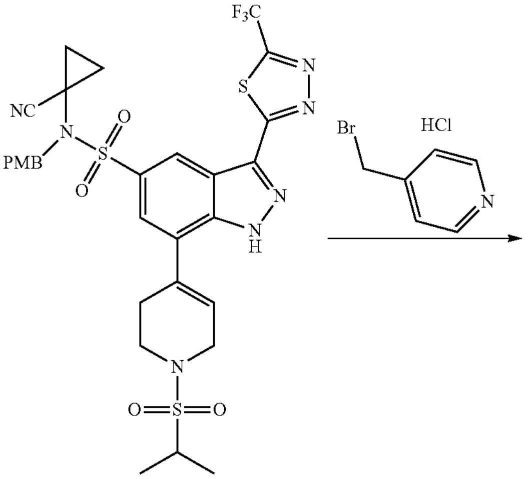

58-b

185

-continued

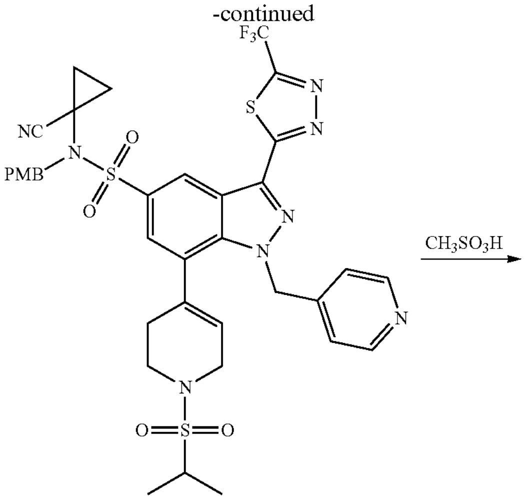

59-a

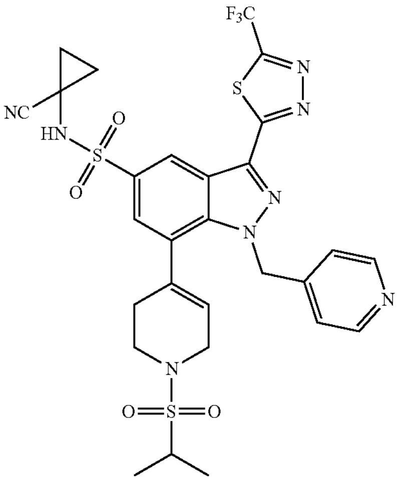

59

Referring to the synthesis of compound 58, compound 59 was synthesized using 4-(bromomethyl)pyridine hydrochloride instead of trifluoroethyl trifluoromethanesulfonate. LC-MS (ESI): m/z 693.2 $(M+H)^+$.

Synthesis of Compound 60

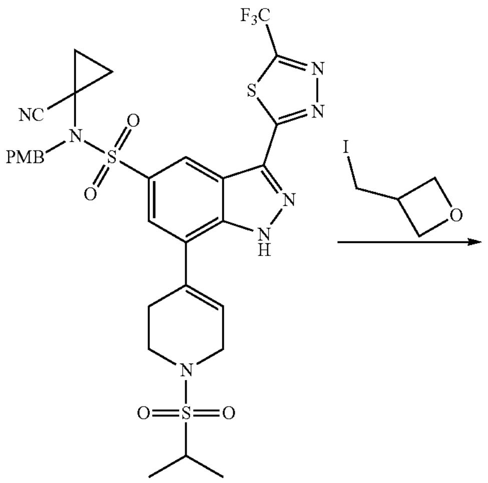

58-b

186

-continued

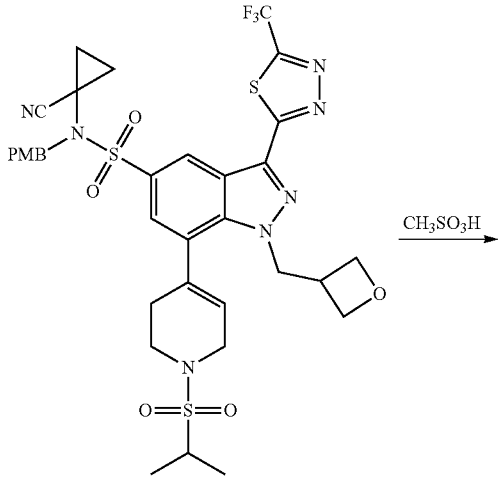

60-a

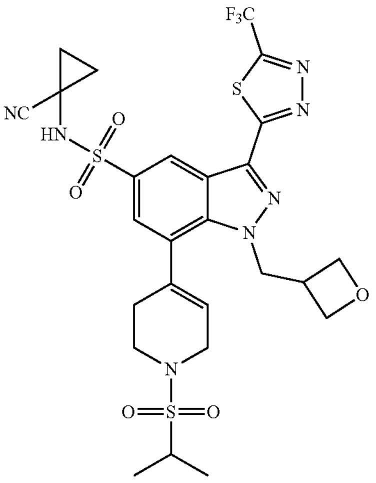

60

Referring to the synthetic method of compound 58, compound 60 was synthesized using 3-iodomethyl oxetane instead of trifluoroethyl trifluoromethanesulfonate to obtain compound 60. LC-MS (ESI): m/z 672.2 $(M+H)^+$.

Synthetic Route of Compound 61

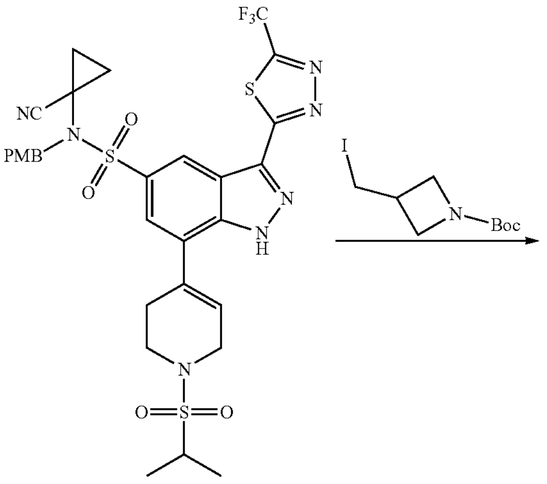

58-b

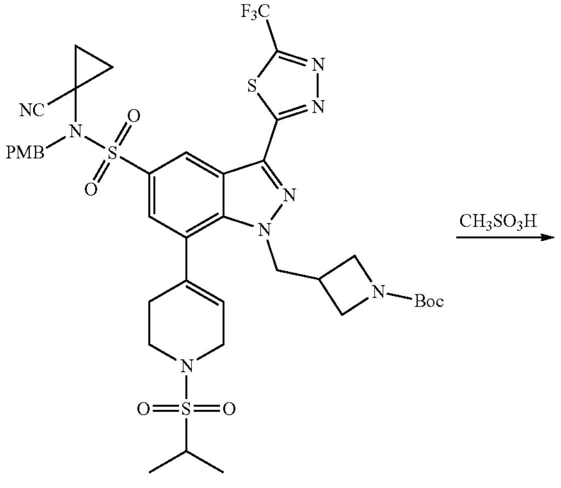

61-a

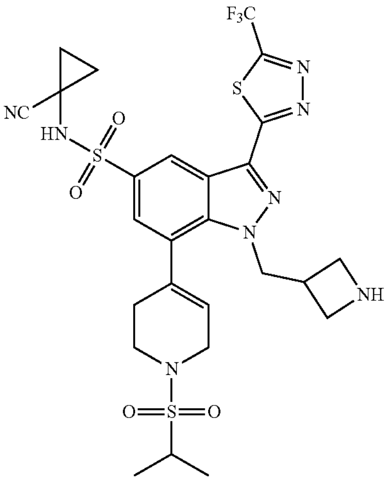

61

Synthesis of Compound 61-a

A reaction vial charged with 58-b (50 mg, 0.07 mmol), 1-Boc-(3-iodomethyl)azetidine (83 mg, 0.28 mmol), potassium carbonate (10 mg, 0.07 mmol) and N,N-dimethylformamide (4 mL) was stirred at room temperature for 48 hours. The reaction mixture was quenched with water (20 mL), the aqueous phase was extracted with ethyl acetate (20 mL*3), and the organic phase was concentrated at reduced pressure and the residue was purified by column chromatography (petroleum ether/ethyl acetate=3/1) to afford compound 61-a (31 mg, 50%). LC-MS (ESI): m/z 891.3 $(M+H)^+$.

Synthesis of Compound 61

A reaction flask charged with 61-a (31 mg, 0.035 mmol), methanesulfonic acid (120 mg, 1.25 mmol), dichloromethane (8 mL) was stirred at room temperature for 3 hours. The reaction mixture was quenched by the addition of ammonia methanol (0.12 mL) and the organic phase was concentrated at reduced pressure and the residue was purified by Prep-HPLC to give compound 61 (6.2 mg, 26%). LC-MS (ESI): m/z 671.3 $(M+H)^+$.

Synthesis of Compound 62

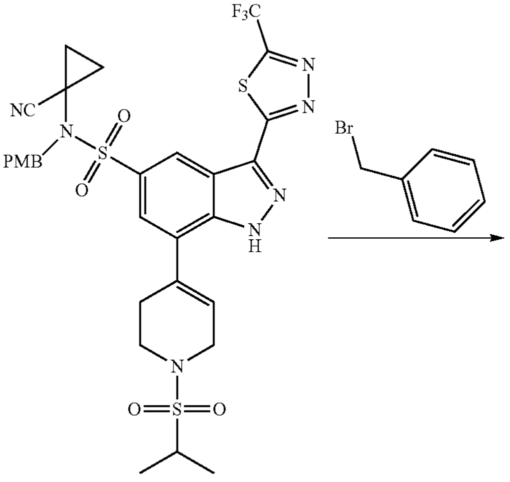

58-b

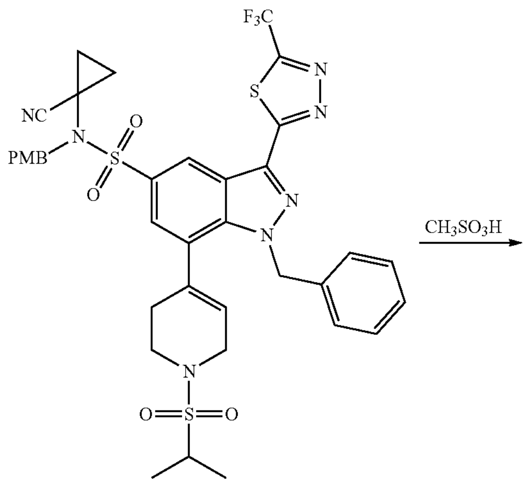

62-a

-continued

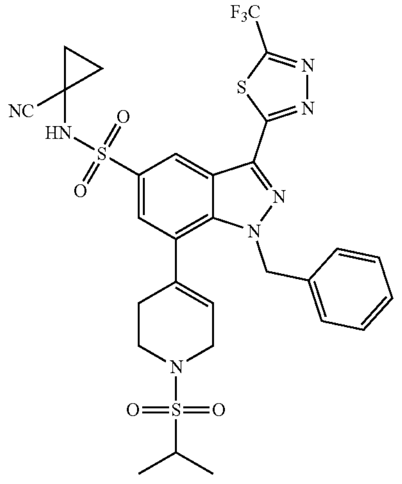

62

Referring to the synthetic method of compound 58, compound 62 was synthesized using benzyl bromide instead of trifluoroethyl trifluoromethanesulfonate. LC-MS (ESI): m/z 692.1 $(M+H)^+$.

Synthetic Route of Compound 63

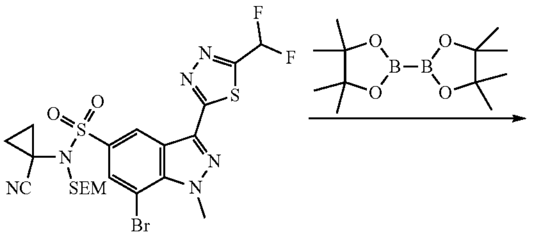

I-1

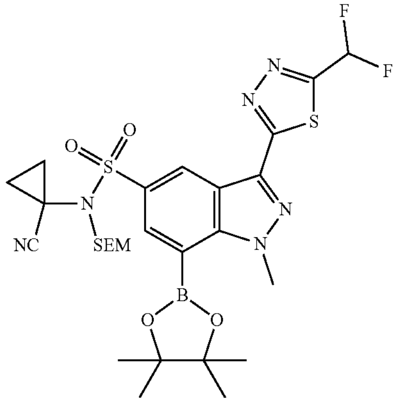

63-d

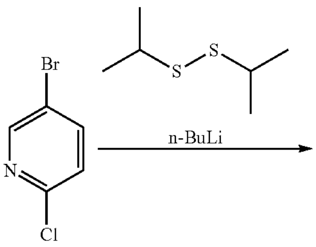

-continued

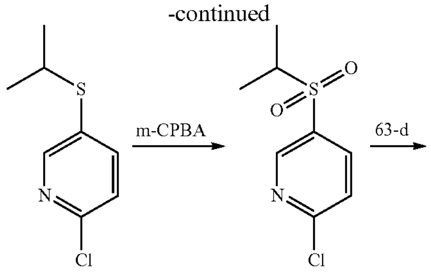

63-c 63-b

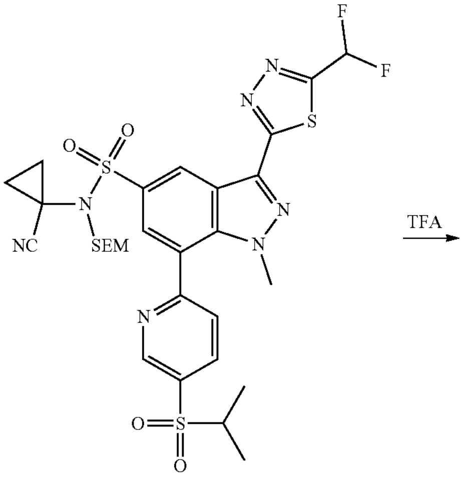

63-a

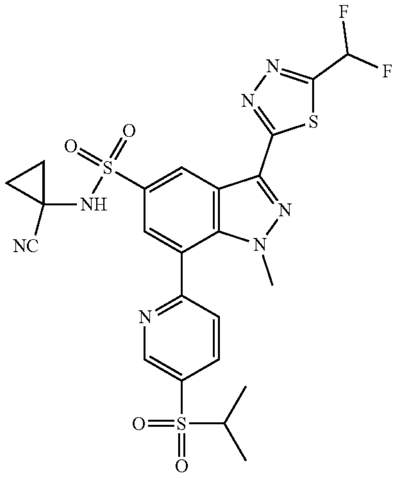

63

Synthesis of Compound 63-d

Compound I-1 (100 mg, 0.16 mmol) was dissolved in 10 mL of toluene at room temperature, and was added pinacol ester of bisboronic acid (123 mg, 0.48 mmol), chloro(2-dicyclohexylphosphino-2',4',6'-triisopropyl-1,1'-biphenylyl)[2-(2'-amino-1,1'-biphenyl)]palladium(II) (13 mg, 0.016 mmol), potassium acetate (48 mg, 0.48 mmol) and 2-dicyclohexylphosphino-2,4,6-triisopropylbiphenyl (15 mg, 0.032 mmol) sequentially. The reaction mixture was stirred at 65° C. under argon for 8 hours. Cooled to room temperature, the reaction mixture was added 50 mL of water, extracted with ethyl acetate (50 mL*2). The organic phase was dried over anhydrous sodium sulfate, filtered, and the filtrate was concentrated at reduced pressure to obtain the crude product 63-d (107 mg), which was used directly in the next reaction without further purification. LC-MS (ESI): m/z=667.2[M+H]$^+$.

Synthesis of Compound 63-c

Compound 5-bromo-2-chloropyridine (3000 mg, 15.59 mmol) was dissolved in 30 mL of anhydrous THF under nitrogen protection at room temperature. The mixture was cooled at −78° C. and was added n-BuLi (7.5 mL, 18.71 mmol, 2.5 M) dropwise. After the dropwise addition, the mixture was stirred under nitrogen protection at −78° C. for 30 min, then was added isopropyl disulfide (2.98 mL, 18.71 mmol) dropwise. After the dropwise addition, the reaction mixture was stirred under nitrogen protection at room temperature for 1 hr. At room temperature, the reaction mixture was slowly added 100 mL of saturated ammonium chloride solution, then extracted with ethyl acetate (100 mL). The organic phase was washed with brine (100 mL), dried over anhydrous sodium sulfate, filtered, and the filtrate was concentrated at reduced pressure, and the residue was purified by a flash column chromatography (PE/EA=10/1) to give compound 63-c (750 mg, 26%). LC-MS (ESI): m/z=188.1 [M+H]$^+$.

Synthesis of Compound 63-b

Compound 63-c (200 mg, 1.07 mmol) was dissolved in 10 mL of DCM at room temperature and was added m-CPBA (541 mg, 2.66 mmol) in batches. The mixture was stirred at room temperature under nitrogen protection for 30 min. The reaction mixture was added 100 mL of saturated sodium bicarbonate solution and extracted with DCM (100 mL). The organic phase was washed sequentially with saturated sodium bicarbonate solution (100 mL), water (200 mL), dried over anhydrous sodium sulfate, filtered, and the filtrate was concentrated at reduced pressure, and the residue was purified by a flash column chromatography (PE/EA=3:1) to give compound 63-b (188 mg, 80%). LC-MS (ESI): m/z=220.1 [M+H]$^+$.

Synthesis of Compound 63-a

A solution of compound 63-d (107 mg, 0.16 mmol) in 18 mL of 1,4-dioxane at room temperature was added compound 63-b (176 mg, 0.80 mmol), 1,1'-di-tert-butylphosphinoferrocene palladium dichloride (21 mg, 0.032 mmol), cesium fluoride (73 mg, 0.48 mmol) and water (2 mL). The reaction mixture was stirred at 80° C. under nitrogen protection for 5 hours. The reaction mixture was cooled to room temperature, concentrated at reduced pressure, and the residue was added 100 mL of water and the aqueous phase was extracted with ethyl acetate (100 mL). The organic phase was dried over anhydrous sodium sulfate, filtered and the filtrate was concentrated at reduced pressure to give the crude product. The crude product was purified by Prep-TLC (PE/EA=2:1) to give the crude compound 63-a (80 mg, 69%), which was directly used in the next reaction without further purification. LC-MS (ESI): m/z=724.3 [M+H]$^+$.

Synthesis of Compound 63

Trifluoroacetic acid (2 mL) was added to a solution of compound 63-a (80 mg, 0.11 mmol) in 6 mL of dichloromethane at room temperature, and the reaction mixture was stirred under nitrogen protection for 1.5 h at room temperature. The reaction mixture was concentrated at reduced pressure and the residue was suspended in 5 mL of saturated sodium bicarbonate, then was added potassium carbonate (200 mg) and ethyl acetate (20 mL). The reaction mixture was stirred for 30 min at room temperature, then 20 mL of water was added to the reaction mixture and extracted with ethyl acetate (50 mL). The organic phase was dried over anhydrous sodium sulfate, filtered, and the filtrate was concentrated at reduced pressure, and the residue was purified by Prep-HPLC ($NH_4HCO_3$) to afford compound 63 (8.2 mg, 13%). LC-MS (ESI): m/z=594.1[M+H]$^+$.

Synthetic Route of Compound 64

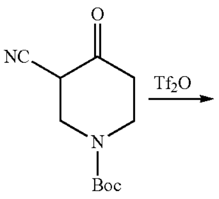

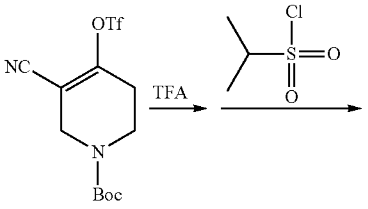

64-c

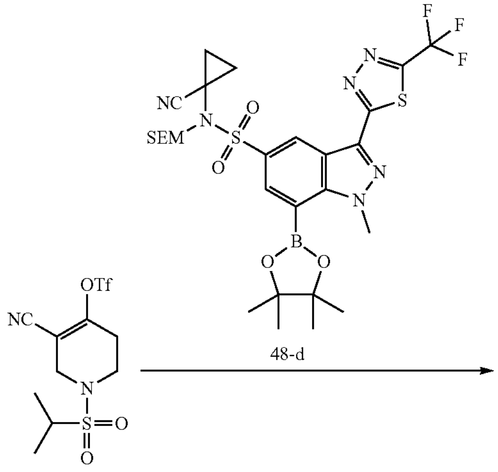

64-b

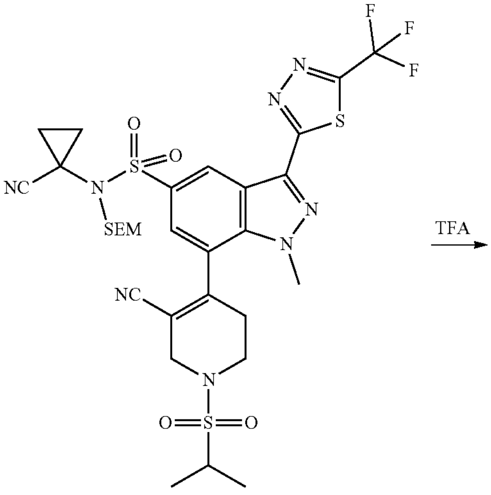

64-a

-continued

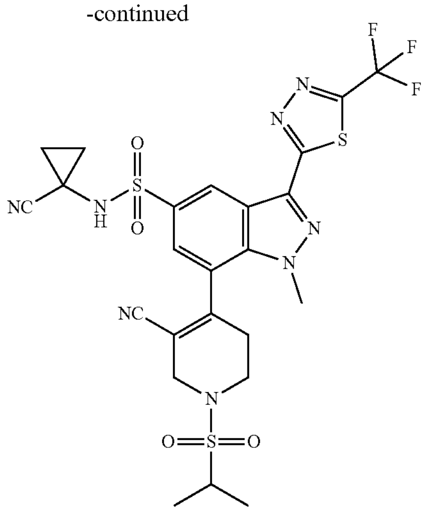

64

Synthesis of Compound 64-c

A solution of compound N-Boc-3-cyano-4-piperidone (1 g, 4.46 mmol) in dichloromethane (10 mL) was added dimethylaminopyridine (110 mg, 0.90 mmol), triethylamine (590 mg, 5.83 mmol), then was added trifluoromethanesulfonic anhydride (1.64 g, 5.81 mmol) dropwise in an ice-cold water bath. The reaction mixture was stirred at room temperature for 4 hours, then was added water (100 mL), extracted with dichloromethane (100 mL). The organic phase was washed with brine (100 mL), dried over sodium sulfate, filtered to remove the desiccant, and the filtrate was concentrated at reduced pressure to obtain the crude product, which was purified by column chromatography (mobile phase, PE/EA 3/1) to obtain 64-c (1.16 g, 73%). $^1$H NMR (400 MHz, DMSO-$d_6$): δ 4.28-4.24 (2H, m), 3.62-3.55 (2H, m), 2.70-2.64 (2H, m), 1.42 (9H, s).

Synthesis of Compound 64-b

Compound 64-c (500 mg, 1.40 mmol) was dissolved in dichloromethane (10 mL), to which trifluoroacetic acid (3 mL) was added, and the reaction mixture was stirred at room temperature for 2 h, then was adjusted to pH 7 to 8 with saturated sodium bicarbonate solution, extracted with dichloromethane (100 mL) containing 10% methanol. The organic phase was washed with brine (50 mL), dried over sodium sulfate, filtered to remove the desiccant, and the filtrate was concentrated at reduced pressure to obtain the crude product, which was dissolved in dichloromethane (10 mL), to which triethylamine (284 mg, 2.81 mmol) was added, and isopropylsulfonyl chloride (300 mg, 2.10 mmol) was added dropwise in an ice-cold water bath, and the reaction mixture was stirred at room temperature for 1 hour. The reaction mixture was concentrated at reduced pressure to obtain the crude product, which was purified by column chromatography (mobile phase, PE/EA 1/1) to obtain 64-b (166 mg, 33%).

Synthesis of Compound 64-a

Compound 64-b (74 mg, 0.20 mmol), 48-d (200 mg, 0.29 mmol), [1,1'-bis(di-tert-butylphosphino)ferrocene]palladium dichloride (40 mg, 0.062 mmol), and cesium fluoride (133 mg, 0.88 mmol) were added to 1,4-dioxane (9 mL) and water (1 mL), the reaction mixture was degassed and purged with nitrogen for 3 times and then stirred at 90° C. for 3 hours. The reaction mixture was filtered through celite, and the filtrate was added water (50 mL) and extracted with dichloromethane (50 mL). The organic phase was washed with brine (50 mL), dried over sodium sulfate, filtered off the desiccant, and the filtrate was concentrated at reduced pressure to obtain the crude product, which was purified by column chromatography (mobile phase, PE/EA 1/1) to obtain 64-a (44 mg, 28%). LC-MS (ESI): m/z 769.2 $(M-H)^-$.

Synthesis of Compound 64

Compound 64-a (44 mg, 0.057 mmol) was dissolved in dichloromethane (3 mL) in an ice-cold water bath, to which trifluoroacetic acid (1 mL) was added, and the reaction mixture was stirred for 2 h at room temperature. The dichloromethane was removed by concentration at reduced pressure, and the residue was adjusted pH to 7 to 8 with saturated sodium bicarbonate solution. The aqueous phase was extracted with dichloromethane (50 mL). The organic phase was washed with brine (50 mL), dried over sodium sulfate, filtered off the desiccant, and the filtrate was concentrated at reduced pressure to obtain the crude product, which was purified by Prep-HPLC (basic conditions) to give Compound 64 (19 mg, 52%). LC-MS (ESI): m/z 639.1 $(M-H)^-$.

Synthetic Route of Compound 65

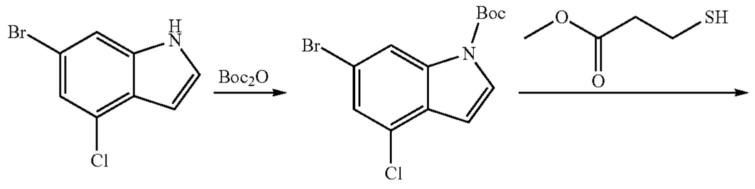

65-g

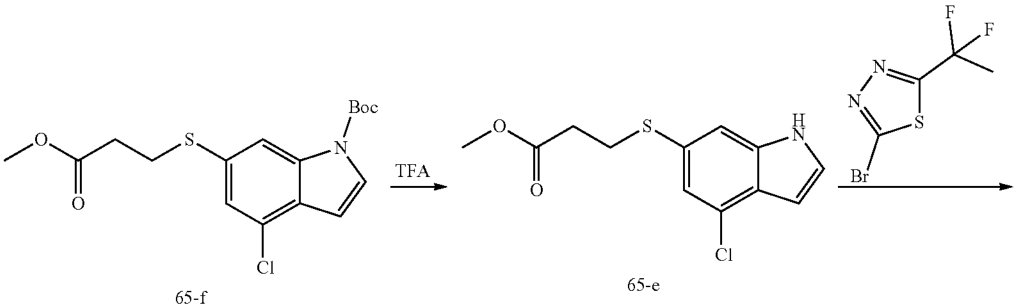

65-f 65-e

-continued
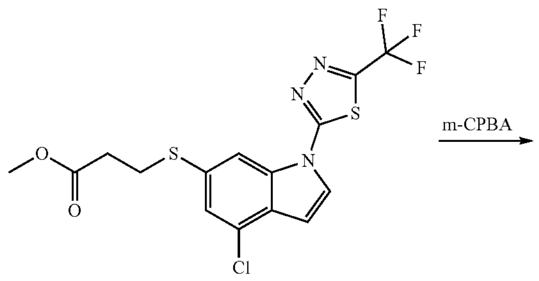
65-d
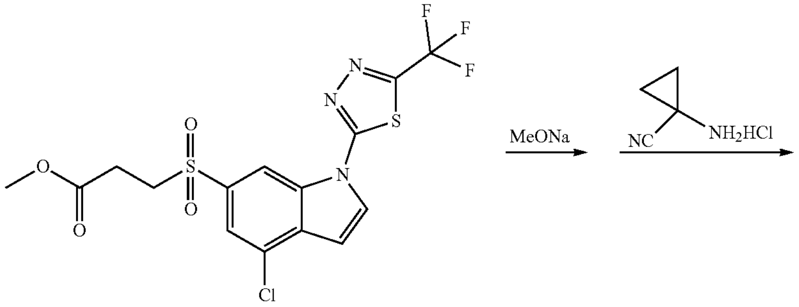
65-c
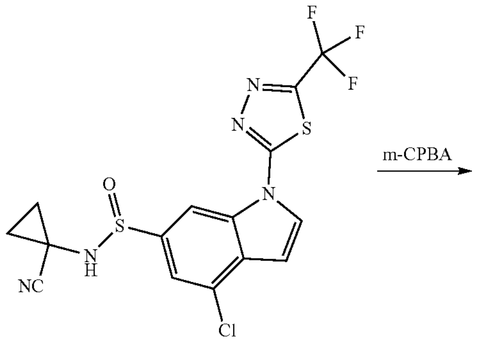
65-b
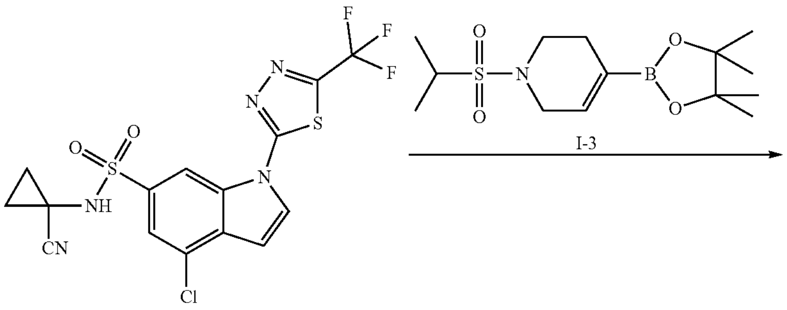
65-a

-continued

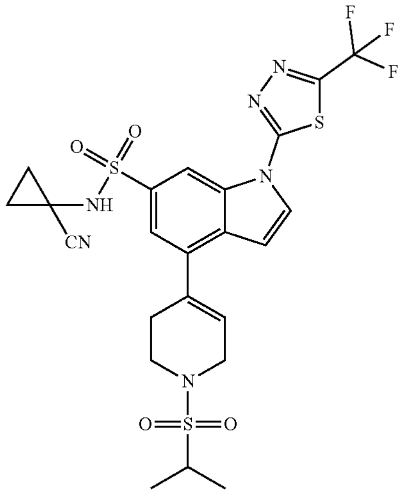

65

Synthesis of Compound 65-g

A reaction flask charged with 6-bromo-4-chloroindole (660 mg, 2.86 mmol), N,N-diisopropylethylamine (1110 mg, 8.59 mmol), 4-dimethylaminopyridine (35 mg, 0.29 mmol), and di-tert-butyl dicarbonate (1250 mg, 5.73 mmol) and dichloromethane (100 mL) was stirred under nitrogen protection at room temperature for 3 hours. The reaction mixture was washed with saturated sodium bisulfate (20 mL), and the organic phase was concentrated, purified by column chromatography (petroleum ether/ethyl acetate=5/1) to obtain compound 65-g (610 mg, 64%).

Synthesis of Compound 65-f

A reaction vial charged with 65-g (610 mg, 1.85 mmol), $Pd_2(dba)_3$ (84 mg, 0.09 mmol), Xantphos (107 mg, 0.19 mmol), 1,4-dioxane (10 mL), N,N-diisopropylethylamine (715 mg, 5.54 mmol) and methyl 3-mercaptopropionate (266 mg, 2.21 mmol) was degassed and purged with nitrogen for three times. The reaction mixture was stirred at 90° C. for 3 hours, then cooled to room temperature, concentrated to remove the solvent, and the residue was purified by column chromatography (petroleum ether/ethyl acetate=5/1, 3/1) to obtain the compound 65-f (620 mg, 91%). LC-MS (ESI): m/z 387.2 $(M+NH_4)^+$.

Synthesis of Compound 65-e

A reaction vial charged with 65-f (620 mg, 1.68 mmol), dichloromethane (6 mL), trifluoroacetic acid (2 mL) and stirred at room temperature for 3 h under nitrogen protection. The reaction mixture was concentrated at reduced pressure and saturated aqueous sodium bicarbonate (20 mL) was added to the residue, which was extracted with dichloromethane (20 mL*2). The organic phase was concentrated at reduced pressure and the residue was purified by column chromatography (petroleum ether/ethyl acetate=3/1, 1/3) to afford compound 65-e (409 mg, 90%).

Synthesis of Compound 65-d

A reaction vial charged with 65-e (410 mg, 1.52 mmol), 2-bromo-5-(trifluoromethyl)-1,3,4-thiadiazole (710 mg, 3.05 mmol), cesium carbonate (990 mg, 3.04 mmol), N,N-dimethylformamide (10 mL) was stirred under nitrogen protection for 4 hours at room temperature. The reaction mixture was added brine (50 mL) and extracted with ethyl acetate (50 mL*3). The organic phase was concentrated at reduced pressure and the residue was purified by column chromatography (petroleum ether/ethyl acetate=3/1, 1/1) to afford compound 65-d (390 mg, 61%). LC-MS (ESI): m/z 422.1 $(M+H)^+$.

Synthesis of Compound 65-c

A reaction flask charged with 65-d (390 mg, 0.93 mmol), m-chloroperoxybenzoic acid (469 mg, 2.31 mmol) and ethyl acetate (40 mL) was stirred in an ice-cold water bath for 10 min, then stirred at room temperature and for 3 hr. The reaction mixture was added saturated aqueous sodium bicarbonate (40 mL), partitioned, and the organic phase was concentrated and purified by column chromatography (dichloromethane/methanol=100/0, 10/1) to afford compound 65-c (292 m g, 70%). LC-MS (ESI): m/z 454.0 $(M+H)^+$.

Synthesis of Compound 65-b

A reaction flask charged with 65-c (120 mg, 0.26 mmol), methanol (10 mL) and dichloromethane (10 mL) in an ice-cold water bath was added sodium methanolate (43 mg, 0.79 mmol). The reaction mixture was stirred for 1 hour in an ice-cold water bath, then in an ice-cold water bath was added 1-aminocyclopropanecarbonitrile hydrochloride (125 mg, 1.06 mmol) and stirred for 15 minutes. The solvent was concentrated at room temperature and the residue was dried by an oil pump for 1 hour. Then 1-aminocyclopropanecarbonitrile hydrochloride (31 mg, 0.26 mmol) and N,N-dimethylformamide (10 mL) were added to the residue, followed by N,N-dimethylaminopyridine (65 mg, 0.53 mmol) and EDCI (152 mg, 0.79 mmol) while stirring in an ice-cold water bath, then the temperature was warmed to room temperature and stirred for 2 hours. The reaction mixture was added water (100 mL) and extracted with ethyl acetate (100 mL*3). The organic phase was concentrated and purified by column chromatography (petroleum ether/ethyl acetate=3/1, 1/3) to give 65-b (73 mg, 63%). LC-MS (ESI): m/z 432.1 $(M+H)^+$.

Synthesis of Compound 65-a

A reaction flask charged with 65-b (73 mg, 0.17 mmol), m-chloroperoxybenzoic acid (44 mg, 0.25 mmol) and dichloromethane (20 mL) was stirred at room temperature for 2 h. The reaction mixture was quenched by addition of saturated aqueous sodium bicarbonate (40 mL) and partitioned. The organic phase was concentrated and purified by column chromatography (petroleum ether/ethyl acetate=6/1 to 1/1) to afford compound 65-a (63 mg, 83%). LC-MS (ESI): m/z 448.0 $(M+H)^+$.

Synthesis of Compound 65

A reaction flask charged with 65-a (30 mg, 0.07 mmol), I-3 (32 mg, 0.10 mmol), [1,1'-bis(di-tert-butylphosphino) ferrocene]palladium(II) dichloride (II) (11 mg, 0.02 mmol), cesium fluoride (31 mg, 0.20 mmol), 1,4-dioxane (9 mL) and water (1 mL) was degassed and purged with nitrogen for three times, and stirred at 100° C. for 8 hours. The reaction mixture was concentrated at reduced pressure, and the residue was washed with ethyl acetate (10 mL*3). The organic phase was concentrated at reduced pressure and the residue was purified by Prep-HPLC to give compound 65 (6.2 mg, 15%). LC-MS (ESI): m/z 601.0 $(M+H)^+$.

Synthetic Route of Compound 66

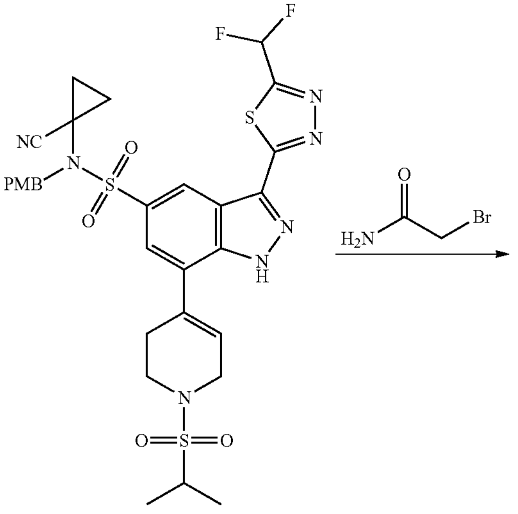

44-b

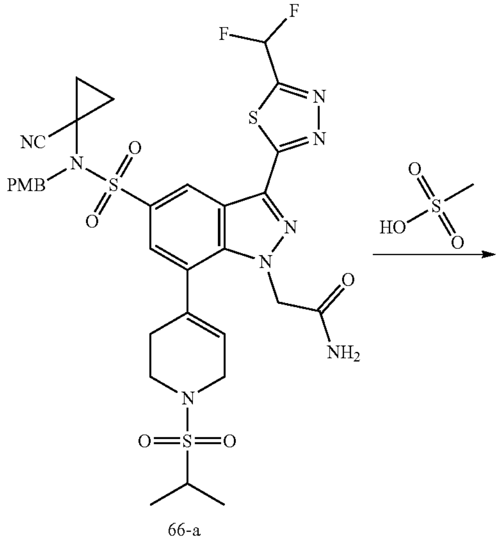

66-a

-continued

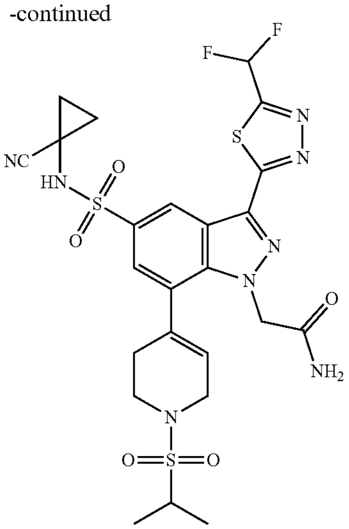

66

Synthesis of Compound 66-a

A solution of compound 44-b (50 mg, 0.071 mmol) in 5 mL of DMF at room temperature was added potassium carbonate (31 mg, 0.22 mmol), potassium iodide (2.4 mg, 0.014 mmol) and 2-bromoacetamide (49 mg, 0.36 mmol) sequentially, and the reaction mixture was stirred at room temperature under nitrogen protection for 36 hours. The reaction mixture was added 50 mL of brine, then extracted with ethyl acetate (50 mL*2), the organic phase was washed with brine (50 mL*5), dried over anhydrous sodium sulfate, filtered, and the filtrate was distilled at reduced pressure to give compound 66-a (crude, 48 mg, 89%), the crude was used directly in the next step. LC-MS (ESI): m/z=761.3 $[M+H]^+$.

Synthesis of Compound 66

A solution of compound 66-a (48 mg, 0.063 mmol) dissolved in 2.5 mL of DCM in an ice-cold water bath was added methanesulfonic acid (180 uL, 2.77 mmol). The reaction mixture was warmed to room temperature and stirred for 1 hour. The reaction mixture was added 50 mL of DCM, and the organic phase was washed with saturated sodium bicarbonate solution (50 mL), dried over anhydrous sodium sulfate, filtered, and the filtrate was concentrated at reduced pressure to give the crude product, which was purified by Prep-HPLC (basic method, $NH_4HCO_3$) to give compound 66 (12.8 mg, 32%). LC-MS (ESI): m/z=641.2 $[M+H]^+$.

Synthetic Route of Compound 67

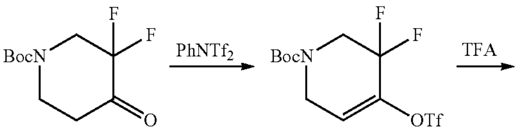

67-d

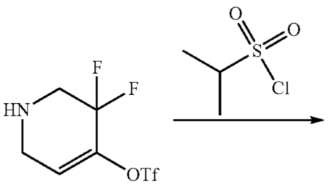

67-c

-continued

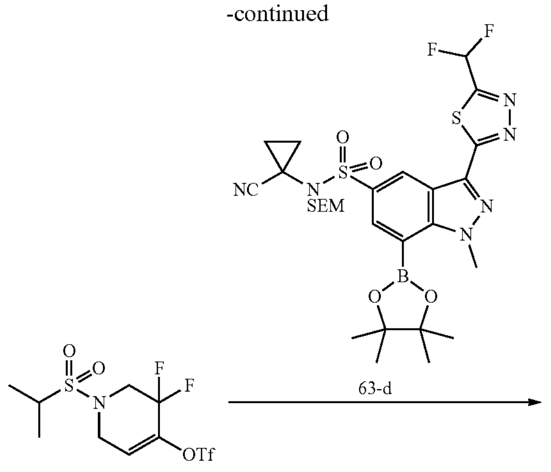

63-d 67-b

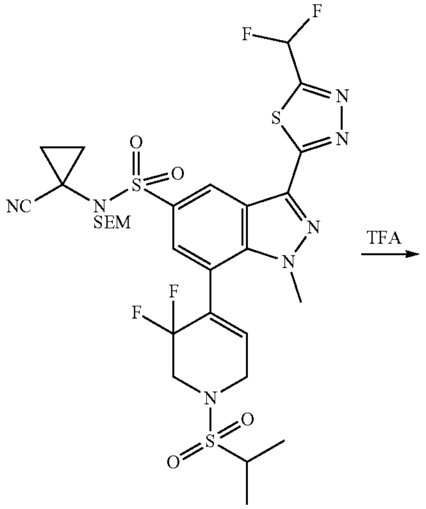

67-a

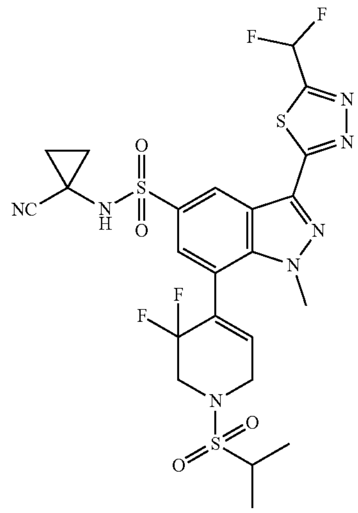

67

Synthesis of Compound 67-d

A reaction vial charged with tert-butyl 3,3-difluoro-4-oxopiperidine-1-carboxylate (5.60 g, 23.81 mmol), N-phenylbis(trifluoromethanesulfonyl)imide (17.01 g, 47.61 mmol), DMAP (0.29 g, 2.37 mmol) and anhydrous dichloromethane (100 mL) was added triethylamine (20.0 mL, 143.89 mmol) dropwise. After addition, the reaction mixture was stirred at room temperature for 18 hours. The reaction mixture was quenched by addition of saturated sodium bicarbonate solution, partitioned, and the organic phase was washed with water, brine, dried over anhydrous sodium sulfate, filtered, and the filtrate was evaporated to dryness. The residue was purified by column chromatography (mobile phase: petroleum ether/ethyl acetate, 100/0 to 80/20) to give 67-d (8.1 g, 93%).

Synthesis of Compound 67-c

A reaction vial charged with 67-d (1.15 g, 3.13 mmol) and dichloromethane (8 mL) was added trifluoroacetic acid (3 mL) dropwise at room temperature. The reaction mixture was stirred at room temperature for 2 hours. The solvent was removed and the residue was dried by an oil pump. To the residue, petroleum ether and methyl tert-butyl ether were added to slurry, filtered, and the solid was washed with petroleum ether and dried by an oil pump to give 67-c (1.19 g, 100%). LC-MS (ESI): m/z 267.9 $(M+H)^+$.

Synthesis of Compound 67-b

A reaction flask charged with 67-c (1.19 g, 3.13 mmol) and dichloromethane (10 mL) in an ice-cold water bath was added triethylamine (2.0 mL, 14.3 mmol), followed by dropwise addition of isopropylsulfonyl chloride (0.60 g, 4.21 mmol) in an ice-cold water bath. After addition, the reaction mixture was stirred in an ice-cold water bath for 1 hour, then at room temperature for 3 hours. The reaction mixture was quenched by addition of saturated sodium bicarbonate. The aqueous phase was extracted once with dichloromethane, and the organic phases were combined, dried over anhydrous sodium sulfate, filtered and evaporated to dryness. The crude was purified by column chromatography (mobile phase: petroleum ether/ethyl acetate, 100/0 to 70/30) to give 67-b (700 mg, 60%).

Synthesis of Compound 67-a

A reaction vial charged with 67-b (260 mg, 0.70 mmol), 63-d (110 mg, 0.17 mmol), Pd(dtbpf)$Cl_2$ (22 mg, 0.034 mmol) and 1,4-dioxane (10 mL) was degassed and purged with nitrogen for three times, then was added a solution of cesium fluoride (210 mg, 1.38 mmol) in water (1 mL) dropwise while stirring. The reaction mixture was stirred at 50° C. for 2 hours under nitrogen protection. The reaction mixture was cooled to room temperature and diluted with ethyl acetate. The organic phase was washed twice with water, washed with brine, dried over anhydrous sodium sulfate, filtered and evaporated to obtain the crude product. The crude was purified by column chromatography (mobile phase: dichloromethane/ethyl acetate, 100/0 to 70/30) to give 67-a (80 mg, 63%). LC-MS (ESI): m/z 764.3 $(M+H)^+$.

Synthesis of Compound 67

A reaction vial charged with 67-a (80 mg, 0.11 mmol) and dichloromethane (3 mL) was added trifluoroacetic acid (0.7 mL) at room temperature. The reaction mixture was stirred at room temperature for 2 hours. The solvent was removed and the residue was diluted with ethyl acetate, and the new mixture was added saturated sodium bicarbonate and anhydrous potassium carbonate and the resulting mixture was stirred for 20 minutes at room temperature. The liquid was partitioned, the aqueous phase was extracted once with ethyl acetate, the organic phases were combined, washed with brine, dried over anhydrous sodium sulfate, filtered, and the filtrate was evaporated, and the crude was purified by Prep-HPLC (ammonium bicarbonate) to give 67 (18 mg, 27%). LC-MS (ESI): m/z 634.2 $(M+H)^+$; $^1$HNMR (DMSO-$d_6$, 400 MHz): δ 9.10 (1H, bs), 8.98 (1H, d, J=1.6 Hz), 7.92-7.50 (2H, m), 6.70 (1H, s), 4.31-4.25 (2H, m), 4.16

(3H, s), 4.15-4.05 (2H, m), 3.56 (1H, p, J=6.8 Hz), 1.45-1.38 (2H, m), 1.33 (6H, d, J=6.8 Hz), 1.28-1.22 (2H, m).

Synthetic Route of Compound 68

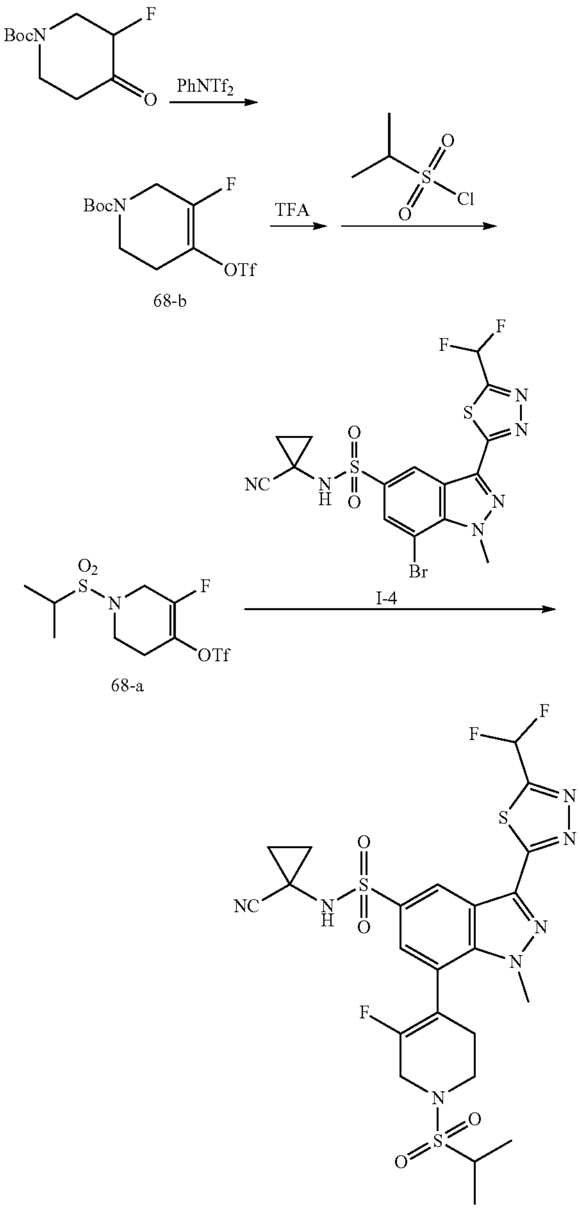

68-b 68-a

68

Synthesis of Compound 68-b

Cooled at −78° C. and under nitrogen protection, a reaction flask charged with a solution of LHMDS in tetrahydrofuran (1M, 17 mL, 17.00 mmol) was added a solution of tert-butyl 3-fluoro-4-oxopiperidine-1-carboxylate (2.9 g, 13.35 mmol) in anhydrous THF (20 mL) slowly dropwise in a period of 30 min. The reaction mixture was stirred at −78° C. for 30 min, then was slowly added a solution of N-phenylbis(trifluoromethanesulfonyl)imide (5.72 g, 16.02 mmol) in anhydrous THF (20 mL) dropwise at −78° C. After addition, the reaction mixture was stirred from −78° C. to room temperature for 1 hour. The solvent was removed, and the residue was added ethyl acetate and petroleum ether, washed with ice-cold water, washed with water, washed with brine, dried over anhydrous sodium sulfate, filtered, and the filtrate was evaporated to dryness, and purified by column chromatography (mobile phase: petroleum ether/ethyl acetate, 100/0 to 85/15) to give 68-b (200 mg, 4.3%).

Synthesis of Compound 68-a

A reaction vial charged with 68-b (200 mg, 0.57 mmol) and dichloromethane (2 mL) was added trifluoroacetic acid (0.7 mL) dropwise in a water bath at room temperature. The reaction mixture was stirred at room temperature for 2 hours. The solvent was removed and the residue was dried by an oil pump to give a solid crude product. A reaction flask charged with the above crude product and dichloromethane (20 mL) in an ice-cold water bath was added triethylamine (0.32 mL, 2.30 mmol) and 2-propylsulfonyl chloride (120 mg, 0.84 mmol). The reaction mixture was stirred from ice-cold water bath to room temperature for 2 h. Supplemental triethylamine (0.32 mL, 2.30 mmol) and 2-propylsulfonyl chloride (120 mg, 0.84 mmol) were added. The reaction mixture was stirred at room temperature for 2 hours. The solvent was removed, and the residue was purified by column chromatography (mobile phase: petroleum ether/ethyl acetate, 100/0 to 70/30) to afford compound 68-a (200 mg, 98%).

Synthesis of Compound 68

A microwave tube charged with 68-a (100 mg, 0.28 mmol), pinacol bis(boronic acid) ester (86 mg, 0.34 mmol), XPHOS (10 mg, 0.021 mmol), XPhos Pd G2 (10 mg, 0.013 mmol) and potassium acetate (100 mg, 1.02 mmol) was degassed and purged with nitrogen, then was added anhydrous toluene (10 mL). Degassed and purged with nitrogen again for 3 times, the reaction mixture was sealed and stirred at 80° C. for 4 hours. The reaction mixture was cooled to room temperature and removed the solvent by rotary evaporation. The crude product was dissolved in 1,4-dioxane (4 mL) and placed into a microwave tube, followed by addition of I-4 (120 mg, 0.25 mmol), Pd(dtbpf)$Cl_2$ (10 mg, 0.015 mmol), cesium fluoride (170 mg, 1.12 mmol) and water (1 mL). Degassed and purged with nitrogen for 3 times and sealed, the reaction mixture was stirred at 100° C. for 6 hours. The reaction mixture was cooled to room temperature, diluted with ethyl acetate, washed with brine, dried over anhydrous sodium sulfate, filtered, and the filtrate was evaporated, and the crude product was dissolved again in 1,4-dioxane (4 mL), placed into a microwave tube, followed by addition of Pd(dtbpf)$Cl_2$ (10 mg, 0.015 mmol), cesium fluoride (170 mg, 1.12 mmol) and water (1 mL). The reaction mixture was degassed and purged with nitrogen for 3 times, then sealed and stirred at 100° C. for 5 hours. The reaction mixture was cooled to room temperature, diluted with ethyl acetate, washed with brine, dried over anhydrous sodium sulfate, filtered, and the filtrate was evaporated, and the crude product was purified by column chromatography (mobile phase: dichloromethane/ethyl acetate, 100/0 to 70/30) to obtain the crude product. The crude was purified by Prep-HPLC (ammonium bicarbonate) to afford compound 68 (27 mg, 16%). LC-MS (ESI): m/z 616.4 $(M+H)^+$; $^1$HNMR (DMSO-$d_6$, 400 MHz): δ 9.21 (1H, bs), 8.91 (1H, d, J=1.6 Hz), 7.88-7.56 (2H, m), 4.30-4.22 (4H, m), 4.13 (1H, d, J=16.8 Hz), 3.64 (2H, t, J=5.5 Hz), 3.59-3.52 (1H, m), 2.70-2.62 (2H, m), 1.45-1.39 (2H, m), 1.33-1.26 (8H, m).

Synthetic Route of Compound 69

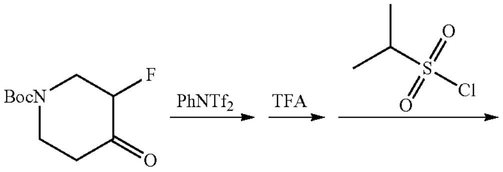

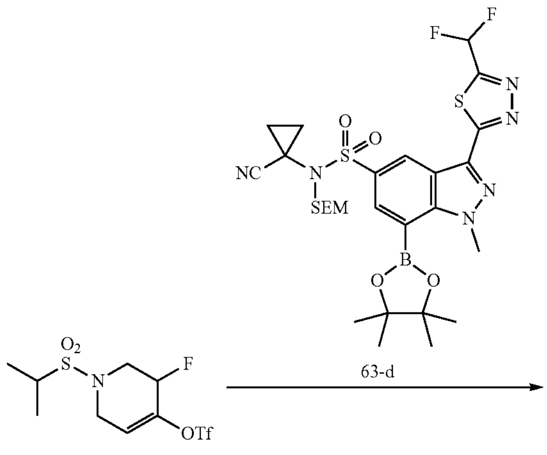

63-d 69-b

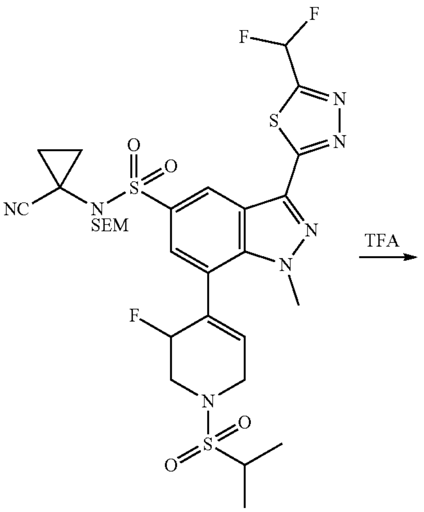

69-a

-continued

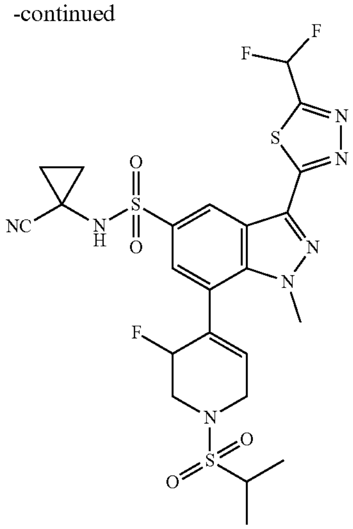

69

Synthesis of Compound 69-b

A reaction vial charged with tert-butyl 3-fluoro-4-oxopiperidine-1-carboxylate (1.5 g, 6.91 mmol), N-phenylbis(trifluoromethanesulfonyl)imide (2.96 g, 8.29 mmol) and anhydrous dichloromethane (20 mL) was added DBU (3.15 g, 20.72 mmol) dropwise at 60° C. under nitrogen protection. The reaction mixture was stirred at 70° C. for 4 hours. The solvent was removed, and the residue was added ethyl acetate/petroleum ether (1:1), washed twice with water, washed with brine, dried over anhydrous sodium sulfate, filtered, and evaporated to dryness to obtain the crude product. The crude product was added dichloromethane (10 mL) and trifluoroacetic acid (3.5 mL), and the reaction mixture was stirred at room temperature for 3 hours. The solvent was removed and the crude product was dried by an oil pump. To the crude product was added dichloromethane (20 mL), followed by addition of triethylamine (4.5 mL, 32.38 mmol) in an ice-cold water bath, and dropwise addition of 2-propylsulfonyl chloride (1.5 mL). After addition, the reaction mixture was stirred in an ice-cold water bath to room temperature for 4 hours. The solvent was removed, and the residue was added ethyl acetate/petroleum ether (1:1), washed twice with water, washed with brine, dried over anhydrous sodium sulfate, filtered, and evaporated to dryness to obtain the crude product. The crude product was purified by column chromatography (mobile phase: petroleum ether/ethyl acetate, 100/0 to 70/30) to obtain 69-b (480 mg, 20%). $^1$HNMR ($CHCl_3$, 400 MHz): δ 6.25 (1H, dt, J=4.8, 2.4 Hz), 4.99 (1H, d, J=49.6 Hz), 4.30 (1H, ddd, J=18.8, 7.8, 4.8 Hz), 4.20-4.11 (1H, m), 3.97 (1H, dd, J=18.8, 10.8 Hz), 3.52-3.37 (1H, m), 3.29 (1H, p, J=6.8 Hz), 1.40 (3H, d, J=6.8 Hz), 1.34 (3H, d, J=6.8 Hz).

Synthesis of Compound 69-a

A reaction flask charged with 69-b (150 mg, 0.42 mmol), 63-d 110 mg, 0.17 mmol), and Pd(dtbpf)$Cl_2$ (15 mg, 0.023 mmol) was degassed and purged with nitrogen for three times, then was added a solution of cesium fluoride (130 mg, 0.86 mmol) in water (1 mL) dropwise while stirring. The reaction mixture was stirred at 55° C. for 2 hours under nitrogen protection, then cooled to room temperature, diluted with ethyl acetate, washed twice with water, washed with brine, dried over anhydrous sodium sulfate, filtered and evaporated to dryness to obtain the crude product. The crude product was purified by column chromatography (mobile phase: dichloromethane/ethyl acetate, 100/0 to 70/30) to obtain 69-a (50 mg, 41%). LC-MS (ESI): m/z 746.3 $(M+H)^+$.

Synthesis of Compound 69

A reaction vial charged with 69-a (50 mg, 0.067 mmol) and dichloromethane (2 mL) was added trifluoroacetic acid (0.7 mL) dropwise at room temperature. The reaction mixture was stirred at room temperature for 2 hours. The solvent was removed and the residue was dried by an oil pump. To the residue was added saturated aqueous sodium bicarbonate, ethyl acetate and anhydrous potassium carbonate. The resulting mixture was stirred at room temperature for 3 minutes. The liquid was partitioned and the organic phase was dried over anhydrous sodium sulfate, filtered and evaporated to dryness. The crude was purified by column chromatography (mobile phase: dichloromethane/ethyl acetate, 100/0 to 70/30) and by Prep-HPLC (ammonium bicarbonate) to give 69 (2.6 mg, 6.3%). LC-MS (ESI): m/z 616.2 $(M+H)^+$.

Synthetic Route of Compound 70

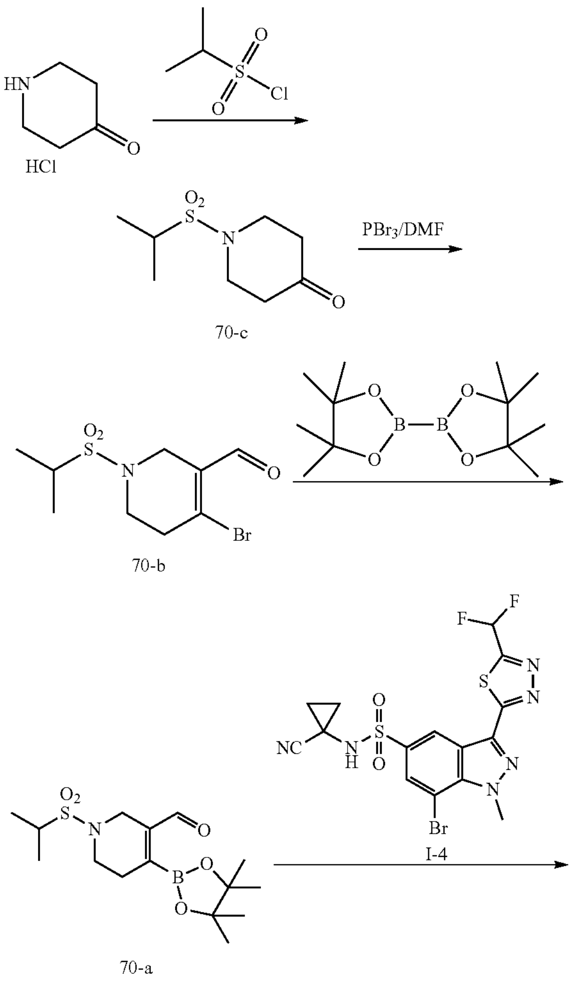

-continued

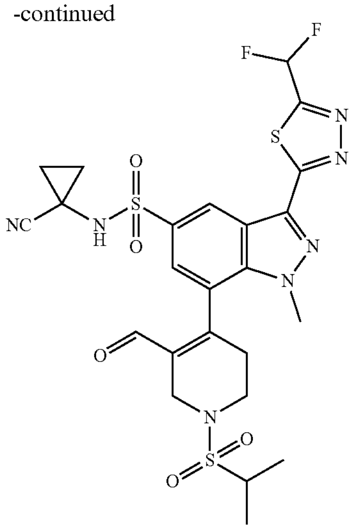

70

Synthesis of Compound 70-c

A reaction flask charged with 4-oxopiperidone hydrochloride (2.72 g, 20.06 mmol), acetone (30 mL) and water (15 mL) cooled in ice-cold water bath was added anhydrous potassium carbonate (7.21 g, 52.16 mmol), followed by dropwise addition of 2-propylsulfonyl chloride (3.38 mL, 30.09 mmol). The reaction mixture was stirred in an ice-cold bath to room temperature for 18 hours. The reaction mixture was quenched by the addition of saturated sodium bicarbonate solution, and the mixture was extracted with dichloromethane three times. The organic phases were combined, washed once with brine, dried by adding anhydrous sodium sulfate and anhydrous magnesium sulfate, filtered, and the filtrate was evaporated to dryness, and the crude product was washed twice with petroleum ether to give compound 70-c (2.7 g, 66%).

Synthesis of Compound 70-b

A reaction flask charged with N,N-dimethylformamide (3.18 mL, 39.46 mmol) and dichloromethane (60 mL) in an ice-cold water bath was added a solution of phosphorus tribromide (2.97 mL, 31.57 mmol) in dichloromethane (10 mL) slowly and dropwise. After addition, the reaction mixture was stirred in an ice-cold water bath for 1 hour, then was added a solution of 70-c (2.7 g, 13.15 mmol) in methylene chloride (20 mL) dropwise. After addition, the reaction mixture was stirred at room temperature overnight. The reaction mixture was cooled and stirred in an ice-cold water bath for 5 min, was added saturated sodium bicarbonate solution slowly and dropwise until no bubbles were formed. The reaction mixture was partitioned, and the aqueous phase was extracted twice with dichloromethane. The organic phases were combined, dried over anhydrous sodium sulfate, filtered, and the filtrate was evaporated, and purified by column chromatography (mobile phase: petroleum ether/ethyl acetate, 100/0 to 70/30) to afford compound 70-b (1.6 g, 41%). LC-MS (ESI): m/z 313.1 $(M+NH_4)^+$.

Synthesis of Compound 70-a 70-b (400 mg, 1.35 mmol), bis-pinacol borate (403 mg, 1.59 mmol), $Pd(dppf)Cl_2$—$CH_2Cl_2$ (80 mg, 0.098 mmol) and potassium acetate (396 mg, 4.04 mmol) were combined in a microwave tube. Degassed and purged with nitrogen, the above mixture was added 1,4-dioxane (10 mL). The reaction mixture was degassed and purged with nitrogen for 3 times, then sealed and stirred at 80° C. for 6 hours. The reaction mixture was cooled to room temperature, and 2 mL of the reaction mixture went directly to the next reaction. The left reaction mixture was diluted with ethyl acetate, washed once with brine, and the aqueous phase was extracted with ethyl acetate for 3 times. The organic phases were combined, evaporated, and dried by an oil pump to obtain the crude product 70-a (463 mg, 100%). LC-MS (ESI): m/z 344.2 $(M+H)^+$.

Synthesis of Compound 70

A solution of crude 70-a (115 mg, 0.34 mmol) in 1,4-dioxane (2 mL), Pd(dtbpf)$Cl_2$ (14 mg, 0.022 mmol), I-4 (107 mg, 0.21 mmol) and a solution of cesium fluoride (110 mg, 0.72 mmol) in water (0.5 mL) were combined in a reaction flask. The reaction mixture was degassed and purged with nitrogen for 3 times, then sealed and stirred at 100° C. for 2 hours. The reaction mixture was cooled to room temperature, diluted with ethyl acetate, washed with brine, evaporated to dryness, and 1/5 of the crude was purified by Prep-HPLC (ammonium bicarbonate) to give 70 (7.6 mg, 28%). LC-MS (ESI): m/z 626.2 $(M+H)^+$. $^1$HNMR (DMSO-$d_6$, 400 MHz) δ 9.33 (1H, s), 8.98 (1H, d, J=1.6 Hz), 7.89-7.55 (2H, m), 4.27-4.12 (5H, m), 3.75-3.68 (1H, m), 3.64-3.51 (2H, m), 2.96-2.73 (2H, m), 1.48-1.34 (4H, m), 1.30 (6H, dd, J=6.8, 2.4 Hz).

Synthetic Route of Compound 71

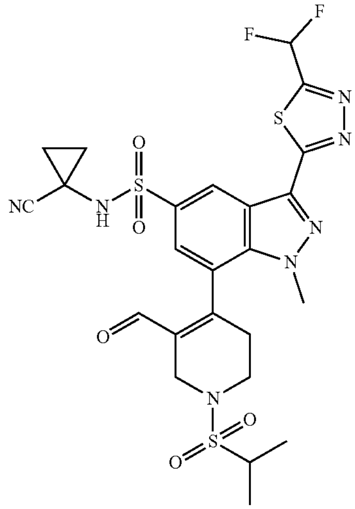

70

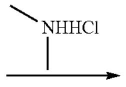

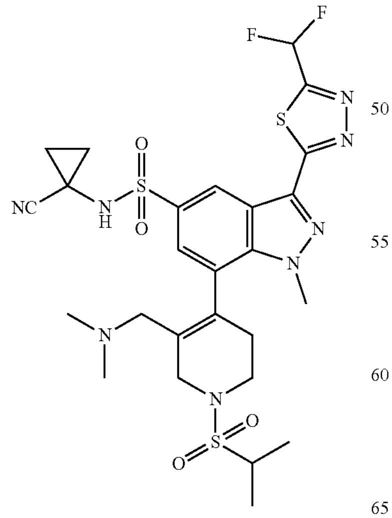

71

Synthesis of Compound 71

A reaction flask charged with 70 (108 mg, 0.17 mmol), dimethylamine hydrochloride (64 mg, 0.79 mmol), anhydrous ethanol (5 mL) and potassium acetate (62 mg, 0.63 mmol) was stirred at room temperature for 10 minutes and then was added sodium triacetoxyborohydride (200 mg, 0.95 mmol). The reaction mixture was stirred at room temperature for 2 hours and then was added sodium triacetoxyborohydride (72 mg, 0.34 mmol) and stirred for 1 hour at room temperature and then placed in a refrigerator overnight. The reaction mixture was quenched by adding ice-cold water to the reaction mixture, extracted twice with ethyl acetate, the organic phase was washed with brine, dried over anhydrous sodium sulfate, filtered and evaporated, and the crude was purified by Prep-HPLC (ammonium bicarbonate) to give 71 (9.2 mg, 8.2%). LC-MS (ESI): m/z 655.3 $(M+H)^+$; $^1$HNMR (DMSO-$d_6$, 400 MHz) δ 9.24 (1H, bs), 8.89 (1H, d, J=1.6 Hz), 7.86-7.55 (2H, m), 4.26-4.12 (4H, m), 3.94 (1H, d, J=18.0 Hz), 3.71-3.65 (1H, m), 3.59-3.30 (3H, m), 2.87 (1H, d, J=13.2 Hz), 2.52 (2H, s), 1.99 (6H, s), 1.53-1.35 (2H, m), 1.36-1.26 (8H, m).

Synthetic Route of Compound 72

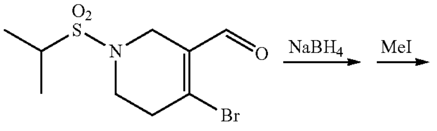

70-b

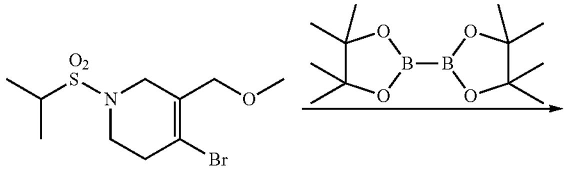

72-b

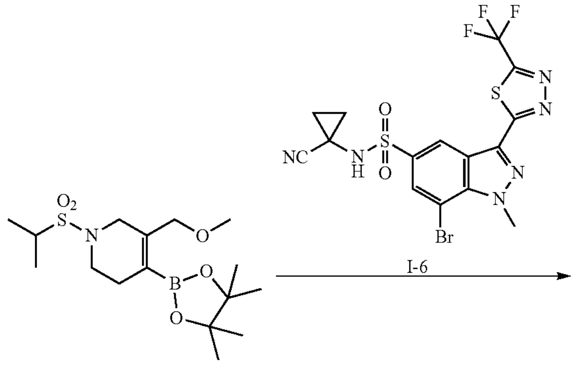

72-a

-continued

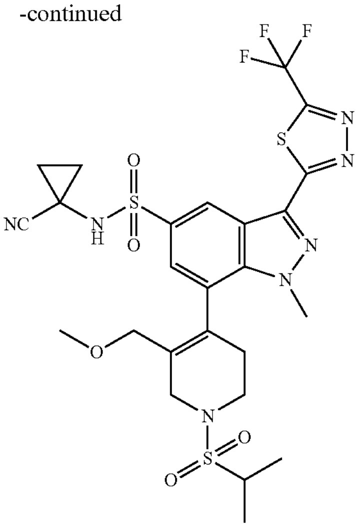

72

Synthesis of Compound 72-b

A reaction flask charged with 70-b (630 mg, 2.13 mmol), tetrahydrofuran (20 mL) and anhydrous methanol (10 mL) was stirred for 5 min in an ice-cold water bath, then was added anhydrous cerium(III) chloride (786 mg, 3.19 mmol) and sodium borohydride (90 mg, 2.38 mmol) and a large number of bubbles generated. The reaction mixture was stirred in an ice-cold water bath for 1 hour, then was quenched by adding water (10 mL), and removed the solvent at room temperature. The residue was added a small amount of anhydrous sodium sulfate solid, and the aqueous phase was extracted with ethyl acetate for three times. The organic phase was dried over anhydrous sodium sulfate, filtered and evaporated to obtain the crude product. The crude product was added into a reaction flask, and anhydrous tetrahydrofuran (10 mL) was added, then in an ice-cold water bath, sodium hydride (170 mg, 4.25 mmol) was added. The reaction mixture was stirred for 1 hour in an ice-cold water bath, and then it was warmed to room temperature and stirred for 15 minutes, then was added iodomethane (0.45 mL, 5.55 mmol). The reaction mixture was stirred for 2 h at room temperature, concentrated to dryness by rotary evaporation. The residue was added ethyl acetate, and ice-cold water slowly. The liquid was partitioned, and the organic phase was washed with brine, dried over anhydrous sodium sulfate, filtered, and the filtrate was evaporated, and the crude was purified by column chromatography (mobile phases: petroleum ether/ethyl acetate, 100/0 to 80/20) to give compound 72-b (350 mg, 53%).

Synthesis of Compound 72-a

A microwave tube charged with 72-b (350 mg, 1.12 mmol), bis-pinacol borate (342 mg, 1.35 mmol), Pd(dppf)$Cl_2$—$CH_2Cl_2$ (46 mg, 0.056 mmol) and potassium acetate (330 mg, 3.36 mmol) was degassed and purged with nitrogen, then was added 1,4-dioxane (10 mL). After degassed and purged with nitrogen for 3 times, the above mixture was sealed and stirred at 80° C. for 8 hours. The reaction mixture was cooled to room temperature, diluted with ethyl acetate, washed with water, the aqueous phase was extracted with ethyl acetate once. The organic phases were combined, washed with brine, dried over anhydrous sodium sulfate, filtered, and the filtrate was evaporated to dryness, and purified by column chromatography (mobile phase: petroleum ether/ethyl acetate, 100/0 to 80/20) to obtain compound 72-a (110 mg, 27%). LC-MS (ESI): m/z 359.9 $(M+H)^+$.

Synthesis of Compound 72

A solution of 72-a (55 mg, 0.15 mmol), Pd(dtbpf)$Cl_2$ (9 mg, 0.014 mmol), I-6 (86 mg, 0.17 mmol), 1,4-dioxane (2 mL) and cesium fluoride (80 mg, 0.53 mmol) in water (0.5 mL) were added into a reaction flask. Degassed and purged with nitrogen 3 times, the reaction mixture was stirred at 100° C. for 3 hours. Cooled to room temperature. The reaction mixture was diluted with ethyl acetate, washed with brine and evaporated to dryness, and the crude was purified by Prep-HPLC (ammonium bicarbonate) to give 72 (30 mg, 30%). LC-MS (ESI): m/z 660.6 $(M+H)^+$. $^1$H NMR (DMSO-$d_6$, 400 MHz): δ 9.28 (1H, bs), 8.90 (1H, d, J=2.0 Hz), 7.65 (1H, d, J=1.6 Hz), 4.20 (3H, s), 4.07 (2H, s), 3.73 (1H, d, J=11.6 Hz), 3.71-3.52 (3H, m), 3.50 (1H, q, J=6.8 Hz), 3.05 (3H, s), 2.59-2.52 (2H, m), 1.47-1.38 (2H, m), 1.37-1.32 (2H, m), 1.30 (6H, d, J=6.8 Hz).

Synthetic Route of Compounds 73 and 74

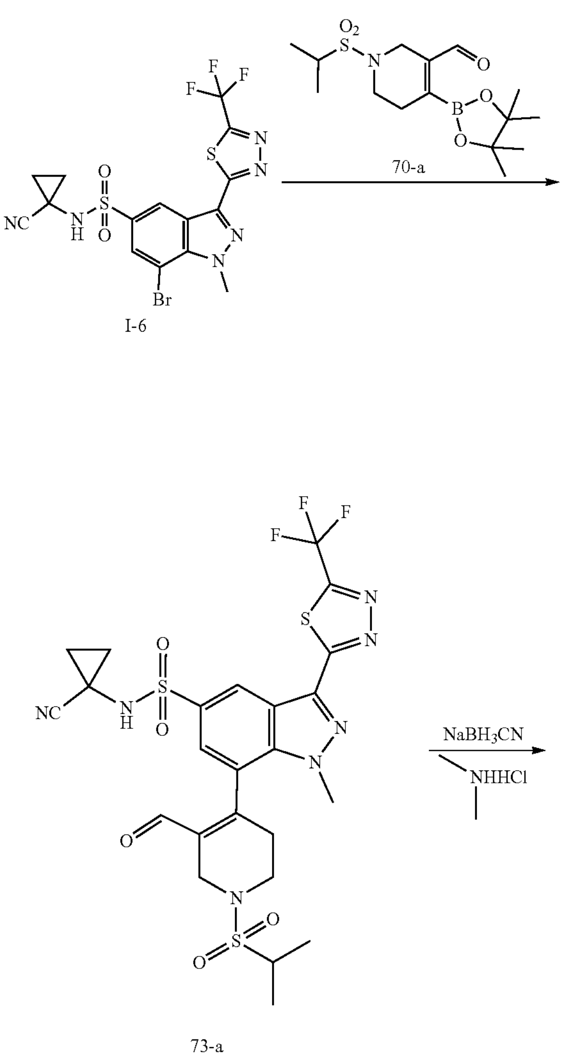

-continued

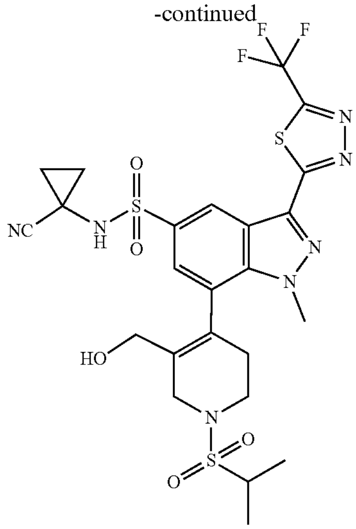

73

+

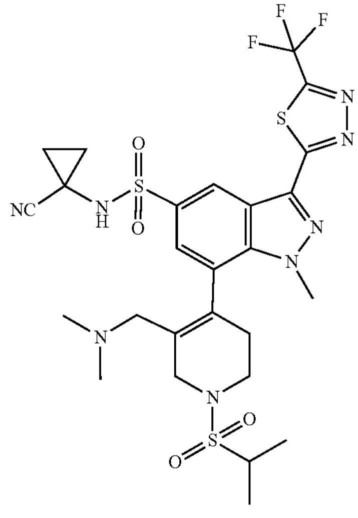

74

Synthesis of Compound 73-a

A solution of 70-a (345 mg, 1.01 mmol), $Pd(dtbpf)Cl_2$ (41 mg, 0.063 mmol), I-6 (335 mg, 0.66 mmol) and cesium fluoride (340 mg, 2.24 mmol) in water (2 mL) were added into a reaction flask. After degassed and purged with nitrogen 3 times, the reaction mixture was stirred at 100° C. for 2 hours. The reaction mixture was cooled to room temperature, diluted with ethyl acetate, washed with brine, evaporated to dryness, and the crude was purified by column chromatography (mobile phases: dichloromethane/ethyl acetate, 100/0 to 70/30) to give compound 73-a (290 mg, 68%). LC-MS (ESI): m/z 644.1 $(M+H)^+$.

Synthesis of Compounds 73 and 74

A reaction vial charged with 73-a (130 mg, 0.20 mmol), dimethylamine hydrochloride (180 mg, 2.21 mmol), potassium acetate (220 mg, 2.24 mmol) and anhydrous ethanol (10 mL) was stirred at room temperature for 1 hour and then was added sodium cyanoborohydride (50 mg, 0.80 mmol), and continued stirring for 30 minutes before sodium cyanoborohydride (50 mg, 0.80 mmol) was added. The reaction mixture was continued stirring for 30 min at room temperature, removed most of the solvent at room temperature. The residue was added brine, and the aqueous phase was extracted twice with ethyl acetate, the organic phase was dried over anhydrous sodium sulfate, filtered, and the filtrate was evaporated and blown to dryness with nitrogen, and the crude product was purified by Prep-HPLC (ammonium bicarbonate) to give 73 (28 mg, 21%), and the other component was purified again by Prep-TLC (8% MeOH/DCM) to give 74 (22 mg, 16%).

73, LC-MS (ESI): m/z 646.1 $(M+H)^+$; $^1$HNMR (DMSO-$d_6$, 400 MHz): δ 9.23 (1H, bs), 8.87 (1H, d, J=2.0 Hz), 7.65 (1H, d, J=1.6 Hz), 4.93 (1H, t, J=5.2 Hz), 4.23 (3H, s), 4.19-4.05 (2H, m), 3.73 (2H, d, J=5.2 Hz), 3.66-3.54 (2H, m), 3.48 (1H, q, J=6.8 Hz), 2.58-2.50 (2H, m), 1.50-1.38 (2H, m), 1.36-1.23 (8H, m).

74, LC-MS (ESI): m/z 673.4 $(M+H)^+$; $^1$HNMR (DMSO-$d_6$, 400 MHz): δ 9.34 (1H, bs), 8.88 (1H, d, J=1.6 Hz), 7.61 (1H, d, J=1.6 Hz), 4.24-4.12 (4H, m), 3.95 (1H, d, J=18.0 Hz), 3.73-3.64 (1H, m), 3.58-3.44 (2H, m), 3.39-3.31 (1H, m), 2.88 (1H, d, J=12.8 Hz), 2.54-2.50 (2H, m), 1.99 (6H, s), 1.48-1.37 (2H, m), 1.37-1.24 (8H, m).

Synthetic Route of Compound 75

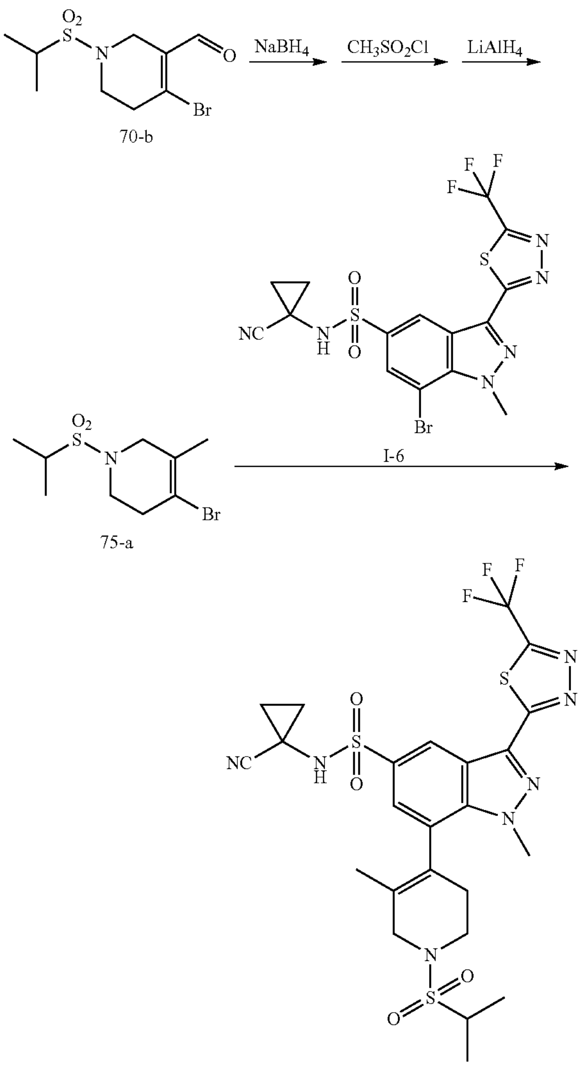

75

Synthesis of Compound 75-a

A reaction flask charged with 70-b (330 mg, 1.11 mmol) and anhydrous methanol (10 mL) was stirred in an ice-cold water bath for 5 minutes, then was added sodium borohydride (22 mg, 0.58 mmol). After stirred for 5 minutes in an ice-cold water bath, the above mixture was added sodium borohydride (30 mg, 0.79 mmol). The reaction mixture was stirred in an ice-cold water bath for 1 hour, then was added saturated aqueous ammonium chloride solution dropwise, removed the methanol and the residue was extracted twice with ethyl acetate. The organic phase was washed with brine, dried over anhydrous sodium sulfate, filtered and evaporated to obtain the crude product. The crude product in anhydrous dichloromethane (10 mL) in an ice-cold water bath was added triethylamine (0.55 mL, 3.96 mmol) and methanesulfonyl chloride (0.2 mL, 2.58 mmol) dropwise. After addition, the reaction mixture was stirred in an ice-cold water bath for 1 hour. After the solvent was removed, the residue was dried by an oil pump, and was added anhydrous tetrahydrofuran (10 mL). Then the mixture was cooled in an ice-salt bath, was added a solution of lithium aluminum hydride in THF (1M, 2.5 mL, 2.50 mmol) slowly and dropwise over 20 min. After addition, the reaction mixture was stirred in an ice-salt bath for 1 hour. The reaction mixture was quenched by the slow addition of $Na_2SO_4{\cdot}10H_2O$, and the reaction mixture was continued stirring for 15 minutes, then diluted by the addition of ethyl acetate, and the reaction mixture was stirred for 15 minutes at room temperature, filtered, and the filtrate was evaporated and purified by column chromatography (mobile phase: petroleum ether/ethyl acetate, 100/0 to 80/20) to afford compound 75-a (95 mg, 30%). LC-MS (ESI): m/z 281.9 $(M+H)^+$.

Synthesis of Compound 75

A microwave tube charged with 75-a (95 mg, 0.34 mmol), bis-pinacol borate (128 mg, 0.50 mmol), $Pd(dppf)Cl_2$—$CH_2Cl_2$ (15 mg, 0.018 mmol) and potassium acetate (100 mg, 1.02 mmol) was degassed and purged with nitrogen, then was added 1,4-dioxane (4 mL). After degassed and purged with nitrogen for 3 times, the reaction mixture was sealed and stirred at 80° C. for 20 hours. The reaction mixture was cooled to room temperature and was added I-6 (100 mg, 0.20 mmol), $Pd(dtbpf)Cl_2$ (10 mg, 0.015 mmol), cesium fluoride (200 mg, 1.32 mmol) and water (1 mL), degassed and purged with nitrogen for 3 times, then sealed and stirred at 100° C. for 2 hours. After additional I-6 (100 mg, 0.20 mmol), $Pd(dtbpf)Cl_2$ (20 mg, 0.031 mmol) and cesium fluoride (120 mg, 0.79 mmol) were added, the reaction mixture was degassed and purged with nitrogen and stirred at 100° C. for 5 h. The reaction mixture was cooled to room temperature, diluted with ethyl acetate, washed with water, and the aqueous phase was extracted with ethyl acetate once. The organic phases were combined, washed with brine, dried over anhydrous sodium sulfate, filtered, and the filtrate was evaporated, and purified by column chromatography (mobile phase: dichloromethane/methanol, 100/0 to 97/3) to give the crude product, which was purified by Prep-HPLC (ammonium bicarbonate) to give compound 75 (32 mg, 15%). LC-MS (ESI): m/z 630.1 $(M+H)^+$; $^1$HNMR (DMSO-$d_6$, 400 MHz): δ 9.26 (1H, bs), 8.87 (1H, d, J=2.0 Hz), 7.64 (1H, d, J=1.6 Hz), 4.19 (3H, s), 4.01-3.88 (2H, m), 3.68-3.51 (2H, m), 3.49 (1H, q, J=6.8 Hz), 1.47 (3H, s), 2.50-2.42 (2H, m), 1.45-1.39 (2H, m), 1.38-1.32 (2H, m), 1.30 (6H, d, J=6.7 Hz).

Synthetic Route of Compound 76

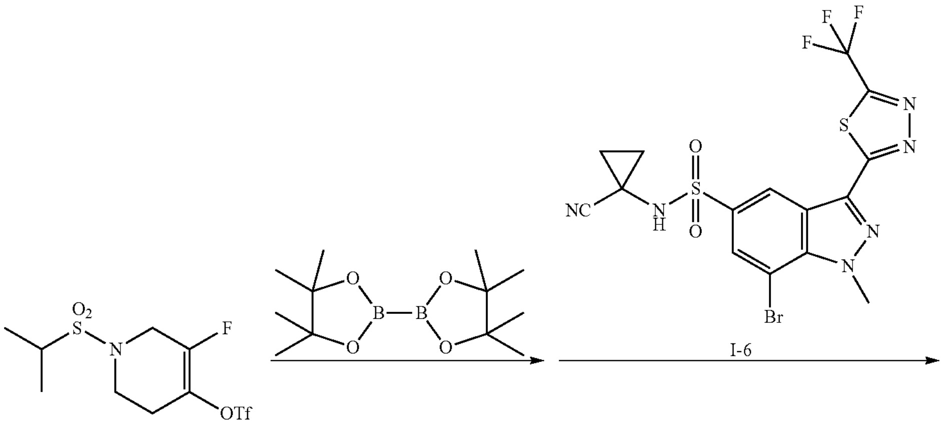

68-a

-continued

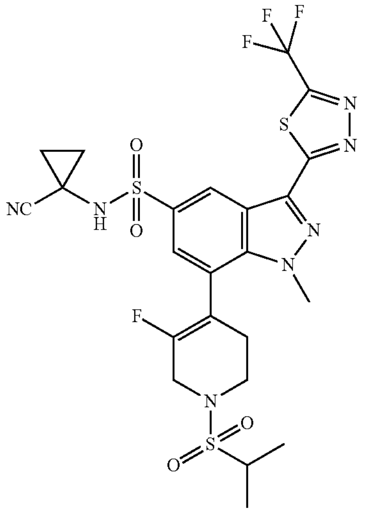

76

Synthesis of Compound 76

A microwave tube charged with 68-a (100 mg, 0.28 mmol), pinacol ester of bisboronic acid (86 g, 0.34 mmol), XPHOS (10 mg, 0.021 mmol), XPhos Pd G2 (10 mg, 0.013 mmol), and potassium acetate (100 mg, 1.02 mmol) was degassed and purged with nitrogen, was added anhydrous toluene (10 mL). After degassed and purged with nitrogen for 3 times, the reaction mixture was sealed and stirred at 80° C. for 4 hours. The reaction mixture was cooled to room temperature, was added I-6 (143 mg, 0.28 mmol), Pd(dtbpf) $Cl_2$ (10 mg, 0.015 mmol), cesium fluoride (170 mg, 1.12 mmol) and water (1 mL). After degassed and purged with nitrogen for 3 times, the reaction mixture was sealed and stirred at 100° C. for 6 hours. The reaction mixture was cooled to room temperature, diluted with ethyl acetate, washed with brine, dried over anhydrous sodium sulfate, filtered, and the filtrate was evaporated, and the crude product was purified by column (mobile phase: dichloromethane/ethyl acetate, 100/0 to 70/30) to obtain the crude product. The crude was purified by Prep-HPLC (ammonium bicarbonate) to give compound 76 (38 mg, 21%). LC-MS (ESI): m/z 634.5 $(M+H)^+$; $^1$HNMR (DMSO-$d_6$, 400 MHz): δ 9.28 (1H, bs), 8.90 (1H, d, J=1.6 Hz), 7.81 (1H, d, J=1.6 Hz), 4.32-4.20 (4H, m), 4.18-4.09 (1H, m), 3.65 (2H, t, J=5.2 Hz), 3.55 (1H, p, J=6.8 Hz), 2.73-2.62 (2H, m), 1.50-1.38 (2H, m), 1.37-1.25 (8H, m).

Synthetic Route of Compound 77

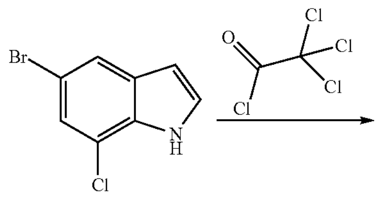

-continued

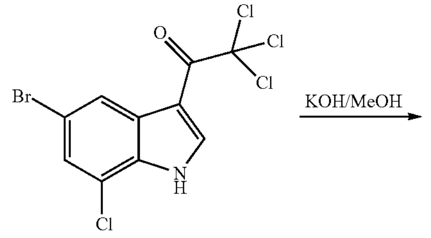

77-i

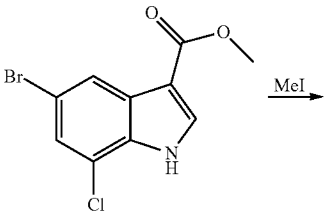

77-h

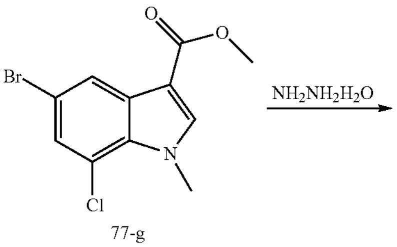

77-g

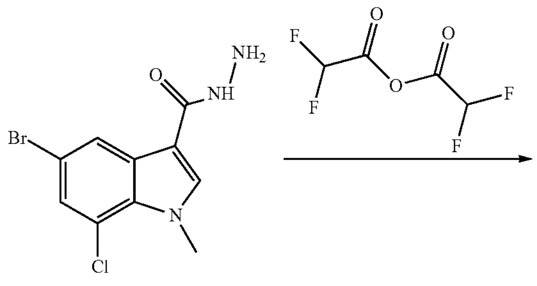

77-f

-continued

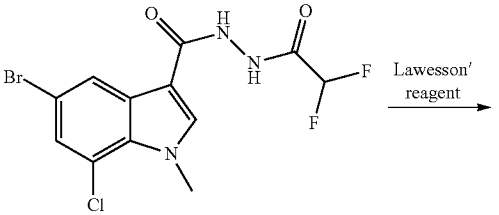

77-e

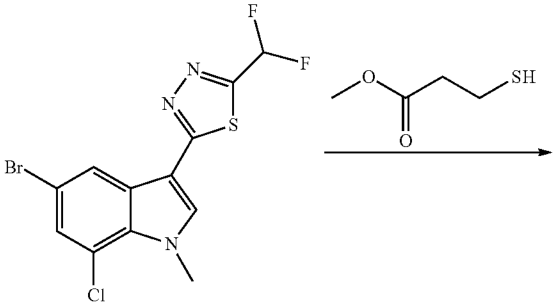

77-d

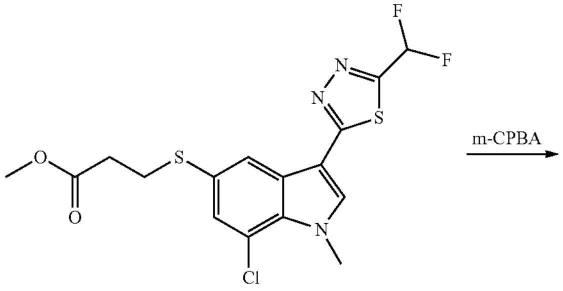

77-c

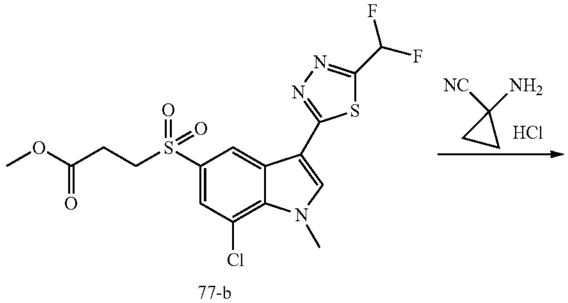

77-b

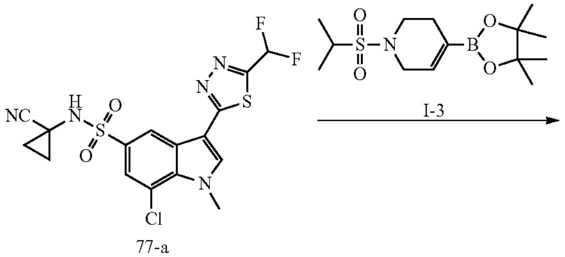

77-a

-continued

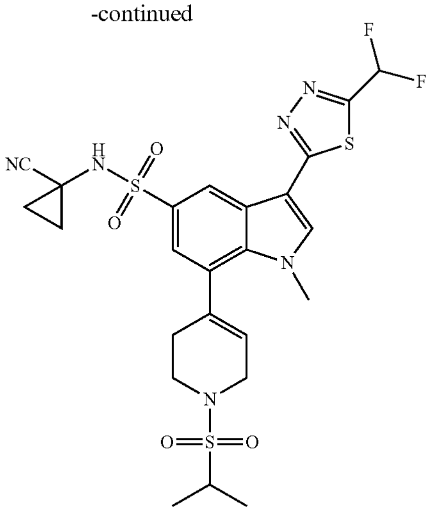

77

Synthesis of Compound 77-i

A solution of 5-bromo-7-chloro-1H-indole (3.0 g, 13.02 mmoL) dissolved in 20 mL of dichloromethane at room temperature was added trichloroacetyl chloride (5.84 mL, 52.06 mmoL), then was added pyridine (4.21 mL, 52.06 mmoL) dropwise under nitrogen protection at room temperature, and after addition the mixture was stirred at 48° C. for 18 hours under nitrogen protection. The reaction mixture was cooled to room temperature, poured into 50 mL of an ice-cold water and extracted with dichloromethane (50 mL*2). The organic phase was dried over anhydrous sodium sulfate, filtered, and the filtrate was concentrated at reduced pressure, and the residue was dried at vacuum for 2 h to afford approximately 10 g (4.89 g theoretically) of the crude product (77-i, 100%), and the crude product was used directly in the next step.

Synthesis of Compound 77-h

A suspension of 77-i (4.89 g, 13.01 mmoL) in 50 mL of methanol at room temperature was added KOH (1.88 g, 33.50 mmoL) in batches, and the reaction mixture was stirred at room temperature under nitrogen protection overnight. After the reaction mixture was concentrated at reduced pressure to about 20 mL, was added 50 mL of water, the pH was adjusted to 6 with 1 M hydrochloric acid. The mixture was extracted with ethyl acetate (50 mL*2), and the organic phase was washed with brine (100 mL), dried over anhydrous sodium sulfate, filtered, the filtrate was concentrated at reduced pressure. The residue was slurried with 20 mL of DCM, filtered, and the filter cake was washed with DCM (5 mL), and the solid was collected, dried at vacuum for 2 h to give a product of 2.8 g. The filtrate was concentrated at reduced pressure and the residue was purified by a flash column chromatography (PE/EA=1:1) to give a product of 380 mg. The two products were combined to give a total of compound 77-h (3.18 g, 85%). LC-MS (ESI): m/z=286.1[M−H]$^-$.

Synthesis of Compound 77-g 77-h (3.15 g, 10.92 mmoL) was dissolved in 20 mL of DMF at room temperature, then in an ice-cold waterbath, the above mixture was added NaH (655 mg, 16.38 mmoL, 60%) in batches under nitrogen protection, then the mixture was stirred under nitrogen protection at room temperature for 30 min followed by dropwise addition of iodomethane (1.02 mL, 16.38 mmoL). After the dropwise addition, the reaction mixture was stirred at room temperature under nitrogen protection for 2 hours. The reaction mixture was quenched with saturated ammonium chloride solution (100 mL) in an ice-cold water bath, and the aqueous phase was extracted with ethyl acetate (100 mL*2), and the organic phase was washed with brine (100 mL*5), dried over anhydrous sodium sulfate, filtered, concentrated at reduced pressure, and the residue was suspended in methanol (10 mL) and stirred for 30 minutes. The mixture was filtered, and the filter cake was washed with methanol (10 mL). The solid was collected and dried at vacuum for 2 hours to give compound 77-g (2.8 g, 85%). $^{1}$H NMR (DMSO-$d_6$, 400 MHz): δ 3.81 (3H, s), 4.11 (3H, s), 7.45 (1H, d, J=1.2 Hz), 8.07 (1H, d, J=1.2 Hz), 8.20 (1H, s).

Synthesis of Compound 77-f

A suspension of 77-g (700 mg, 2.31 mmoL) in 20 mL of ethanol at room temperature was added hydrazine hydrate (4 mL, 67.92 mmoL, 85%), and the reaction mixture was stirred at 85° C. under nitrogen protection for 72 hours. The reaction mixture was cooled in an ice-cold water bath, filtered, and the filter cake was washed with ethanol (10 mL), collected and dried at vacuum for 2 h to give compound 77-f (305 mg, 44%). LC-MS (ESI): m/z=302.0[M+H]$^+$.

Synthesis of Compound 77-e

TEA (400 uL, 2.88 mmoL) was added to a solution of 77-f (290 mg, 0.96 mmoL) in 20 mL of DCM at room temperature. Placed in an ice-cold water bath, the above mixture was added difluoroacetic anhydride (131 uL, 1.05 mmoL) dropwise, and after addition, the reaction mixture was stirred for 6 hours in an ice-cold water bath. The reaction mixture was filtered and the filter cake was washed with DCM (5 mL), the solid was collected and dried at vacuum for 2 h to give compound 77-e (238 mg, 65%). LC-MS (ESI): m/z=379.9 [M+H]$^+$.

Synthesis of Compound 77-d 77-e (238 mg, 0.62 mmoL) was dissolved in 10 mL of 1,4-dioxane at room temperature, and Lawesson's reagent (379 mg, 0.94 mmoL) was added to the above mixture. The resulting mixture was stirred for 3 h at 80° C. under nitrogen protection. The reaction mixture was concentrated at reduced pressure, and the residue was dissolved in 100 mL of dichloromethane, washed sequentially with saturated sodium bicarbonate (100 mL), water (100 mL). The organic phase was dried over anhydrous sodium sulfate, filtered, and the filtrate was concentrated at reduced pressure, and the residue was purified by a flash column chromatography (PE/EA=1:1) to give compound 77-d (172 mg, 73%). LC-MS (ESI): m/z=378.0[M+H]$^+$.

Synthesis of Compound 77-c

A solution of 77-d (172 mg, 0.45 mmoL) in 10 mL of 1,4-dioxane at room temperature was added tris(dibenzylideneacetone)dipalladium (42 mg, 0.045 mmoL), 4,5-bis (diphenylphosphino)-9,9-dimethylxanthene (52 mg, 0.091 mmoL), DIPEA (225 uL, 1.36 mmoL), and methyl 3-mercaptopropionate (56 uL, 0.50 mmoL), and the reaction mixture was stirred at 80° C. under nitrogen protection for 3 hours. The reaction mixture was cooled to room temperature, concentrated at reduced pressure and the residue was purified by a flash column chromatography (PE/EA=1:1) to afford compound 77-c (170 mg, 90%). LC-MS (ESI): m/z=418.5[M+H]$^+$.

Synthesis of Compound 77-b

A solution of 77-c (170 mg, 0.41 mmoL) in 10 mL of DCM was added m-CPBA (248 mg, 1.22 mmoL) under nitrogen protection in an ice-cold water bath. After addition, the mixture was stirred under nitrogen protection in an ice-cold water bath for 2 hours. The reaction mixture was added saturated sodium bicarbonate (50 mL), extracted with DCM (100 mL). The organic phase was washed with saturated sodium bicarbonate (100 mL), dried over anhydrous sodium sulfate, filtered, and the filtrate was concentrated at reduced pressure, and the residue was purified by a flash column chromatography (DCM/MeOH=20:1) to give compound 77-b (205 mg, crude). LC-MS (ESI): m/z=450.1[M+H]$^+$.

Synthesis of Compound 77-a 77-b (120 mg, 0.27 mmol) was dissolved in a mixed solvent of methanol (10 mL) and DCM (15 mL) at room temperature. In an ice-cold water bath, the above mixture was added sodium methanolate (43 mg, 0.80 mmol) and stirred under nitrogen protection at room temperature for 60 min. In an ice-cold water bath, the reaction mixture was added 1-aminocyclopropanecarbonitrile hydrochloride (127 mg, 1.07 mmol) and stirred in an ice-cold water bath for 15 minutes, then concentrated at reduced pressure and dried at vacuum for 2 hours. The residue was dissolved in dry DMF (5 mL) and placed in an ice-cold water bath, was added 1-aminocyclopropanecarbonitrile hydrochloride (32 mg, 0.27 mmol), triethylamine (74 uL, 0.53 mmol), NCS (107 mg, 0.80 mmol) sequentially. The reaction mixture was stirred for 1 hour at room temperature. The reaction mixture was quenched by addition of water (50 mL) and the mixture was extracted with ethyl acetate (50 mL*2). The organic phase was washed sequentially with water (100 mL), brine (100 mL*3), dried over anhydrous sodium sulfate, filtered, and the filtrate was concentrated at reduced pressure, and the residue was purified by a flash column chromatography (DCM/MeOH=10:1) to afford compound 77-a (90 mg, 76%). LC-MS (ESI): m/z=444.1[M+H]$^+$.

Synthesis of Compound 77

Compound 77-a (30 mg, 0.068 mmol) was dissolved in 18 mL of 1,4-dioxane at room temperature, then was added compound I-3 (32 mg, 0.10 mmol), 1,1'-di-tert-butylphosphinoferrocene palladium dichloride (8.8 mg, 0.014 mmol), cesium fluoride (31 mg, 0.20 mmol) and water (2 mL). The reaction mixture was stirred at 100° C. under nitrogen protection for 18 hours. The reaction mixture was cooled to room temperature, concentrated at reduced pressure, and the residue was purified by a flash column chromatography (PE/EA=1:3) to obtain the crude product. The crude product was purified by Prep-HPLC (basic method, $NH_4HCO_3$) to afford compound 77 (13.5 mg, 33%). LC-MS (ESI): m/z=597.2 [M+H]$^+$.

Synthetic Route of Compound 78

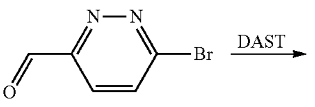

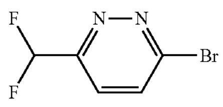

78-g

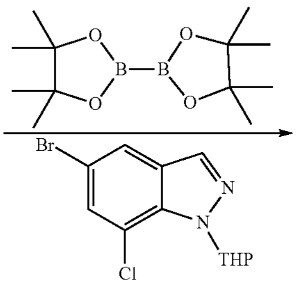

15-g

-continued

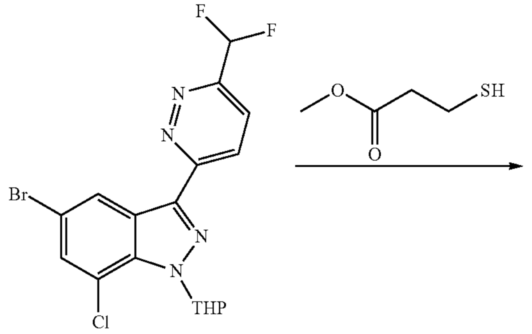

78-f

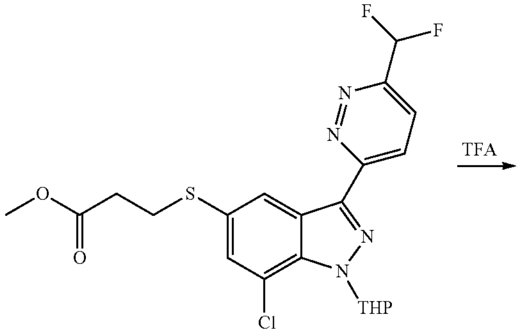

78-e

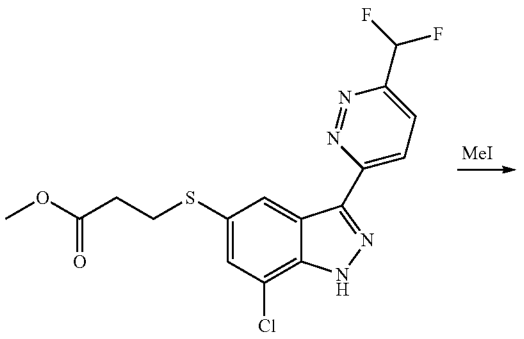

78-d

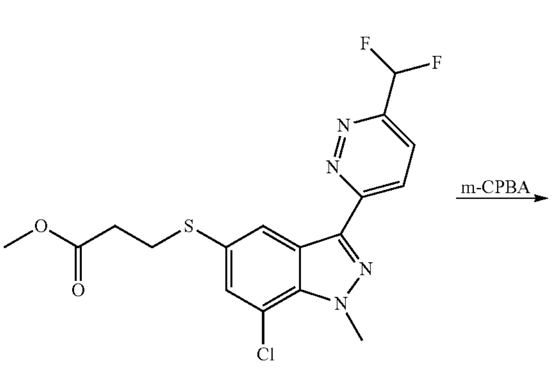

78-c

-continued

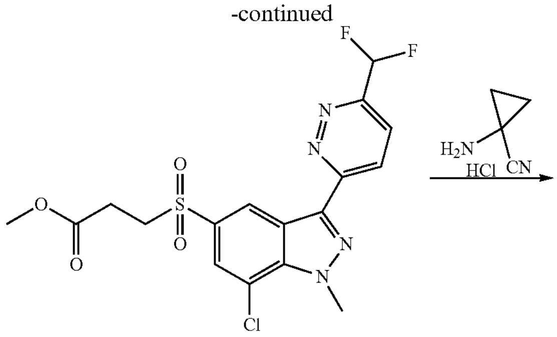

78-b

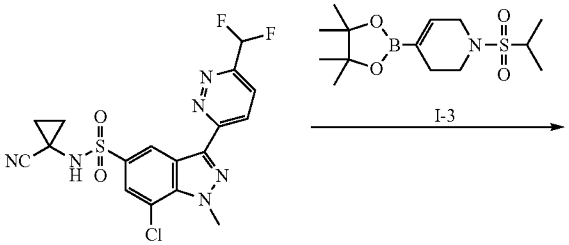

78-a

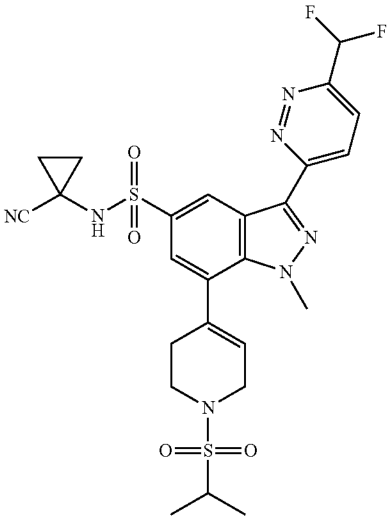

78

Synthesis of Compound 78-g

To a solution of 6-bromopyridazine-3-carbaldehyde (1.0 g, 5.35 mmol) in dichloromethane (20 mL) was added diethylaminosulfur trifluoride (DAST) (1.06 mL, 8.06 mmol) in an ice-cold water bath. After addition, the reaction mixture was stirred at room temperature overnight. Upon completion, the reaction mixture was added saturated sodium bicarbonate solution (10 mL) and stirred for 30 minutes. Separated the liquid, and the aqueous phase was extracted with dichloromethane. The organic phases were combined, washed with brine, dried over anhydrous sodium sulfate, filtered and evaporated to dryness. The crude product was purified by a flash column chromatography (mobile phase: ethyl acetate/petroleum ether 0% to 50%) to give compound 78-g (900 mg, 81%). $^1$HNMR (DMSO-$d_6$, 400 MHz): δ 7.28 (1H, t, J=54.0 Hz), 8.02 (1H, t, J=8.8 Hz), 8.29 (1H, d, J=8.8 Hz).

Synthesis of Compound 78-f

A sealed tube charged with pinacol ester of bisboronic acid (724 mg, 2.85 mmol), 4,4'-di-tert-butyl-2,2'-dipyridine (125 mg, 0.19 mmol) and methyl tert-butyl ether (10 mL) was added methoxy(cyclooctadiene)iridium dimer (102 mg, 0.38 mmol) under nitrogen protection. After degassed and purged with nitrogen for 2 times, the above mixture was stirred at room temperature for 10 min, then was added a solution of 15-g (600 mg, 1.90 mmol) in methyl tert-butyl ether (10 mL), degassed and purged with nitrogen 3 times, stirred at 85° C. for 3.5 hours. The reaction mixture was concentrated to obtain the crude borate ester.

To the resulting crude borate ester was added toluene (20 mL) and water (10 mL), and 78-g (397 mg, 1.90 mmol), palladium acetate (43 mg, 0.19 mmol), Xantphos (220 mg, 0.38 mmol), and N-methylmorpholine (0.63 mL, 5.70 mmol), and the reaction mixture was degassed and purged with nitrogen twice, stirred at 40° C. for 18 hours. Upon completion, the reaction mixture was diluted with ethyl acetate, washed with water, washed with saturated sodium chloride, dried over anhydrous sodium sulfate, filtered, concentrated, and purified by column chromatography (mobile phase: ethyl acetate/petroleum ether 0% to 50%) to give compound 78-f (300 mg, 36%). LC-MS (ESI): m/z=443.0 $(M+H)^+$.

Synthesis of Compound 78-e

A three-necked vial charged with 78-f (300 mg, 0.68 mmol), Xantphos (39 mg, 0.068 mmol), 1,4-dioxane (20 mL), DIPEA (0.35 mL, 2.03 mmol), and methyl 3-mercaptopropionate (0.09 mL, 0.81 mmol) with degassed and purged with nitrogen twice and added $Pd_2(dba)_3$ (31 mg, 0.034 mmol), then degassed and purged with nitrogen 3 times and refluxed at 85° C. for 2 hours. The reaction mixture was cooled to room temperature, evaporated to dryness, and purified by column chromatography (mobile phase: mobile phase: ethyl acetate/petroleum ether 0% to 50%) to afford compound 78-e (300 mg, 92%). LC-MS (ESI): m/z=483.5 $[M+H]^+$.

Synthesis of Compound 78-d

To a solution of 78-e (300 mg, 0.62 mmol) in dichloromethane (10 mL) was added TFA (3 mL) at room temperature. After addition, the reaction was stirred at room temperature overnight. Upon completion, the solvent was removed by rotary evaporation at room temperature, diluted by addition of ethyl acetate, washed with saturated sodium bicarbonate, washed with brine water, dried over anhydrous sodium sulfate, filtered, and evaporated to obtain compound 78-d (200 mg, 81%). LC-MS (ESI): m/z=398.8 $[M+H]^+$.

Synthesis of Compound 78-c

To a solution of 78-d (200 mg, 0.50 mmol) in DMF (10 mL) was added cesium carbonate (327 mg, 1.00 mmol) and iodomethane (0.081 mL, 1.00 mmol) at room temperature. After addition, the reaction was stirred at room temperature overnight. Upon completion, the reaction mixture was diluted by adding ethyl acetate, washed with water, washed with brine, dried over anhydrous sodium sulfate, filtered, and evaporated to dryness. The residue was purified by a flash column chromatography (mobile phase: ethyl acetate/petroleum ether 0% to 50%) to afford compound 78-c (200 mg, 96%). LC-MS (ESI): m/z=413.1 $[M+H]^+$.

Synthesis of Compound 78-b

To a solution of 78-c (200 mg, 0.48 mmol) in dichloromethane (10 mL) was added m-CPBA (251 mg, 1.45 mmol) in an ice-cold water bath. After addition, the reaction mixture was kept at 0° C. and stirred for 1 hour. Upon completion, the solvent was removed by rotary evaporation at room temperature, diluted by adding ethyl acetate, washed with saturated sodium bicarbonate, washed with brine, dried over anhydrous sodium sulfate, filtered and evaporated to dryness. The crude product was purified by a flash column chromatography (mobile phase: ethyl acetate/petroleum ether, 0% to 100%) to afford compound 78-b (160 mg, 74%). LC-MS (ESI): m/z=445.1 $[M+H]^+$.

Synthesis of Compound 78-a

A reaction flask charged with 78-b (160 mg, 0.36 mmol), methanol (10 mL) and dichloromethane (10 mL) was cooled to 0° C. in an ice-cold water bath, was added sodium methanol (58 mg, 1.08 mmol) and the reaction mixture was kept in an ice-cold water bath for 1 hour. 1-aminocyclopropanecarbonitrile hydrochloride (171 mg, 1.44 mmol) was added and the solvent was removed by concentration at room temperature and then the residue was dried at vacuum for 20 min. DMF (8 mL) and a small amount of 3A molecular sieves were added. After stirring for 3 min in an ice-cold water bath, the resulting mixture was added triethylamine (0.10 mL, 0.72 mmol) and 1-aminocyclopropanecarbonitrile hydrochloride (43 mg, 0.36 mmol), followed by addition of NCS (96 mg, 0.72 mmol) in an ice-cold water bath. The reaction mixture was stirred in an ice-cold water bath for 1 hour. The mixture was diluted with ethyl acetate, washed with sodium bisulfite solution, washed with water, washed with brine, dried over anhydrous sodium sulfate, filtered and evaporated to dryness. The crude was purified by a flash column chromatography (mobile phase: ethyl acetate/petroleum ether, 0% to 100%) to give 78-a (120 mg, 76%). LC-MS (ESI): m/z=439.0 $[M+H]^+$.

Synthesis of Compound 78

A reaction vial charged with 78-a (50 mg, 0.11 mmol), I-3 (54 mg, 0.17 mmol), [1,1'-bis(di-tert-butylphosphino)ferrocene]palladium dichloride (15 mg, 0.023 mmol), cesium fluoride (52 mg, 0.34 mmol), 1,4-dioxane (9 mL) and $H_2O$ (1 mL) was degassed and purged with nitrogen for 3 times, then was stirred at 100° C. for 5 hours. Upon completion, the reaction mixture was cooled to room temperature, concentrated at reduced pressure to remove the organic solvent. The residue was diluted with ethyl acetate, and the organic phase was washed with water, brine, dried over anhydrous sodium sulfate, filtered, and the filtrate was concentrated at reduced pressure to obtain the crude product. The crude product was purified by a flash column chromatography (mobile phase: ethyl acetate/petroleum ether: 0% to 100%) to give compound 78 (20 mg, 30%). LC-MS (ESI): m/z=592.0 $[M+H]^+$.

Synthetic Route of Compound 79

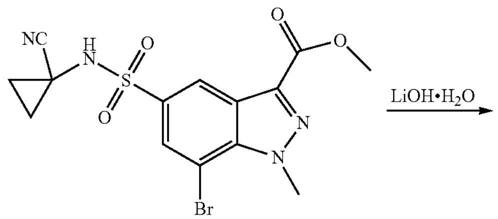

I-1-d

-continued

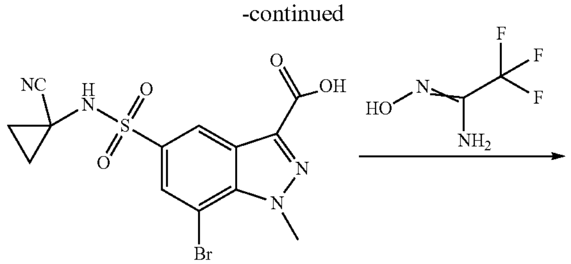

79-b

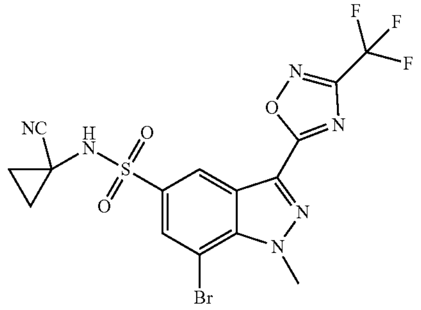

79-a

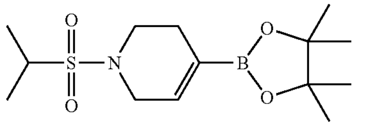

I-3

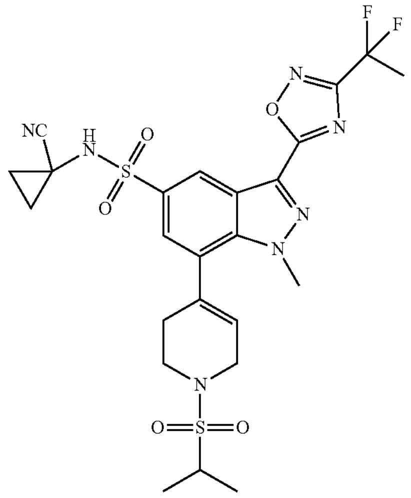

79

Synthesis of Compound 79-b

Compound I-1-d (200 mg, 0.48 mmol) was dissolved in tetrahydrofuran (3 mL), to which was added a solution of lithium hydroxide monohydrate (102 mg, 2.43 mmol) in 1 mL of water, and the reaction mixture was stirred at room temperature for 1.5 h. The reaction mixture was concentrated, to which was added water (3 mL), and the pH was adjusted to 3-4 by dropwise addition of 6 M hydrochloric acid, and filtered. The precipitated solid was washed with a small amount of water and the solid was dried to give 79-b (188 mg, 97%).

Synthesis of Compound 79-a

Compound 79-b (230 mg, 0.58 mmol) was dissolved in dry N,N-dimethylformamide (20 mL). In an ice-cold water bath, the above mixture was added (1Z)-2,2,2-trifluoro-N'-hydroxyacetamidine (81 mg, 0.63 mmol), dimethylaminopyridine (70 mg, 0.57 mmol), 1-hydroxybenzotriazole (117 mg, 0.87 mmol) and 1-(3-dimethylaminopropyl)-3-ethylcarbodiimide hydrochloride (166 mg, 0.87 mmol), and the reaction mixture was stirred at room temperature for 12 hours. To the reaction mixture was added water (200 mL), extracted with ethyl acetate (100 mL), and the organic phase was washed with brine (100 mL), dried over sodium sulfate, filtered to remove the desiccant and the filtrate was concentrated at reduced pressure to obtain the crude product, which was purified by column chromatography (mobile phase, DCM/EA 10/1) to give 79-a (84 mg, 30%).

Synthesis of Compound 79

Compound 79-a (84 mg, 0.17 mmol), I-3 (81 mg, 0.26 mmol), [1,1'-bis(di-tert-butylphosphino)ferrocene]palladium dichloride (22 mg, 0.034 mmol), and cesium fluoride (78 mg, 0.51 mmol) were added to 1,4-dioxane (18 mL) and water (2 mL). After degassed and purged with nitrogen for three times, the reaction mixture was stirred at 90° C. for 6 h. The reaction mixture was filtered through celite, and the filtrate was added water (50 mL) and extracted with dichloromethane (50 mL). The organic phase was washed with brine (50 mL), dried over sodium sulfate, filtered off the desiccant, and the filtrate was concentrated at reduced pressure to obtain the crude product, which was purified by column chromatography (mobile phase, PE/EA 1/1), and then by Prep-HPLC (basic conditions) to obtain compound 79 (41 mg, 40%). LC-MS (ESI): m/z 598.2 $(M-H)^-$; $^1$HNMR (400 MHz, DMSO-$d_6$): δ 9.30 (1H, s), 8.64 (1H, s), 7.73 (1H, s), 6.01 (1H, s), 4.31 (3H, s), 4.12-4.04 (2H, m), 3.70-3.58 (2H, m), 3.55-3.43 (1H, m), 2.63-2.53 (2H, m), 1.48-1.40 (2H, m), 1.36-1.24 (8H, m).
Synthetic Route of Compound 80
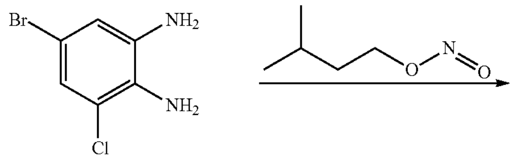
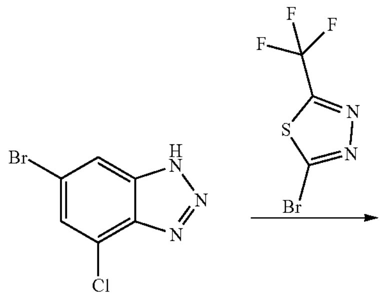
80-f
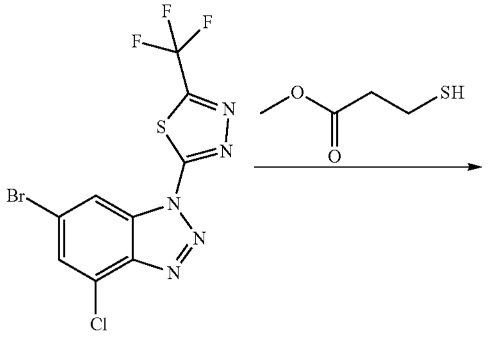
80-e
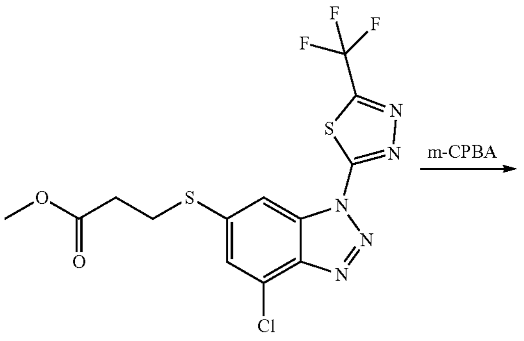
80-d
-continued
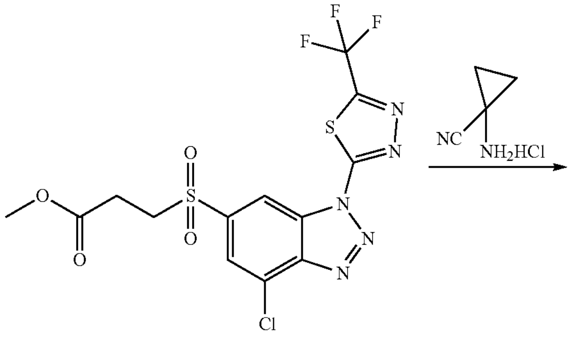
80-c
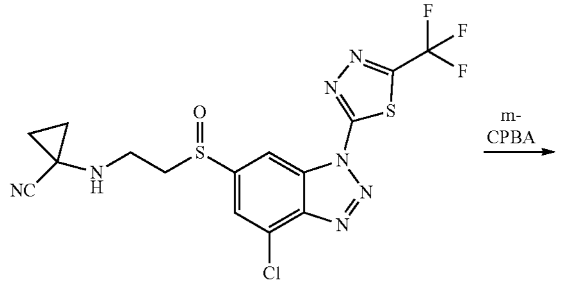
80-b
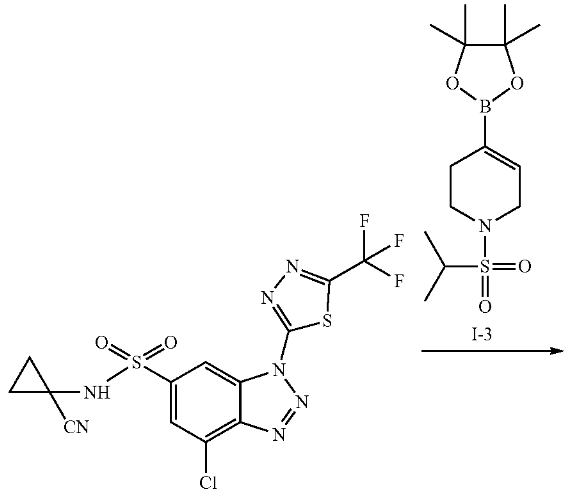
80-a -continued

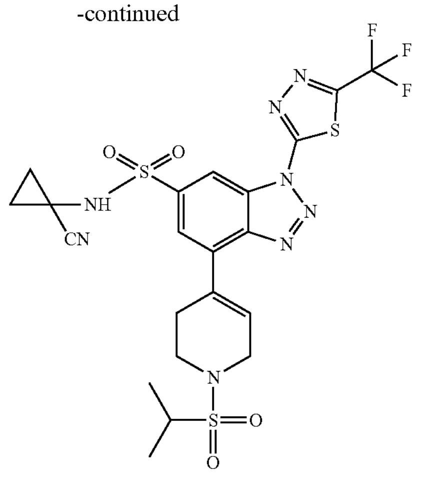

80

Synthesis of Compound 80-f

Compound 5-bromo-3-chlorobenzene-1,2-diamine (1 g, 4.52 mmol) was dissolved in acetonitrile (10 mL), to which isoamyl nitrite (2.6 g, 22.19 mmol) was added, and the reaction mixture was stirred for 3 hours at 60° C. The reaction mixture was concentrated under reduced pressure to give the crude product, which was purified by column chromatography (mobile phase, EA) to give compound 80-f (900 mg, 86%).

Synthesis of Compound 80-e

Compound 80-f (300 mg, 1.29 mmol) was dissolved in N,N-dimethylformamide (5 mL), to which was added cesium carbonate (630 mg, 1.93 mmol) and 2-bromo-5-trifluoromethyl-1,3,4-thiazole (451 mg, 1.94 mmol). The reaction mixture was stirred at 50° C. for 12 hours, then was added water (100 mL), extracted with ethyl acetate (50 mL). The organic phase was washed with brine (50 mL), dried over sodium sulfate, filtered to remove the desiccant, and the filtrate was concentrated under reduced pressure to give the crude product, which was purified by column chromatography (mobile phase, PE/EA 10/1) to give compound 80-e (350 mg, 71%).

Synthesis of Compound 80-d

Compound 80-e (210 mg, 0.55 mmol), methyl 3-mercaptopropionate (75 mg, 0.62 mmol), tris(dibenzylideneacetone)dipalladium (50 mg, 0.055 mmol), 4,5-bis(diphenylphosphino)-9,9-dimethyloxanthene (63 mg, 0.11 mmol), diisopropylethylamine (212 mg, 1.64 mmol) were added into 1,4-dioxane (15 mL). The reaction mixture was degassed and purged with nitrogen for three times and stirred in an oil bath at 80° C. for 3 hours. The reaction mixture was concentrated under reduced pressure to give the crude product, which was purified by column chromatography (mobile phase, PE/EA 10/1) to give compound 80-d (187 mg, 81%).

Synthesis of Compound 80-c

Compound 80-d (187 mg, 0.44 mmol) was dissolved in dichloromethane (10 mL) in an ice-water bath, to which m-chloroperoxybenzoic acid (269 mg, 1.56 mmol) was added, and the reaction mixture was stirred for 2 h at room temperature. The reaction mixture was added saturated sodium bicarbonate solution (50 mL), extracted with dichloromethane (50 mL). The organic phase was washed with brine (50 mL), dried over sodium sulfate, filtered to remove the desiccant, and the filtrate was concentrated under reduced pressure to obtain the crude product, which was purified by column chromatography (mobile phase, PE/EA 1/1) to obtain compound 80-c (200 mg, 99%).

Synthesis of Compound 80-b

Compound 80-c (200 mg, 0.44 mmol) was dissolved in dichloromethane (10 mL) and methanol (10 mL), to which sodium methanol (71 mg, 1.31 mmol) was added in an ice-water bath, and the reaction mixture was stirred in an ice-water bath for 30 min, then was added 1-amino-1-cyclopropyl cyanide hydrochloride (156 mg, 1.32 mmol) and stirred for 10 minutes at room temperature. The mixture was concentrated under reduced pressure and dried at vacuum by an oil pump for 3 hours. The resulting residue was dissolved in N,N-dimethylformamide (10 mL), to which was added 1-amino-1-cyclopropylcyanide hydrochloride (104 mg, 0.88 mmol), dimethylaminopyridine (54 mg, 0.44 mmol), 1-(3-dimethylaminopropyl)-3-ethylcarbodiimide hydrochloride (168 mg, 0.88 mmol) and the reaction mixture was stirred at room temperature for 1 hour, was added water (100 mL) and extracted with ethyl acetate (100 mL). The organic phase was washed with water (100 mL) and brine (100 mL) sequentially, dried over sodium sulfate, filtered to remove the desiccant and concentrated under reduced pressure to obtain the crude product, which was purified by column chromatography (mobile phase, PE/EA 3/1) to give 80-b (18 mg, 9%). LC-MS (ESI): m/z 434.0 $(M+H)^+$.

Synthesis of Compound 80-a

Compound 80-b (18 mg, 0.041 mmol) was dissolved in dichloromethane (5 mL) and m-chloroperoxybenzoic acid (33 mg, 0.19 mmol) was added to it in an ice-water bath. The reaction mixture was stirred for 4 hours at room temperature. The reaction mixture was added saturated sodium bicarbonate solution (50 mL) and extracted with dichloromethane (50 mL). The organic phase was washed with brine (50 mL), dried over sodium sulfate, filtered to remove the desiccant and concentrated under reduced pressure to give the crude product, which was purified by column chromatography (mobile phase, PE/EA 3/1) to give compound 80-a (18 mg, 96%). LC-MS (ESI): m/z 450.0 $(M+H)^+$.

Synthesis of Compound 80

Compound 80-a (18 mg, 0.040 mmol), I-3 (19 mg, 0.060 mmol), [1,1'-bis(di-tert-butylphosphino)ferrocene]palladium dichloride (8 mg, 0.012 mmol), and cesium fluoride (18 mg, 0.12 mmol) were added to 1,4-dioxane (9 mL) and water (1 mL) and the reaction mixture was degassed and purged with nitrogen for three times and then stirred at 100° C. for 5 h. The reaction mixture was filtered through celite. The filtrate was added water (50 mL) and extracted with dichloromethane (50 mL). The organic phase was washed with brine (50 mL), dried over sodium sulfate, filtered off the desiccant, and the filtrate was concentrated under reduced pressure to obtain the crude product, which was purified by column chromatography (mobile phase, PE/EA 1/2), and then by prep-HPLC (basic conditions) to obtain compound 80 (2 mg, 8.3%). LC-MS (ESI): m/z 603.0 $(M+H)^+$.

Synthetic Route of Compound 81

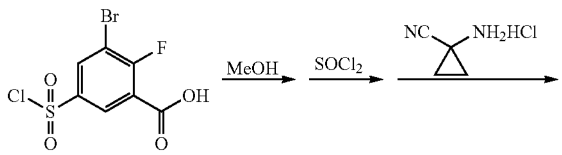

-continued

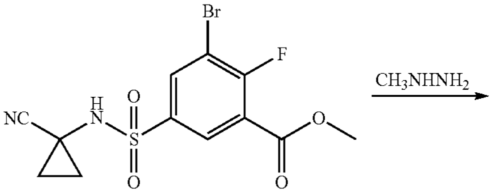

81-d

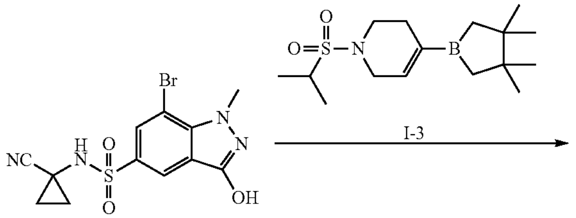

81-c

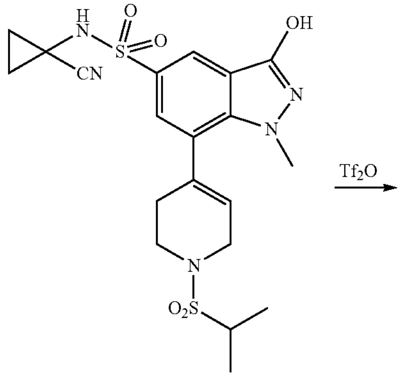

81-b

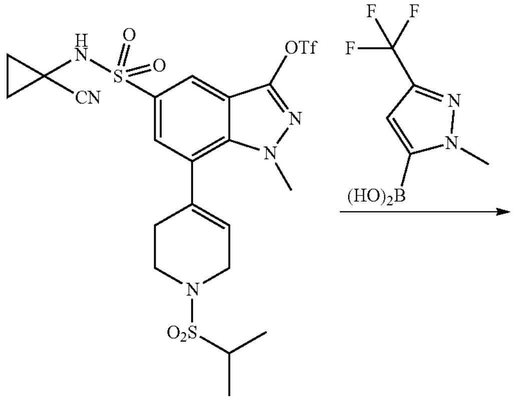

81-a

-continued

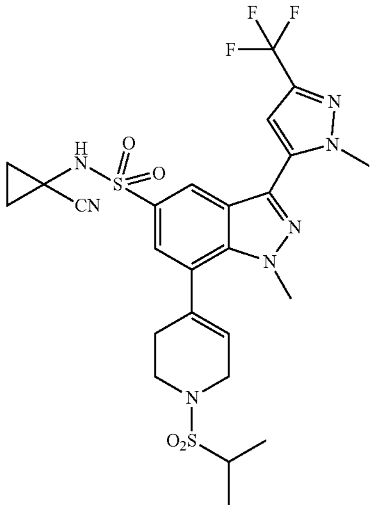

81

Synthesis of Compound 81-d

A reaction flask charged with 3-bromo-5-(chlorosulfonyl)-2-fluorobenzoic acid (950 mg, 2.99 mmol) was added anhydrous methanol (20 mL) dropwise in an ice-cold water bath, followed by slow dropwise addition of sulfoxide chloride (2 mL). The reaction mixture was stirred at 80° C. for 3 hours. The reaction mixture was concentrated to dryness. The residue was added to a small amount of ice-cold water, then added a small amount of anhydrous sodium sulfate solid, and solid was precipitated, filtered, and dried to obtain the crude product 1 (600 mg). To the crude 1 was added sulfoxide chloride (3 mL) dropwise, the reaction mixture was stirred at 80° C. for 3 hours. The solvent was removed to give crude 2. 1-Amino-1-cyclopropyl cyanide hydrochloride (420 mg, 3.54 mmol) was added to a reaction flask, pyridine (1 mL, 12.36 mmol) was added to the reaction flask, and the reaction mixture was stirred in an ice-cold water bath for 5 min before dichloromethane (5 mL) was added. A suspension of crude 2 in dichloromethane (5 mL) was added dropwise. After addition, the reaction mixture was stirred in an ice-cold water bath for 1 hour. The solvent was removed at room temperature, diluted with ethyl acetate, washed with brine, dried over anhydrous sodium sulfate, filtered, and the filtrate was evaporated to give compound 81-d (630 mg, 56% yield). LC-MS (ESI): m/z 375.1 $(M-H)^-$.

Synthesis of Compound 81-c

A reaction vial charged with 81-d (630 mg, 1.67 mmol) and anhydrous ethanol (20 mL) was added methylhydrazine (0.35 mL, 6.61 mmol) dropwise at room temperature. After addition, the reaction mixture was stirred at room temperature for 4 hours, then was removed most of the solvent. The residue was added ethyl acetate, brine and a small amount of sodium bisulfate solid. The liquid partitioned, and the aqueous phase was extracted with ethyl acetate three times. The organic phases were combined, dried over anhydrous sodium sulfate, filtered and evaporated to give compound 81-c (600 mg, 97% yield). LC-MS (ESI): m/z 371.0 $(M+H)^+$.

Synthesis of Compound 81-b

A reaction flask charged with 81-c (600 mg, 1.62 mmol), 1-3 (680 mg, 2.16 mmol), $Pd(dtbpf)Cl_2$ (100 mg, 0.16 mmol), 1,4-dioxane (24 mL) and a solution of cesium fluoride (860 mg, 5.66 mmol) in water (6 mL) was degassed and purged with nitrogen gas for three times and then stirred at 100° C. for 5 hours. The reaction mixture was cooled to room temperature, removed most of the solvent, added ethyl acetate, brine and a small amount of sodium bisulfate solid. The liquid was partitioned, and the aqueous phase was extracted with ethyl acetate twice. The organic phases were combined, dried over anhydrous sodium sulfate, filtered and evaporated to dryness. The crude was purified by column chromatography (mobile phase: dichloromethane/methanol, 100/0 to 94/6) to afford compound 81-b (280 mg, 36% yield). LC-MS (ESI): m/z 480.2 $(M+H)^+$.

Synthesis of Compound 81-a

A reaction flask charged with 81-b (280 mg, 0.58 mmol) and dichloromethane (6 mL) in an ice-cold water bath was added pyridine (0.189 mL, 2.34 mmol), and trifluoromethanesulfonic anhydride (330 mg, 1.17 mmol) slowly and dropwise. After addition, the reaction mixture was stirred in an ice-cold water bath for 2 hours. The reaction mixture was quenched by adding water, partitioned and the aqueous phase was extracted with dichloromethane once. The organic phases were combined, washed with saturated sodium bicarbonate, washed with brine, dried over anhydrous sodium sulfate, filtered, and the filtrate was evaporated to give 81-a (340 mg, 95% yield). LC-MS(ESI): m/z 610.1 $(M-H)^-$.

Synthesis of Compound 81

A microwave tube charged with 81-a (65 mg, 0.11 mmol), (1-methyl-3-trifluoromethyl-1H-pyrazol-5-yl)boronic acid (45 mg, 0.23 mmol), $Pd(dppf)Cl_2$ (8 mg, 0.011 mmol), 1,4-dioxane (2 mL) and a solution of cesium fluoride (65 mg, 0.43 mmol) in water (0.5 mL) was degassed and purged with nitrogen for 3 times and sealed. The reaction mixture was stirred at 100° C. for 2 hours. The reaction mixture was cooled to room temperature, diluted with ethyl acetate, washed with brine, and the aqueous phase was extracted with ethyl acetate once. The organic phases were combined, dried over anhydrous sodium sulfate, filtered, evaporated and purified by Prep-HPLC (ammonium bicarbonate) to give 81 (23 mg, 35% yield). LC-MS(ESI): m/z 612.3 $(M+H)^+$; $^1H$ NMR (DMSO-$d_6$, 400 MHz): δ 9.12 (1H, bs), 8.28 (1H, d, J=1.6 Hz), 7.63 (1H, d, J=1.2 Hz), 7.34 (1H, s), 6.07-5.94 (1H, m), 4.21 (3H, s), 4.18 (3H, s), 4.10-4.03 (2H, m), 3.63 (2H, t, J=5.5 Hz), 3.51-3.45 (1H, m), 2.61-2.52 (2H, m), 1.46-1.39 (2H, m), 1.35-1.26 (8H, m).

Synthetic Route of Compound 82

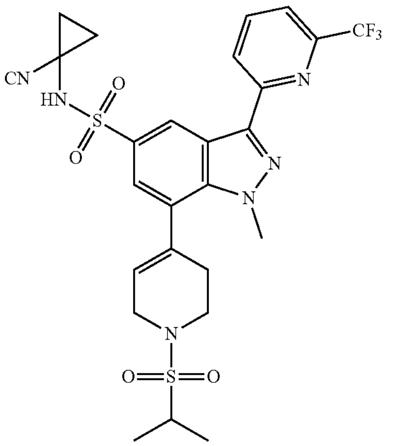

With reference to the synthesis of compound 81, compound 82 was synthesized using 6-(trifluoromethyl) pyridin-2-yl-2-boronic acid instead of (1-methyl-3-trifluoromethyl-1H-pyrazol-5-yl)boronic acid. LC-MS (ESI): m/z 609.0 $(M+H)^+$.

Synthetic Route of Compound 83

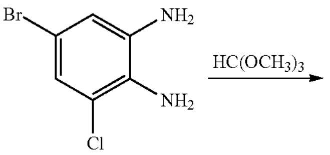

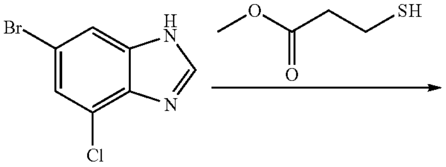

83-j

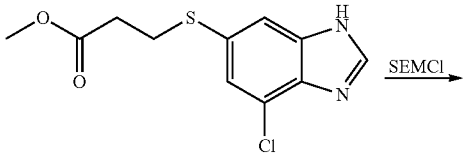

83-i

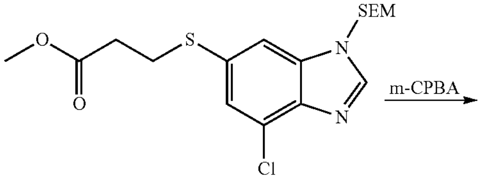

83-h

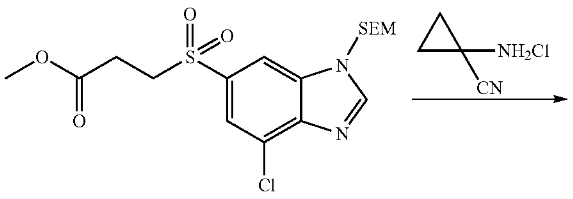

83-g

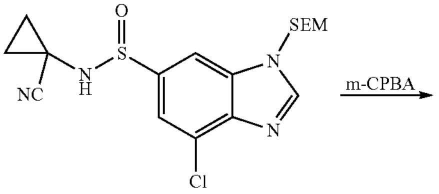

83-f

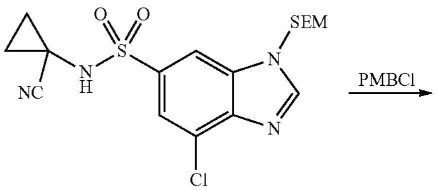

83-e

-continued

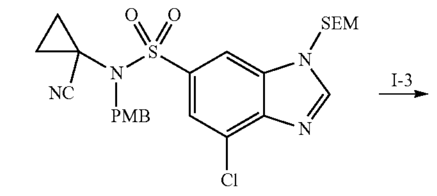

83-d

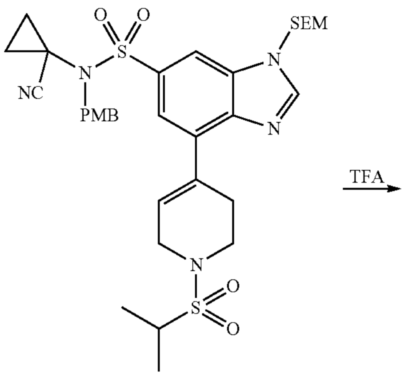

83-c

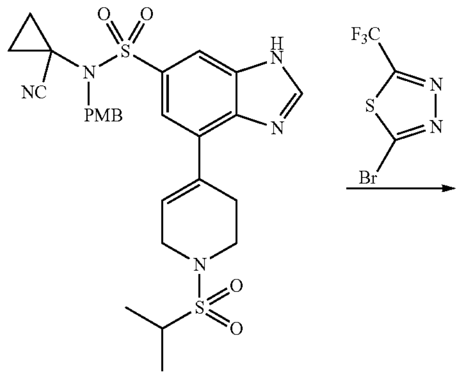

83-b

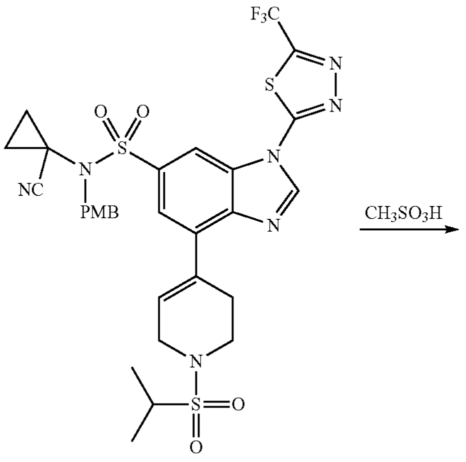

83-a

-continued

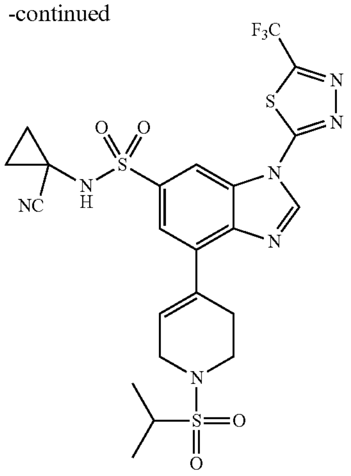

83

Synthesis of Compound 83-j

To a solution of 5-bromo-3-chlorobenzene-1,2-diamine (1.0 g, 4.52 mmol) in acetic acid (10 mL) was added trimethyl orthoformate (2.48 mL, 22.58 mmol) at room temperature. After addition, the reaction was stirred at 45° C. for 2 hours, then stirred at 80° C. overnight. At the end of the reaction, the organic solvent was removed by concentration under reduced pressure. The crude product was purified by a flash column chromatography (mobile phase: ethyl acetate/petroleum ether 0% to 100%) to afford compound 83-j (1.0 g, 96%). LC-MS (ESI): m/z=231.0 $[M+H]^+$.

Synthesis of Compound 83-i

A three-necked vial charged with 83-j (800 mg, 3.46 mmol), Xantphos (200 mg, 0.34 mmol), 1,4-dioxane (20 mL), DIPEA (1.81 mL, 10.37 mmol), and methyl 3-mercaptopropionate (498 mg, 4.15 mmol) was degassed and purged with nitrogen for 3 times, then was added $Pd_2(dba)_3$ (158 mg, 0.17 mmol), degassed and purged with nitrogen for 3 times. The reaction mixture was refluxed at 90° C. for 3 hours. The reaction mixture was cooled to room temperature, evaporated to dryness, and purified by column chromatography (mobile phase: mobile phase: ethyl acetate/petroleum ether 0% to 100%) to give compound 83-i (900 mg, 96%). LC-MS (ESI): m/z=271.1 $[M+H]^+$.

Synthesis of Compound 83-h

To a solution of 83-i (900 mg, 3.32 mmol) in dichloromethane (10 mL) was added DIPEA (1.16 mL, 6.65 mmol) and 2-(trimethylsilyl)ethoxymethyl chloride (1.18 mL, 6.65 mmol) at room temperature. After addition, the reaction was stirred at room temperature for 1 hour. At the end of the reaction, water was added to quench the reaction. The aqueous phase was extracted with dichloromethane, and the organic phases were combined, washed with brine, dried over anhydrous sodium sulfate, filtered, and the filtrate was evaporated to dryness. The crude product was purified by a flash column chromatography (mobile phase: ethyl acetate/petroleum ether 0% to 50%) to afford compound 83-h (1.0 g, 75%). LC-MS (ESI): m/z=401.2 $[M+H]^+$.

Synthesis of Compound 83-g

To a solution of 83-h (1.0 g, 2.49 mmol) in dichloromethane (10 mL) was added m-CPBA (1.08 g, 6.24 mmol) in an ice-cold water bath. After addition, the reaction mixture was kept at 0° C. and stirred for 1 hour. At the end of the reaction, the reaction mixture was diluted by adding dichloromethane, washed with saturated sodium bicarbonate solution, washed with brine, dried over anhydrous sodium sulfate, filtered and evaporated to dryness. The crude product was purified by a flash column chromatography (mobile phase: ethyl acetate/petroleum ether, 0% to 100%) to give compound 83-g (900 mg, 83%). LC-MS (ESI): m/z=433.1 $[M+H]^+$.

Synthesis of Compound 83-f

A reaction flask was charged with 83-g (900 mg, 2.08 mmol), methanol (10 mL) and dichloromethane (10 mL) was cooled to 0° C. in an ice-cold water bath, then was added sodium methanol (337 mg, 6.24 mmol) and the reaction mixture was kept in an ice-cold water bath for 1 hour. 1-Amino-1-cyclopropyl cyanide hydrochloride (986 mg, 8.32 mmol) was added and the solvent was removed by concentration under reduced pressure at room temperature and dried at vacuum for 20 min. DMF (8 mL) and a small amount of 3A molecular sieves were added. After stirring for 3 min in an ice-cold water bath, the above mixture was added triethylamine (0.58 mL, 4.16 mmol) and 1-amino-1-cyclopropyl cyanide hydrochloride (246 mg, 2.08 mmol), then in an ice-cold water bath, was added EDCI (797 mg, 4.16 mmol) and DMAP (254 mg, 2.08 mmol). The reaction mixture was stirred in an ice-cold water bath for 1 hour, then was diluted with ethyl acetate, washed with water, washed with brine, dried over anhydrous sodium sulfate, filtered and evaporated to dryness. The crude was purified by a flash column chromatography (mobile phase: ethyl acetate/petroleum ether, 0% to 100%) to afford 83-f (800 mg, 94%). LC-MS (ESI): m/z=411.1 $[M+H]^+$.

Synthesis of Compound 83-e

To a solution of 83-f (800 mg, 1.95 mmol) in dichloromethane (10 mL) was added m-CPBA (504 mg, 2.92 mmol) in an ice-cold water bath. After addition, the reaction was kept at 0° C. and stirred for 1 hour. Upon completion, the reaction mixture was diluted dichloromethane, washed with saturated sodium bicarbonate solution, brine, dried over anhydrous sodium sulfate, filtered, and the filtrate was evaporated to dryness. The crude product was purified by a flash column chromatography (mobile phase: ethyl acetate/petroleum ether, 0% to 100%) to give compound 83-e (800 mg, 96%). LC-MS (ESI): m/z=427.1 $[M+H]^+$.

Synthesis of Compound 83-d

To a solution of 83-e (800 mg, 1.87 mmol) in DMF (10 mL) was added potassium carbonate (647 mg, 4.48 mmol) and 4-methoxybenzyl chloride (0.38 mL, 2.81 mmol) at room temperature. After addition, the reaction was stirred at room temperature overnight. At the end of the reaction, the reaction mixture was diluted by adding ethyl acetate, washed with water, washed with brine, dried over anhydrous sodium sulfate, filtered and evaporated to dryness. The residue was purified by a flash column chromatography (mobile phase: ethyl acetate/petroleum ether 0% to 100%) to afford compound 83-d (800 mg, 78%). LC-MS (ESI): m/z=547.2 $[M+H]^+$.

Synthesis of Compound 83-c

A reaction vial charged with 83-d (400 mg, 0.73 mmol), 1-3 (346 mg, 1.10 mmol), [1,1'-bis(di-tert-butylphosphino) ferrocene]palladium dichloride (94 mg, 0.15 mmol), cesium fluoride (333 mg, 2.19 mmol), 1,4-dioxane (18 mL) and $H_2O$ (2 mL) was degassed and purged with nitrogen for 3 times, then was heated and stirred at 100° C. for 4 hours. At the end of the reaction, the reaction mixture was cooled to room temperature, concentrated under reduced pressure to remove the organic solvent, the residue was diluted with ethyl acetate, and the organic phase was washed with water, brine, dried over anhydrous sodium sulfate, filtered, and concentrated under reduced pressure to obtain the crude product. The crude product was purified by a flash column chromatography (mobile phase: ethyl acetate/petroleum ether: 0% to 100%) to give compound 83-c (400 mg, 78%). LC-MS (ESI): m/z=700.5 $[M+H]^+$.

Synthesis of Compound 83-b

To a solution of 83-c (400 mg, 0.57 mmol) in dichloromethane (20 mL) was added TFA (10 mL) at room temperature. After addition, the reaction was stirred at room temperature for 4 hours. At the end of the reaction, the reaction mixture was removed the solvent by concentration under reduced pressure at room temperature, diluted by addition of ethyl acetate, washed with saturated sodium bicarbonate solution, washed with brine, dried over anhydrous sodium sulfate, filtered, and the filtrate was evaporated to give compound 83-b (250 mg, 77%). LC-MS (ESI): m/z=570.3 $[M+H]^+$.

Synthesis of Compound 83-a

To a solution of 83-b (50 mg, 0.088 mmol) in DMF (5 mL) was added cesium carbonate (43 mg, 0.13 mmol) and 2-bromo-5-trifluoromethyl-1,3,4-thiazole (31 mg, 0.13 mmol) at room temperature. After addition, the reaction was stirred at room temperature overnight. At the end of the reaction, the reaction mixture was diluted with the addition of ethyl acetate, washed with water, washed with brine, dried over anhydrous sodium sulfate, filtered and evaporated to dryness. The residue was purified by a flash column chromatography (mobile phase: ethyl acetate/petroleum ether 0% to 100%) to afford compound 83-a (40 mg, 63%). LC-MS (ESI): m/z=722.2 $[M+H]^+$.

Synthesis of Compound 83

To a solution of 83-a (40 mg, 0.055 mmol) in dichloromethane (12 mL) was added methanesulfonic acid (0.3 mL) at room temperature. After addition, the reaction was stirred at room temperature for 2 hours. At the end of the reaction, the reaction was quenched by the addition of saturated aqueous sodium bicarbonate solution and the aqueous phase was extracted with dichloromethane. The organic phases were combined, washed with water, brine, dried over anhydrous sodium sulfate, filtered and evaporated to dryness. The crude product was purified by a flash column chromatography (mobile phase: ethyl acetate/petroleum ether 0% to 100%) to give compound 83 (10 mg, 30%). LC-MS (ESI): m/z=602.2 $[M+H]^+$.

Synthetic Route of Compound 84

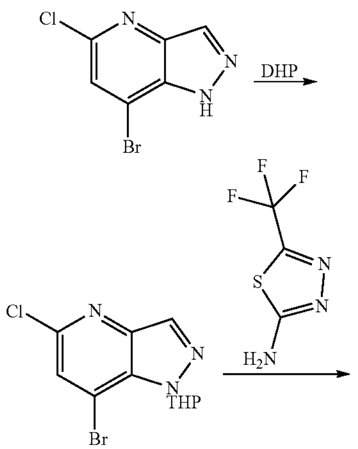

84-d

-continued

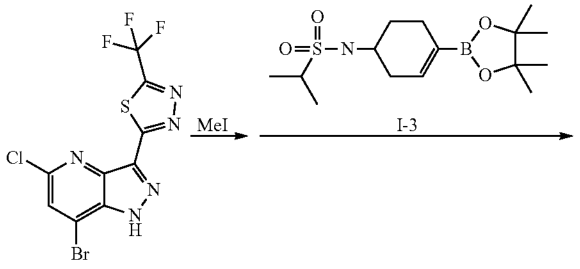

84-c

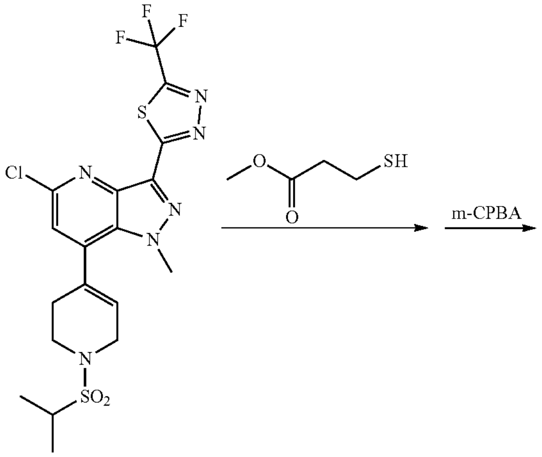

84-b

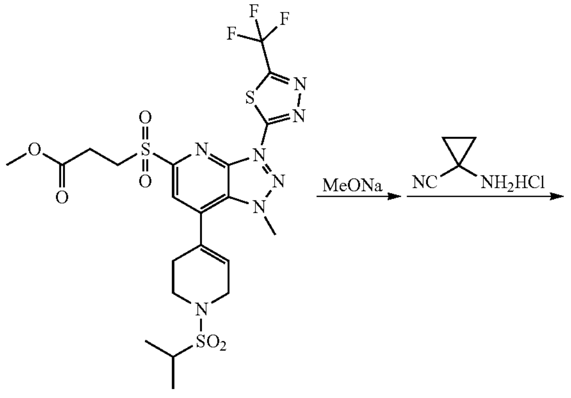

84-a

-continued

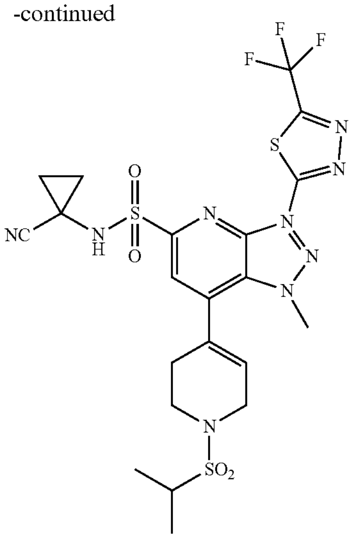

84

Synthesis of Compound 84-d

A reaction flask charged with 7-bromo-5-chloro-1H-pyrazolo[4,3-b]pyridine (1.02 g, 4.39 mmol), 3,4-dihydro-2H-pyran (10 mL) and trifluoroacetic acid (0.3 mL) was stirred at 90° C. for 2 hours. The reaction mixture was cooled to room temperature, diluted by adding ethyl acetate, washed once with saturated sodium bicarbonate water, washed with brine water, dried over anhydrous sodium sulfate, filtered, evaporated, and purified by column chromatography (mobile phase: petroleum ether/ethyl acetate, 100/0 to 70/30) to give 84-d (1.35 g, 97% yield). LC-MS (ESI): m/z 316.0 $(M+H)^+$.

Synthesis of Compound 84-c

A reaction vial charged with 84-d (660 mg, 2.09 mmol), 2-amino-5-trifluoromethyl-1,3,4-thiadiazole (528 mg, 3.12 mmol), palladium acetate (45 mg, 0.20 mmol) and anhydrous acetonitrile (20 mL) was added tert-butyl nitrite (309 mg, 3.00 mmol) dropwise at room temperature in a water bath. After addition, the reaction mixture was stirred at room temperature for 2 hours. The reaction mixture was removed solvent, and the residue was diluted with a small amount of ethyl acetate, petroleum ether. Solid was precipitated and the supernatant was separated. The residual solid was diluted with a small amount of ethyl acetate, petroleum ether, and solid precipitated, and the supernatant was separated. The residual solid was evaporated to dryness to give compound 84-c (380 mg, 47% yield). LC-MS(ESI): m/z 383.9 $(M+H)^+$.

Synthesis of Compound 84-b

To a reaction vial charged with 84-c (250 mg, 0.65 mmol), DMF (4 mL) and anhydrous potassium carbonate (270 mg, 1.95 mmol). Iodomethane (0.106 mL, 1.30 mmol) was added dropwise at room temperature. The reaction mixture was stirred for 1 h at room temperature and then was added water and extracted twice with ethyl acetate. The organic phase was washed with water, brine, dried over anhydrous sodium sulfate, filtered and evaporated to obtain the crude product. The crude product in a reaction flask was added I-3 (205 mg, 0.65 mmol), Pd(dtbpf)$Cl_2$ (42 mg, 0.065 mmol), 1,4-dioxane (10 mL) and a solution of cesium fluoride (300 mg, 1.98 mmol) in water (2 mL). After degassed and purged with nitrogen for 3 times, the reaction mixture was stirred at 100° C. for 2 hours. The reaction mixture was removed most of the solvent, diluted with ethyl acetate, washed with water, and the aqueous phase was extracted with ethyl acetate once. The organic phases were combined, washed with brine, dried over anhydrous sodium sulfate, filtered and evaporated to dryness. The crude was purified by column chromatography (mobile phase: petroleum ether/ethyl acetate, 100/0 to 60/40) to give compound 84-b (150 mg, 46% yield). LC-MS (ESI): m/z 507.2 $(M+H)^+$.

Synthesis of Compound 84-a

A microwave tube charged with 84-b (153 mg, 0.30 mmol), XANTPHOS (15 mg, 0.026 mmol), $Pd_2(dba)_3$ (13 mg, 0.014 mmol), 1,4-dioxane (3 mL), triethylamine (0.168 mL, 1.21 mmol) and methyl 3-mercaptopropionate (73 mg, 0.61 mmol) was degassed and purged with nitrogen gas once and sealed. The reaction mixture was stirred at 100° C. for 2 hours, then was cooled to room temperature and concentrated to dryness to obtain the crude product. The crude product was dissolved in dichloromethane (6 mL) and to which m-CPBA (156 mg, 0.90 mmol) was added in an ice-cold water bath. The reaction mixture was stirred in an ice-cold water bath for 2 hours. After addition of m-CPBA (51 mg, 0.30 mmol), the reaction mixture was stirred in an ice-cold waterbath for 1 hour. After addition of m-CPBA (51 mg, 0.30 mmol), the reaction mixture was stirred in an ice-cold water bath for 1 hour. The reaction mixture was removed solvent at room temperature, diluted with ethyl acetate, washed with saturated sodium bicarbonate, washed with aqueous sodium bicarbonate, washed with sodium bisulfite, washed with aqueous sodium bicarbonate, dried over anhydrous sodium sulfate, filtered, evaporated to dryness, and the crude was purified by column chromatography (mobile phase: petroleum ether/ethyl acetate, 100/0 to 40/60) to give compound 84-a (100 mg, 53% yield). LC-MS (ESI): m/z 623.1 $(M+H)^+$.

Synthesis of Compound 84

A reaction flask charged with 84-a (100 mg, 0.16 mmol) in an ice-cold water bath was added anhydrous dichloromethane (4.0 mL), anhydrous methanol (1.3 mL) and sodium methanolate (8.7 mg, 0.16 mmol). The reaction mixture was stirred in an ice-cold water bath for 20 min, then was added 1-amino-1-cyclopropyl cyanide hydrochloride (58 mg, 0.49 mmol) and continued stirring in an ice-cold water bath for 5 min. The solvent was removed at room temperature, and the residue was added a small amount of dichloromethane, concentrated to dryness at room temperature and dried by an oil pump for 10 minutes, was added 1-Amino-1-cyclopropyl cyanide hydrochloride (19 mg, 0.16 mmol), DMF (3 mL) and triethylamine (0.021 mL, 0.15 mmol), then in an ice-cold water bath was added NCS (30 mg, 0.23 mmol). The reaction mixture was stirred for 1 h at 20° C. Ice-cold water was added to the reaction mixture, followed by a small amount of sodium bisulfate solid and extracted twice with ethyl acetate. The organic phases were combined, dried over anhydrous sodium sulfate. Filtered, and the filtrate was concentrated to dryness. Most of the DMF was blown off with nitrogen. The residue was added dichloromethane (5 mL), NCS (2 mg, 0.015 mmol), and concentrated to dryness to give the crude product, which was purified by Prep-HPLC purification (ammonium bicarbonate) to give compound 84 (23 mg, 23% yield). LC-MS(ESI): m/z 617.2 $(M+H)^+$; $^1H$ NMR (DMSO-$d_6$, 400 MHz): δ 9.57 (1H, bs), 7.96 (1H, s), 6.18-6.09 (1H, m), 4.27 (3H, s), 4.13-4.05 (2H, m), 3.64 (2H, t, J=5.6 Hz), 3.48 (1H, p, J=6.8 Hz), 2.71-2.60 (2H, m), 1.55-1.40 (4H, m), 1.30 (6H, d, J=6.8 Hz).

Synthetic Route of Compound 85

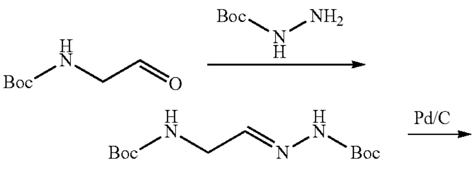

85-g

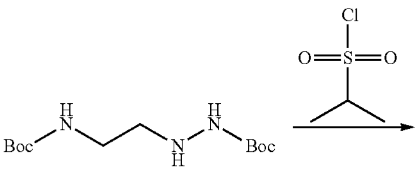

85-f

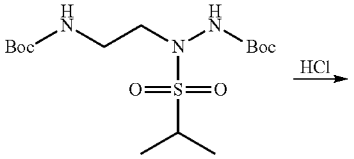

85-e

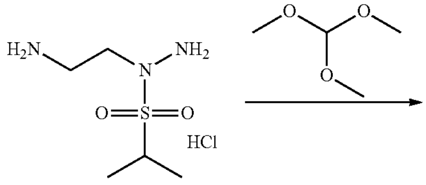

85-d

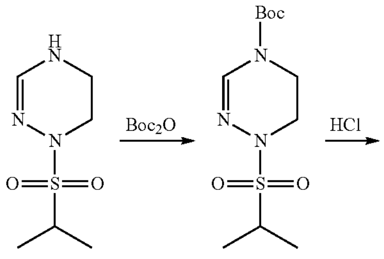

85-b-1 85-c

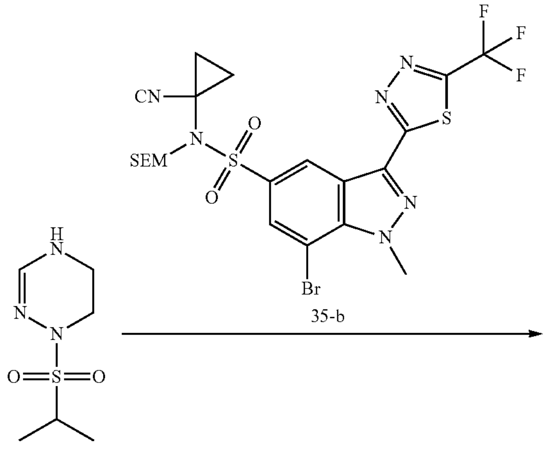

35-b 85-b-2

-continued

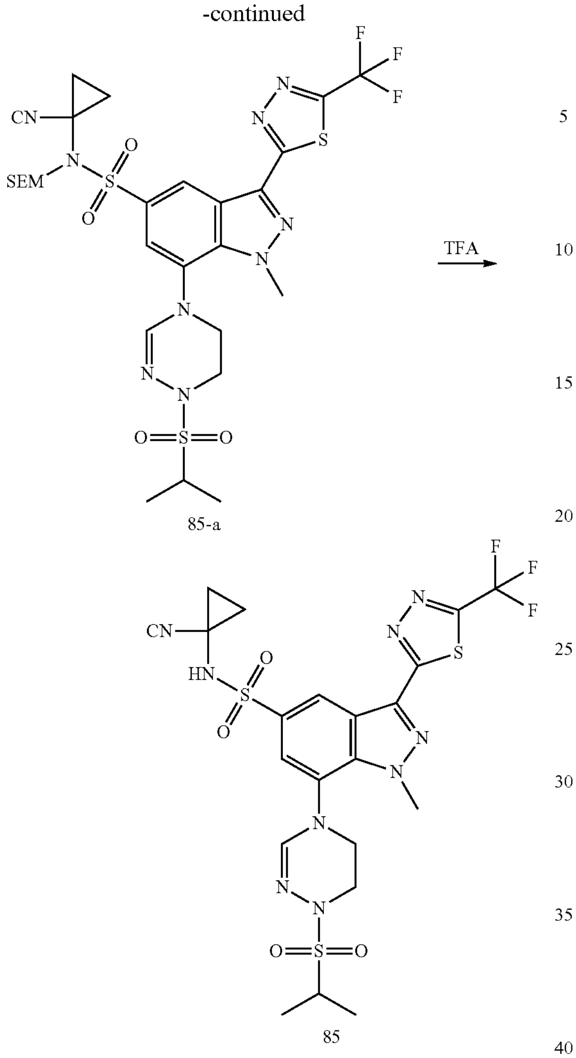

85-a

85

Synthesis of Compound 85-g

At room temperature under nitrogen protection, N-tert-butoxycarbonyl-2-aminoacetaldehyde (2.91 g, 18.28 mmol) was added to a solution of tert-butoxycarbohydrazide (2.30 g, 17.40 mmol) dissolved in 50 mL of methylcyclohexane. The reaction mixture was stirred at 100° C. under nitrogen protection for 1 hour and then cooled to room temperature and continued stirring overnight. To the reaction mixture was added 100 mL of n-hexane and stirred for 10 minutes. The mixture was filtered and the filter cake was washed with n-hexane (10 mL*2). The solid was collected and dried at vacuum for 1 hour to give compound 85-g (3.5 g, 74%).

Synthesis of Compound 85-f

Palladium carbon (0.50 g) was added to a solution of compound 85-g (3.5 g, 12.81 mmol) in 100 mL of ethanol at room temperature. The mixture was stirred under hydrogen protection at room temperature for 36 hours. The reaction mixture was filtered and the filtrate was concentrated under reduced pressure to give the crude compound 85-f (3.5 g, 99%), which was used directly in the next step. LC-MS (ESI): m/z=276.3[M+H]$^+$.

Synthesis of Compound 85-e

Potassium carbonate (5.72 g, 41.39 mmol) was added to a solution of compound 85-f (1.90 g, 6.90 mmol) in 20 mL of DMF at room temperature and. The mixture was cooled in an ice-cold water bath and was added isopropylsulfonyl chloride (3.87 mL, 34.50 mmol). The mixture was warmed to room temperature and stirred for 2 days. Potassium carbonate (5.72 g, 41.39 mmol) and isopropylsulfonyl chloride (3.87 mL, 34.50 mmol) were made up at room temperature and the mixture was stirred for 24 hours at room temperature. To the reaction mixture was added 100 mL of water, extracted with ethyl acetate (100 mL*2), and the organic phase was washed with brine (100 mL*5), dried over anhydrous sodium sulfate, filtered, and the filtrate was concentrated under reduced pressure, and the residue was purified by a flash column chromatography (PE/EA=1:1, potassium permanganate color development) to give compound 85-e (205 mg, 7.8%). LC-MS (ESI): m/z=382.2[M+H]$^+$.

Synthesis of Compound 85-d

A solution of hydrogen chloride in 1,4-dioxane (10 mL, 4 M) was added to a solution of compound 85-e (267 mg, 0.70 mmol) in 10 mL of dichloromethane in an ice-cold water bath. The reaction mixture was stirred under nitrogen protection at room temperature for 2 hours. The reaction mixture was concentrated under reduced pressure to give the crude compound 85-d (177 mg, 99%), which was used directly in the next reaction without further purification. LC-MS (ESI): m/z=182.2 [M+H]$^+$.

Synthesis of Compound 85-b-1

At room temperature, trimethyl orthoformate (5 mL) was added to a solution of compound 85-d (177 mg, 0.70 mmol) in 20 mL of glacial acetic acid. The reaction mixture was stirred at 60° C. under nitrogen for 1 hour and then at 100° C. for 3 hours. The reaction mixture was cooled to room temperature and concentrated under reduced pressure. To the residue were added 2 mL of saturated sodium bicarbonate solution and 1 g of sodium bicarbonate solid and concentrated under reduced pressure. Ethanol (10 mL) was added to the residue and concentrated under reduced pressure. To the residue was added a mixed solvent of dichloromethane and methanol (10/1, 50 mL), dried over anhydrous sodium sulfate, filtered, and the filtrate was concentrated under reduced pressure to give the crude compound 85-b-1 (133 mg, 99%). The crude product was directly used in the next reaction without further purification. LC-MS (ESI): m/z=192.2 [M+H]$^+$.

Synthesis of Compound 85-c

Di-tert-butyl dicarbonate (120 mg, 0.55 mmol) and DMAP (4.5 mg, 0.037 mmol) were added to a solution of compound 85-b-1 (70 mg, 0.37 mmol) dissolved in 10 mL of THF at room temperature. The reaction mixture was stirred at 80° C. under nitrogen for 3 hours, cooled to room temperature, concentrated under reduced pressure and the residue was purified by a flash column chromatography (PE/EA=1:1) to give compound 85-c (25 mg, 23%). LC-MS (ESI): m/z=292.2 [M+H]$^+$.

Synthesis of Compound 85-b-2

Compound 85-c (25 mg, 0.086 mmol) was dissolved in 5 mL of dichloromethane at room temperature, to which was added a solution of hydrogen chloride in 1,4-dioxane (1 mL, 4 M) in an ice-water bath, and the reaction mixture was stirred under nitrogen for 2 h at room temperature. A solution of hydrogen chloride in 1,4-dioxane (4.5 mL, 4M) was made up at room temperature and the reaction mixture was stirred under nitrogen at room temperature for 18 hours. The reaction mixture was concentrated under reduced pressure. To the residue were added 2 mL of saturated sodium bicarbonate solution and 1 g of sodium bicarbonate solid and concentrated under reduced pressure. Ethanol (10 mL) was added to the residue and concentrated under reduced pressure. To the residue was added a mixed solvent of dichloromethane and methanol (10/1, 30 mL), dried over anhydrous sodium sulfate, filtered, and the filtrate was concentrated under reduced pressure and dried at vacuum to give the crude compound 85-b-2 (18 mg). The crude product was directly used in the next reaction without further purification. LC-MS (ESI): m/z=192.1 $[M+H]^+$.

Synthesis of Compound 85-a

Compound 35-b (60 mg, 0.094 mmol), 85-b-2 (18 mg, 0.094 mmol), (SP-4-1)-[1,3-bis[2,6-bis(1-ethylpropyl)phenyl]-4,5-dichloro-1,3-dihydro-2H-imidazolylidene]dichloro (3-chloropyridinium-kN)palladium (24 mg, 0.028 mmol), RuPhos (13 mg, 0.028 mmol), cesium carbonate (92 mg, 0.28 mmol) and 1,4-dioxane (2 mL) were combined in a sealed tube, and the reaction mixture was stirred at 88° C. protected by nitrogen for 18 hours. The reaction mixture was cooled to room temperature, was added 50 mL of water and extracted with ethyl acetate (50 mL*2). The organic phase was dried over anhydrous $Na_2SO_4$, filtered, and the filtrate was concentrated under reduced pressure, and the residue was purified by a flash column chromatography (DCM/MeOH=30:1) to afford the crude compound 85-a (60 mg, 85%). The crude product was directly used in the next step without further purification. LC-MS (ESI): m/z=748.2$[M+H]^+$.

Synthesis of Compound 85

Trifluoroacetic acid (2 mL) was added to a solution of compound 85-a (60 mg, 0.080 mmol) in 6 mL of dichloromethane at room temperature, and the reaction mixture was stirred under nitrogen for 2 h at room temperature. The reaction mixture was concentrated under reduced pressure and the residue was suspended in 2 mL of saturated sodium bicarbonate, was added potassium carbonate (200 mg) and ethyl acetate (50 mL). The reaction mixture was stirred at room temperature for 1 h. 50 mL of water was added and the reaction mixture was extracted with ethyl acetate (50 mL), the organic phase was dried over anhydrous sodium sulfate, filtered, and the filtrate was concentrated under reduced pressure, and the residue was isolated and purified by Prep-TLC (DCM/MeOH=20:1) to obtain the crude product, which was further purified by Prep-HPLC ($NH_4HCO_3$) to obtain compound 85 (5.2 mg, 11%). LC-MS(ESI): m/z=618.2 $[M+H]^+$.

Bioactivity Test

PARG Enzyme Inhibition Assay

Experimental Procedure.

PARG in vitro assays were conducted in standard 384-well plates in a total volume of 15 μL. 5 μL of PARG (389-976) (manufactured by Chempartner Chemical Co., Ltd.) in buffer (50 mM Tris-HCL 7.5, 30 mM KCl, 1 mM EDTA, 3 mM DTT, tween-20 0.01%, BSA 0.025%) was added at a final concentration of 1.5 pM to the 384-well plates containing the compounds to be tested, which was incubated for 30 min at room temperature. To the above mixture was added 5 μL Bio PARylated His-TEV-PARP1 (2-1014) substrate (manufactured by Chempartner Chemical Co., Ltd.) at a final concentration of 12 nM, after addition, the resulting mixture was incubated for 30 minutes at room temperature. Then to the mixture was added detection reagent (5 μL) which was buffered with 50 mM Tris-HCL 7.5, 30 mM KCl, 1 mM EDTA, 3 mM DTT, tween-20 0.01%, BSA 0.025%, and consisted of 3 μM of compound PDD00017273 and 9 nM Mab anti-6HIS XL665 (Cisbio: 61HISXLA) and 0.9 nM streptavidin affinity terbium cryptate (Cisbio:610SATLA), all at 3× working concentrations (final concentrations of 1 μM, 3 nM and 0.3 nM, respectively). After 120 min incubation in the dark at room temperature, TR-FRET signals were measured at Ex 340 and Em 665 and Em 615. The ratio for each well was calculated as Em 665/Em 615 and the compound inhibition rate was calculated based on the obtained data.

Results of PARG Bioactivity (Enzyme Inhibition Assay) Assay.

TABLE 1

PARG biochemical activity of representative compounds of the present disclosure

| Compound No. | $IC_{50}$ (PARG enzyme) |
|---|---|
| 1 | ***** (0.20 nM) |
| 2 | ***** (0.27 nM) |
| 3 | **** (1.64 nM) |
| 4 | **** |
| 5 | ***** (0.33 nM) |
| 6 | ***** |
| 7 | **** (1.18 nM) |
| 8 | **** |
| 9 | **** |
| 10 | **** |
| 11 | ***** |
| 12 | ***** |
| 13 | **** |
| 14 | ***** |
| 15 | ***** |
| 16 | **** (1.18 nM) |
| 17 | **** |
| 18 | ***** (0.12 nM) |
| 19 | ***** (0.12 nM) |
| 20 | ***** (0.06 nM) |
| 21 | ***** |
| 22 | ***** |
| 23 | ***** |
| 24 | ***** |
| 25 | ***** (0.34 nM) |
| 26 | ***** (0.16 nM) |
| 27 | **** |
| 28 | **** |
| 29 | *** |
| 30 | ***** (0.61 nM) |
| 31 | **** (1.14 nM) |
| 32 | **** (1.03 nM) |
| 33 | ***** |
| 34 | *** |
| 35 | ***** |
| 36 | ***** |
| 37 | ***** |
| 38 | ***** |
| 39 | ***** |
| 40 | ***** |
| 41 | ** |
| 42 | **** |
| 43 | ** |
| 44 | — |
| 45 | ***** |
| 46 | ***** |
| 47 | **** |
| 48 | *** |
| 49 | ** |
| 50 | *** |
| 51 | **** |

TABLE 1-continued

PARG biochemical activity of representative compounds of the present disclosure

| Compound No. | $IC_{50}$ (PARG enzyme) |
|---|---|
| 52 | **** |
| 53 | ***** |
| 54 | *** |
| 55 | ***** |
| 56 | ***** |
| 57 | *** |
| 58 | **** |
| 59 | **** |
| 60 | **** |
| 61 | ***** |
| 62 | *** |
| 63 | ** |
| 64 | ***** |
| 65 | **** |
| 66 | **** |
| 67 | ***** |
| 68 | ***** |
| 69 | ***** |
| 70 | ***** |
| 71 | ***** |
| 72 | ***** |
| 73 | ***** |
| 74 | **** |
| 75 | ***** |
| 76 | ***** |
| 77 | **** |
| 78 | **** |
| 79 | ***** |
| 80 | *** |
| 81 | ** |
| 82 | — |
| 83 | **** |
| 84 | ** |
| 85 | ***** |
| comparative compound 1' | **** (1.90 nM) |
| PDD 00017273 | **** |

***** represents $IC_{50}$ < 1 nM;
**** represents 1 nM ≤ $IC_{50}$ < 10 nM;
*** represents 10 nM ≤ $IC_{50}$ < 100 nM;
** represents 100 nM ≤ $IC_{50}$ < 1 μM;
* represents $IC_{50}$ ≥ 1 μM
#PPD 00017273 is a PARG inhibitor reported in the literature.

Cellular Assay CTG Assay for Proliferation Inhibition Assay of Compounds on Cell Lines The assay was conducted on either 384-well plates or 96-well plates. The procedures are as follows:

The cell suspensions were added to 384- or 96-well plates (384-well plate: 50 μL; 96-well plate: 100 μL) except for peripheral wells. The plates were incubated in a carbon dioxide incubator overnight, HCC1395, HCC1428 and NCI-H460 were placed in a carbon dioxide incubator of 5%, 370 overnight. Prepared compounds (10 concentration gradients by serial 3-fold dilution) were added to the wells using the HPD300 micro-dosing instrument. The cell plates were incubated in a carbon dioxide incubator for 7 days. HCC1395, HCC1428 and NCI-H460 were incubated in a 5%, 37° $CO_2$ incubator. On the day of plate measurement, 384- or 96-well plates were first equilibrated at room temperature for 10-30 minutes, then to the 384- or 96-well plate was added CellTiter Glo reagent (384-well plate: 25 μL; 96-well plate: 100 μL), shaken for 10 minutes away from light, and incubated for 10 minutes. The incubated plates were placed into Victor NIVO reader plates, and the pharmacodynamic inhibition curves were plotted and $IC_{50}$ values were calculated using XLFit.

TABLE 2

Proliferation inhibition assay of cell lines by representative compounds of the present disclosure

| Compound No. | $IC_{50}$ (μM) (HCC1395) | $IC_{50}$ (μM) (HCC1428) | $IC_{50}$ (μM) (NCI-H460) |
|---|---|---|---|
| 6 | 0.4421 | — | — |
| 7 | 0.3059 | 0.5376 | 0.3116 |
| 9 | 0.1971 | 1.1741 | 0.1470 |
| 12 | 0.1693 | 0.1507 | 0.1485 |
| 14 | 0.1262 | 0.3989 | 0.1216 |
| 15 | 0.0955 | 0.1165 | 0.0561 |
| 18 | 0.0423 | 0.2153 | 0.0408 |
| 19 | 0.0532 | 0.1955 | 0.0414 |
| 22 | 0.6054 | 1.0911 | 0.7137 |
| 23 | 0.1831 | 0.4657 | 0.1238 |
| 25 | 0.2063 | 0.1525 | 0.1854 |
| 26 | — | 0.0865 | 0.1387 |
| 32 | 0.1774 | 0.2321 | 0.2096 |
| Comparative compound 1' | 1.2888 | 1.3768 | 0.7964 |
| 2 | — | 0.413 | — |
| 3 | 0.3860 | — | — |
| 5 | 0.2221 | 0.1322 | 0.1828 |
| 20 | 3.9488 | 3.0176 | 2.8150 |
| 21 | 1.4560 | 2.0899 | 0.8907 |
| 24 | 0.6498 | 0.5779 | 0.4933 |
| 30 | 0.7867 | 0.4499 | 0.6558 |
| 31 | 0.6412 | 0.5066 | 0.4565 |
| 33 | 0.6914 | 0.6158 | 0.4996 |
| 35 | 0.2839 | 0.6977 | 0.1622 |
| 36 | 0.1267 | 0.0978 | 0.0729 |
| 37 | 0.0621 | — | — |
| 38 | 0.4319 | 0.3998 | 0.3658 |
| 39 | 0.8269 | 0.3692 | 0.4290 |
| 40 | 0.3004 | 0.4540 | 0.2606 |
| 44 | 1.0478 | — | 1.0691 |
| 45 | 0.1620 | 0.1435 | 0.1336 |
| 46 | — | 1.703 | — |
| 47 | — | 1.912 | — |
| 48 | 2.0403 | — | 2.0531 |
| 50 | — | 2.333 | — |
| 51 | — | 2.517 | — |
| 52 | 1.3758 | 1.0633 | — |
| 53 | 0.3915 | 0.2073 | |
| 55 | 0.8360 | 0.2082 | — |
| 56 | 0.0475 | 0.0472 | — |
| 58 | 0.2527 | 0.2007 | 0.2165 |
| 59 | 0.3569 | — | 0.2697 |
| 60 | 0.1813 | 0.0778 | 0.1153 |
| 61 | 1.6269 | 1.6762 | — |
| 64 | — | 0.0882 | — |
| 67 | — | 0.2031 | — |
| 68 | — | 0.4700 | — |
| 69 | 0.2961 | — | 0.2916 |
| 70 | 0.2697 | 0.3428 | — |
| 71 | 0.3080 | 0.3421 | — |
| 72 | 0.0587 | 0.1262 | — |
| 73 | 0.0462 | 0.0576 | — |
| 74 | 0.1558 | 0.0621 | — |
| 75 | 0.0352 | — | — |
| 76 | 0.1560 | 0.1847 | 0.1310 |
| 78 | 0.5002 | 0.5317 | 0.4256 |
| 79 | 0.1955 | 0.0833 | — |

Although specific embodiments of the present disclosure have been described above, it will be appreciated by those skilled in the art that these embodiments are merely illustrative and that many changes or modifications can be made to these embodiments without departing from the principles and spirit of the present disclosure. The scope of protection of the present disclosure is therefore defined by the appended claims.

What is claimed for:

1. A compound represented by formula I, a pharmaceutically acceptable salt thereof, a stereoisomer thereof, an isomer thereof or an isotopic compound thereof:

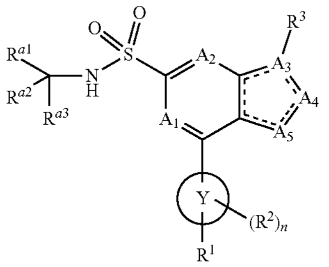

I wherein, "⎓" represents a single bond or a double bond; both rings of

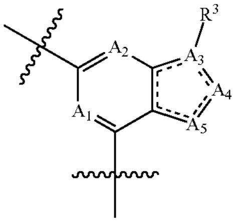

are aromatic;

$A_1$ and $A_2$ are independently N or $CR^{b1}$; $R^{b1}$ is hydrogen or halogen;

$A_3$ is C or N;

$A_4$ is N, $CR^4$ or $NR^4$;

$A_5$ is NR, N, $CR^5$, S or O;

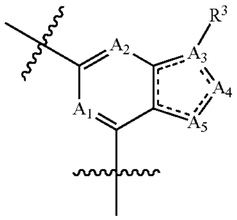

is

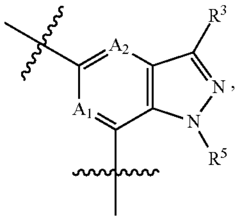

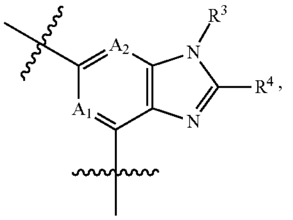

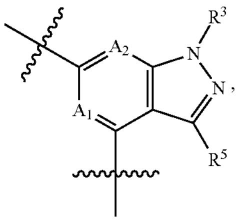

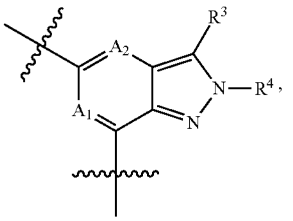

-continued

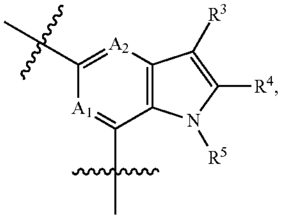

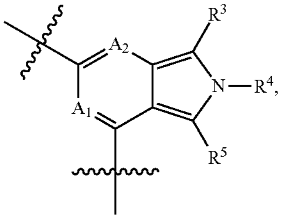

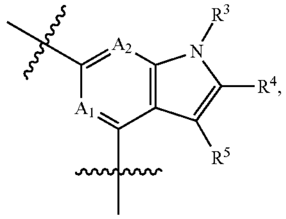

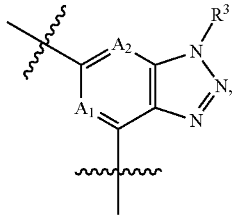

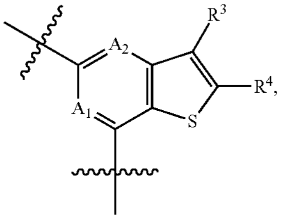

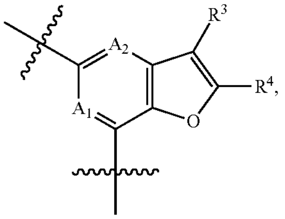

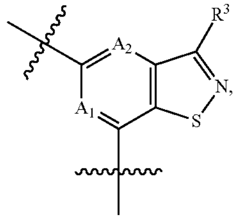

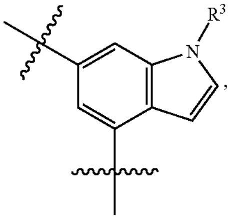

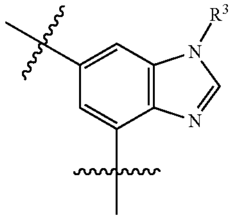

or

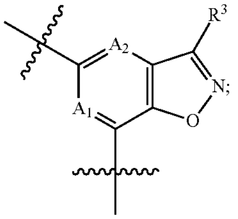

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a-1}$, $C(=O)R^{a-2}$, $-NR^{a-31}R^{a-32}$, $-C(=O)OR^{a-4}$, $-C(=O)NR^{a-1}R^{a-52}$, or, $C_{1-6}$ alkyl substituted with one or more $R^{a1-1}$, $R^{a1-1}$ is independently halogen, hydroxyl or $-OC_{1-6}$ alkyl;

or, $R^{a2}$ and $R^{a3}$ together with the carbon atom to which they are attached form $C_{3-7}$ cycloalkane, $C_{3-7}$ cycloalkane substituted with one or more $R^{a2-1}$, "3- to 8-membered heterocycloalkyl containing 1 to 3 heteroatoms independently selected from O, S and N", or, "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, =O, hydroxyl, $C_{1-6}$ alkyl, $C_{1-6}$ alkyl substituted with one or more halogen, $-OC_{1-6}$ alkyl, or, $-OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogen;

ring Y is $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, "5- to 6-membered heteroaryl containing 1 to 4 heteroatoms independently selected from O, S and N" fused with "5- to 6-membered heterocycloalkyl containing 1 to 3 heteroatoms independently selected from O, S and N", or, "4- to 8-membered heterocycloalkenyl containing 1 to 3 heteroatoms independently selected from O, S and N";

n is 0, 1, 2, 3, 4, 5 or 6;

$R^2$ is halogen, hydroxyl, cyano, oxo, $C_{1-6}$ alkyl, $C_{1-6}$ alkyl substituted with one or more $R^{2-1}$ $C_{2-6}$ alkenyl, $C_{2-6}$ alkynyl, —$OC_{1-6}$ alkyl, —$SC_{1-6}$ alkyl, —$OC_{1-6}$ alkyl substituted with one or more $R^{2-2}$, —C(═O)$R^{2a}$, —$NR^{2b1}R^{2b2}$, —C(═O)$OR^{2c}$, —C(═O)$NR^{2d1}R^{2d2}$, $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N"; or, when n is 2, 3, 4, 5 or 6, two optional $R^2$ are connected, together with the atoms to which they are attached, independently form 3- to 8-membered carbon ring or "3- to 8-membered heterocycle containing 1 to 3 heteroatoms independently selected from O, S and N";

$R^{2-1}$ and $R^{2-2}$ are independently halogen, cyano, $C_{1-6}$ alkyl-O—, hydroxyl, —C(═O)$R^{22a}$, —$NR^{22b1}R^{22b2}$, —C(═O)$OR^{22c}$, —C(═O)$NR^{22d1}R^{22d2}$, —S(O)$_2$ $NR^{22e1}R^{22e2}$ or —S(O)$_2R^{22f}$;

$R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$ and $R^{22f}$ are independently hydrogen, $C_{1-6}$ alkyl, or, $C_{1-6}$ alkyl substituted with one or more halogen;

$R^1$ is

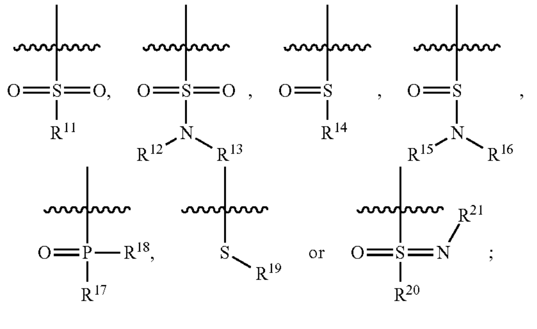

$R^{11}$, $R^{12}$, $R^{13}$, $R^{14}$, $R^{15}$, $R^{16}$, $R^{17}$, $R^{18}$, $R^{19}$ and $R^{20}$ are independently $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, $C_{6-20}$ aryl substituted with one or more $R^{1-4}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-5}$, $C_{4-8}$ cycloalkenyl, $C_{4-8}$ cycloalkenyl substituted with one or more $R^{1-6}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-7}$;

$R^{21}$ is hydrogen or $C_{1-6}$ alkyl;

$R^{1-1}$, $R^{1-2}$, $R^{1-3}$, $R^{1-4}$, $R^{1-5}$, $R^{1-6}$ and $R^{1-7}$ are halogen, hydroxyl, cyano, $C_{1-6}$ alkyl, $C_{2-6}$ alkenyl, $C_{2-6}$ alkynyl, —$OC_{1-6}$ alkyl, —$SC_{1-6}$ alkyl, —$OC_{1-6}$ alkyl substituted with one or more $R^{1-1-1}$, —$SC_{1-6}$ alkyl substituted with one or more $R^{1-1-2}$, —C(═O)$R^{1a}$, —$NR^{1b1}R^{1b2}$, —C(═O)$OR^{1c}$, —C(═O)$NR^{1d1}R^{1d2}$, —S(O)$_2$ $NR^{1e1}R^{1e2}$, —S(O)$_2R^{1f}$, $C_{3-10}$ cycloalkyl, $C_{3-10}$ cycloalkyl substituted with one or more $R^{1-1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{4-8}$ cycloalkenyl, $C_{4-8}$ cycloalkenyl substituted with one or more $R^{1-1-7}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently azide, halogen, hydroxyl, cyano, oxo, $C_{1-6}$ alkyl, $C_{2-6}$ alkenyl, $C_{2-6}$ alkynyl, —$OC_{1-6}$ alkyl, —C(═O)$R^{11a}$, —$NR^{11b1}R^{11b2}$, —C(═O)$OR^{11c}$, —C(═O)$NR^{11d1}R^{11d2}$, —S(O)$_2$ $NR^{11e1}R^{11e2}$, —S(O)$_2R^{11f}$, $C_{3-10}$ cycloalkyl, or, "4- to 12-membered heterocycloalkyl containing 1 to 3 heteroatoms independently selected from O, S and N"; provided that when multiple substituents are present, the substituents are the same or different;

$R^{1a}$, $R^{1b1}$, $R^{1b2}$, $R^{1c}$, $R^{1d1}$, $R^{1d2}$, $R^{1e1}$, $R^{1e2}$, $R^{1f}$, $R^{11a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen or $C_{1-6}$ alkyl;

$R^3$ is "5- to 6-membered heteroaryl containing 1 to 4 heteroatoms independently selected from O, S and N", or, "5- to 6-membered heteroaryl containing 1 to 4 heteroatoms independently selected from O, S and N" substituted with one or more $R^{3-1}$;

$R^{3-1}$ is halogen, hydroxyl, cyano, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, —$SC_{1-6}$ alkyl, —$OC_{1-6}$ alkyl substituted with one or more halogen, or, —$SC_{1-6}$ alkyl substituted with one or more halogen; provided that when multiple substituents are present, the substituents are the same or different;

$R^4$ is hydrogen, halogen, $C_{1-6}$ alkyl, or, $C_{1-6}$ alkyl substituted with one or more $R^{4-1}$; $R^{4-1}$ is halogen, hydroxyl, $C_{3-12}$ cycloalkyl, —$OC_{1-6}$ alkyl or —$SC_{1-6}$ alkyl; provided that when multiple substituents are present, the substituents are the same or different;

$R^5$ is

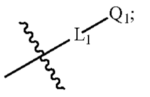

$L_1$ is a bond, $C_{1-6}$ alkylene or $C_{1-6}$ alkylene substituted with deuterium;

$Q_1$ is hydrogen, deuterium, halogen, cyano, $C_{2-6}$ alkenyl, $C_{2-6}$ alkynyl, hydroxyl, —$OC_{1-6}$ alkyl, —C(═O)$R^{5a}$, —$NR^{5b1}R^{5b2}$, —C(═O)$OR^{5c}$, —C(═O)$NR^{5d1}R^{5d2}$, —$OC_{1-6}$ alkyl substituted with one or more $R^{5-1}$, $C_{6-20}$ aryl, $C_{6-20}$ aryl substituted with one or more $R^{5-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-3}$, $C_{3-12}$ cycloalkyl, $C_{3-12}$ cycloalkyl substituted with one or more $R^{5-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-5}$, $C_{4-8}$ cycloalkenyl, $C_{4-8}$ cycloalkenyl substituted with one or more $R^{5-6}$, "4- to 8-membered heterocycloalkenyl containing 1 to 3 heteroatoms independently selected from O, S and N", "4- to 8-membered heterocycloalkenyl containing 1 to 3 heteroatoms independently selected from O, S and N" substituted with one or more $R^{5-7}$ or $C_{1-6}$ alkyl substituted with one or more $R^{5-8}$; provided that when multiple substituents are present, the substituents are the same or different;

$R^{5-1}$, $R^{5-2}$, $R^{5-3}$, $R^{5-4}$, $R^{5-5}$, $R^{5-6}$, $R^{5-7}$ and $R^{5-8}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(═O)$R^{51a}$, —$NR^{51b1}R^{51b2}$, —C(═O)$OR^{51c}$ or —C(═O)$NR^{51d1}R^{51d2}$; provided that when multiple substituents are present, the substituents are the same or different;

$R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$ and $R^{51d2}$ are independently hydrogen, $C_{1-6}$ alkyl, or $C_{1-6}$ alkyl substituted with one or more halogen;

or, $R^2$ and $R^5$ are connected together with the atoms to which they are attached independently form "5- to 12-membered heterocyclic olefin containing 1 to 3 heteroatoms independently selected from O, S and N";

or, $R^{a-3}$ and $R^{a-32}$, $R^{a-51}$ and $R^{a-52}$, $R^{2b1}$ and $R^{2b2}$, $R^{2d1}$ and $R^{2d2}$, $R^{22b1}$ and $R^{22b2}$, $R^{22d1}$ and $R^{22d2}$, $R^{22e1}$ and $R^{22e2}$, $R^{1b1}$ and $R^{1b2}$, $R^{1d1}$ and $R^{1d2}$, $R^{1e1}$ and $R^{1e2}$, $R^{11b1}$ and $R^{11b2}$, $R^{11d1}$ and $R^{11d2}$, $R^{11e1}$ and $R^{11e2}$, $R^{5b1}$ and $R^{5b2}$, $R^{5d1}$ and $R^{5d2}$, $R^{51b1}$ and $R^{51b2}$, $R^{51d1}$ and $R^{51d2}$ together with the N to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-2}$-1;

$R^{1-2-1}$ is independently hydrogen, $C_{1-6}$ alkyl, or $C_{1-6}$ alkyl substituted with one or more halogen;

the compound represented by formula I is not one of the following compounds:

N-(1-Cyanocyclopropyl)-3-(5-(difluoromethyl)-1,3,4-thiadiazol-2-yl)-1-methyl-7-(4-(methylsulfonyl)piperazin-1-yl)-1H-indazole-5-sulfonamide;

N-(1-cyanocyclopropyl)-3-(5-(difluoromethyl)-1,3,4-thiadiazol-2-yl)-7-(4-(isopropylsulfonyl)piperazin-1-yl)-methyl-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-(2,2,2-trifluoroethyl)-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-methyl-1H-indazole-5-sulfonamide;

N-(1-Cyanocyclopropyl)-3-(5-(difluoromethyl)-1,3,4-thiadiazol-2-yl)-7-(4-(isopropylsulfonyl)piperazin-1-yl)-1-(2,2,2-trifluoroethyl)-1H-indazole-5-sulfonamide.

2. A compound represented by formula I, a pharmaceutically acceptable salt thereof, a stereoisomer thereof, an isomer thereof or an isotopic compound thereof according to claim 1, the compound represented by formula I is shown as formula II:

II

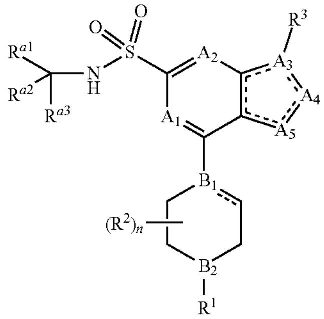

wherein,  is a single bond or a double bond; $B_1$ is N, C or CH, $B_2$ is N or CH, other group definitions are described according to claim 1.

3. A compound represented by formula I, a pharmaceutically acceptable salt thereof, a stereoisomer thereof, an isomer thereof or an isotopic compound thereof according to claim 1, the compound represented by formula I is shown as formula III:

III

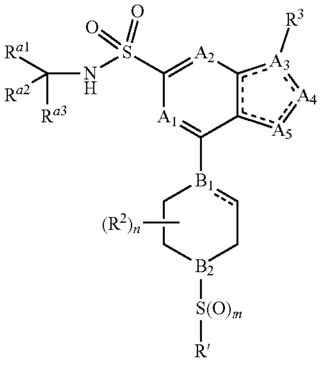

wherein, is a single bond or a double bond; Bi is N, C or CH, $B_2$ is N or CH, m is 0, 1 or 2;

R' is $R^{11}$, $NR^{12}R^{13}$, $R^{14}$ or $R^{19}$;

$R^{11}$, $R^{12}$, $R^{13}$, $R^{14}$ and $R^{19}$ as well as other group definitions are described according to claim 1.

4. A compound represented by formula I, a pharmaceutically acceptable salt thereof, a stereoisomer thereof, an isomer thereof or an isotopic compound thereof according to claim 1, wherein, the compound represented by formula I is defined as solution 1, solution 2, solution 3 or solution 4:

solution 1:

is a single bond or a double bond;

both rings of

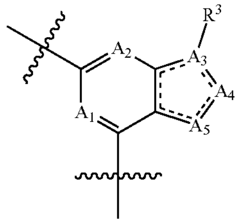

are aromatic;

$A_1$ and $A_2$ are independently N or $CR^{b1}$, $R^{b1}$ is hydrogen or halogen;

$A_3$ is C or N;

$A_4$ is N, $CR^4$ or $NR^4$;

As is $NR^5$, N, $CR^5$, S or O;

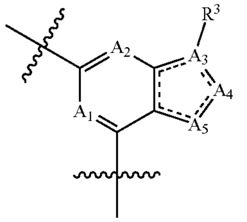

is

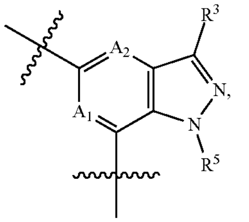

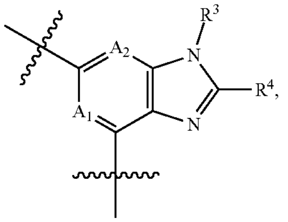

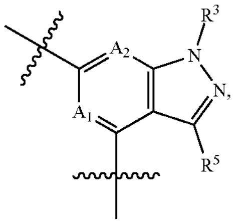

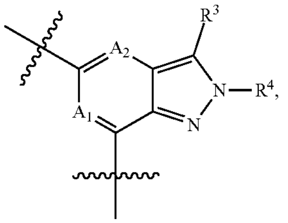

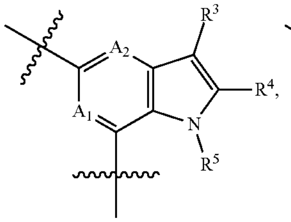

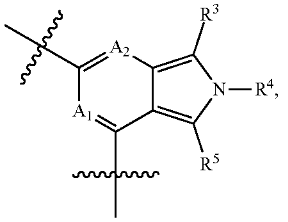

-continued

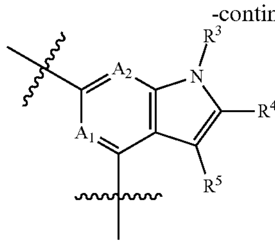

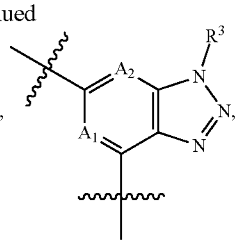

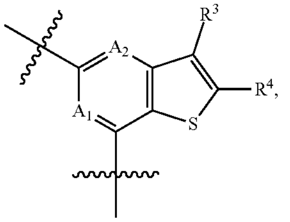

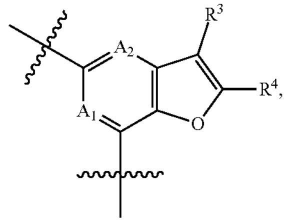

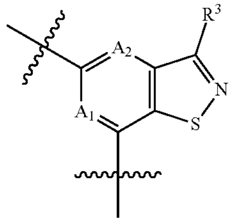

or

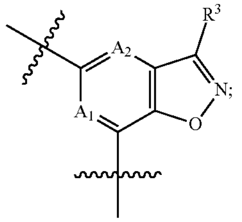

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a-1}$, $—C(=O)R^{a-2}$, $—NR^{a-31}R^{a-32}$, $—C(=O)OR^{a-4}$, $—C(=O)NR^{a-51}R^{a-52}$, or, $C_{1-6}$ alkyl substituted with one or more $R^{a1-1}$, $R^{a1-1}$ is halogen, hydroxyl or $—OC_{1-6}$ alkyl;

or, $R^{a2}$ and $R^{a3}$ together with the carbon atom to which they are attached form $C_{3-7}$ cycloalkane, $C_{3-7}$ cycloalkane substituted with one or more $R^{a2-1}$, 3- to 8-membered heterocycloalkyl containing 1 to 3 heteroatoms independently selected from O, S and N, or, "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, =O, hydroxyl, $C_{1-6}$ alkyl, $C_{1-6}$ alkyl substituted with one or more halogen, $—OC_{1-6}$ alkyl, or, $—OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogen;

Ring Y is $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N";

n is 0, 1, 2, 3, 4, 5 or 6;

$R^2$ is halogen, hydroxyl, cyano, oxo, $C_{1-6}$ alkyl, $C_{1-6}$ alkyl substituted with one or more $R^{2-1}$ $C_{2-6}$ alkenyl, $C_{2-6}$ alkynyl, $—OC_{1-6}$ alkyl, $—SC_{1-6}$ alkyl, $—OC_{1-6}$ alkyl substituted with one or more $R^{2-2}$, $—C(=O)R^{2a}$, $—NR^{2b1}R^{2b2}$, $—C(=O)OR^{2c}$, $—C(=O)NR^{2d1}R^{2d2}$, $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N"; or, when n is 2, 3, 4, 5 or 6, two optional $R^2$ are connected, together with the atoms to which they are attached, independently form 3- to 8-membered carbon ring or "3- to 8-membered heterocycle containing 1 to 3 heteroatoms independently selected from O, S and N";

$R^{2-1}$ and $R^{2-2}$ are independently halogen, cyano, $C_{1-6}$ alkyl-O—, hydroxyl, —C(=O)$R^{22a}$, —$NR^{22b1}R^{22b2}$, —C(=O)O$R^{22c}$, —C(=O)$NR^{22d1}R^{22d2}$, —$S(O)_2NR^{22e1}R^{22e2}$ or —$S(O)_2R^{22f}$;

$R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$ and $R^{22f}$ are independently hydrogen, $C_{1-6}$ alkyl, or, $C_{1-6}$ alkyl substituted with one or more halogen;

$R^1$ is

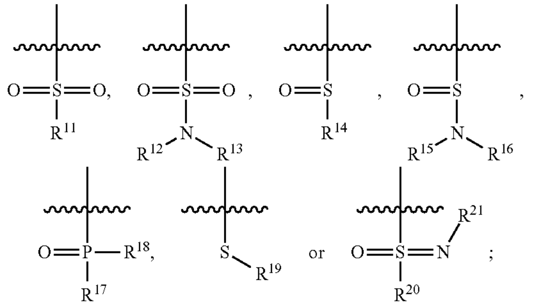

$R^{11}$, $R^{12}$, $R^{13}$, $R^{14}$, $R^{15}$, $R^{16}$, $R^{17}$, $R^{18}$, $R^{19}$ and $R^{20}$ are independently $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, $C_{6-20}$ aryl substituted with one or more $R^{1-4}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-5}$, $C_{4-8}$ cycloalkenyl, $C_{4-8}$ cycloalkenyl substituted with one or more $R^{1-6}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-7}$;

$R^{21}$ is hydrogen or $C_{1-6}$ alkyl;

$R^{1-1}$, $R^{1-2}$, $R^{1-3}$, $R^{1-4}$, $R^{1-5}$, $R^{1-6}$ and $R^{1-7}$ are halogen, hydroxyl, cyano, $C_{1-6}$ alkyl, $C_{2-6}$ alkenyl, $C_{2-6}$ alkynyl, —$OC_{1-6}$ alkyl, —$SC_{1-6}$ alkyl, —$OC_{1-6}$ alkyl substituted with one or more $R^{1-1-1}$, —$SC_{1-6}$ alkyl substituted with one or more $R^{1-1-2}$, —C(=O)$R^{1a}$, —$NR^{1b1}R^{1b2}$, —C(=O)O$R^{1c}$, —C(=O)$NR^{1d1}R^{1d2}$, —$S(O)_2NR^{1e1}R^{1e2}$, —$S(O)_2R^{1f}$, $C_{3-10}$ cycloalkyl, $C_{3-10}$ cycloalkyl substituted with one or more $R^{1-1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$ $C_{4-8}$ cycloalkenyl, $C_{4-8}$ cycloalkenyl substituted with one or more $R^{1-1-7}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently azide, halogen, hydroxyl, cyano, oxo, $C_{1-6}$ alkyl, $C_{2-6}$ alkenyl, $C_{2-6}$ alkynyl, —$OC_{1-6}$ alkyl, —C(=O)$R^{11a}$, —$NR^{11b1}R^{11b2}$, —C(=O)O$R^{11c}$, —C(=O)$NR^{11d1}R^{11d2}$, —$S(O)_2NR^{11e1}R^{11e2}$, —$S(O)_2R^{11f}$, $C_{3-10}$ cycloalkyl, or, "4- to 12-membered heterocycloalkyl containing 1 to 3 heteroatoms independently selected from O, S and N"; provided that when multiple substituents are present, the substituents are the same or different;

$R^{1a}$, $R^{1b}$, $R^{1b2}$, $R^{1c}$, $R^{1d1}$, $R^{1d2}$, $R^{1e1}$, $R^{1e2}$, $R^{1f}$, $R^{11a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen or $C_{1-6}$ alkyl;

$R^3$ is "5- to 6-membered heteroaryl containing 1 to 4 heteroatoms independently selected from O, S and N", or, "5- to 6-membered heteroaryl containing 1 to 4 heteroatoms independently selected from O, S and N" substituted with one or more $R^{3-1}$;

$R^{3-1}$ is independently halogen, hydroxyl, cyano, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, —$SC_{1-6}$ alkyl, —$OC_{1-6}$ alkyl substituted with one or more halogen, or, —$SC_{1-6}$ alkyl substituted with one or more halogen; provided that when multiple substituents are present, the substituents are the same or different;

$R^4$ is hydrogen, halogen, $C_{1-6}$ alkyl, or, $C_{1-6}$ alkyl substituted with one or more $R^{4-1}$; $R^{4-1}$ is halogen, hydroxyl, —$OC_{1-6}$ alkyl or —$SC_{1-6}$ alkyl; provided that when multiple substituents are present, the substituents are the same or different;

$R^5$ is

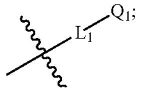

$L_1$ is a bond, $C_{1-6}$ alkylene or $C_{1-6}$ alkylene substituted with deuterium;

$Q_1$ is hydrogen, deuterium, halogen, cyano, $C_{2-6}$ alkenyl, $C_{2-6}$ alkynyl, hydroxyl, —$OC_{1-6}$ alkyl, —C(=O)$R^{5a}$, —$NR^{5b1}R^{5b2}$, —C(=O)O$R^{5c}$, —C(=O)$NR^{5d1}R^{5d2}$, —$OC_{1-6}$ alkyl substituted with one or more $R^{5-1}$, $C_{6-20}$ aryl, $C_{6-20}$ aryl substituted with one or more $R^{5-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-3}$, $C_{3-12}$ cycloalkyl, $C_{3-12}$ cycloalkyl substituted with one or more $R^{5-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-5}$, $C_{4-8}$ cycloalkenyl, $C_{4-8}$ cycloalkenyl substituted with one or more $R^{5-6}$, "4- to 8-membered heterocycloalkenyl containing 1 to 3 heteroatoms independently selected from O, S and N", or "4- to 8-membered heterocycloalkenyl containing 1 to 3 heteroatoms independently selected from O, S and N" substituted with one or more $R^{5-7}$; provided that when multiple substituents are present, the substituents are the same or different;

$R^{5-1}$, $R^{5-2}$, $R^{5-3}$, $R^{5-4}$, $R^{5-5}$, $R^{5-6}$ and $R^{5-7}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(═O)$R^{51a}$, —$NR^{51b1}R^{51b2}$, —C(═O)$OR^{51c}$ or —C(═O)$NR^{51d1}R^{51d2}$; provided that when multiple substituents are present, the substituents are the same or different;

$R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$ and $R^{51d2}$ are independently hydrogen, $C_{1-6}$ alkyl, or $C_{1-6}$ alkyl substituted with one or more halogen;

or, $R^2$ and $R^5$ are connected together with the atoms to which they are attached independently form "5- to 12-membered heterocyclic olefin containing 1 to 3 heteroatoms independently selected from O, S and N";

or, $R^{a-31}$ and $R^{a-32}$, $R^{a-51}$ and $R^{a-52}$, $R^{2b1}$ and $R^{2b2}$, $R^{2d1}$ and $R^{2d2}$, $R^{22b1}$ and $R^{22b2}$, $R^{22d1}$ and $R^{22d2}$, $R^{22e1}$ and $R^{22e2}$, $R^{1b1}$ and $R^{1b2}$, $R^{1d1}$ and $R^{1d2}$, $R^{1e1}$ and $R^{1e2}$, $R^{11b1}$ and $R^{11b2}$, $R^{11d1}$ and $R^{11d2}$, $R^{11e1}$ and $R^{11e2}$, $R^{5b1}$ and $R^{5b2}$, $R^{5d1}$ and $R^{5d2}$, $R^{51b1}$ and $R^{51b2}$, $R^{51d1}$ and $R^{51d2}$ together with the N to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-2-1}$;

$R^{1-2-1}$ is independently hydrogen, $C_{1-6}$ alkyl, or $C_{1-6}$ alkyl substituted with one or more halogen;

the compound represented by formula I is not one of the following compounds:

N-(1-Cyanocyclopropyl)-3-(5-(difluoromethyl)-1,3,4-thiadiazol-2-yl)-1-methyl-7-(4-(methylsulfonyl)piperazin-1-yl)-1H-indazole-5-sulfonamide;

N-(1-cyanocyclopropyl)-3-(5-(difluoromethyl)-1,3,4-thiadiazol-2-yl)-7-(4-(isopropylsulfonyl)piperazin-1-yl)-methyl-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-(2,2,2-trifluoroethyl)-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-methyl-1H-indazole-5-sulfonamide;

N-(1-Cyanocyclopropyl)-3-(5-(difluoromethyl)-1,3,4-thiadiazol-2-yl)-7-(4-(isopropylsulfonyl)piperazin-1-yl)-1-(2,2,2-trifluoroethyl)-1H-indazole-5-sulfonamide;

solution 2:

⫽ is a single bond or a double bond;

$A_1$ and $A_2$ are independently N or $CR^{b1}$; $R^{b1}$ is hydrogen or halogen;

$A_3$ is C or N;

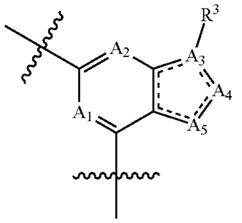

is

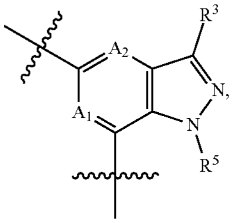

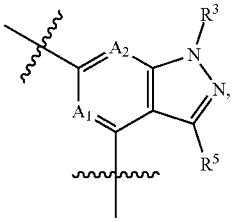

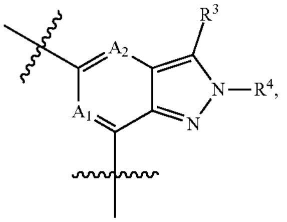

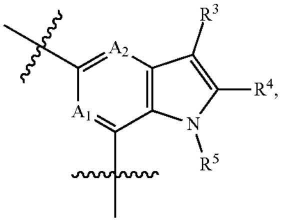

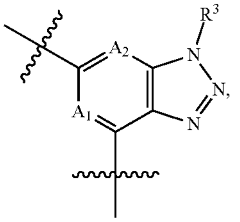

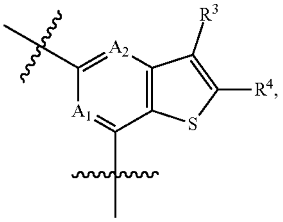

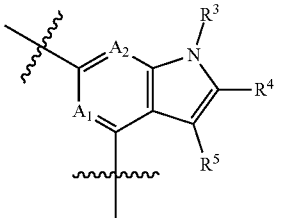

or

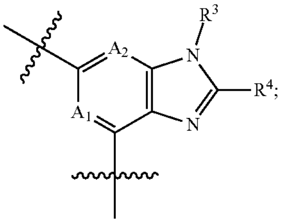

$R^4$ is hydrogen or $C_{1-6}$ alkyl substituted with one or more $R^{4-1}$; $R^{4-1}$ is $C_{3-12}$ cycloalkyl;

provided that when multiple substituents are present, the substituents are the same or different;

$R^5$ is

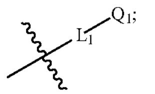

$L_1$ is a bond, $C_{1-6}$ alkylene or $C_{1-6}$ alkylene substituted with deuterium;

$Q_1$ is hydrogen, deuterium, halogen, —$OC_{1-6}$ alkyl, —$NR^{5b1}R^{5b2}$, —C(═O)$NR^{5d1}R^{5d2}$, —$C_{6-20}$ aryl, "5- to 12-membered heteroaryl containing 1 to 4 heteroatoms independently selected from O, S and N", $C_{3-12}$ cycloalkyl, $C_{1-6}$ alkyl substituted with one or more $R^{5-8}$ or "4- to 12-membered heterocycloalkyl containing 1 to 3 heteroatoms independently selected from O, S and N";

provided that when multiple substituents are present, the substituents are the same or different;

$R^{5b1}$, $R^{5b2}$, $R^{5d1}$ and $R^{5d2}$ are independently hydrogen or $C_{1-6}$ alkyl;

$R^{5-8}$ is independently halogen;

$R^{a1}$, $R^{a2}$ and $R^{a3}$ are independently cyano, $C_{1-6}$ alkyl, —C(═O)$NR^{a-51}R^{a-52}$, or, $C_{1-6}$ alkyl substituted with one or more $R^{a1-1}$, $R^{a1-1}$ is independently halogen;

or, $R^{a2}$ and $R^{a3}$ together with the carbon atom to which they are attached form $C_{3-7}$ cycloalkane; provided that when multiple substituents are present, the substituents are the same or different;

$R^{a-51}$ and $R^{a-52}$ are independently hydrogen;

Ring Y is "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, "5- to 6-membered heteroaryl containing 1 to 4 heteroatoms independently selected from O, S and N" fused with "5- to 6-membered heterocycloalkyl containing 1 to 3 heteroatoms independently selected from O, S and N", or, "4- to 8-membered heterocycloalkenyl containing 1 to 3 heteroatoms independently selected from O, S and N";

n is 0, 1 or 2;

$R^2$ is halogen, hydroxyl, cyano, $C_{1-6}$ alkyl, $C_{1-6}$ alkyl substituted with one or more $R^{2-1}$, —C(═O)$R^{2a}$, —C(═O)$OR^{2c}$ or —C(═O)$NR^{2d1}R^{2d2}$; or, when n is 2, two optional $R^2$ are connected, together with the atoms to which they are attached, independently form "3- to 8-membered heterocycle containing 1 to 3 heteroatoms independently selected from O, S and N";

$R^{2-1}$ is independently $C_{1-6}$ alkyl-O—, hydroxyl or —C(═O)$NR^{22d1}R^{22d2}$;

$R^{2a}$, $R^{2c}$, $R^{2d1}$, $R^{2d2}$, $R^{22b1}$ and $R^{22b2}$ are independently hydrogen or $C_{1-6}$ alkyl;

$R^1$ is

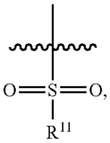,
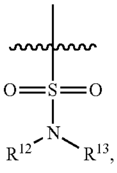,
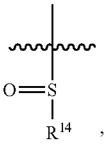,
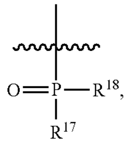,

-continued

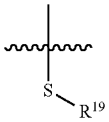
or
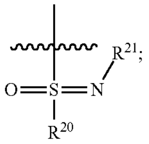

$R^{11}$, $R^{12}$, $R^{13}$, $R^{14}$, $R^{17}$, $R^{18}$, $R^{19}$ and $R^{20}$ are independently $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, "5- to 12-membered heteroaryl containing 1 to 4 heteroatoms independently selected from O, S and N";

$R^{21}$ is hydrogen or $C_{1-6}$ alkyl;

$R^{1-1}$, $R^{1-2}$ and $R^{1-3}$ are $C_{1-6}$ alkyl or —$OC_{1-6}$ alkyl;

$R^3$ is "5- to 6-membered heteroaryl containing 1 to 4 heteroatoms independently selected from O, S and N" substituted with one or more $R^{3-1}$;

$R^{3-1}$ is independently $C_{1-6}$ alkyl or $C_{1-6}$ alkyl substituted with one or more halogen; provided that when multiple substituents are present, the substituents are the same or different;

the compound represented by formula I is not one of the following compounds:

N-(1-Cyanocyclopropyl)-3-(5-(difluoromethyl)-1,3,4-thiadiazol-2-yl)-1-methyl-7-(4-(methylsulfonyl)piperazin-1-yl)-1H-indazole-5-sulfonamide;

N-(1-cyanocyclopropyl)-3-(5-(difluoromethyl)-1,3,4-thiadiazol-2-yl)-7-(4-(isopropylsulfonyl)piperazin-1-yl)-methyl-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-(2,2,2-trifluoroethyl)-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-methyl-1H-indazole-5-sulfonamide;

N-(1-Cyanocyclopropyl)-3-(5-(difluoromethyl)-1,3,4-thiadiazol-2-yl)-7-(4-(isopropylsulfonyl)piperazin-1-yl)-1-(2,2,2-trifluoroethyl)-1H-indazole-5-sulfonamide;

solution 3:

the compound represented by formula I is shown as formula III-1 or III-2:

III-1

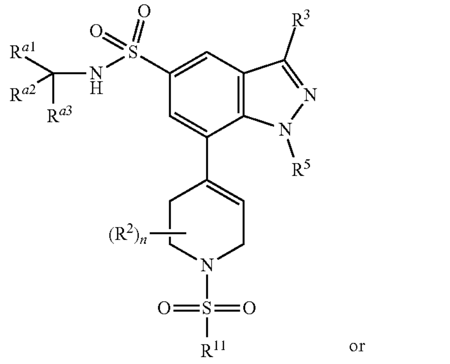

or

III-2

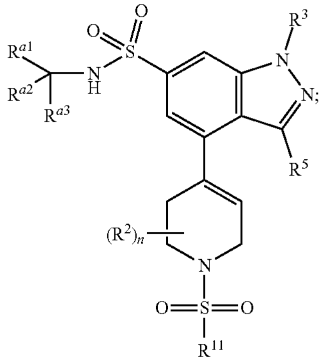

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a1}$, $C(=O)R^{a-2}$, $-NR^{a-31}R^{a-32}$, $-C(=O)OR^{a-4}$, $-C(=O)NR^{a-51}R^{a-52}$, or, $C_{1-6}$ alkyl substituted with one or more $R^{a1-1}$, $R^{a1-1}$ is halogen, hydroxyl or $-OC_{1-6}$ alkyl;

or, $R^{a2}$ and $R^{a3}$ together with the carbon atom to which they are attached form $C_{3-7}$ cycloalkane, $C_{3-7}$ cycloalkane substituted with one or more $R^{a2-1}$, 3- to 8-membered heterocycloalkyl containing 1 to 3 heteroatoms independently selected from O, S and N, or, "3- to 8-membered heterocycloalkyl containing 1 to 3 heteroatoms independently selected from O, S and N" substituted with one or more $R^{a2}$-2; provided that when multiple substituents are present, the substituents are the same or different;

$R^{a2-1}$ and $R^{a2-2}$ are independently halogen, =O, hydroxyl, $C_{1-6}$ alkyl, $C_{1-6}$ alkyl substituted with one or more halogen, $-OC_{1-6}$ alkyl, or, $-OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogen;

n is 0, 1, 2, 3, 4, 5 or 6;

$R^2$ is halogen, hydroxyl, cyano, oxo, $C_{1-6}$ alkyl, $C_{1-6}$ alkyl substituted with one or more $R^{2-1}$, $C_{2-6}$ alkenyl, $C_{2-6}$ alkynyl, $-OC_{1-6}$ alkyl, $-OC_{1-6}$ alkyl substituted with one or more $R^{2-2}$, $C(=O)R^{2a}$, $-NR^{2b1}R^{2b2}$, $-C(=O)OR^{2c}$, $-C(=O)NR^{2d1}R^{2d2}$, $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N"; or, when n is 2, 3, 4, 5 or 6, two optional $R^2$ are connected, together with the atoms to which they are attached, independently form 3- to 8-membered carbon ring or "3- to 8-membered heterocycle containing 1 to 3 heteroatoms independently selected from O, S and N";

$R^{2-1}$ and $R^{22}$ are independently halogen, cyano, $C_{1-6}$ alkyl-O—, hydroxyl, $-C(=O)R^{22a}$, $-NR^{22b1}R^{22b2}$, $-C(=O)OR^{22c}$, $-C(=O)NR^{22d1}R^{22d2}$, $-S(O)_2NR^{22e1}R^{22e2}$ or $-S(O)_2R^{22f}$;

$R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$ and $R^{22f}$ are independently hydrogen, $C_{1-6}$ alkyl, or, $C_{1-6}$ alkyl substituted with one or more halogen;

$R^{11}$ is $C_{1-6}$ alkyl, $-OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, $C_{6-20}$ aryl substituted with one or more $R^{1-4}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-5}$, $C_{4-8}$ cycloalkenyl, $C_{4-8}$ cycloalkenyl substituted with one or more $R^{1-6}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-7}$;

$R^{1-1}$, $R^{1-2}$, $R^{1-3}$, $R^{1-4}$, $R^{1-5}$, $R^{1-6}$ and $R^{1-7}$ are halogen, hydroxyl, cyano, $C_{1-6}$ alkyl, $C_{2-6}$ alkenyl, $C_{2-6}$ alkynyl, $-OC_{1-6}$ alkyl, $-SC_{1-6}$ alkyl, $-OC_{1-6}$ alkyl substituted with one or more $R^{1-1-1}$, $-SC_{1-6}$ alkyl substituted with one or more $R^{1-1-2}$, $-C(=O)R^{1a}$, $-NR^{1b1}R^{1b2}$, $-C(=O)OR^{1c}$, $-C(=O)NR^{1d1}R^{1d2}$, $-S(O)_2NR^{1e1}R^{1e2}$, $-S(O)_2R^{1f}$, $C_{3-10}$ cycloalkyl, $C_{3-10}$ cycloalkyl substituted with one or more $R^{1-1-3}$ "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{4-8}$ cycloalkenyl, $C_{4-8}$ cycloalkenyl substituted with one or more $R^{1-1-7}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently azide, halogen, hydroxyl, cyano, oxo, $C_{1-6}$ alkyl, $C_{2-6}$ alkenyl, $C_{2-6}$ alkynyl, $-OC_{1-6}$ alkyl, $-C(=O)R^{11a}$, $-NR^{11b1}R^{11b2}$, $-C(=O)OR^{11c}$, $-C(=O)NR^{11d1}R^{11d2}$, $-S(O)_2NR^{11e1}R^{11e2}$, $-S(O)_2R^{11f}$, $C_{3-10}$ cycloalkyl, or, "4- to 12-membered heterocycloalkyl containing 1 to 3 heteroatoms independently selected from O, S and N"; provided that when multiple substituents are present, the substituents are the same or different;

$R^{1a}$, $R^{1b1}$, $R^{1b2}$, $R^{1c}$, $R^{1d1}$, $R^{1d2}$, $R^{1e1}$, $R^{1e2}$, $R^{1f}$, $R^{11a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen or $C_{1-6}$ alkyl;

$R^3$ is "5- to 6-membered heteroaryl containing 1 to 4 heteroatoms independently selected from O, S and N", or, "5- to 6-membered heteroaryl containing 1 to 4 heteroatoms independently selected from O, S and N" substituted with one or more $R^{3-1}$;

$R^{3-1}$ is independently halogen, hydroxyl, cyano, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, —$SC_{1-6}$ alkyl, —$OC_{1-6}$ alkyl substituted with one or more halogen, or, —$SC_{1-6}$ alkyl substituted with one or more halogen; provided that when multiple substituents are present, the substituents are the same or different;

$R^5$ is

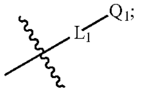

$L_1$ is a bond, $C_{1-6}$ alkylene or $C_{1-6}$ alkylene substituted with deuterium;

$Q_1$ is hydrogen, deuterium, halogen, cyano, $C_{2-6}$ alkenyl, $C_{2-6}$ alkynyl, hydroxyl, —$OC_{1-6}$ alkyl, —C(═O)$R^{5a}$, —$NR^{5b1}R^{5b2}$, —C(═O)$OR^{5c}$, —C(═O)$NR^{5d1}R^{5d2}$, —$OC_{1-6}$ alkyl substituted with one or more $R^{5-1}$, $C_{6-20}$ aryl, $C_{6-20}$ aryl substituted with one or more $R^{5-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-3}$, $C_{3-12}$ cycloalkyl, $C_{3-12}$ cycloalkyl substituted with one or more $R^{5-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-5}$, $C_{4-8}$ cycloalkenyl, $C_{4-8}$ cycloalkenyl substituted with one or more $R^{5-6}$, "4- to 8-membered heterocycloalkenyl containing 1 to 3 heteroatoms independently selected from O, S and N", "4- to 8-membered heterocycloalkenyl containing 1 to 3 heteroatoms independently selected from O, S and N" substituted with one or more $R^{5-7}$, or $C_{1-6}$ alkyl substituted with one or more $R^{5-8}$; provided that when multiple substituents are present, the substituents are the same or different;

$R^{5-1}$, $R^{5-2}$, $R^{5-3}$, $R^{5-4}$, $R^{5-5}$, $R^{5-6}$, $R^{5-7}$ and $R^{5-8}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(═O)$R^{51a}$, —$NR^{51b1}R^{51b2}$, —C(═O)$OR^{51c}$ or —C(═O)$NR^{51d1}R^{51d2}$; provided that when multiple substituents are present, the substituents are the same or different;

$R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$ and $R^{51d2}$ are independently hydrogen, $C_{1-6}$ alkyl, or $C_{1-6}$ alkyl substituted with one or more halogen;

or, $R^2$ and $R^5$ are connected together with the atoms to which they are attached independently form "5- to 12-membered heterocyclic olefin containing 1 to 3 heteroatoms independently selected from O, S and N";

or, $R^{a-31}$ and $R^{a-32}$, $R^{a-51}$ and $R^{a-52}$, $R^{2b1}$ and $R^{2b2}$, $R^{2d1}$ and $R^{2d2}$, $R^{22b1}$ and $R^{22b2}$, $R^{22d1}$ and $R^{22d2}$, $R^{22e1}$ and $R^{22e2}$, $R^{1b1}$ and $R^{1b2}$, $R^{1d1}$ and $R^{1d2}$, $R^{1e1}$ and $R^{1e2}$, $R^{11b1}$ and $R^{11b2}$, $R^{11d1}$ and $R^{11d2}$, $R^{11e1}$ and $R^{11e2}$, $R^{5b1}$ and $R^{5b2}$, $R^{5d1}$ and $R^{5d2}$, $R^{51b1}$ and $R^{51b2}$, $R^{51d1}$ and $R^{51d2}$ together with the N to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-2}$-1;

$R^{1-2-1}$ is independently hydrogen, $C_{1-6}$ alkyl, or $C_{1-6}$ alkyl substituted with one or more halogen;

solution 4:

in the compound represented by formula I, $A_1$ and $A_2$ are independently $CR^{b1}$, $R^{b1}$ is hydrogen;

$A_3$ is C or N;

$A_4$ is N, $CR^4$ or $NR^4$; $R^4$ is hydrogen;

$A_5$ is $NR^5$, $CR^5$ or S;

$R^{a1}$ is halogen, cyano, $C_{1-6}$ alkyl, —C(═O)$NR^{a-51}R^{a-52}$, or, $C_{1-6}$ alkyl substituted with one or more $R^{a-1}$, $R^{a1-1}$ is independently halogen;

$R^{a2}$ and $R^{a3}$ together with the carbon atom to which they are attached form $C_{3-7}$ cycloalkane;

Ring Y is "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N";

n is 0, 1 or 2;

$R^2$ is hydroxyl, $C_{1-6}$ alkyl substituted with one or more $R^{2-1}$, —C(═O)$OR^{2c}$; or, when n is 2, two $R^2$ are connected, together with the atoms to which they are attached, independently form "3- to 8-membered heterocycle containing 1 to 3 heteroatoms independently selected from O, S and N";

$R^{2-1}$ is independently hydroxyl;

$R^{2c}$ is hydrogen;

$R^1$ is

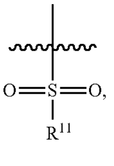
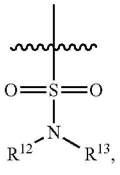
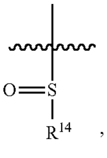
,
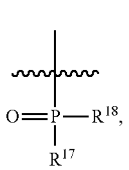
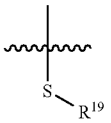
or
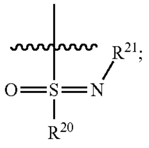

$R^{11}$, $R^{12}$, $R^{13}$, $R^{14}$, $R^{17}$, $R^{18}$, $R^{19}$ and $R^{20}$ are independently $C_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", or "4- to 12-membered heterocycloalkyl containing 1 to 3 heteroatoms independently selected from O, S and N" substituted with one or more $R^{1-3}$;

$R^{21}$ is hydrogen or $C_{1-6}$ alkyl;

$R^{1-1}$, $R^{1-2}$ and $R^{1-3}$ are independently $C_{1-6}$ alkyl or —$OC_{1-6}$ alkyl;

$R^3$ is "5- to 6-membered heteroaryl containing 1 to 4 heteroatoms independently selected from O, S and N" substituted with one or more $R^{3-1}$;

$R^{31}$ is independently $C_{1-6}$ alkyl substituted with one or more halogen; provided that when multiple substituents are present, the substituents are the same or different;

$R^5$ is

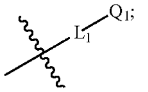

$L_1$ is a bond, $C_{1-6}$ alkylene or $C_{1-6}$ alkylene substituted with deuterium;

$Q_1$ is hydrogen, deuterium or —$OC_{1-6}$ alkyl.

5. A compound represented by formula I, a pharmaceutically acceptable salt thereof, a stereoisomer thereof, an isomer thereof or an isotopic compound thereof according to claim 4, wherein, in the compound represented by formula III-1 is defined as solution 1 or solution 2, solution 1:

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a1}$, $C(=O)R^{a-2}$, —$NR^{a-31}R^{a-32}$, —$C(=O)OR^{a-4}$, —$C(=O)NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

or, $R^{a2}$ and $R^{a3}$ together with the carbon atom to which they are attached form $C_{3-7}$ cycloalkane, $C_{3-7}$ cycloalkane substituted with one or more $R^{a2-1}$, 3- to 8-membered heterocycloalkyl containing 1 to 3 heteroatoms independently selected from O, S and N, or, "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, =O, hydroxyl, $C_{1-6}$ alkyl, $C_{1-6}$ alkyl substituted with one or more halogen, —$OC_{1-6}$ alkyl, or, —$OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogen;

n is 0, 1, 2, 3, 4, 5 or 6;

$R^2$ is independently halogen, hydroxyl, cyano, oxo, $C_{1-6}$ alkyl, $C_{1-6}$ alkyl substituted with one or more $R^{2-1}$, $C_{2-6}$ alkenyl, $C_{2-6}$ alkynyl, —$OC_{1-6}$ alkyl, —$OC_{1-6}$ alkyl substituted with one or more $R^{2-2}$, —$C(=O)R^{2a}$, —$NR^{2b1}R^{2b2}$, —$C(=O)OR^{2c}$, —$C(=O)NR^{2d1}R^{2d2}$, $C_{3-10}$ cycloalkyl, "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, or, "4- to 8-membered heterocycloalkenyl containing 1 to 3 heteroatoms independently selected from O, S and N"; or, when n is 2, 3, 4, 5 or 6, two optional $R^2$ are connected, together with the atoms to which they are attached, independently form 3- to 8-membered carbon ring or "3- to 8-membered heterocycle containing 1 to 3 heteroatoms independently selected from O, S and N";

$R^{2-1}$ and $R^{2-2}$ are independently halogen, cyano, $C_{1-6}$ alkyl-O—, hydroxyl, —$C(=O)R^{22a}$, —$NR^{22b1}R^{22b2}$, —$C(=O)OR^{22c}$, —$C(=O)NR^{22d1}R^{22d2}$, —$S(O)_2NR^{22e1}R^{22e2}$ or —$S(O)_2R^{22f}$;

$R^{2a}$, $R^{2b1}$, $R^{2b2}$, $R^{2c}$, $R^{2d1}$, $R^{2d2}$, $R^{22a}$, $R^{22b1}$, $R^{22b2}$, $R^{22c}$, $R^{22d1}$, $R^{22d2}$, $R^{22e1}$, $R^{22e2}$ and $R^{22f}$ are independently hydrogen, $C_{1-6}$ alkyl, or, $C_{1-6}$ alkyl substituted with one or more halogen;

$R^{11}$ is independently $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, $C_{6-20}$ aryl substituted with one or more $R^{1-4}$ "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-5}$, $C_{4-8}$ cycloalkenyl, $C_{4-8}$ cycloalkenyl substituted with one or more $R^{1-6}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-7}$;

$R^{1-1}$, $R^{1-2}$, $R^{1-3}$, $R^{1-4}$, $R^{1-5}$, $R^{1-6}$ and $R^{1-7}$ are halogen, hydroxyl, cyano, $C_{1-6}$ alkyl, $C_{2-6}$ alkenyl, $C_{2-6}$ alkynyl, —$OC_{1-6}$ alkyl, —$SC_{1-6}$ alkyl, —$OC_{1-6}$ alkyl substituted with one or more $R^{1-1-1}$, —$SC_{1-6}$ alkyl substituted with one or more $R^{1-1-2}$, —$C(=O)R^{1a}$, —$NR^{1b1}R^{1b2}$, —$C(=O)OR^{1c}$, —$C(=O)NR^{1d1}R^{1d2}$, —$S(O)_2NR^{1e1}R^{1e2}$, —$S(O)_2R^{1f}$, $C_{3-10}$ cycloalkyl, $C_{3-10}$ cycloalkyl substituted with one or more $R^{1-1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-1-4}$ $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{4-8}$ cycloalkenyl, $C_{4-8}$ cycloalkenyl substituted with one or more $R^{1-1-7}$, "4- to 8-membered heterocycloalkenyl containing 1 to 3 heteroatoms independently selected from O, S and N", or, "4- to 8-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently azide, halogen, hydroxyl, cyano, oxo, $C_{1-6}$ alkyl, $C_{2-6}$ alkenyl, $C_{2-6}$ alkynyl, —$OC_{1-6}$ alkyl, —C(═O)$R^{11a}$, —$NR^{11b1}R^{11b2}$, —C(═O)$OR^{11c}$, —C(═O)$NR^{11d1}R^{11d2}$, —$S(O)_2NR^{11e1}R^{11e2}$, —$S(O)_2R^{11f}$, $C_{3-10}$ cycloalkyl, or, "4- to 12-membered heterocycloalkyl containing 1 to 3 heteroatoms independently selected from O, S and N"; provided that when multiple substituents are present, the substituents are the same or different;

$R^{1a}$, $R^{1b1}$, $R^{1b2}$, $R^{1c}$, $R^{1d1}$, $R^{1d2}$, $R^{1e1}$, $R^{1e2}$, $R^{1f}$, $R^{11a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen or $C_{1-6}$ alkyl;

$R^3$ is "5- to 6-membered heteroaryl containing 1 to 4 heteroatoms independently selected from O, S and N", or, "5- to 6-membered heteroaryl containing 1 to 4 heteroatoms independently selected from O, S and N" substituted with one or more $R^{3-1}$;

$R^{3-1}$ is independently halogen, hydroxyl, cyano, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, —$SC_{1-6}$ alkyl, —$OC_{1-6}$ alkyl substituted with one or more halogen, or, —$SC_{1-6}$ alkyl substituted with one or more halogen; provided that when multiple substituents are present, the substituents are the same or different;

$R^5$ is

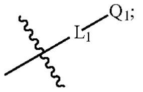

$L_1$ is a bond, $C_{1-6}$ alkylene or $C_{1-6}$ alkylene substituted with deuterium;

$Q_1$ is hydrogen, deuterium, halogen, cyano, $C_{2-6}$ alkenyl, $C_{2-6}$ alkynyl, hydroxyl, —$OC_{1-6}$ alkyl, —C(═O)$R^{5a}$, —$NR^{5b1}R^{5b2}$, —C(═O)$OR^{5c}$, —C(═O)$NR^{5d1}R^{5d2}$, —$OC_{1-6}$ alkyl substituted with one or more $R^{5-1}$, $C_{6-20}$ aryl, $C_{6-20}$ aryl substituted with one or more $R^{5-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-3}$, $C_{3-12}$ cycloalkyl, $C_{3-12}$ cycloalkyl substituted with one or more $R^{5-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-5}$, $C_{4-8}$ cycloalkenyl, $C_{4-8}$ cycloalkenyl substituted with one or more $R^{5-6}$, "4- to 8-membered heterocycloalkenyl containing 1 to 3 heteroatoms independently selected from O, S and N", or "4- to 8-membered heterocycloalkenyl containing 1 to 3 heteroatoms independently selected from O, S and N" substituted with one or more $R^{5-7}$; provided that when multiple substituents are present, the substituents are the same or different;

$R^{5-1}$, $R^{5-2}$, $R^{5-3}$, $R^{5-4}$, $R^{5-5}$, $R^{5-6}$ and $R^{5-7}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(═O)$R^{51a}$, —$NR^{51b1}R^{51b2}$, —C(═O)$OR^{51c}$ or —C(═O)$NR^{51d1}R^{51d2}$; provided that when multiple substituents are present, the substituents are the same or different;

$R^{5a}$, $R^{5b1}$, $R^{5b2}$, $R^{5c}$, $R^{5d1}$, $R^{5d2}$, $R^{51a}$, $R^{51b1}$, $R^{51b2}$, $R^{51c}$, $R^{51d1}$ and $R^{51d2}$ are independently hydrogen, $C_{1-6}$ alkyl, or $C_{1-6}$ alkyl substituted with one or more halogen;

or, $R^2$ and $R^5$ are connected together with the atoms to which they are attached independently form "5- to 12-membered heterocyclic olefin containing 1 to 3 heteroatoms independently selected from O, S and N";

or, $R^{a-31}$ and $R^{a-32}$, $R^{a-51}$ and $R^{a-52}$, $R^{2b1}$ and $R^{2b2}$, $R^{2d1}$ and $R^{2d2}$, $R^{22b1}$ and $R^{22b2}$, $R^{22d1}$ and $R^{22d2}$, $R^{22e1}$ and $R^{22e2}$, $R^{1b1}$ and $R^{1b2}$, $R^{1d1}$ and $R^{1d2}$, $R^{1e1}$ and $R^{1e2}$, $R^{11b1}$ and $R^{11b2}$, $R^{11d1}$ and $R^{11d2}$, $R^{11e1}$ and $R^{11e2}$, $R^{5b1}$ and $R^{5b2}$, $R^{5d1}$ and $R^{5d2}$, $R^{51b1}$ and $R^{51b2}$, $R^{51d1}$ and $R^{51d2}$ together with the N to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-2-1}$;

$R^{1-2-1}$ is independently hydrogen, $C_{1-6}$ alkyl, or $C_{1-6}$ alkyl substituted with one or more halogen;

Solution 2:

$R^{a1}$, $R^{a2}$ and $R^{a3}$ are independently cyano, $C_{1-6}$ alkyl, —C(═O)$NR^{a-51}R^{a-52}$, or, $C_{1-6}$ alkyl substituted with one or more $R^{a1-1}$, $R^{a1-1}$ is independently halogen;

or, $R^{a2}$ and $R^{a3}$ together with the carbon atom to which they are attached form $C_{3-7}$ cycloalkane;

$R^{a-51}$ and $R^{a-52}$ are independently hydrogen;

n is 0, 1 or 2;

$R^2$ is halogen, cyano, $C_{1-6}$ alkyl, $C_{1-6}$ alkyl substituted with one or more $R^{2-1}$, —C(═O)$R^{2a}$, —C(═O)$OR^{2c}$ or —C(═O)$NR^{2d1}R^{2d2}$;

$R^{2-1}$ is independently $C_{1-6}$ alkyl-O—, hydroxyl or —C(═O)$NR^{22d1}R^{22d2}$;

$R^{2a}$, $R^{2c}$, $R^{2d1}$, $R^{2d2}$, $R^{22b1}$ and $R^{22b2}$ are independently hydrogen or $C_{1-6}$ alkyl;

$R^{11}$ is $C_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", or "4- to 12-membered heterocycloalkyl containing 1 to 3 heteroatoms independently selected from O, S and N" substituted with one or more $R^{1-3}$, $C_{6-20}$ aryl or "5- to 12-membered heteroaryl containing 1 to 4 heteroatoms independently selected from O, S and N";

$R^{1-1}$, $R^{1-2}$ and $R^{1-3}$ are independently $C_{1-6}$ alkyl or —$OC_{1-6}$ alkyl;

$R^3$ is "5- to 6-membered heteroaryl containing 1 to 4 heteroatoms independently selected from O, S and N" substituted with one or more $R^3$-1;

$R^{3-1}$ is independently $C_{1-6}$ alkyl or $C_{1-6}$ alkyl substituted with one or more halogen; provided that when multiple substituents are present, the substituents are the same or different;

$R^5$ is

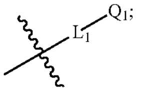

$L_1$ is a bond, $C_{1-6}$ alkylene or $C_{1-6}$ alkylene substituted with deuterium;

$Q_1$ is deuterium, —$OC_{1-6}$ alkyl, —$NR^{5b1}R^{5b2}$, —C(═O)$NR^{5d1}R^{5d2}$, $C_{6-20}$ aryl, "5- to 12-membered heteroaryl containing 1 to 4 heteroatoms independently selected from O, S and N", $C_{3-12}$ cycloalkyl, substituted with $R^{5-8}$ or "4- to 12-membered heterocycloalkyl containing 1 to 3 heteroatoms independently selected from O, S and N"; provided that when multiple substituents are present, the substituents are the same or different;

$R^{5-8}$ is independently halogen;

$R^{5b1}$, $R^{5b2}$, $R^{5d1}$ and $R^{5d2}$ are independently hydrogen or $C_{1-6}$ alkyl;

the compound represented by formula I is not one of the following compounds:

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-(2,2,2-trifluoroethyl)-1H-indazole-5-sulfonamide;

N-(1-cyanocyclopropyl)-3-(5-(difluoromethyl)-1,3,4-thiadiazol-2-yl)-7-(1-(isopropylsulfonyl)-1,2,3,6-tetrahydropyridin-4-yl)-1-methyl-1H-indazole-5-sulfonamide.

6. A compound represented by formula I, a pharmaceutically acceptable salt thereof, a stereoisomer thereof, an isomer thereof or an isotopic compound thereof according to claim 1, wherein, $A_1$ and $A_2$ are independently $CR^{b1}$, $R^{b1}$ is hydrogen or halogen;

and/or, $A_4$ is N or $CR^4$; $R^4$ is hydrogen or $C_{1-6}$ alkyl substituted with one or more $R^{4-1}$; $R^{4-1}$ is $C_{3-12}$ cycloalkyl;

and/or, $A_5$ is N, $NR^5$, $CR^5$ or S;

and/or, $R^5$ is

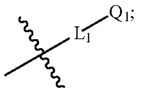

$L_1$ is a bond, $C_{1-6}$ alkylene or $C_{1-6}$ alkylene substituted with deuterium;

$Q_1$ is hydrogen, deuterium, halogen, —$OC_{1-6}$ alkyl, —$NR^{5b1}R^{5b2}$, —C(═O)$NR^{5d1}R^{5d2}$, —$C_{6-20}$ aryl, "5- to 12-membered heteroaryl containing 1 to 4 heteroatoms independently selected from O, S and N", $C_{3-12}$ cycloalkyl, $C_{1-6}$ alkyl substituted with one or more $R^{5-8}$ or "4- to 12-membered heterocycloalkyl containing 1 to 3 heteroatoms independently selected from O, S and N"; provided that when multiple substituents are present, the substituents are the same or different;

$R^{5b1}$, $R^{5b2}$, $R^{5d1}$ and $R^{5d2}$ are independently hydrogen or $C_{1-6}$ alkyl;

$R^{5-8}$ is independently halogen;

and/or, $R^{a1}$ is cyano, $C_{1-6}$ alkyl, —C(═O)$NR^{a-51}R^{a-52}$, or, $C_{1-6}$ alkyl substituted with one or more $R^{a-1}$, $R^{a1-1}$ is independently halogen;

and/or, $R^{a2}$ and $R^{a3}$ together with the carbon atom to which they are attached form $C_{3-7}$ cycloalkane;

and/or, $R^{a-51}$ and $R^{a-52}$ are independently hydrogen;

and/or, ring Y is "4- to 12-membered heterocycloalkyl containing 1 to 3 heteroatoms independently selected from O, S and N", $C_{6-20}$ aryl, "5- to 12-membered heteroaryl containing 1 to 4 heteroatoms independently selected from O, S and N", $C_{4-8}$ cycloalkenyl, "5- to 6-membered heteroaryl containing 1 to 4 heteroatoms independently selected from O, S and N" fused with "5- to 6-membered heterocycloalkyl containing 1 to 3 heteroatoms independently selected from O, S and N", or, "4- to 8-membered heterocycloalkenyl containing 1 to 3 heteroatoms independently selected from O, S and N";

and/or, n is 0, 1 or 2;

and/or, $R^2$ is independently halogen, hydroxyl, cyano, $C_{1-6}$ alkyl, $C_{1-6}$ alkyl substituted with one or more $R^{2-1}$, —C(═O)$R^{2a}$, —C(═O)$OR^{2c}$ or —C(═O)$NR^{2d1}R^{2d2}$; or, when n is 2, two $R^2$ are connected, together with the atoms to which they are attached, independently form "3- to 8-membered heterocycle containing 1 to 3 heteroatoms independently selected from O, S and N";

and/or, $R^{2-1}$ is independently $C_{1-6}$ alkyl-O—, hydroxyl or —C(═O)$NR^{22d1}R^{22d2}$;

and/or, $R^{2a}$, $R^{2c}$, $R^{2d1}$, $R^{2d2}$, $R^{22b1}$ and $R^{22b2}$ are independently hydrogen or $C_{1-6}$ alkyl;

and/or, $R^1$ is

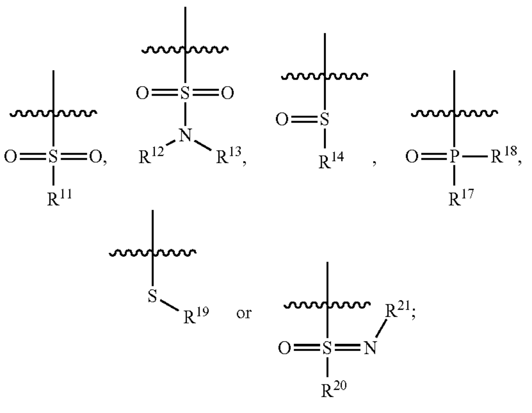

or and/or, $R^{11}$, $R^{12}$, $R^{13}$, $R^{14}$, $R^{17}$, $R^{18}$, $R^{19}$ and $R^{20}$ are independently $C_{1-6}$ alkyl, —$OC_{1-6}$ alkyl, $C_{1-6}$ alkyl substituted with one or more $R^{1-1}$, $C_{3-10}$ cycloalkyl, $C_{3-10}$ cycloalkyl substituted with one or more $R^{1-2}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-3}$, $C_{6-20}$ aryl, "5- to 12-membered heteroaryl containing 1 to 4 heteroatoms independently selected from O, S and N";

and/or, $R^{21}$ is hydrogen or $C_{1-6}$ alkyl;

and/or, $R^{1-1}$, $R^{1-2}$ and $R^{1-3}$ are $C_{1-6}$ alkyl or —$OC_{1-6}$ alkyl;

and/or, $R^3$ is "5- to 6-membered heteroaryl containing 1 to 4 heteroatoms independently selected from O, S and N" substituted with one or more $R^{3-1}$;

and/or, $R^{3-1}$ is independently $C_{1-6}$ alkyl or $C_{1-6}$ alkyl substituted with one or more halogen; provided that when multiple substituents are present, the substituents are the same or different.

7. A compound represented by formula I, a pharmaceutically acceptable salt thereof, a stereoisomer thereof, an isomer thereof or an isotopic compound thereof according to claim 1, wherein, $R^{a1}$ is cyano, $C_{1-6}$ alkyl, —C(═O)$NR^{a-51}R^{a-52}$, or, $C_{1-6}$ alkyl substituted with one or more $R^{a1-1}$, $R^{a1-1}$ is independently halogen, $R^{a2}$ and $R^{a3}$ together with the carbon atom to which they are attached form $C_{3-7}$ cycloalkane;

and/or, when $R^1$ is

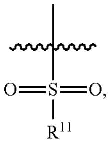

$R^{11}$ is $C_{1-6}$ alkyl, “4- to 12-membered heterocycloalkyl containing 1 to 3 heteroatoms independently selected from O, S and N”, $C_{3-10}$ cycloalkyl, $C_{1-6}$ alkyl substituted with one or more $R^{1-1}$, $C_{3-10}$ cycloalkyl substituted with one or more $R^{1-2}$, “4- to 12-membered heterocycloalkyl containing 1 to 3 heteroatoms independently selected from O, S and N” substituted with one or more $R^{1-3}$, $C_{6-20}$ aryl or “5- to 12-membered heteroaryl containing 1 to 4 heteroatoms independently selected from O, S and N”; $R^{1-1}$ is —$OC_{1-6}$ alkyl; $R^{1-2}$ and $R^{1-3}$ are independently $C_{1-6}$ alkyl;

and/or, when $R^1$ is

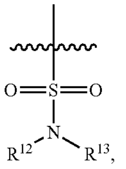

$R^{12}$ and $R^{13}$ are independently $C_{1-6}$ alkyl;

and/or, when $R^1$ is

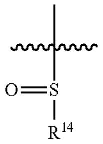
or
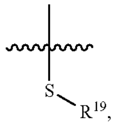

$R^{14}$ and $R^{19}$ are independently $C_{1-6}$ alkyl;

and/or, when $R^1$ is

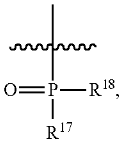

$R^{17}$ and $R^{18}$ are independently $C_{1-6}$ alkyl or —$OC_{1-6}$ alkyl;

and/or, when $R^1$ is

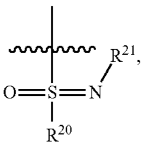

$R^{20}$ is $C_{1-6}$ alkyl;

and/or, when $Q_1$ is “5- to 12-membered heteroaryl containing 1 to 4 heteroatoms independently selected from O, S and N”, the $Q_1$ is “5- to 6-membered heteroaryl containing 1 to 2 heteroatoms independently selected from N”;

and/or, when $Q_1$ is “4- to 12-membered heterocycloalkyl containing 1 to 3 heteroatoms independently selected from O, S and N”, the $Q_1$ is “4- to 6-membered heterocycloalkyl containing 1 to 2 heteroatoms independently selected from O, S and N”;

and/or, when $Q_1$ is $C_{1-6}$ alkyl substituted with one or more $R^{5-8}$, the $Q_1$ is $C_{1-6}$ alkyl substituted with two or three $R^{5-8}$;

and/or, when ring Y is “4- to 12-membered heterocycloalkyl containing 1 to 3 heteroatoms independently selected from O, S and N”, the ring Y is “4- to 8-membered heterocycloalkyl containing 1 to 2 heteroatoms N”;

and/or, when ring Y is “5- to 12-membered heteroaryl containing 1 to 4 heteroatoms independently selected from O, S and N”, the ring Y is “5- to 6-membered heteroaryl containing 1 to 2 heteroatoms independently selected from O and N”;

and/or, when ring Y is $C_{4-8}$ cycloalkenyl, the ring Y is $C_{5-7}$ cycloalkenyl;

and/or, when ring Y is “5- to 6-membered heteroaryl containing 1 to 4 heteroatoms independently selected from O, S and N” fused with “5- to 6-membered heterocycloalkyl containing 1 to 3 heteroatoms independently selected from O, S and N”, the ring Y is “5- to 6-membered heteroaryl containing 1 to 2 heteroatoms N” fused with “5- to 6-membered heterocycloalkyl containing 1 heteroatom N”;

and/or, when ring Y is “4- to 8-membered heterocycloalkenyl containing 1 to 3 heteroatoms independently selected from O, S and N”, the ring Y is “5- to 7-membered heterocycloalkenyl containing 1 to 3 heteroatoms independently selected from O and N”;

and/or, when n is 2, two $R^2$ are connected, together with the atoms to which they are attached, independently form “3- to 8-membered heterocycle containing 1 to 3 heteroatoms independently selected from O, S and N”, the “3- to 8-membered heterocycle containing 1 to 3 heteroatoms independently selected from O, S and N” is “3- to 6-membered heterocycle containing 1 to 2 heteroatoms independently selected from O, S and N”;

and/or, when $R^{11}$, $R^{12}$, $R^{13}$, $R^{14}$, $R^{17}$, $R^{18}$, $R^{19}$ and $R^{20}$ are independently “4- to 12-membered heterocycloalkyl containing 1 to 3 heteroatoms independently selected from O, S and N” or “4- to 12-membered heterocycloalkyl containing 1 to 3 heteroatoms independently selected from O, S and N” substituted with one or more $R^{1-3}$, the “4- to 12-membered heterocycloalkyl containing 1 to 3 heteroatoms independently selected from O, S and N” is “4- to 6-membered heterocycloalkyl containing 1 to 2 heteroatoms independently selected from O and N”;

and/or, when $R^{11}$, $R^{12}$, $R^{13}$, $R^{14}$, $R^{17}$, $R^{18}$, $R^{19}$ and $R^{20}$ are independently “5- to 12-membered heteroaryl containing 1 to 4 heteroatoms independently selected from O, S and N”, the “5- to 12-membered heteroaryl containing 1 to 4 heteroatoms independently selected from O, S and N” is “5- to 6-membered heteroaryl containing 1 to 2 heteroatoms independently selected from O, S and N”;

and/or, when $R^3$ is “5- to 6-membered heteroaryl containing 1 to 4 heteroatoms independently selected from O, S and N” substituted with one or more $R^{3-1}$, the “5- to 6-membered heteroaryl containing 1 to 4 heteroatoms independently selected from O, S and N" is "5- to 6-membered heteroaryl containing 1 to 3 heteroatoms independently selected from O, S and N";

and/or, when $R^{3-1}$ is $C_{1-6}$ alkyl substituted with one or more halogen, the $C_{1-6}$ alkyl substituted with one or more halogen is $C_{1-2}$ alkyl substituted with two or three halogen.

8. A compound represented by formula I, a pharmaceutically acceptable salt thereof, a stereoisomer thereof, an isomer thereof or an isotopic compound thereof according to claim 1, wherein,

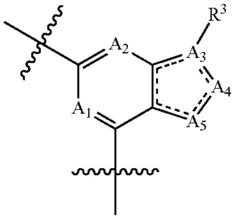
is

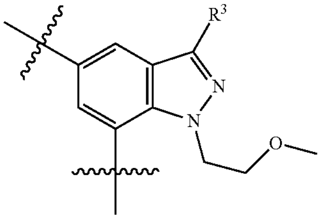
,
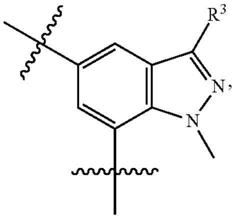

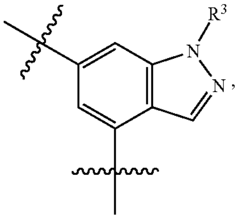
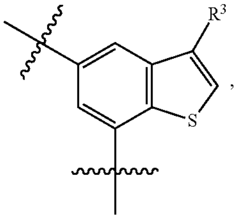
,

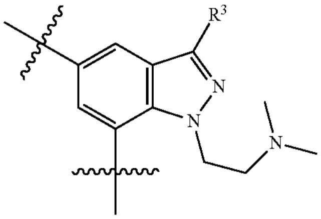
,
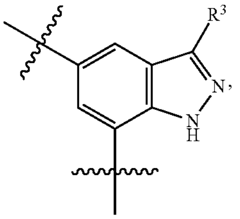

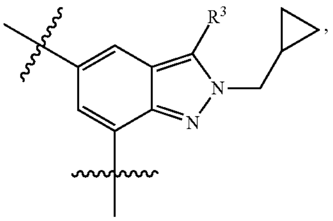

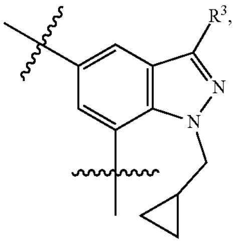

-continued

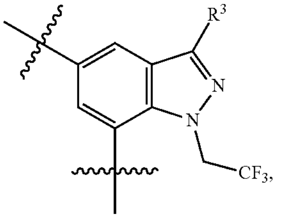

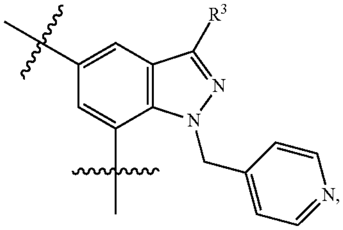

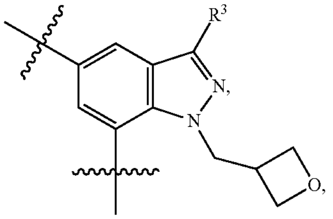

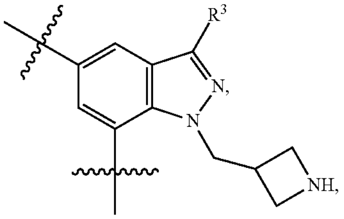

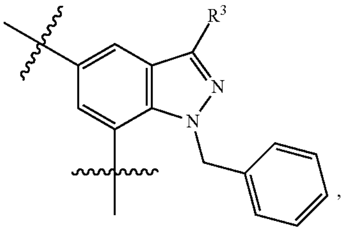

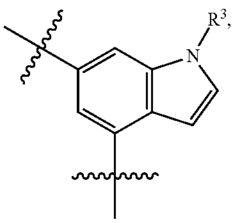
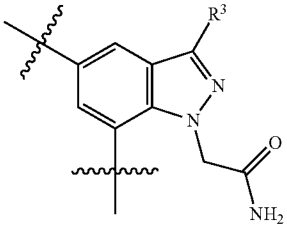
,

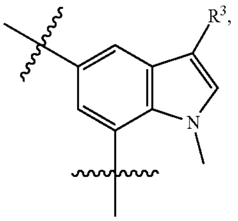
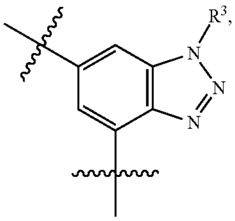

-continued
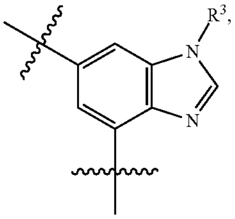
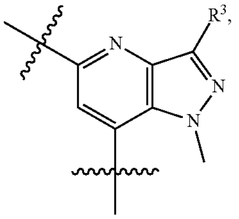
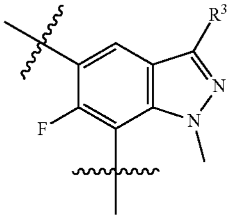
or
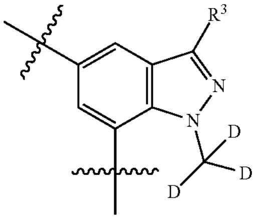
and/or, $R^3$ is
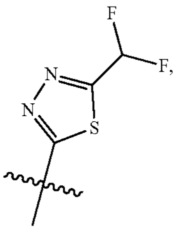
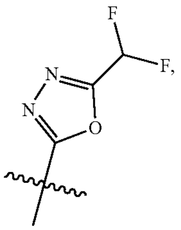
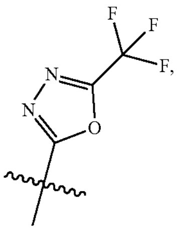
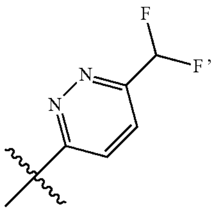
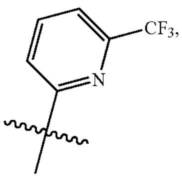
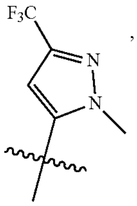
,
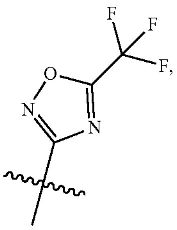
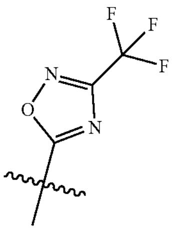
or
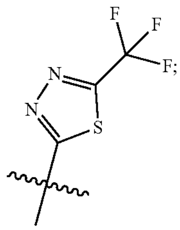
; and/or,
-continued
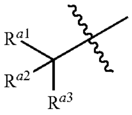
is
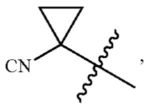
,
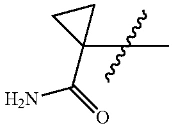
,
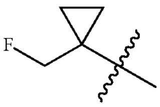
or
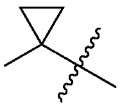
;
and/or, ring Y is
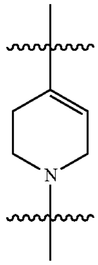
,
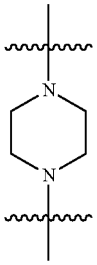
,
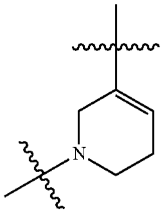
,
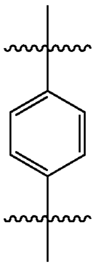
,
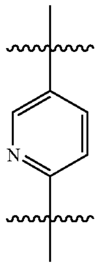
,
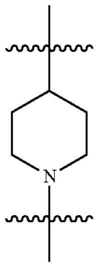
,
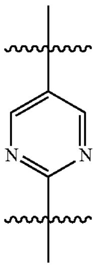
,
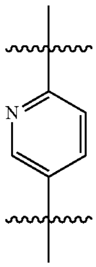
,
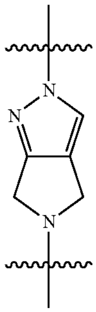
or
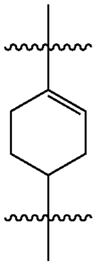
; and/or, -continued
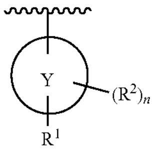 is 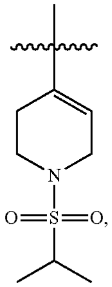 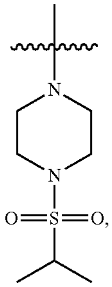
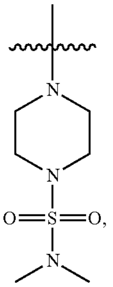 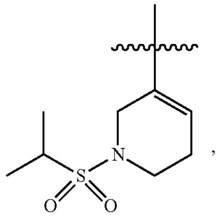 ,
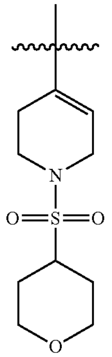 , 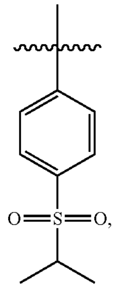 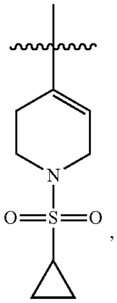 ,
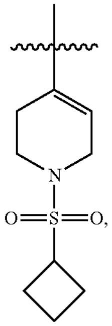 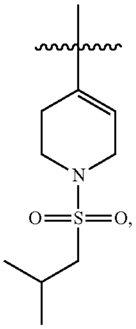 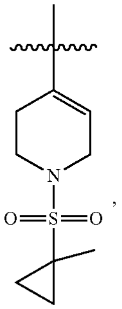 ,
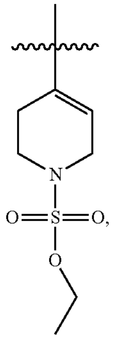 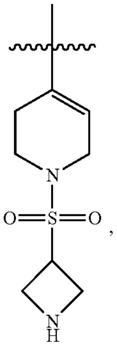 , 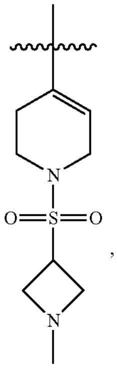 ,
-continued
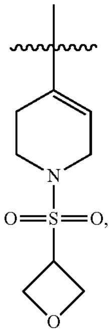 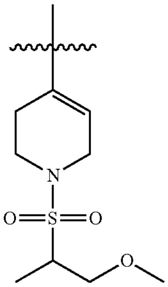 ,
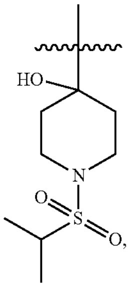 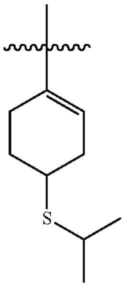 , 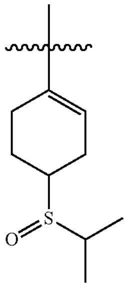 ,
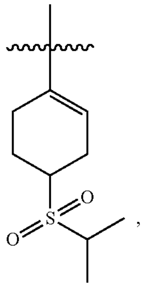 , 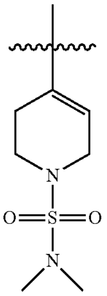 , 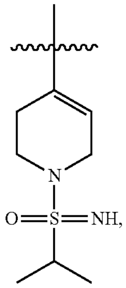
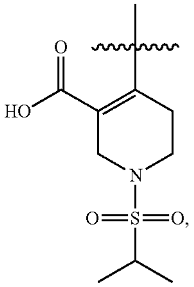 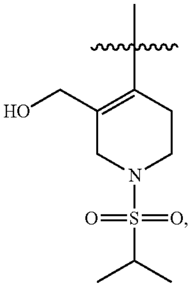
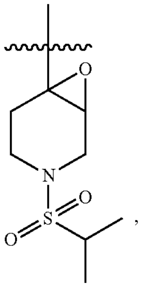 , 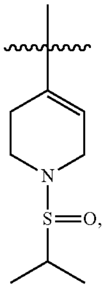 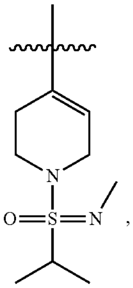 , -continued
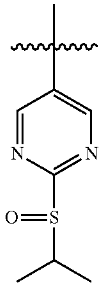,
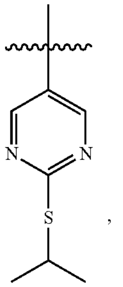,
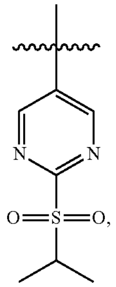
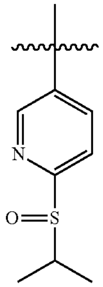
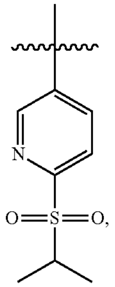
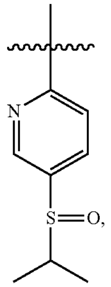
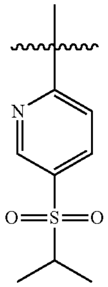,
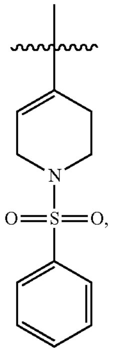
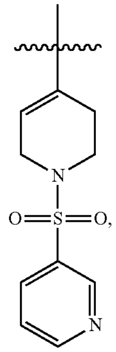
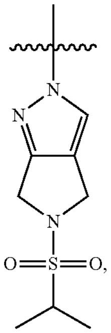
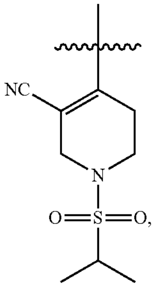
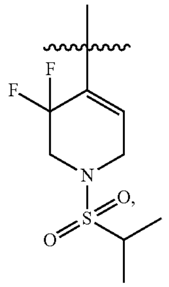,
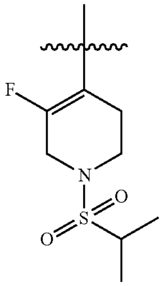,
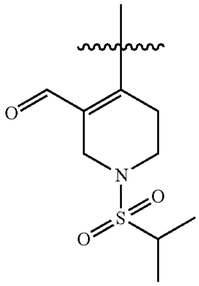,
-continued
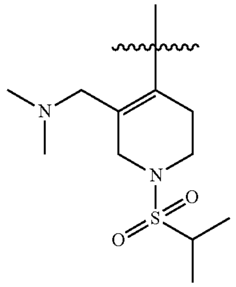,
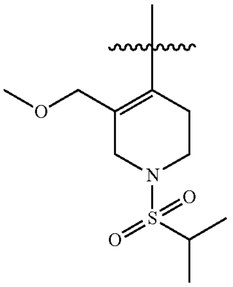,
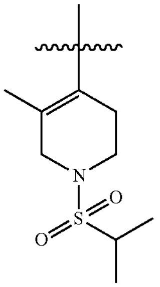,
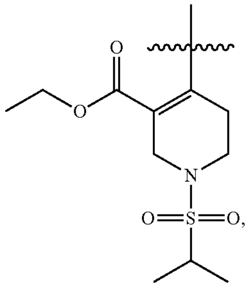
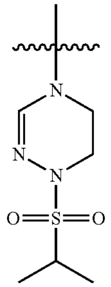
or
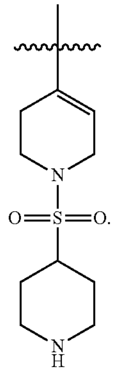
9. A compound represented by formula I, a pharmaceutically acceptable salt thereof, a stereoisomer thereof, an isomer thereof or an isotopic compound thereof according to claim 1, wherein, the compound represented by formula I as described above can be any one of the following structures:
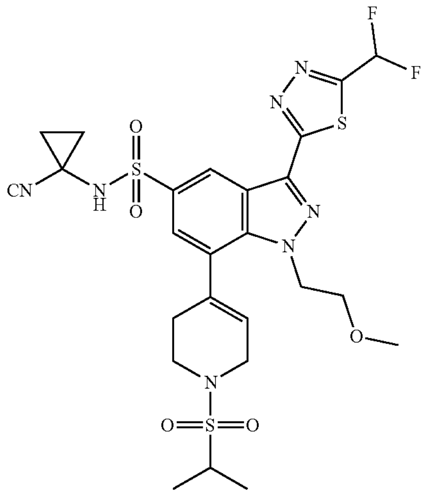

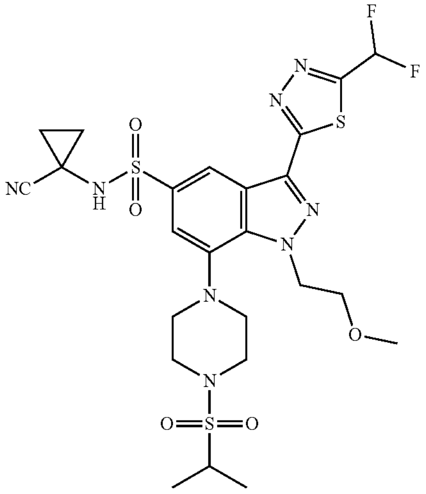
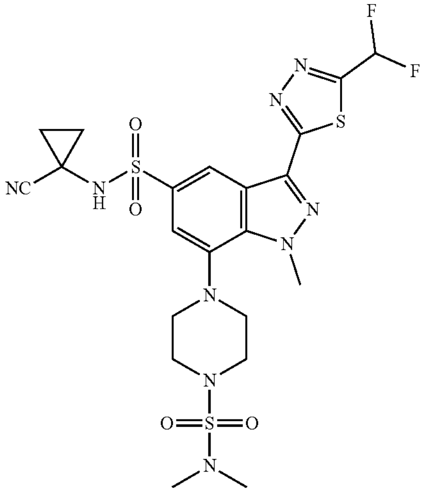
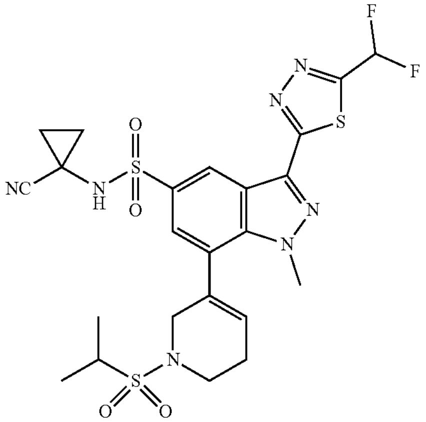
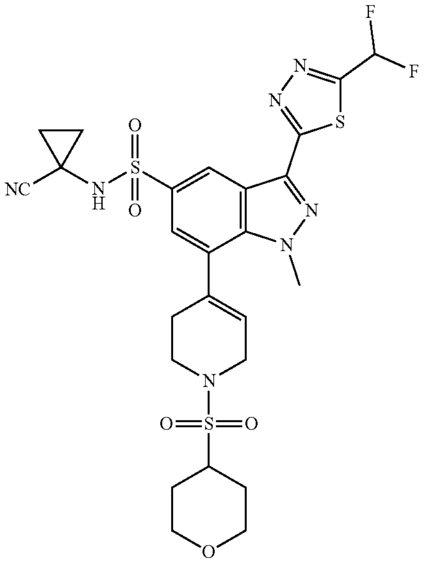
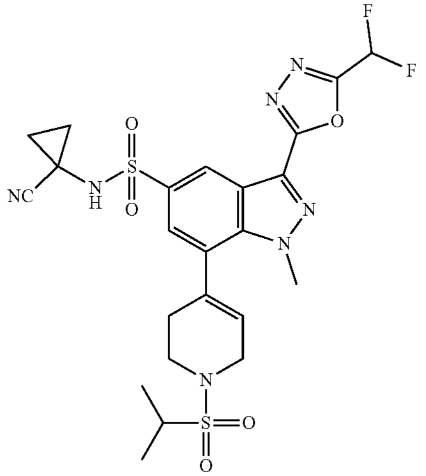
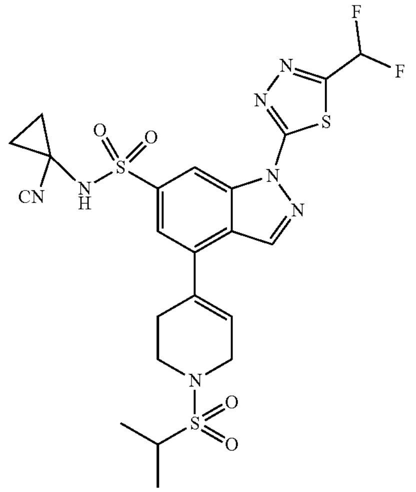

-continued
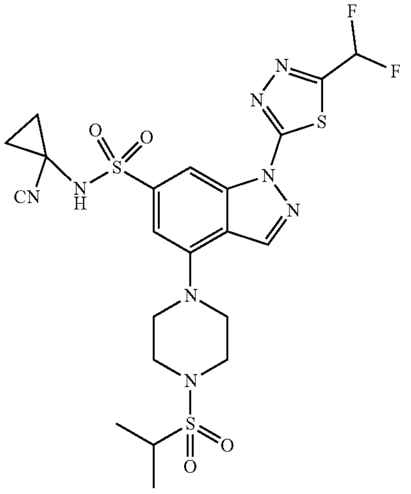
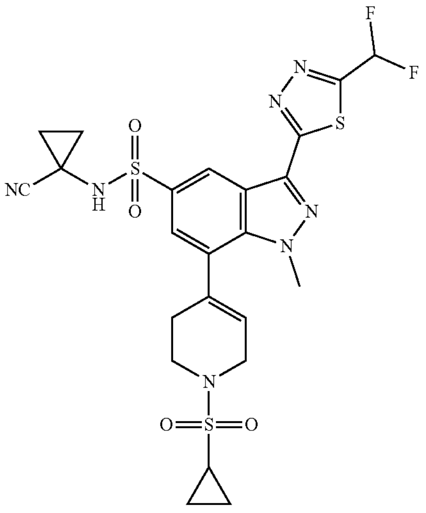
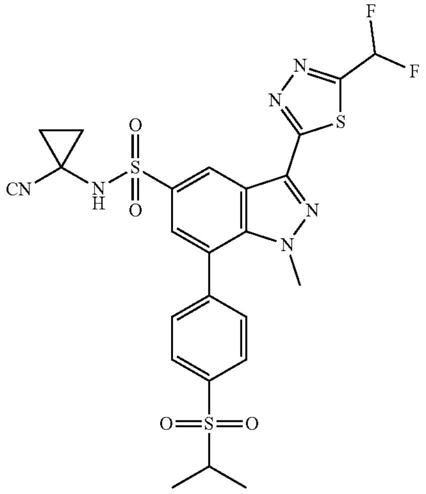
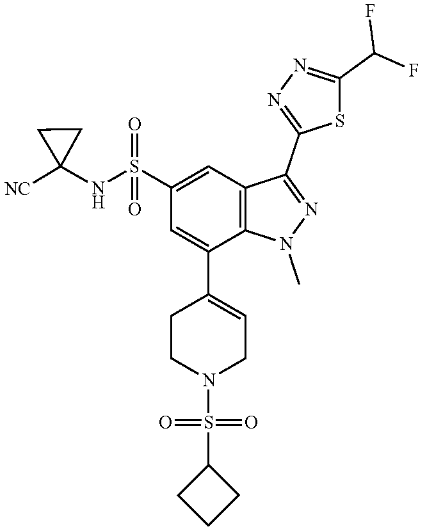
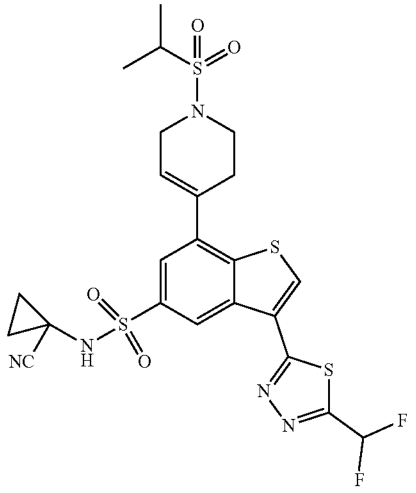
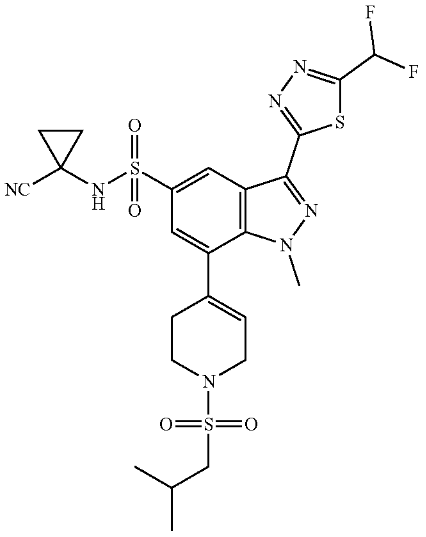
-continued -continued
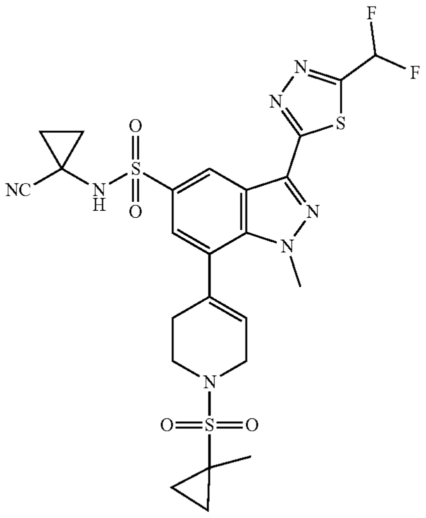
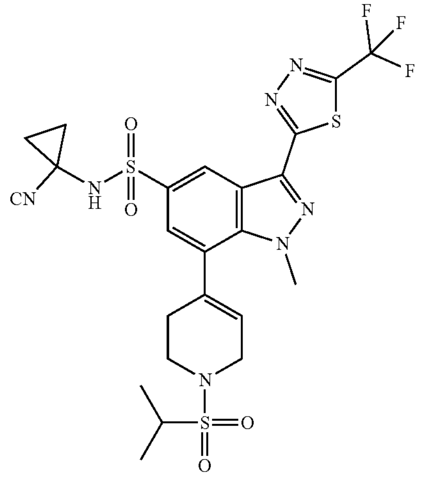
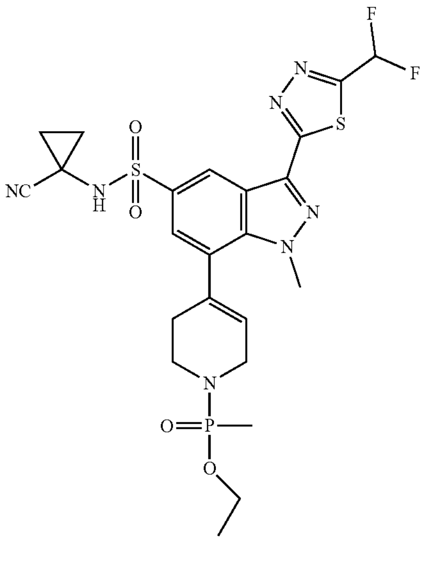
-continued
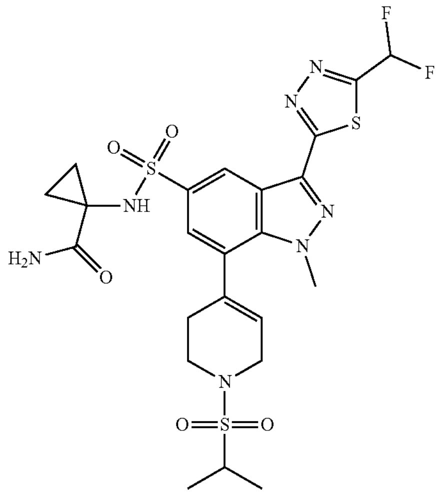
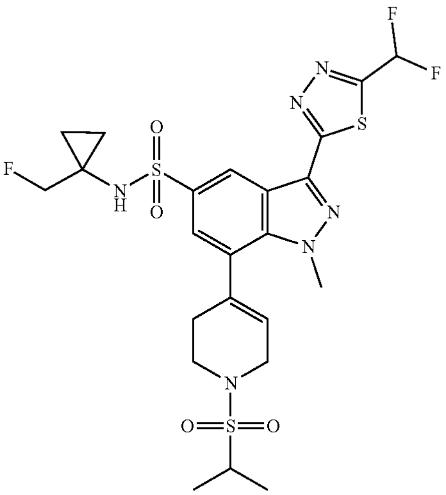
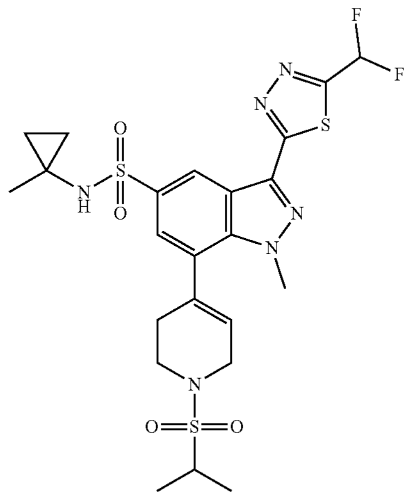

-continued
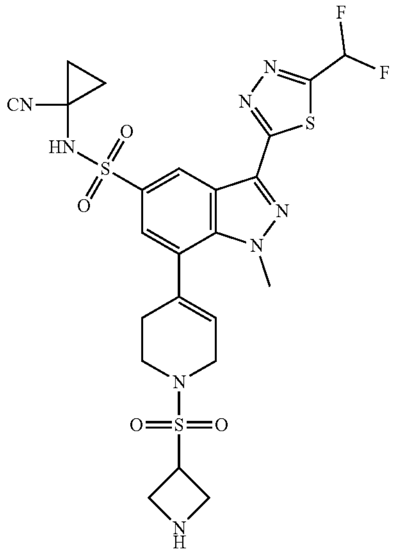
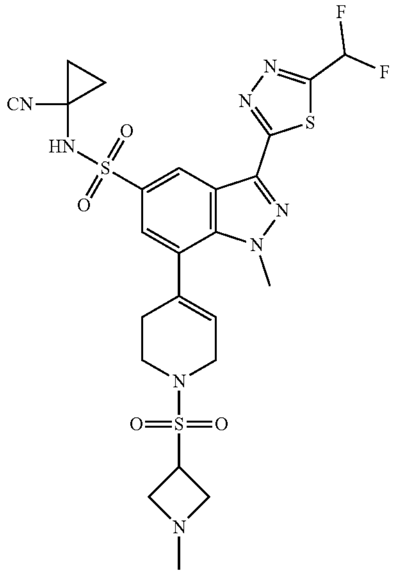
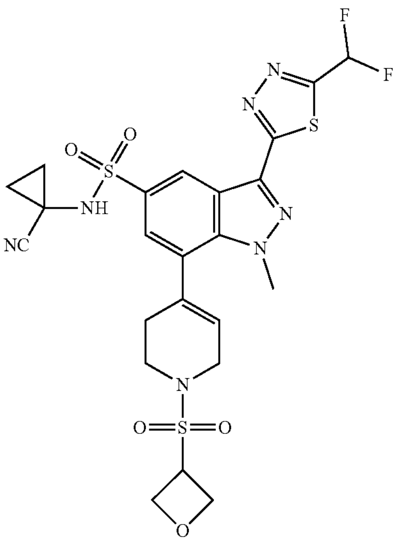
-continued
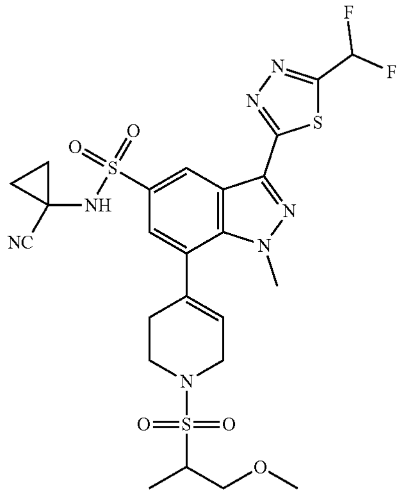
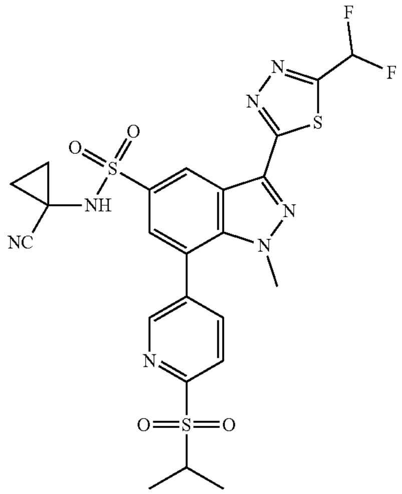
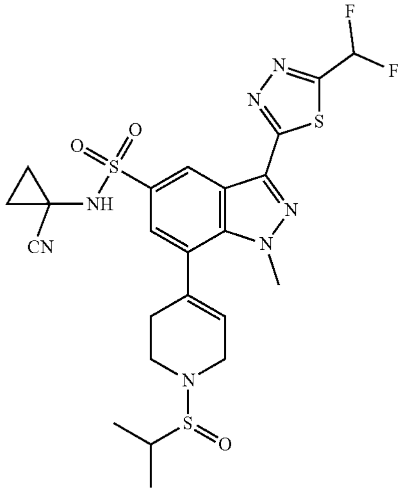

-continued
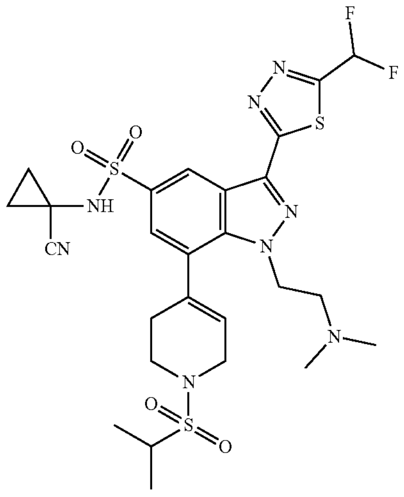
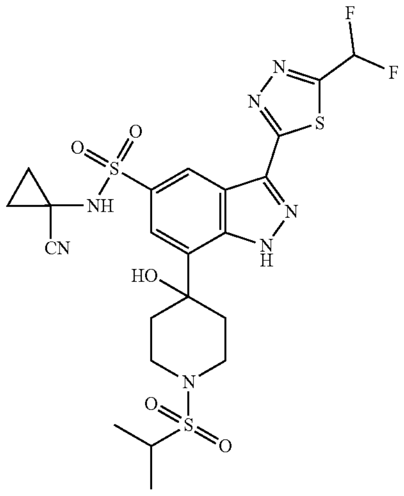
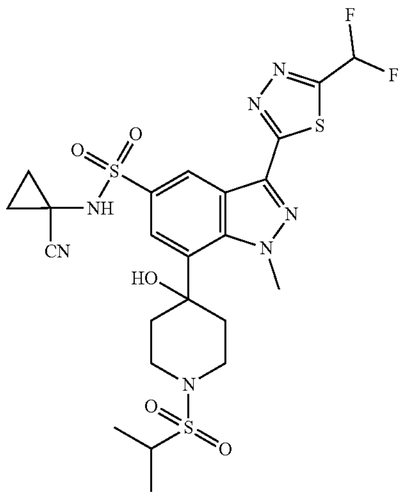
-continued
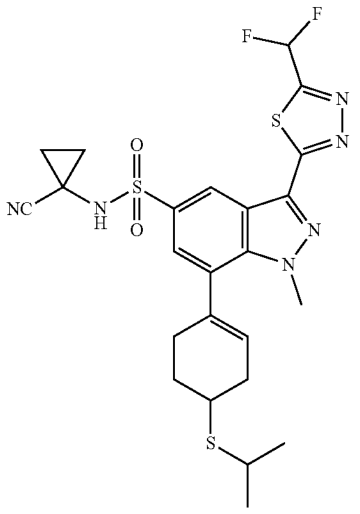
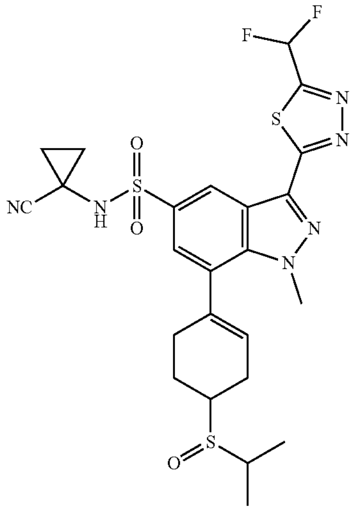
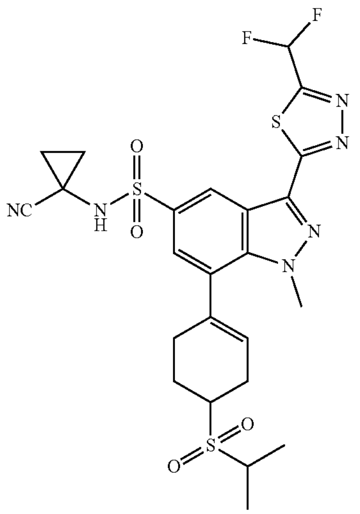

-continued
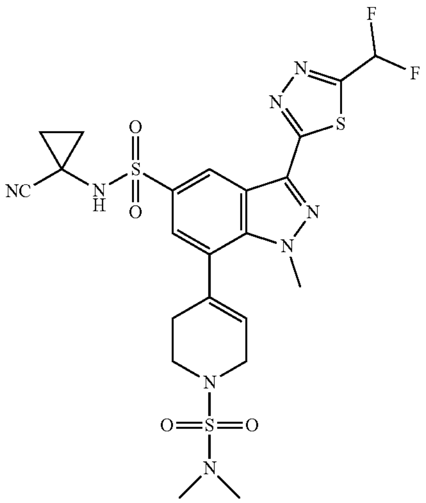
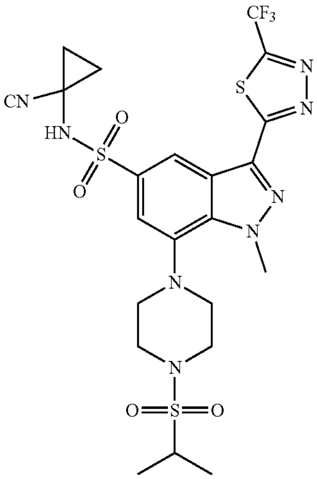
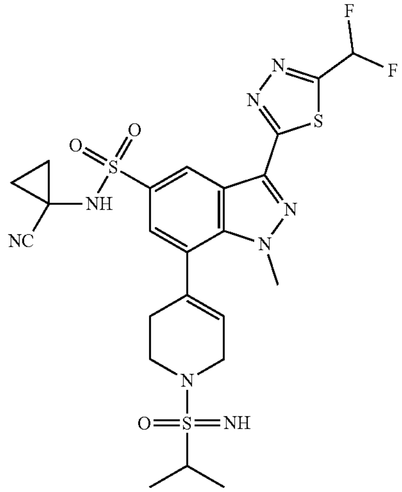
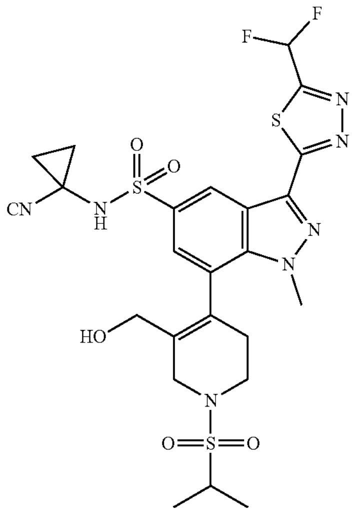
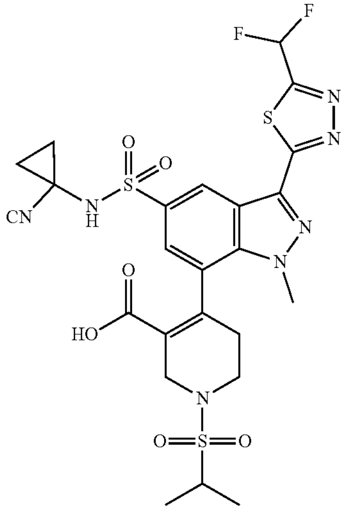
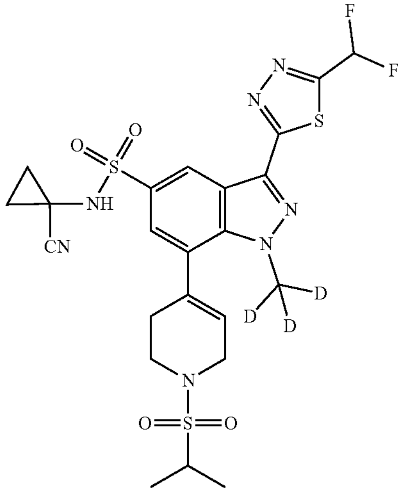
-continued

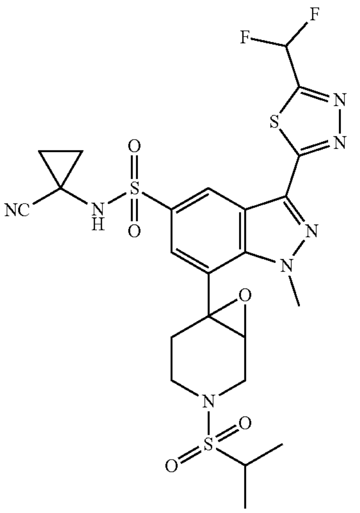
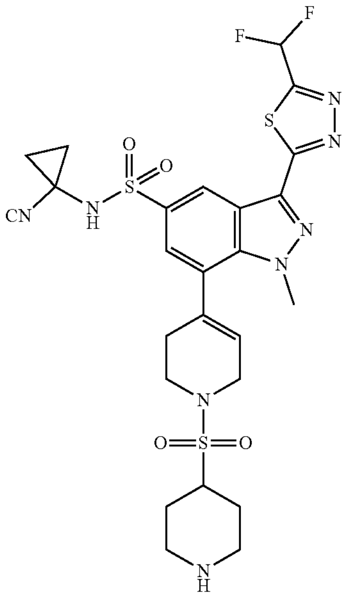
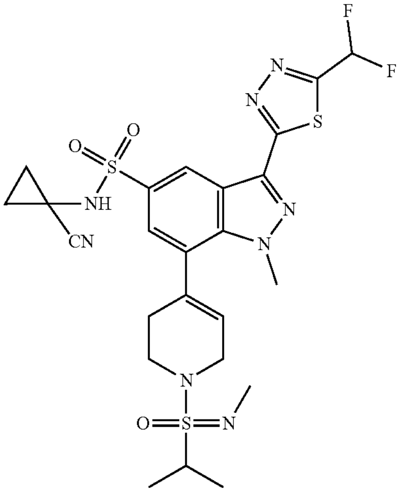
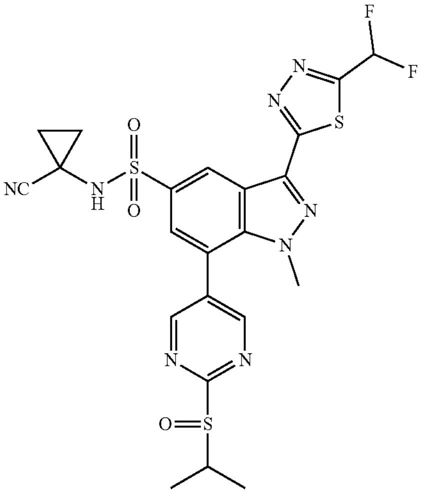
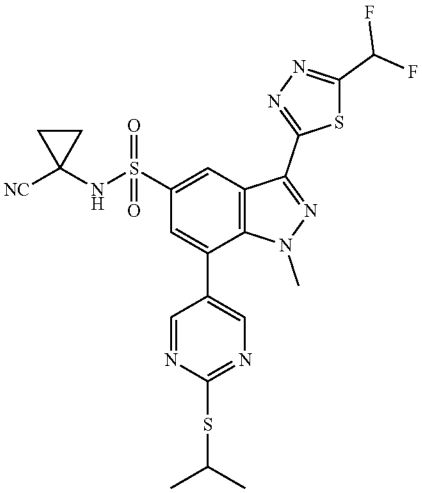
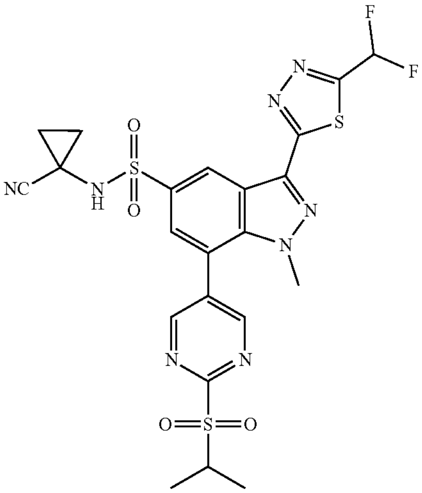

-continued
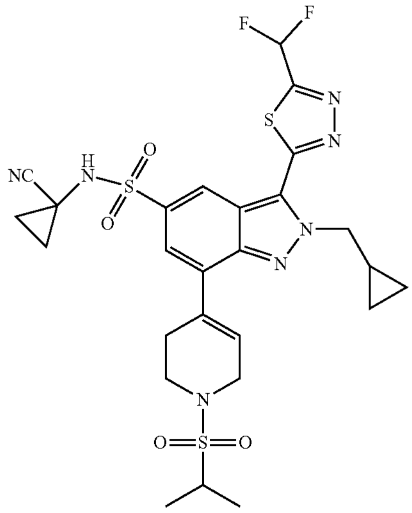
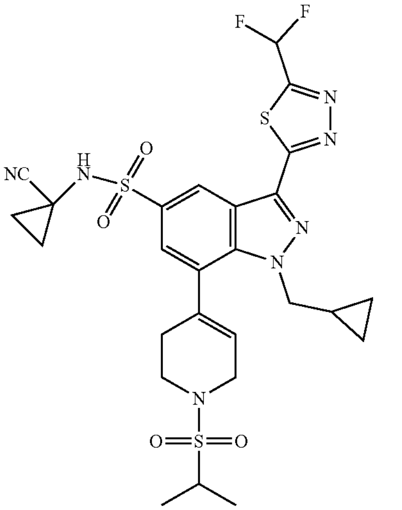
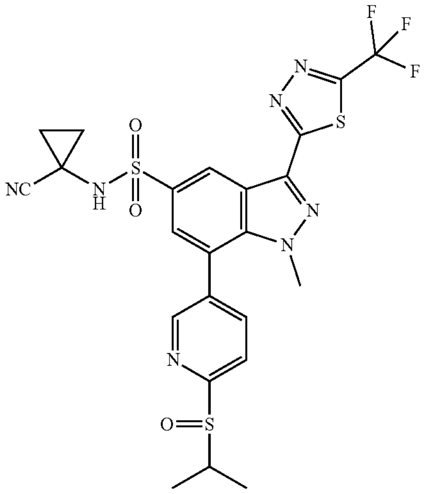
-continued
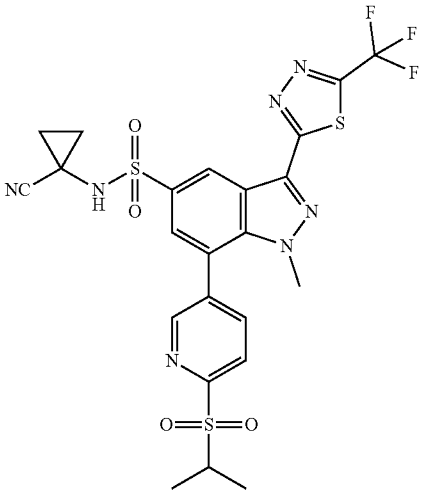
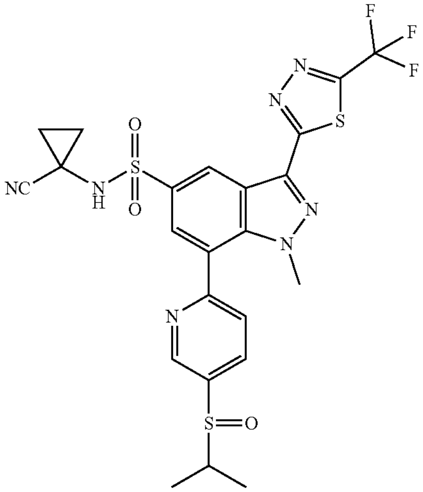
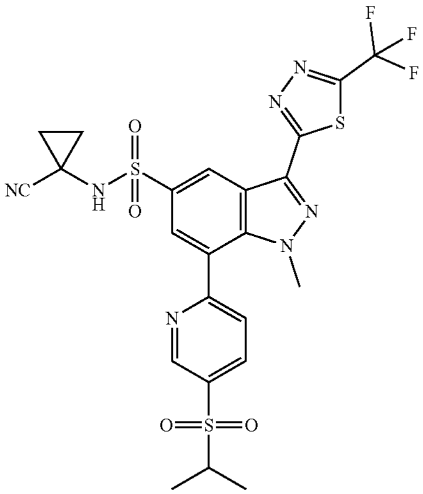

-continued
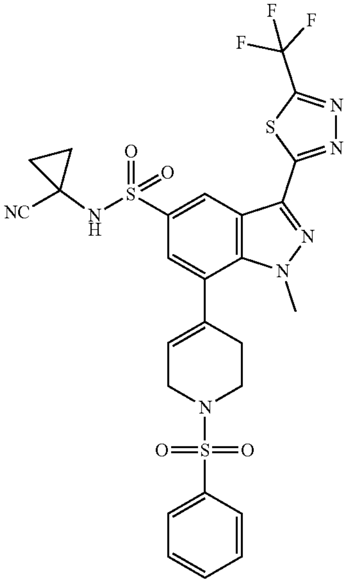
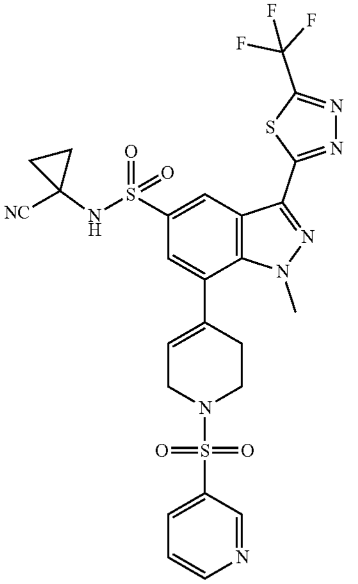
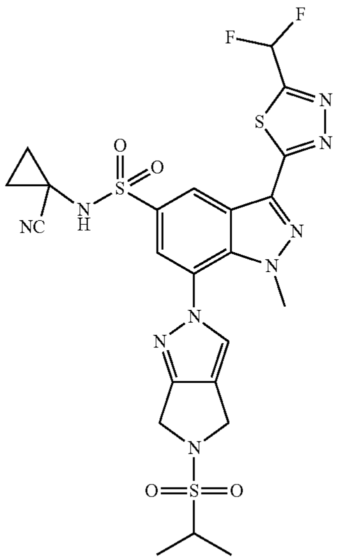
-continued
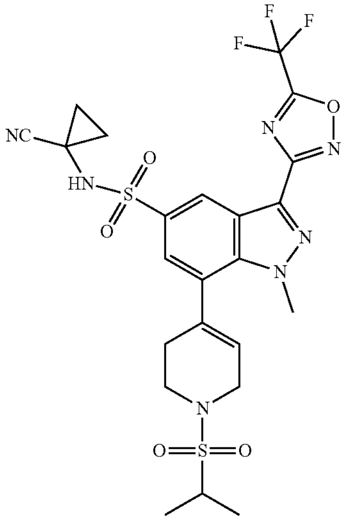
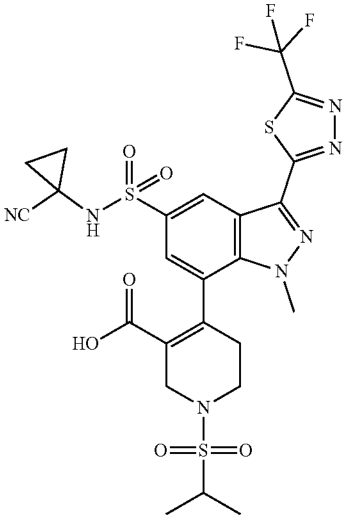
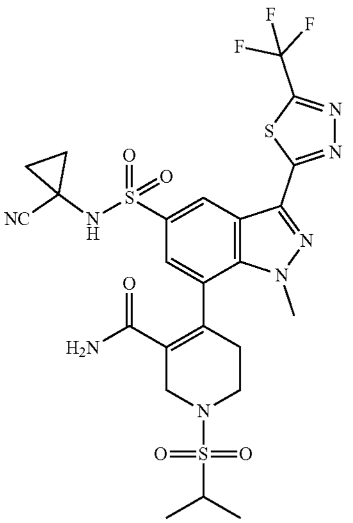

-continued
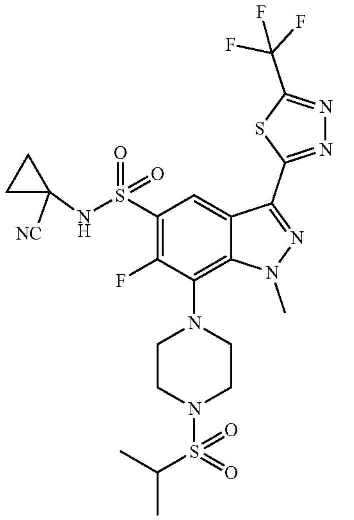
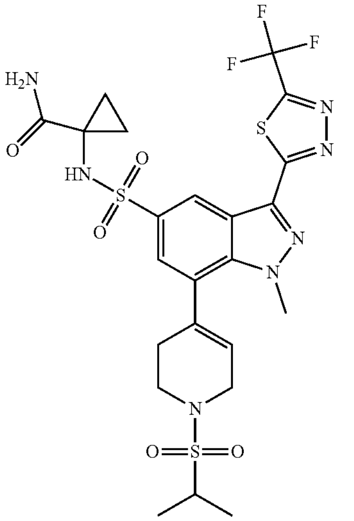
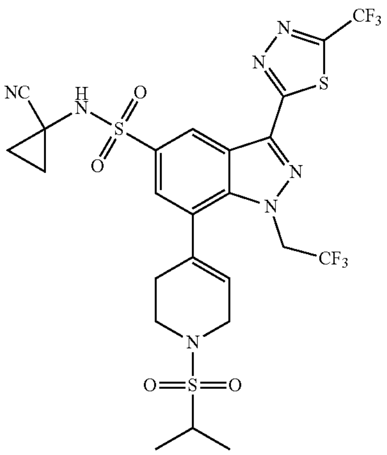
-continued
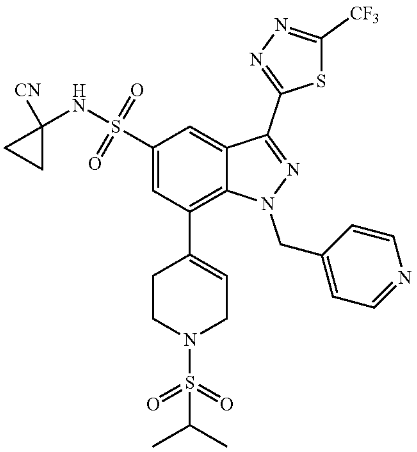
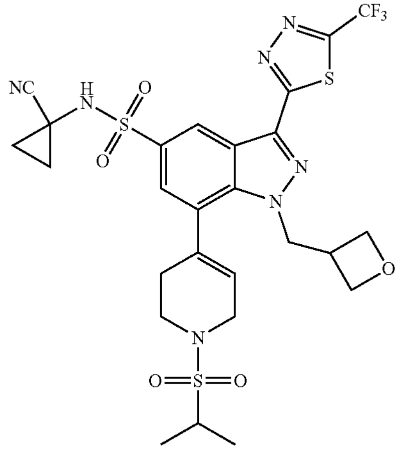
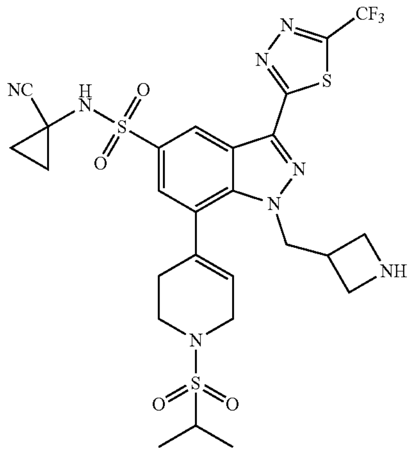

-continued
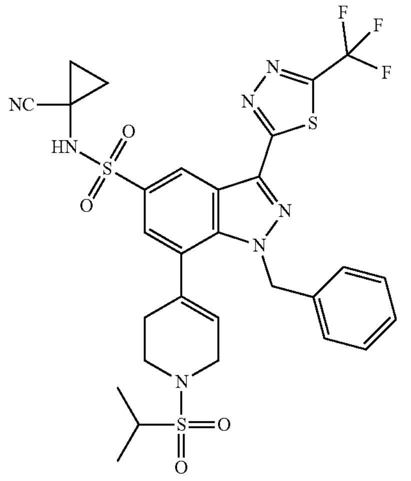
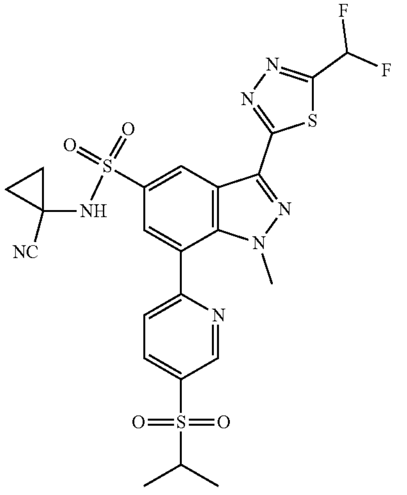
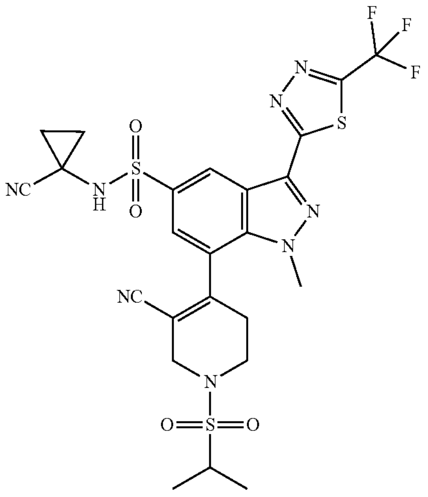
-continued
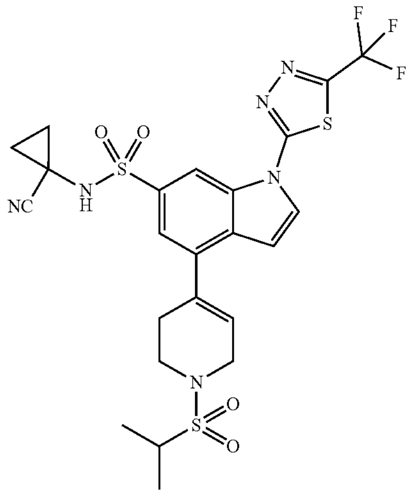
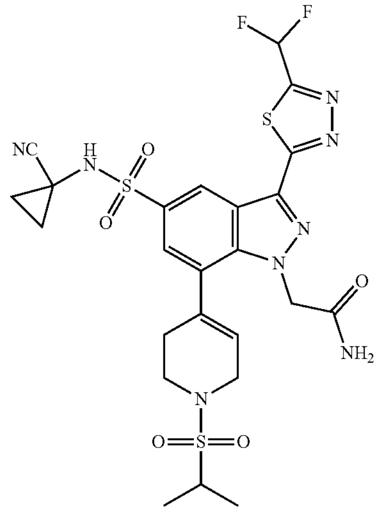
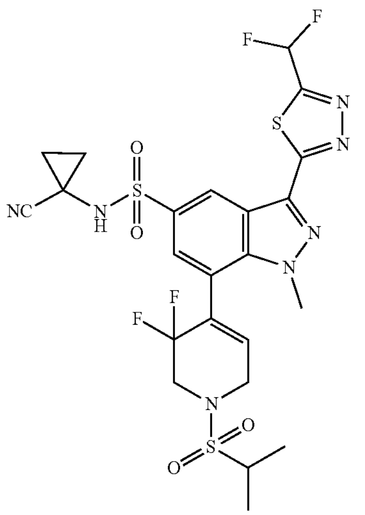

-continued
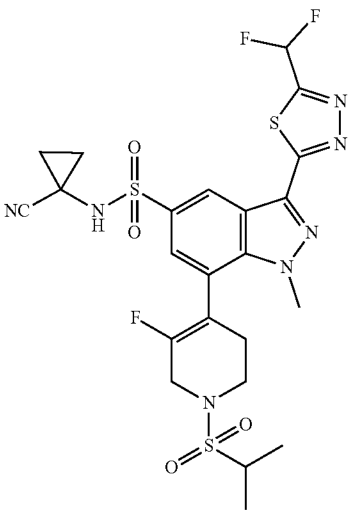
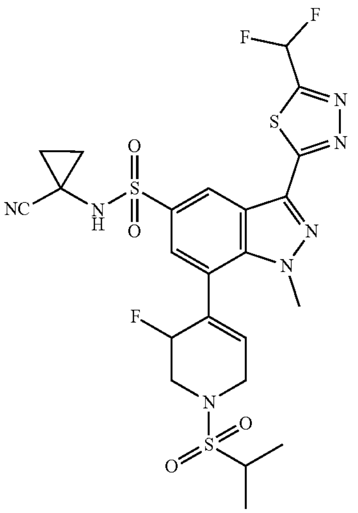
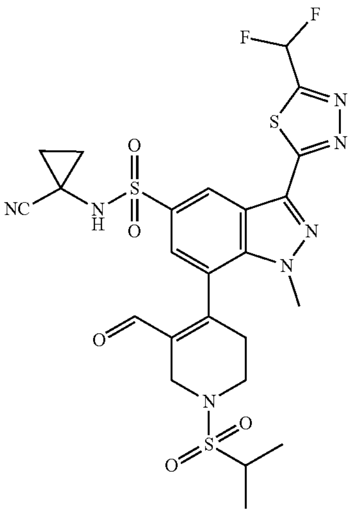
-continued
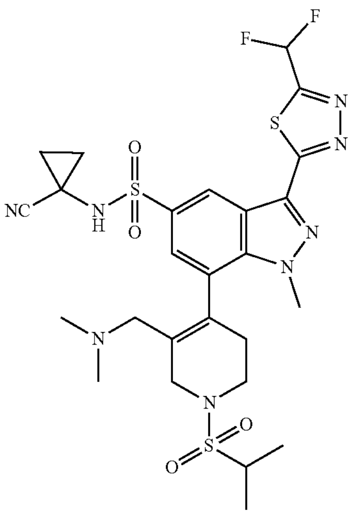
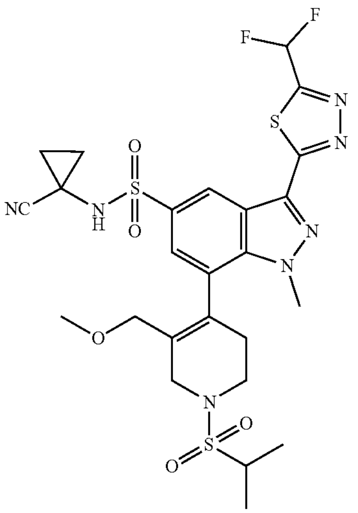
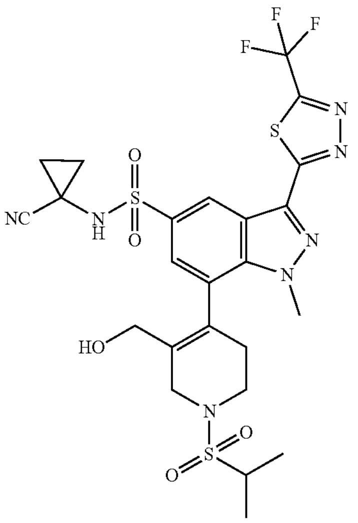

-continued
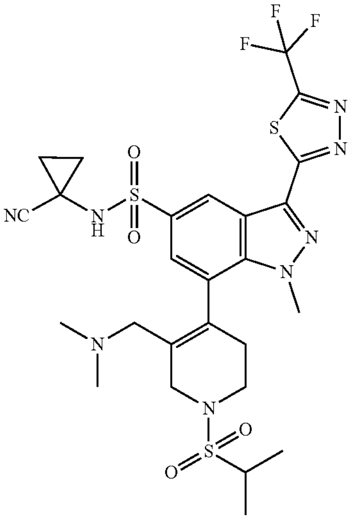
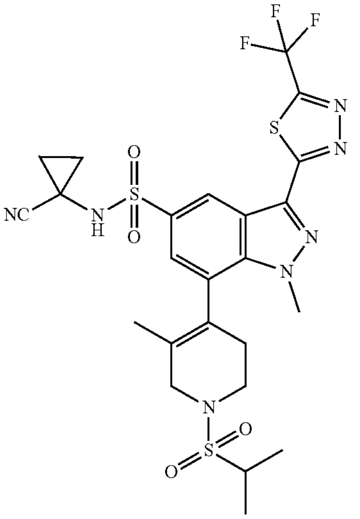
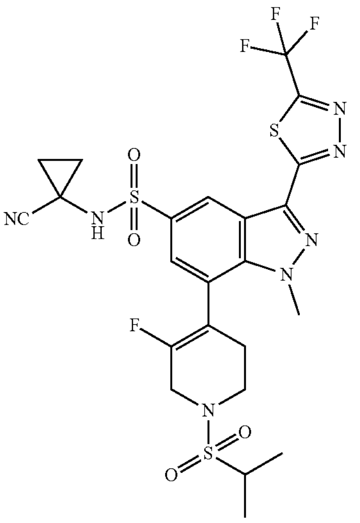
-continued
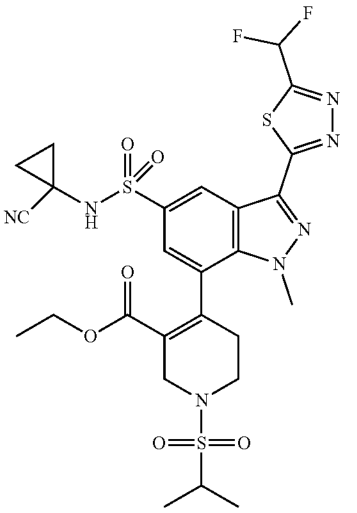
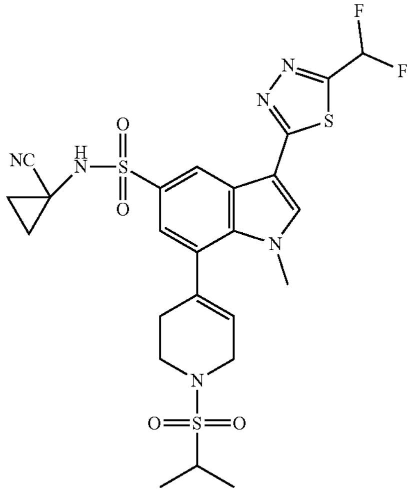
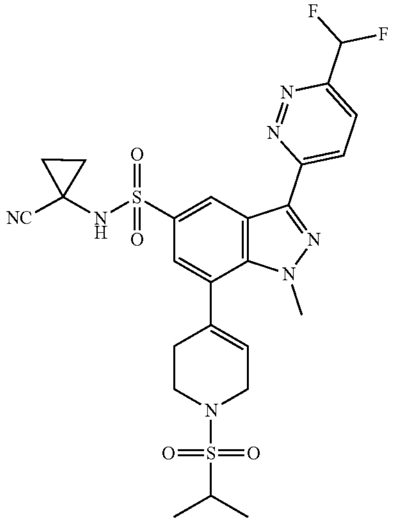

-continued
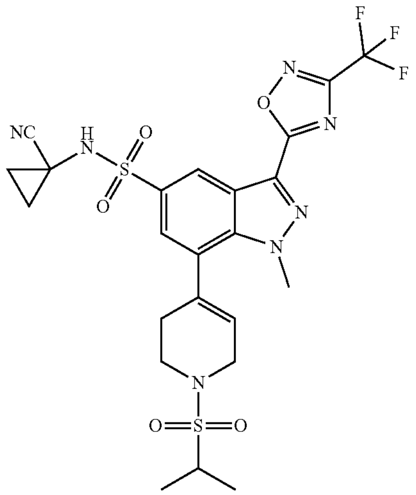
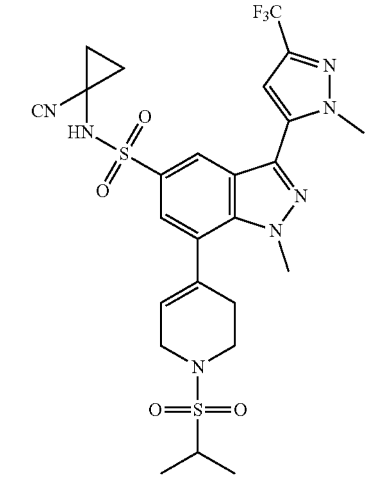
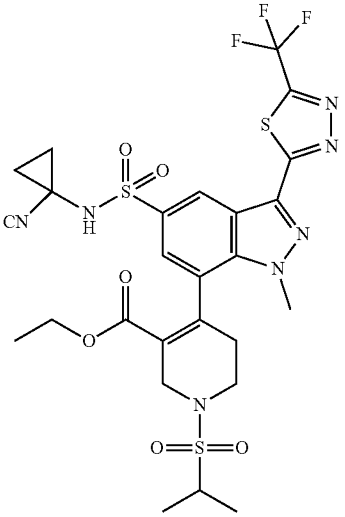
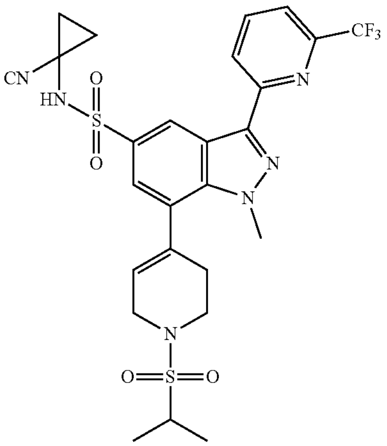
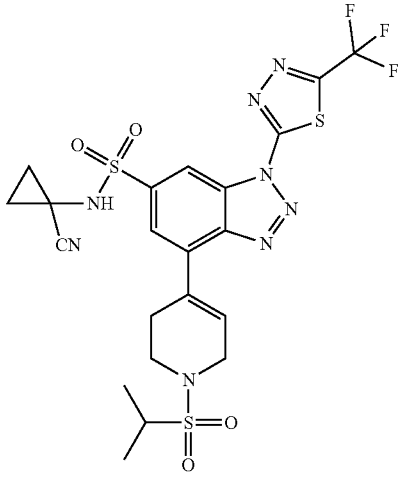
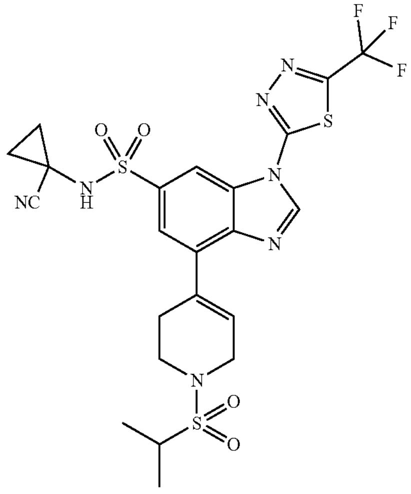

-continued

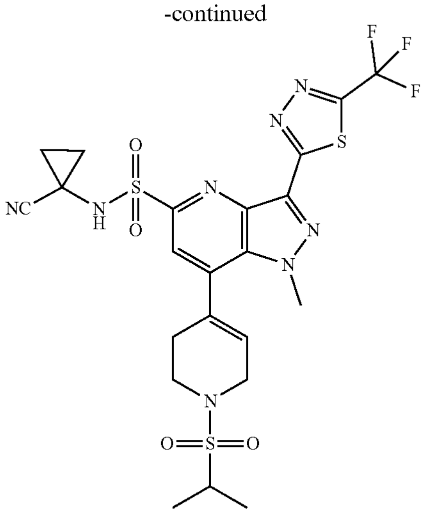

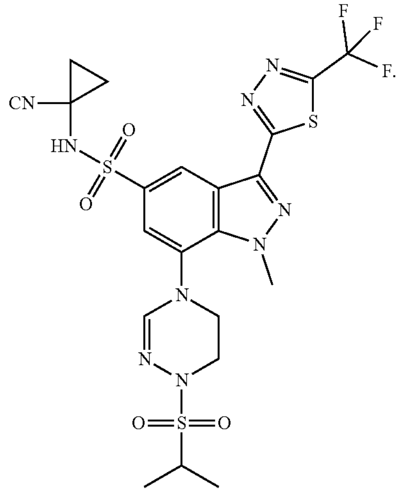

10. A pharmaceutical composition comprising a substance A and a pharmaceutically acceptable excipient, wherein the substance A is a therapeutically effective amount of the compound of formula I, the pharmaceutically acceptable salt thereof, the stereoisomer thereof, the tautomer thereof or the isotopically labeled compound thereof according to claim 1.

11. A method for inhibiting PARG in a subject in need thereof, comprising: administering a therapeutically effective amount of a substance A to the subject, wherein the substance A is the compound of formula I, the pharmaceutically acceptable salt thereof, the stereoisomer thereof, the tautomer thereof or the isotopically labeled compound thereof according to claim 1.

12. A method for treating a PARG related disease in a subject in need thereof, comprising: administering an effective amount of a substance A, wherein the substance A is the compound containing structure of a heteroaromatic ring of formula I, the pharmaceutically acceptable salt thereof, the stereoisomer thereof, the tautomer thereof or the isotopically labeled compound thereof according to claim 1.

13. A method for treating a cancer, comprising: administering a therapeutically effective amount of a substance A to the subject, wherein the substance A is the compound of formula I, the pharmaceutically acceptable salt thereof, the stereoisomer thereof, the tautomer thereof or the isotopically labeled compound thereof according to claim 1; the cancer is selected from the group consisting of colon cancer, appendicle cancer, pancreatic cancer, MYH-related polyposis, hematologic cancer, breast cancer, endometrial cancer, gallbladder cancer, bile duct cancer, prostate cancer, lung cancer, brain cancer, ovarian cancer, cervical cancer, testicular cancer, kidney cancer, head or neck cancer, bone cancer, skin cancer, rectal cancer, liver cancer, esophageal cancer, stomach cancer, thyroid cancer, bladder cancer, lymphoma, leukemia and melanoma.

* * * * *